United States Patent
Varma et al.

(10) Patent No.: US 11,903,984 B1
(45) Date of Patent: *Feb. 20, 2024

(54) **COMPOSITIONS COMPRISING *PROPIONIBACTERIUM ACNES* BACTERIOPHAGES FOR TREATING ACNE**

(71) Applicant: PHI THERAPEUTICS, INC., San Francisco, CA (US)

(72) Inventors: Yug Varma, San Francisco, CA (US); Nancy Van Prooyen, San Francisco, CA (US)

(73) Assignee: PHI THERAPEUTICS, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/819,050

(22) Filed: Aug. 11, 2022

Related U.S. Application Data

(63) Continuation of application No. 16/606,158, filed as application No. PCT/US2018/028556 on Apr. 20, 2018.

(Continued)

(51) Int. Cl.
*C12N 15/09* (2006.01)
*A61K 35/76* (2015.01)
(Continued)

(52) U.S. Cl.
CPC ............ *A61K 35/76* (2013.01); *A61K 9/0014* (2013.01); *A61K 31/05* (2013.01); *A61K 31/327* (2013.01);
(Continued)

(58) Field of Classification Search
CPC ....................................................... C12N 15/09
See application file for complete search history.

(56) References Cited

U.S. PATENT DOCUMENTS

| 5,034,506 A | 7/1991 | Summerton et al. |
| 5,235,033 A | 8/1993 | Summerton et al. |

(Continued)

FOREIGN PATENT DOCUMENTS

| EP | 0817613 B1 | 3/2005 |
| KR | 20120115920 A | 10/2012 |

(Continued)

OTHER PUBLICATIONS

NCBI Blast, a Blast search of SEQ ID No. 1 on the NIH National Center for Biotechnology Information blastn suite web site, https://blast.ncbi.nlm.nih.gov/Blast.cgi?PROGRAM=blastn&BLAST_SPEC=GeoBlast&PAGE_TYPE=BlastSearch, Apr. 19, 2023.*

(Continued)

*Primary Examiner* — Rosanne Kosson
(74) *Attorney, Agent, or Firm* — QUARLES & BRADY LLP

(57) ABSTRACT

Provided herein are, inter alia, compositions, systems, and methods for preventing or treating acne. Included are compositions, combinations, systems, and methods comprising at least one *Propionibacterium acnes* bacteriophage, at least one anti-acne compound, and a pharmaceutically acceptable carrier. Also included are compositions, combinations, and systems comprising a *Propionibacterium acnes* bacteriophage and an enzyme. Methods for preventing or treating acne are also provided.

18 Claims, 11 Drawing Sheets

Specification includes a Sequence Listing.

Related U.S. Application Data

(60) Provisional application No. 62/488,326, filed on Apr. 21, 2017.

(51) Int. Cl.
| | |
|---|---|
| *A61K 9/00* | (2006.01) |
| *A61K 38/47* | (2006.01) |
| *A61K 31/60* | (2006.01) |
| *A61P 17/10* | (2006.01) |
| *A61K 31/05* | (2006.01) |
| *A61K 33/04* | (2006.01) |
| *A61K 45/06* | (2006.01) |
| *A61K 31/327* | (2006.01) |
| *A61K 35/741* | (2015.01) |

(52) U.S. Cl.
CPC .............. *A61K 31/60* (2013.01); *A61K 33/04* (2013.01); *A61K 35/741* (2013.01); *A61K 38/47* (2013.01); *A61K 45/06* (2013.01); *A61P 17/10* (2018.01); *C12Y 302/01052* (2013.01)

(56) References Cited

U.S. PATENT DOCUMENTS

| | | | |
|---|---|---|---|
| 6,034,506 | A | 3/2000 | Hall et al. |
| 6,235,033 | B1 | 5/2001 | Brace et al. |
| 9,068,159 | B2 | 6/2015 | Holland et al. |
| 9,125,919 | B2 | 9/2015 | Maloney et al. |
| 9,526,738 | B2 | 12/2016 | Stasko et al. |
| 2008/0299159 | A1 | 12/2008 | Aimi et al. |
| 2015/0086581 | A1 | 3/2015 | Li et al. |
| 2016/0338979 | A1 | 11/2016 | Huang |

FOREIGN PATENT DOCUMENTS

| | | | |
|---|---|---|---|
| KR | 20150141385 A | 12/2015 | |
| WO | 2007/007055 A1 | 1/2007 | |
| WO | 2015/118150 A2 | 8/2015 | |
| WO | 2016130024 A1 | 8/2016 | |
| WO | WO-2016130024 A1 * | 8/2016 | ............. C12N 75/55 |
| WO | 2017200873 A1 | 11/2017 | |
| WO | 2018/195415 A1 | 10/2018 | |
| WO | WO-2019113066 A1 * | 6/2019 | ............. A61K 35/76 |

OTHER PUBLICATIONS

Result 6, alignment of SEQ ID No. 1 and SEQ ID No. 14 of Weinstock et al. (WO 2019/113066 A1), search of SEQ ID No. 1 in the PTO's database of published patent applications performed on Apr. 27, 2023.*

Blast2 search of SEQ ID No. 1 vs. P. acnes phage PA3, NIH National Center for Biotechnology Information blast2 suite web site, https://blast.ncbi.nlm.nih.gov/Blast.cgi?PAGE=MegaBlast&PROGRAM=blastn&BLAST_PROGRAMS=megaBlast&PAGE_TYPE=BlastSearch&BLAST_SPEC=blast2seq&DATABASE=n/a&QUERY=&SUBJECTS=, May 1, 2023.*

CVS Pharmacy, CVS Acne Treatment—Resorcinol, Sulfur Cream, Drug Facts and Product Information, Revised Jul. 2010, 5 pages.

Genbank, Propionibacterium Phage PA6, Complete Genome, GenBank ID: DQ431235.1, 2007, 13 pages.

Lu et al., Dispersing Biofilms with Engineered Enzymatic Bacteriophage, Proceedings of the National Academy of Sciences, 2007, 104(27):11197-11202.

Farrar et al., Genome Sequence and Analysis of a Propionibacterium Acnes Bacteriophage, Journal of Bacteriology, 2007, 189(11):4161-4167.

Achermann et al., Propionibacterium Acnes: From Commensal to Opportunistic Biofilm-Associated Implant Pathogen, Clinical Microbiology Reviews, 2014, 27(3):419-440.

Jonczyk-Matysiak et al., Prospects of Phage Application in the Treatment of Acne Caused by Propionibacterium Acnes, Frontiers in Microbiology, 2017, vol. 8, Article 164, pp. 1-11.

Ister et al., *Staphylococcus aureus* Biofilms: Recent Developments in Biofilm Dispersal, Frontiers in Cellular and Infection Microbiology, 2014, vol. 4, Article 178, pp. 1-9.

Marinellli et al., Propionibacterium Acnes Bacteriophages Display Limited Genetic Diversity and Broad Killing Activity Against Bacterial Skin Isolates, MBio, 2012, 3(5):e00279-12, pp. 1-13.

Altschul et al.(Oct. 1990) "Basic Local Alignment Search Tool", Journal of Molecular Biology, 215(3):403-410.

Altschul et al. (Sep. 1, 1997) "Gapped BLAST and PSI-Blast: A New Generation of Protein Database Search Programs", Nucleic Acids Research, 25(17):3389-3402.

Coenye et al. (May 2007) "Biofilm Formation by Propionibacterium Acnes is Associated with Increased Resistance to Antimicrobial Agents and Increased Production of Putative Virulence Factors", Research in Microbiology, 158 (4):386-392.

Database Genbank "Cutibacterium acnes KPA171202, complete sequence", NCBI Reference Sequence: NC_006085.1.

Fligiel et al. (Jun. 1984) "Protein Degradation Following Treatment with Hydrogen Peroxide", The American Journal of Pathology, 115(3):418-425.

Grice et al. ( 2009) "Topographical and Temporal Diversity of the Human Skin Microbiome", Science, 324(5931): 1190-1192.

Henikoff et al. (Nov. 1992) "Amino Acid Substitution Matrices from Protein Blocks", Proceedings of the National Academy of Sciences of the United States of America, 89(22): 10915-10919.

Jahns et al. (2014) "Three Dimensional Distribution of Propionibacterium Acnes Biofilms in Human Skin", Experimental Dermatology, 23:687-689.

Kachlany et al. (Nov. 2000) "Nonspecific Adherence by Actinobacillus Actinomycetemcomitans Requires Genes Widespread in Bacteria and Archaea", Journal of Bacteriology, 182(21):6169-6176.

Verbeeck et al.(1985) "Plasma Protein Binding of Salicylic Acid, Phenytoin, Chlorpromazine, Propranolol and Pethidine Using Equilibrium Dialysis and Ultracentrifugation", Arzneimittelforschung, 35(6):903-906.

Kocha et al. (Feb. 1997) "Hydrogen Peroxide-Mediated Degradation of Protein: Different Oxidation Modes of Copper- and Iron-Dependent Hydroxyl Radicals on the Degradation of Albumin", Biochimica et Biophysica Acta, 1337 2):319-326.

Lee et al. (Jun. 1995) "Protein Binding of Acetylsalicylic Acid and Salicylic Acid in Porcine and Human Serum", Veterinary and Human Toxicology , 37(3):224225.

Needleman et al. (Mar. 28, 1970) "A General Method Applicable to the Search for Similarities in the Amino Acid Sequence of Two Proteins", Journal of Molecular Biology, 48(3):443-453.

Pearson et al. (Apr. 1988) "Improved Tools For Biological Sequence Comparison", Proceedings of the National Academy of Sciences, 85:2444-2448.

Schreiner et al. (Jun. 10, 2003) "Tight-Adherence Genes of Actinobacillus Actinomycetemcomitans are Required for Virulence in a Rat Model", Proceedings of the National Academy of Sciences of the United States of America, 100 (12):7295-7300.

Smith et al. (Dec. 1981) "Comparison of Biosequences", Advances in Applied Mathematics, 2(4):482-489.

Suh et al. (2015) "What's New in the Physiopathology of Acne", British Journal of Dermatology, 172(suppl 1): 13-19.

Swindle et al. (Mar. 2012) "Swine as Models in Biomedical Research and Toxicology Testing", Veterinary Pathology, 49(2):344-356.

Tomich et al.(May 2007) "The Tad Locus: Postcards from the Widespread Colonization Island", Nature Reviews Microbiology, 5(5):363-375.

Tyner et al. (May 27, 2016) "Propionibacterium Acnes biofilm—A sanctuary for Staphylococcus Aureus?", Anaerobe, 40:63-67.

* cited by examiner

COMPOSITIONS COMPRISING *PROPIONIBACTERIUM ACNES* BACTERIOPHAGES FOR TREATING ACNE

CROSS-REFERENCE TO RELATED APPLICATIONS

This application claims the benefit of priority to U.S. Provisional Application No. 62/488,326, filed Apr. 21, 2017, which is hereby incorporated by reference in its entirety and or all purposes.

GOVERNMENT SUPPORT

This invention was made with government support under Grant No. 1R43AR068172-01 awarded by the National Institutes of Health. The government has certain rights in the invention.

INCORPORATION-BY-REFERENCE OF SEQUENCE LISTING

The content of the text file named "052004-503001WO_SequenceListing.TXT", which was created on Apr. 20, 2018, and is 101,782 bytes in size, is hereby incorporated by reference in its entirety.

BACKGROUND

Acne is a nearly universal condition that affects more than 80% of all people worldwide. This chronic skin condition is complex but the main etiological agent is *Propionibacterium acnes* whose overgrowth leads to inflammation that causes pimples. Despite a clear need for innovation, there has not been a novel acne drug in over 30 years. Current treatments including benzoyl peroxide and antibiotics are quite ineffective, and the most effective treatment—isotretinoin—is limited to a small set of patients due to dangerous side effects (including birth defects, liver damage, and suicide).

New methods and compositions for treating for acne are needed.

BRIEF SUMMARY

Provided herein are, inter alia, compositions, combinations, systems, and methods for preventing or treating acne.

In an aspect, provided herein is a composition comprising, consisting essentially of, or consisting of at least one *Propionibacterium acnes* bacteriophage, at least one anti-acne compound, and a pharmaceutically acceptable carrier.

In an aspect, provided herein is a composition that includes at least one *Propionibacterium acnes* bacteriophage, no more than one anti-acne compound, and a pharmaceutically acceptable carrier.

In an aspect, provided herein is a composition that includes active ingredients consisting of at least one *Propionibacterium acnes* bacteriophage and no more than one anti-acne compound, and a pharmaceutically acceptable carrier.

In an aspect, provided herein is a composition that includes at least one *Propionibacterium acnes* bacteriophage, at least one anti-acne compound, and a pharmaceutically acceptable carrier, wherein the composition does not comprise a probiotic bacterium.

In an aspect, provided herein is a composition that includes a *Propionibacterium acnes* bacteriophage and an enzyme.

In an aspect, provided herein is a combination comprising, consisting essentially of, or consisting of at least one *Propionibacterium acnes* bacteriophage and at least one anti-acne compound, wherein each of the at least one *Propionibacterium acnes* bacteriophage and the at least one anti-acne compound is in a composition that further includes a pharmaceutically acceptable carrier.

In an aspect, provided herein is a combination that includes a *Propionibacterium acnes* bacteriophage and an enzyme.

In an aspect, provided herein is a method of preventing or treating acne in a subject in need thereof, the method including administering an effective amount of a composition or combination provided herein.

DETAILED DESCRIPTION

Figure 1:
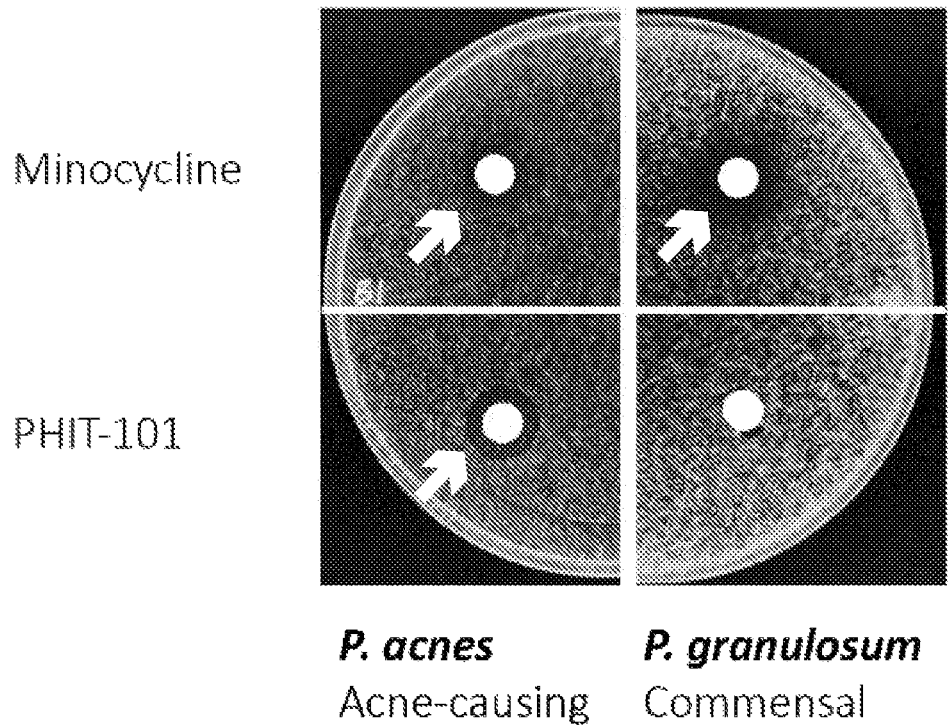
FIG. 1. *P. acnes* (acne-causing, left half plate) or *P. granulosum* (commensal, right half plate) bacteria was plated on RCM-agar petri dishes. Sterile half-pads soaked in either minocycline or PHIT-101 ($10^7$ pfu/mL) were placed on each plate. After anaerobic incubation at 37° C. for 3 days, zones of killing (arrows) appear, indicating that minocycline kills both pathogenic and commensal bacteria while PHIT-101 kills the acne-causing bacteria without disturbing commensal *P. granulosum*.

Provided herein, are, inter alia, compositions, combinations, methods, and systems for treating and preventing acne.

Salicylic acid and benzoyl peroxide are the most commonly used anti-acne agents in over-the-counter (OTC) products. The stability of phages in combination with these anti-acne agents is unknown, especially since phages diverge widely in their stability and response to external physical and chemical factors. The redox properties of benzoyl peroxide and sulfur can potentially cause the degradation of the protein coat of the phage. Previous studies have shown that exposure to peroxide increases the rate of protein degradation by destabilizing the protein and increasing its susceptibility to proteolysis (Fligiel et al. Protein degradation following treatment with hydrogen peroxide. *Am J Pathol* 1984, 115 (3), 418-25; Kocha et al. Hydrogen peroxide-mediated degradation of protein: different oxidation modes of copper- and iron-dependent hydroxyl radicals on the degradation of albumin. *Biochim Biophys Acta* 1997, 1337 (2), 319-26). Salicylic acid is noted for its protein-binding ability (Lee et al. Protein binding of acetylsalicylic acid and salicylic acid in porcine and human serum. *Vet Hum Toxicol* 1995, 37 (3), 224-5; Verbeeck and Cardinal, Plasma protein binding of salicylic acid, phenytoin, chlorpromazine, propranolol and pethidine using equilibrium dialysis and ultracentrifugation. *Arzneimittelforschung* 1985, 35 (6), 903-6), and a high affinity for the protein coat of the capsid or the tail fibers would render the phage unviable.

Surprisingly, a *Propionibacterium acnes* bacteriophage was found to be stable in compositions that include salicylic acid. See, for example, FIG. 15. Thus, salicylic acid is shown to be well tolerated by the phage and is a suitable anti-acne agent for co-formulation. In embodiments, the anti-keratolytic activity of the salicylic acid complements phage activity by enabling deeper penetration of the phage, thereby increasing its killing efficiency. In embodiments, phages as described herein may be combined with salicylic acid in compositions for preventing and treating acne.

While benzoyl peroxide is not suitable for co-formulation with the phage tested (see FIG. 16) for formulations that will be stored for more than, e.g., a few days, benzoyl peroxide can be used along with a phage product as part of an anti-acne combination (e.g., a kit). In embodiments, the benzoyl peroxide is an active ingredient in a cleanser, which is applied to the skin and washed off prior to the application of a comprising the phage composition/formulation. In embodiments, the anti-keratolytic and transient antibacterial action of the benzoyl peroxide complements the specific deeper and targeted killing of *P. acnes* by the bacteriophage.

In embodiments, a *Propionibacterium acnes* bacteriophage and an anti-acne compound (such as salicylic acid and/or sulfur) are in a single composition that is topically administered to the skin of a subject. In embodiments, a kit that includes a *Propionibacterium acnes* bacteriophage and an anti-acne compound (e.g. in separate containers, such as bottles) is provided. In embodiments, a *Propionibacterium acnes* bacteriophage is in one composition and an anti-acne compound (such as benzoyl peroxide, salicylic acid, and/or sulfur) is in another composition, and each composition is topically administered to the skin of a subject. In embodiments, the *Propionibacterium acnes* bacteriophage is administered to the subject, and then the anti-acne compound is administered to the subject. In embodiments, the anti-acne compound is administered to the subject, and then the *Propionibacterium acnes* bacteriophage is administered to the subject. In embodiments, the subject's face is washed between when the anti-acne compound and the *Propionibacterium acnes* bacteriophage (in either order) are topically administered to the face of the subject.

In embodiments, the effective dose of the anti-acne compound (such as benzoyl peroxide, salicylic acid, or sulfur) when used in combination with the *Propionibacterium acnes* bacteriophage is less than would be required if the anti-acne compound was used alone. In embodiments, the effective dose of the anti-acne compound (such as benzoyl peroxide, salicylic acid, or sulfur) when used in combination with the *Propionibacterium acnes* bacteriophage is less than 90%, 80%, 70%, 60%, 50%, 40%, 30%, 20%, or 10% less than the dose that would be required if the anti-acne compound was used alone.

Definitions

The following definitions are included for the purpose of understanding the present subject matter and for constructing the appended patent claims. The abbreviations used herein have their conventional meanings within the chemical and biological arts.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure As used herein a "*Propionibacterium acnes* bacteriophage" is a bacteriophage that infects, replicates within, and kills *P. acnes* cells. In embodiments, a *P. acnes* bacteriophage is a lytic *P. acnes* bacteriophage. In embodiments, a *P. acnes* bacteriophage is capable of lysing a *P. acnes* bacterium and incapable of lysing any bacterium which is not *P. acnes*. In embodiments, a *P. acnes* bacteriophage is incapable of sustaining lysogeny in a bacterium. In embodiments, the use of a bacteriophage that can lyse *P. acnes* but is incapable of sustaining lysogeny has the advantage that the bacteriophage cannot lie dormant within a bacterium, but must lyse the bacterium and hence kill it. In embodiments, a *P. acnes* bacteriophage lacks the ability to express at least one gene necessary for sustaining lysogeny. The term "lacks the ability to express at least one gene necessary for sustaining lysogeny" is intended to indicate that the *P. acnes* bacteriophage lacks the ability to produce a fully functional protein product necessary to sustain lysogeny, for example, as the result of one or more point mutations or full or partial deletions of the genome. In embodiments, the *P. acnes* bacteriophage has a genome that lacks all or part of at least one gene necessary for sustaining lysogeny (e.g., artificially or naturally, e.g., the strain is or is derived from a strain that lacks all or part of at least one gene necessary for sustaining lysogeny). In embodiments, the *P. acnes* bacteriophage may comprise defects (e.g. mutations, insertions or deletions) in the genome in non-coding regions that may, nonetheless, affect the ability of the phage to sustain lysogeny, for example defects in the genome integration site(s) (e.g. a/att/site) or in a repressor binding site. In embodiments, a *P. acnes* bacteriophage is naturally occurring and isolated, with the added advantage that artificial mutations need not be introduced into the bacteriophage. In embodiments, a *P. acnes* bacteriophage is capable of lysing a plurality of strains of the *P. acnes* bacterium. In embodiments, a *P. acnes* bacteriophage is capable of lysing at least about 5, 10, 15, 20, 25, 30 or more strains of the *P. acnes* bacterium. Non-limiting examples of *P. acnes* bacteriophages are disclosed herein. In embodiments, the *P. acnes* bacteriophage has a genome having sequence identity of at least about 80%, 81%, 82%, 83%, 84%, 85%, 86%, 87%, 88%, 89%, 90%, 95%, 99%, 99.1%, 99.2%, 99.3%, 99.4%, 99.5%, 99.6%, 99.7%, 99.8%, 99.9% with SEQ ID NO: 1. In embodiments, a *P. acnes* bacteriophage has a genome having the sequence of SEQ ID NO: 1, or includes the sequence of SEQ ID NO: 1. In embodiments, the genome of the *P. acnes* bacteriophage has no insertions or deletions compared to SEQ ID NO: 1. In embodiments, the genome of the *P. acnes* bacteriophage has no insertions or deletions, and only conservative substitutions compared to SEQ ID NO: 1. In embodiments, the *P. acnes* bacteriophage is one of the following exemplary isolates of *P. acnes* bacteriophages that have been deposited under the terms of the Budapest Treaty at The National Collection of Industrial, Marine and Food Bacteria (NCIMB), Ferguson Building, Craibstone Estate, Bucksburn, Aberdeen, AB21 9YA, United Kingdom, under the following accession numbers: Accession no. NCIMB 41332 (isolate PA6); Accession no. NCIMB 41334 (isolate 1874); Accession no. NCIMB 41333 (isolate 1878); Accession no. NCIMB 41335 (isolate 1905); Accession no. NCIMB 41349 (isolate 1894); Accession no. NCIMB 41350 (isolate 103609); Accession no. NCIMB 41351 (isolate 103672). In embodiments, a non-limiting example of a host bacterium, *P. acnes*, AT1 has been deposited as NCIMB 41336. In embodiments, a *P. acnes* bacteriophage has a genome having sequence identity of at least about 80%, 81%, 82%, 83%, 84%, 85%, 86%, 87%, 88%, 89%, 90%, 95%, or 99% with the genome of the bacteriophage deposited under Accession No. NCIMB 41349. In embodiments, a P. acnes bacteriophage has a genome having sequence identity of at least 87% with the genome of the bacteriophage deposited under Accession No. NCIMB 41350. In embodiments, a P. acnes bacteriophage has a genome having sequence identity of at least 88% with the genome of the bacteriophage deposited under Accession No. NCIMB 41351. Additional non-limiting descriptions relating to P. acnes bacteriophages are provided in U.S. Pat. No. 9,068,159 B2, issued Jun. 30, 2015, the entire content of which is incorporated herein by reference. The terms "phage" and "bacteriophage" are used interchangeably herein.

As used herein, "degrading" a biofilm means cleaving a covalent bond of at least one compound that forms part of a biofilm (e.g., by enzymatic activity). Non-limiting examples of compounds that may form a part of a biofilm include polymers, glycosides, proteins, polysaccharides, and nucleic acids. As used herein, a "P. acnes biofilm degrading enzyme" is an enzyme that degrades at least one compound that forms part of a P. acnes biofilm.

The enzymes as provided herein include any naturally occurring forms, homologs, isoforms or variants that maintain the enzymatic activity (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form.

The term "isolated," when applied to a bacterium or bacteriophage, refers to a bacterium or bacteriophage that has been (1) separated from at least some of the components with which it was associated when initially produced (whether in nature or in an experimental setting), and/or (2) produced, prepared, purified, and/or manufactured by the hand of man, e.g. using artificial culture conditions such as (but not limited to) growing on a plate and/or in a fermenter. Isolated bacteria include those bacteria that are cultured, even if such cultures are not monocultures. In embodiments, the isolated bacteria are bacteria that are cultured as a monoculture (e.g., on a plate or in liquid culture such as in a fermenter). Isolated bacteria and bacteriophages may be separated from at least about 10%, about 20%, about 30%, about 40%, about 50%, about 60%, about 70%, about 80%, about 90%, about 95%, about 96%, about 97%, about 99% or more of the other components with which they were initially associated (e.g., by weight). In embodiments, isolated bacteria are more than about 80%, about 85%, about 90%, about 91%, about 92%, about 93%, about 94%, about 95%, about 96%, about 97%, about 98%, about 99%, or more than about 99% pure (e.g., by weight). In embodiments, isolated bacteriophages are more than about 80%, about 85%, about 90%, about 91%, about 92%, about 93%, about 94%, about 95%, about 96%, about 97%, about 98%, about 99%, or more than about 99% pure (e.g., by weight). In embodiments, a composition provided herein includes one or more isolated bacteriophages. In embodiments, a composition provided herein includes an isolated bacteriophage. In embodiments, a bacteriophage that is administered is an isolated bacteriophage. In embodiments, a composition provided herein includes one or more isolated bacteria. In embodiments, a composition provided herein includes an isolated bacterium. In embodiments, a bacterium that is administered is an isolated bacterium.

A "control" sample or value refers to a sample that serves as a reference, usually a known reference, for comparison to a test sample. For example, a test sample can be taken from a test condition, e.g., in the presence of a test compound (e.g., enzyme) or phage, and compared to samples from known conditions, e.g., in the absence of the test compound, phage, or bacterium (negative control), or in the presence of a known compound, phage, or bacterium (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life, the degradation of a biofilm or a component thereof, or bacterial cell lysis) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Polynucleotides are polymers of any length, including longer lengths, e.g., 200, 300, 500, 1000, 2000, 3000, 5000, 7000, 10000, 20000, 30000, 40000 etc. Polynucleotides and oligonucleotides will generally contain phosphodiester bonds, although in some cases, nucleic acid analogs are included that may have alternate backbones, that include, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The term "bp" and the like refer, in the usual and customary sense, to the indicated number of base pairs.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. In embodiments, the percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire nucleic acid or polypeptide sequence or individual portions or domains of a nucleic acid or polypeptide), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. In embodiments, the identify exists over a region that is about or at least about 20, 50, 100, 1000, 2500, 5000, 7500, 10000, 15000, 20000, 25000, or 30000 amino acids or nucleotides in length to about, less than about, or at least about 31000, 32000, 33000, 34000 or 35000 amino acids or nucleotides in length. Optionally, the identity exists over a region that is at least about 10 to about 100, about 20 to about 75, about 30 to about 50 amino acids or nucleotides in length. Optionally, the identity exists over a region that is at least about 50 amino acids in length, or more preferably over a region that is 100 to 500 or 1000 or more amino acids in length. Included herein are phages comprising nucleic acids (e.g., a genome or a portion thereof) having sequences that are substantially identical to any of SEQ ID NOs: 1, 11, 13, 15, 17, 19, 21, 23, 25, or 27. Non-limiting examples of phages provided herein comprise genomes having sequences that are substantially identical to SEQ ID NO: 1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions in which a sequence may be compared to a reference sequence of the same number of contiguous positions after the two sequences are optimally aligned. In embodiments, a comparison window includes about or at least about 20, 50, 100, 1000, 2500, 5000, 7500, 10000, 15000, 20000, 25000, or 30000 to about, less than about, or at least about 31000, 32000, 33000, 34000 or 35000 contiguous positions. In embodiments, a comparison window includes about or at least about 20 to about, less than about, or at least about 31000 contiguous positions. In embodiments, a comparison window includes about or at least about 25000 to about, less than about, or at least about 31000 contiguous positions. In embodiments, a comparison window includes about or at least about 26000 to about, less than about, or at least about 31000 contiguous positions. In embodiments, a comparison window includes about or at least about 27000 to about, less than about, or at least about 31000 contiguous positions. In embodiments, a comparison window includes about or at least about 28000 to about, less than about, or at least about 31000 contiguous positions. In embodiments, a comparison window includes about or at least about 29000 to about, less than about, or at least about 31000 contiguous positions. In embodiments, a comparison window includes about or at least about 30000 to about, less than about, or at least about 31000 contiguous positions. In embodiments, a comparison includes about 20 to about 600, about 50 to about 200, or about 100 to about 150 contiguous positions. In embodiments, the comparison window is the entire length of a reference sequence, such as the sequence of a bacteriophage genome. Methods of alignment of sequences for comparison are well-known in the art. In embodiments, optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of algorithms suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. As will be appreciated by one of skill in the art, the software for performing BLAST analyses is publicly available through the website of the National Center for Biotechnology Information (NCBI). In embodiments, BLAST and BLAST 2.0 are used, with the parameters described herein, to determine percent sequence identity for the nucleic acids and proteins. In embodiments, a BLAST algorithm involves first identifying high scoring sequence pairs (HSPs) by identifying short words of length W in the query sequence, which either match or satisfy some positive-valued threshold score T when aligned with a word of the same length in a database sequence. In embodiments, T is referred to as the neighborhood word score threshold (Altschul et al., supra). In embodiments, these initial neighborhood word hits act as seeds for initiating searches to find longer HSPs containing them. In embodiments, the word hits are extended in both directions along each sequence for as far as the cumulative alignment score can be increased. In embodiments, cumulative scores are calculated using, for nucleotide sequences, the parameters M (reward score for a pair of matching residues; always >0) and N (penalty score for mismatching residues; always <0). In embodiments, for amino acid sequences, a scoring matrix is used to calculate the cumulative score. In embodiments, extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. In embodiments, the BLAST algorithm parameters W, T, and X determine the sensitivity and speed of the alignment. In embodiments, the NCBI BLASTN or BLASTP program is used to align sequences. In embodiments, the BLASTN or BLASTP program uses the defaults used by the NCBI. In embodiments, the BLASTN program (for nucleotide sequences) uses as defaults: a word size (W) of 28; an expectation threshold (E) of 10; max matches in a query range set to 0; match/mismatch scores of 1, −2; linear gap costs; the filter for low complexity regions used; and mask for lookup table only used. In embodiments, the BLASTP program (for amino acid sequences) uses as defaults: a word size (W) of 3; an expectation threshold (E) of 10; max matches in a query range set to 0; the BLOSUM62 matrix (see Henikoff & Henikoff, Proc. Natl. Acad. Sci. USA 89:10915 (1992)); gap costs of existence: 11 and extension: 1; and conditional compositional score matrix adjustment.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions to a peptide, polypeptide, or protein sequence which alters a single amino acid is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "disease" refers to any deviation from the normal health of a mammal and includes a state when disease symptoms are present, as well as conditions in which a deviation (e.g., dysbiosis, infection, gene mutation, genetic defect, etc.) has occurred, but symptoms are not yet manifested. In embodiments, the disease is acne. In embodiments, the disease includes dermal dysbiosis. In embodiments, methods, compositions, systems, phages, and probiotic bacteria provided herein are suitable for use in a subject that is a member of the Vertebrate class, Mammalia, including, without limitation, primates (such as humans), livestock, work animals, and domestic pets (e.g., a companion animal). In embodiments, a subject is a human subject. As used herein, a "symptom" of a disease includes and clinical or laboratory manifestation associated with the disease, and is not limited to what a subject can feel or observe.

As used herein, the term "dermal dysbiosis" means a difference in the skin microbiota compared to a healthy or general population. In embodiments, the dysbiosis is on the surface of the skin, within skin (e.g., within a skin region or layer of skin cells), within a gland, and/or within a pore of the skin. In embodiments, the dysbiosis is within sweat and/or sebum. In embodiments, the skin is on the face (e.g., the forehead, one or more cheeks, the nose, or the chin of a subject). In embodiments, the skin is on the shoulders, chest, or back. In embodiments, dermal dysbiosis includes a change in microbiota commensal species diversity as compared to a healthy or general population and may include decrease of beneficial microorganisms and/or increase of pathobionts (pathogenic or potentially pathogenic microorganisms) and/or decrease of overall microbiota species diversity. Many factors can lead to dysbiosis, including hormonal changes (e.g., during adolescence), infrequent washing, cosmetic use, antibiotic use, psychological and physical stress, radiation, and dietary changes.

In embodiments, compositions are administered to a subject suffering from acne in a "therapeutically effective dose." Amounts effective for this use may depend upon the severity of the disease and the general state of the patient's health. Single or multiple administrations of the compositions may be administered depending on the dosage and frequency as required and tolerated by the patient. A "patient" or "subject" includes both humans and other animals, particularly mammals. Thus the methods are applicable to both human therapy and veterinary applications.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the bacteriophages, probiotic bacteria, and/or compounds of the invention. One of skill in the art will recognize that other pharmaceutical excipients are useful in the present invention.

The term "contacting" may include allowing two species to react, interact, or physically touch, wherein the two species may be, for example, an enzyme as described herein and a biofilm that includes a substrate of the enzyme. In another example, the two species may be a bacteriophage and a cell of a species that the bacteriophage infects. In embodiments contacting includes, for example, allowing a bacteriophage as described herein to interact with a *P. acnes* cell. In embodiments contacting includes, for example, allowing an enzyme as described herein to interact with a *P. acnes* biofilm.

"Patient" or "subject in need thereof" refers to a living member of the animal kingdom suffering from or who may suffer from the indicated disorder. In embodiments, the subject is a member of a species that includes individuals who naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human.

The terms "subject," "patient," "individual," etc. are not intended to be limiting and can be generally interchanged. That is, an individual described as a "patient" does not necessarily have a given disease, but may be merely seeking medical advice.

As used herein the abbreviation "sp." for species means at least one species (e.g., 1, 2, 3, 4, 5, or more species) of the indicated genus. The abbreviation "spp." for species means 2 or more species (e.g., 2, 3, 4, 5, 6, 7, 8, 9, 10 or more) of the indicated genus. In embodiments, methods and compositions provided herein comprise a single species within an indicated genus or indicated genera, or 2 or more (e.g., a plurality that includes more than 2) species within an indicated genus or indicated genera. In embodiments, 1, 2, 3, 4, 5, or more or all or the indicated species is or are isolated. In embodiments, the indicated species are administered together. In embodiments, each of the indicated species is present in a single composition that includes each of the species. In embodiments, each of the species is administered concurrently, e.g., within about 1, 2, 3, 4, 5, 6, 7, 8, 9, 10, 30, or 60, 1-5, 1-10, 1-30, 1-60, or 5-15 seconds or minutes of each other.

In this disclosure, "comprises," "comprising," "containing," and "having" and the like can have the meaning ascribed to them in U.S. Patent law and can mean "includes," "including," and the like. Thus, the transitional term "comprising," which is synonymous with "including," "containing," or "characterized by," is inclusive or open-ended and does not exclude additional, unrecited features, integers, steps, operations, elements, and/or components. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. By contrast, the transitional phrase "consisting of" excludes any feature, integer, element, step, operation, component, and/or ingredient not specified.

As used herein, the term "about" in the context of a numerical value or range means ±10% of the numerical value or range recited or claimed, unless the context requires a more limited range.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," herein and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

As used in the description herein and throughout the claims that follow, the meaning of "a," "an," and "the" includes plural reference unless the context clearly dictates otherwise.

As used herein, "treating" or "treatment" of a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean inhibiting the progression of the condition, disorder or disease, slowing the progression of the condition, disorder or disease temporarily, although in some instances, it involves halting the progression of the condition, disorder or disease permanently. In the case of treating acne, the terms can refer to reducing, e.g., dermal dysbiosis and/or the number or size of cystic lesions, whiteheads (closed plugged pores), blackheads (open plugged pores—in which oil exposed to the air has a dark color, e.g., brown or black), mall red, tender bumps (papules), pimples (pustules; papules with pus at their tips), large, solid, painful lumps beneath the surface of the skin (nodules).

As used herein, the terms "treat" and "prevent" are not intended to be absolute terms. In embodiments, treatment can refer to a 10%, 20%, 30%, 40%, 50%, 60%, 70%, 80%, 90%, or 100% reduction in the severity of an established disease, condition, or symptom of the disease or condition. In embodiments, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. In embodiments, references to decreasing, reducing, or inhibiting include a change of 10%, 20%, 30%, 40%, 50%, 60%, 70%, 80%, 90% or greater as compared to a control level and such terms can include but do not necessarily include complete elimination. Treatment can refer to any delay in onset, amelioration of symptoms, improvement in patient skin appearance, etc. The effect of treatment can be compared to an individual or pool of individuals not receiving the treatment, or to the same patient prior to treatment or at a different time during treatment. In embodiments, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques. In embodiments, treatment is effective to reduce at least one symptom of acne. In embodiments, treatment is effective to reduce the level of pimples (pustules) on the face, forehead, chest, back, and/or shoulders of the subject. In embodiments, treatment is effective to reduce the level of whiteheads (closed plugged pores) on the face, forehead, chest, back, and/or shoulders of the subject. In embodiments, treatment is effective to reduce the level of blackheads (open plugged pores) on the face, forehead, chest, back, and/or shoulders of the subject. In embodiments, treatment is effective to reduce the level of papules on the face, forehead, chest, back, and/or shoulders of the subject. In embodiments, treatment is effective to reduce the level of solid, painful lumps beneath the surface of the skin (nodules) on the face, forehead, chest, back, and/or shoulders of the subject. In embodiments, treatment is effective to reduce the level of cystic lesions on the face, forehead, chest, back, and/or shoulders of the subject. In embodiments, the level (e.g., number) is reduced compared to before treatment has begun. In embodiments, the level (e.g., number) is reduced compared to a corresponding subject who is afflicted with *acnes* but who has not received treatment. In embodiments, the level (e.g., number) is reduced compared to a corresponding subject who is afflicted with *acnes* but who has not received treatment comprising a bacteriophage.

The terms "effective amount," "effective dose," "therapeutically effective amount," etc. refer to the amount of an agent that is sufficient to ameliorate a disorder, as described herein. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "diagnosis" refers to a relative probability a subject has a given metabolic disorder. Symptoms and diagnostic criteria are summarized herein. Similarly, the term "prognosis" refers to a relative probability that a certain future outcome may occur in the subject. For example, in the context of the present invention, prognosis can refer to the likelihood that an individual will develop acne. Prognosis can also refer to the likely severity of the disease (e.g., severity of symptoms, rate of functional decline, etc.). The terms are not intended to be absolute, as will be appreciated by any one of skill in the field of medical diagnostics.

Compositions and Combinations Comprising Bacteriophages

In an aspect, provided herein is a composition comprising, consisting essentially of, or consisting of at least one *P. acnes* bacteriophage, at least one anti-acne compound, and a pharmaceutically acceptable carrier.

In an aspect, provided herein is a composition that includes at least one *Propionibacterium acnes* bacteriophage, no more than one anti-acne compound, and a pharmaceutically acceptable carrier.

In an aspect, provided herein is a composition that includes active ingredients consisting of at least one *Propionibacterium acnes* bacteriophage and no more than one anti-acne compound, and a pharmaceutically acceptable carrier.

In an aspect, provided herein is a composition that includes at least one *P. acnes* bacteriophage, at least one anti-acne compound, and a pharmaceutically acceptable carrier, wherein the composition does not comprise a probiotic bacterium.

In embodiments, the at least one anti-acne compound is benzoyl peroxide. In embodiments, the benzoyl peroxide is present at a concentration of 2.5% to 10% (weight/volume). In embodiments, the benzoyl peroxide is present at a concentration of less than 2.5% but greater than about 0.1%, 0.5%, 1%, 1.5%, or 2% (weight/volume). In embodiments, the benzoyl peroxide is present at a concentration of 2.5% to 10%, e.g., about 2.5%, 3%, 3.5%, 4%, 4.5%, 5%, 5.5%, 6%, 6.5%, 7%, 7.5%, 8%, 8.5%>, 9%, 9.5% or 10% (weight/volume). In embodiments, the benzoyl peroxide is present at a concentration of less than 2.5% but greater than about 0.1%, 0.5%, 1%, 1.5%, or 2% (weight/volume).

In embodiments, the at least one anti-acne compound is salicylic acid. In embodiments, the salicylic acid is present at a concentration of 0.5% to 2% (weight/volume). In embodiments, the salicylic acid is present at a concentration of less than 0.5% but greater than about 0.1% (weight/volume). In embodiments, the salicylic acid is present at a concentration of 0.5% to 2%, e.g., about 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (weight/volume). In embodiments, the salicylic acid is present at a concentration of less than 0.5% but greater than about 0.1% (weight/volume).

In embodiments, the at least one anti-acne compound is sulfur. In embodiments, the sulfur is present at a concentration of 3% to 10% (weight/volume). In embodiments, the sulfur is present at a concentration of less than 3% but greater than about 0.1%, 0.5%, 1%, 1.5%, 2%, or 2.5% (weight/volume). In embodiments, the sulfur is present at a concentration of 3% to 10%, e.g., about 3%, 3.5%, 4%, 4.5%, 5%, 5.5%, 6%, 6.5%, 7%, 7.5%, 8%, 8.5%, 9%, 9.5%, or 10% (weight/volume). In embodiments, the sulfur is present at a concentration of less than 3% but greater than about 0.1%, 0.5%, 1%, 1.5%, 2%, or 2.5% (weight/volume). In embodiments, resorcinol is present at a concentration of 2% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume).

In embodiments, the at least one anti-acne compound is resorcinol and sulfur. In embodiments, the resorcinol is present at a concentration of 2% and sulfur is present at a concentration of 3% to 8% (weight/volume). In embodiments, resorcinol is present at a concentration of 2% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume).

In embodiments, the at least one anti-acne compound includes resorcinol monoacetate and sulfur. In embodiments, the resorcinol monoacetate is present at a concentration of 3% and sulfur is present at a concentration of 3% to 8% (weight/volume). In embodiments, resorcinol monoacetate is present at a concentration of 3% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume).

In embodiments, the *P. acnes* bacteriophage is present in an amount of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ plaque forming units (pfu). In embodiments, the *P. acnes* bacteriophage is present in an amount of about $1\times10^6$ to $1\times10^{11}$ pfu. In embodiments, the *P. acnes* bacteriophage is present in an amount of about $1\times10^6$ to $1\times10^8$, about $1\times10^8$ to $1\times10^9$, about $1\times10^9$ to $1\times10^{10}$, about $1\times10^9$ to $1\times10^{11}$ or about $1\times10^{10}$ to $1\times10^{11}$ pfu.

In embodiments, a probiotic bacterium is present in an amount of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ colony forming units (cfu). In embodiments, the probiotic bacterium is present in an amount of about $1\times10^6$ to $1\times10^{11}$ cfu. In embodiments, the probiotic bacterium is present in an amount of about $1\times10^6$ to $1\times10^8$, about $1\times10^8$ to $1\times10^9$, about $1\times10^9$ to $1\times10^{10}$, about $1\times10^9$ to $1\times10^{11}$ or about $1\times10^{10}$ to $1\times10^{11}$ cfu.

In embodiments, the anti-acne compound is an antibiotic, a retinoid, or an alpha-hydroxy acid.

In an aspect, provided herein is a composition that includes a *P. acnes* bacteriophage and an enzyme.

In an aspect, provided herein is a combination comprising, consisting essentially of, or consisting of at least one *P. acnes* bacteriophage, at least one anti-acne compound, wherein each of the at least one *P. acnes* bacteriophage and the at least one anti-acne compound is in a composition that further includes a pharmaceutically acceptable carrier.

In an aspect, provided herein is a combination that includes a *P. acnes* bacteriophage and an enzyme.

In embodiments, the *P. acnes* bacteriophage has a linear double stranded DNA genome.

In embodiments, the *P. acnes* bacteriophage is within the bacteriophage family Siphoviridae.

In embodiments, the bacteriophage is a wild-type bacteriophage. In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genomic sequence of a wild-type *P. acnes* bacteriophage. A non-limiting example of an genomic sequence for a wild-type *P. acnes* bacteriophage is as follows:

```
                                                        (SEQ ID NO: 1)
  1   AGTGAAATAC  CTCCCTTTTG  TGGTTTTGTC  TGTTTGTCGA  CTTTTTGTGT  TGGTGGTGAG

61   TGTTGTGCAG  CCTGAGCTTC  CTGAGTCTCG  TGAGTGGTGT  GGGGAGACGC  GTCGTTGGTG

121   GCGTGTGTGG  GGTGAGGATA  GTCGCGCGCC  GTATGTGTCT  GATGAGGAGT  GGTTGTTTCT

181   TATGGATGCT  GCGGTGATTC  ATGATTGTGT  GTGGCGTGAG  GGTCGCGCGG  ATTTGGTGGC

241   TTCGCTTCGT  GCGCATGTGA  AGGCTTTTAT  GGGCATGTTG  GATAGGTATT  CGGTTGATGT

301   GGCGTCTGGT  GGCCGTGGTG  GGGGTTCTGC  TGTGGCGATG  ATTGACCGGT  ATAGGAAGCG

361   TAGGGGGGCT  TGAGTAGGTG  TCTGGTGTTG  TTGGGTCTCA  GGTTCCTCGT  CACCGTGTGG

421   CTGCGGCGTA  TTCGGTGTCT  GCTGGGGGTG  ATGCTGGGGA  GCTTGGTCGT  GCGTATGGGT

481   TGACGCCTGA  TCCGTGGCAG  CAGCAGGTGT  TGGATGATTG  GCTGGCTGTC  GGTAGCAATG

541   GCAGGCTTGC  TTCTGGTGTG  TGTGGGGTGT  TTGTTCCGCG  GCAGAATGGC  AAGAATGCTA

601   TTTTGGAGAT  TGTGGAGTTG  TTTAAGGCGA  CTATTCAGGG  TCGCCGTATT  TTGCATACGG

661   CTCACGAGTT  GAAGTCGGCT  CGTAAGGCGT  TTATGCGGTT  GAGGTCGTTT  TTTGAGAATG

721   AGCGGCAGTT  TCCTGACTTG  TATCGTATGG  TGAAGTCGAT  TCGTGCGACG  AATGGTCAGG

781   AGGCTATTGT  GTTGCATCAT  CCGGATTGTG  CCACTTTTGA  GAAGAAGTGT  GGCTGCAGCG
```

-continued

```
 841 GTTGGGGTTC GGTTGAGTTT GTGGCTCGTA GCCGGGGTTC GGCTCGCGGG TTTACGGTTG
 901 ATGATTTGGT GTGTGATGAG GCTCAGGAGT TGTCGGATGA GCAGTTGGAG GCTTTGCTTC
 961 CTACGGTAAG TGCTGCCCCG TCTGGTGATC CGCAGCAGAT TTTCCTTGGT ACGCCGCCTG
1021 GGCCGTTGGC TGATGGTTCT GTGGTGTTGC GTTTGCGTGG CAGGCGCTT GGTGGCGGTA
1081 AAAGGTTTGC GTGGACGGAG TTTTCGATTC CTGACGAGTC TGATCCGGAT GATGTGTCGC
1141 GGCAGTGGCG GAAGTTGGCG GGGGATACGA ATCCGGCGTT GGGGCGTCGC CTGAATTTTG
1201 GGACCGTAAG CGATGAGCAT GAGTCGATGT CTGCTGCCGG TTTTGCTCGG GAGCGGCTTG
1261 GCTGGTGGGA TCGTGGCCAG TCTGCTGCGT CTGTGGTTCC TGCTGATAAG TGGGCTCAGT
1321 CTGCGGTGGA TGAGGCGAGT CTGGTTGGCG GGAAAGTGTT TGGTGTCTCG TTTTCTCGTT
1381 CTGGGGATCG GGTTGCTTTG GCGGGTGCCG GCAAGACTGA TGCTGGGGTT CATGTTGAGG
1441 TTATTGATGG GCTGTCGGGA ACGATTGTTG ATGGTGTGGG CCGGTTGGCT GACTGGTTGG
1501 CGGTTCGTTG GGGTGATACT GACCGGATCA TGGTTGCCGG GTCTGGTGCG GTGTTGTTGC
1561 AGAAGGCGTT GACGGATCGT GGTATTCCGG GCCGTGGCGT GGTGGTTGCT GATACTGGCG
1621 TTTATGTGGA GGCTTGTCAG GCGTTTCTTG AGGGTGTCAG GTCGGGTGTG ATCAGTCATC
1681 CTCGTGCTGA TTCTCGCCGT GACATGTTGG ATATTGCTGT GAGGTCGGCT GTGCAGAAGC
1741 GTAAGGGGTC TGCGTGGGGT TGGGGTTCCT CGTTTAAGGA TGGTTCTGAG GTTCCTTTGG
1801 AGGCTGTGTC TTTGGCGTTT TTGGGGGCTA AACGTGTTCG TCGTGGCCGT CGGGAGCGTA
1861 GTGGTAGGAA GCGGGTGTCT GTGGTATGAA CTCGGATGAG TTGGCTCTGA TTGAGGGCAT
1921 GTACGATCGT ATCCAAAGGT TGTCTTCGTG GCATTGTTGT ATTGAGGGCT ACTATGAGGG
1981 CTCTAATCGG GTGCGTGACC TTGGTGTGGC TATTCCGCCG GAGTTGCAGC GTGTGCAGAC
2041 TGTGGTGTCG TGGCCTGGTA TAGCTGTGGA TGCTTTGGAG GAGCGTCTGG ATTGGCTTGG
2101 CTGGACTAAT GGTGACGGCT ACGGCCTTGA TGGTGTGTAT GCTGCGAATC GGCTTGCTAC
2161 GGCGTCGTGT GATGTGCATT TGGATGCGCT GATTTTTGGG TTGTCGTTTG TTGCGATCAT
2221 TCCTCATGGT GATGGTACGG TGTCGGTTCG TCCGCAGTCA CCAAAGAATT GTACGGGCAA
2281 GTTTTCGGCT GACGGGTCTC GTTTGGATGC GGGTTTGGTG GTGCAGCAGA CGTGTGATCC
2341 TGAGGTTGTT GAGGCTGAGC TTTTGCTTCC TGATGTGATT GTTCAGGTGG AGCGGCGGGG
2401 TTCGCGTGAA TGGGTTGAGG TGGATCGTAT ACCGAATGTG TTGGGTGCGG TTCCGTTGGT
2461 GCCTATTGTG AATCGTCGCC GTACTTCTAG GATTGATGGC CGTTCGGAGA TTACGAGGTC
2521 TATTAGGGCT TACACGGATG AGGCTGTGCG CACACTGTTG GGGCAGTCTG TGAATCGTGA
2581 TTTTTATGCG TATCCTCAGC GTTGGGTGAC TGGCGTGAGC GCGGATGAGT TTTCGCAGCC
2641 TGGCTGGGTC CTGTCGATGG CTTCTGTGTG GGCTGTGGAT AAGGATGATG ACGGTGACAC
2701 TCCGAATGTG GGGTCGTTTC CTGTCAATAG TCCTACACCG TATTCGGATC AGATGAGACT
2761 GTTGGCGCAG TTGACTGCGG GTGAGGCGGC TGTTCCGGAA CGCTATTTCG GGTTTATCAC
2821 GTCTAACCCA CCTAGTGGGG AGGCTTTGGC TGCCGAGGAA TCTCGGCTTG TGAAGCGTGC
2881 TGAGCGGCGT CAAACGTCGT TTGGTCAGGG TTGGCTGTCG GTTGGTTTTT TGGCTGCCAA
2941 GGCGTTGGAT TCTCGTGTTG ATGAGGCCGA TTTTTTTGGT GATGTTGGTT TGCGTTGGCG
3001 TGATGCTTCG ACGCCTACCC GGGCGGCTAC GGCTGATGCT GTGACGAAGC TTGTTGGTGC
3061 CGGTATTTTG CCTGCTGATT CTCGTACGGT GTTGGAGATG TTGGGGCTTG ATGATGTGCA
3121 GGTTGAGGCT GTGATGCGTC ATCGTGCTGA GTCGTCTGAC CCGTTGGCGG TGCTTGCTGG
3181 GGCTATATCG CGTCAAACTA ACGAGGTATG ATAGGCGATG GCTTCGGGGG TTGAGGCGAG
```

```
3241  GCTTGCGGCG ACTGAGTATC AGCGTGAGGC GGTCAGGTTT GCTGGGAAGT ATGCGGGCTA

3301  TTATTCTGAG CTTGGTCGTT TGTGGCGTGC CGGCAGGATG AGTGACACGC AGTATGTGCG

3361  TTTGTGTGTG GAGTTGGAGC GTGCCGGCCA TGATGGTTCG GCATCGTTGG CTGCCAGGTT

3421  TGTGTCGGAT TTTCGCCGGT TGAATGGTGT GGATCCGGGT TTGATTGTGT ATGACGAGTT

3481  TGATGCTGCG GCGGCTTTGG CTAGGTCTAT TTCGACCACG AAGATTCTTG AGAGTGACCC

3541  GGATAGGGCG AATGACACGA TTGATGCGAT GGCGGCGGGT TTTGATCGGG CTGTTATGAA

3601  TGCTGGCCGT GACACGGTTG AGTGGTCTGC GGGTGCGCAG GGTAGGTCGT GGCGTCGGGT

3661  GACGGATGGT GATCCGTGTG CTTTTTGTGC CATGTTGGCT ACGAGGTCGG ATTATACGAC

3721  AAAAGAGAGG GCACTTACTA CTGGACATAC TCGGCGTCAT AAGCGTGGTG GTAAGCGTCC

3781  GTTTGGTTCG AAGTATCATG ATCATTGTGG TTGTACGGTG GTTGAGGTTG TTGGCCCTTG

3841  GGAACCAAAT AGGGCTGATG CCGAGTATCA GAGGACGTAT GAGAAGGCCT GTGAGTGGGT

3901  TGATGATCAT GGGTTGCAGC AATCGCCTGG CAATATTTTG AAGGCTATGC GTACTGTTGG

3961  CGACATGAGA TAATTTGATG TGGTTTCCGG TTGTGCGCCC CCGGTTATTG GTGCACAGGG

4021  TTGTCTCCCG CACGGGGGTC AACAATATTG TGTTGTTTTC CGCAAGGAGT GTAGGGTTAG

4081  GCTATGGCCG ATCAGAGTGT TGAGGAACAG AATGTTGACA ATGATGTTGT GGAGTCCGGA

4141  AAGGATAACG GCATTGTTGA TACAGTAAAA GACGATGGCG GCAGGAGGT AGCCGACAAT

4201  CAGTTGAAGA ATGAAGGCGA GGGTAAATCG CCGGGGACTG ATTGGAAGGC TGAGGCCCGT

4261  AAGTGGGAGT CTCGTGCTAA AAGTAATTTT GCCGAGTTGG AGAAGCTTCG CGCCTCGGAT

4321  GGTGATGCGG GGTCTACGAT TGATGAGCTT CGCCGCAAGA ATGAGGAACT CGAAGACCGG

4381  ATCAATGGGT TGTTCTTGA GGGTGTGAAG CGCGAGGTGG CTGCCGAGTG TGGCCTGTCG

4441  GGTGATGCTG TCGCTTTCTT GTCGGGTGGC GATAAGGAGT CGCTTGCCGA GTCTGCGAAA

4501  GCTTTGAAGG GTTTGATCGA CCATAGTAGT GGTGGCGCGG GTGTGCGCCG TCTTGCGGGG

4561  AGTGCCCCCG TTGATGATGT TAAACGACGT GAGGGTGTCG CGTTTGTGGA TGCTCTTGTC

4621  AATAATTCTA GGAGATGATT TGTGATGGCT GACGATTTTC TTTCTGCAGG GAAGCTTGAG

4681  CTTCCTGGTT CTATGATTGG TGCGGTTCGT GACCGTGCTA TCGATTCTGG TGTTTTGGCG

4741  AAGCTTTCGC CGGAGCAGCC GACTATTTTC GGGCCTGTGA AGGGTGCCGT GTTTAGTGGT

4801  GTTCCTGCGC CCAAGATTGT TGGTGAGGGC GAGGTTAAGC CTTCCGCGTC TGTTGATGTT

4861  TCGGCGTTTA CTGCGCAGCC TATCAAGGTT GTGACTCAGC AGCGTGTCTC GGATGAGTTT

4921  ATGTGGGCTG ATGCTGATTA CCGTCGGGT GTGCTTCAGG ATCTGATTTC CCCGGCTCTT

4981  GGTGCTTCGA TTGGTCGCGC CGTGGATCTG ATTGCTTTCC ATGGTATTGA TCCTGCCACT

5041  GGTAAAGCGG CTTCCGCTGT GCATACTTCG CTGAATAAGA CGAAGAATAT TGTTGATGCC

5101  ACGGATTCTG CTACGGCTGA TCTTGTTAAG GCTGTCGGCC TGATTGCTGG TGCTGGTTTG

5161  CAGGTTCCTA ACGGGGTTGC TTTGGATCCG GCGTTCTCGT TTGCGCTGTC TACTGAGGTG

5221  TATCCGAAGG GGTCTCCGCT TGCCGGTCAG CCTATGTATC CTGCCGCCGG GTTTGCCGGT

5281  TTGGATAATT GGCGCGGGCT GAATGTTGGT GCTTCTTCGA CTGTTTCTGG CGCCCCGGAG

5341  ATGTCGCCTG CCTCTGGCGT TAAGGCTATT GTTGGTGATT CTCTCGTGT TCATTGGGGT

5401  TTCCAGCGTA ACTTCCCGAT CGAGCTTATC GAGTATGGTG ACCCGGATCA GACTGGGCGT

5461  GACTTGAAGG GCCATAATGA GGTTATGGTT CGTGCCGAGG CTGTCCTGTA TGTTGCGATT

5521  GAGTCGCTTG ATTCGTTTGC TGTTGTGAAG GAGAAGGCTG CCCCGAAGCC TAATCCGCCG

5581  GCCGAGAACT GATTCATTTG TTGCGGTGAT GTTTTCTATG TGCAGGGGGT GGTGTTGATG

5641  GGTATCATTT TGAAGCCTGA GGATATTGAG CCTTTCGCCG ATATTCCTAG AGAGAAGCTT
```

-continued

```
5701 GAGGCGATGA TTGCCGATGT GGAGGCTGTG GCTGTCAGTG TCGCCCCCTG TATCGCTAAA

5761 CCGGATTTCA AATACAAGGA TGCCGCTAAG GCTATTCTGC GCAGGGCCCT GTTGCGCTGG

5821 AATGATACCG GGGTTTCGGG TCAGGTGCAG TACGAGTCTG CGGGCCCGTT TGCTCAGACT

5881 ACACGGTCGA ATACTCCCAC GAATTTGTTG TGGCCTTCTG AGATTGCCGC GTTGAAGAAG

5941 TTGTGTGAGG GTGATGGTGG GGCTGGTAAA GCGTTCACTA TTACACCGAC CATGAGGAGT

6001 AGTGTGAATC ATTCTGAGGT GTGTTCCACG GTGTGGGGTG AGGGTTGCTC GTGCGGATCT

6061 GATATTAACG GCTATGCTGG CCCTTTGTGG GAGATATGAT ATGACCGGTT TTCCTTACGG

6121 TGAAACGGTT GTGATGCTTC AACCGACTGT TCGTGTCGAT GATCTTGGCG ACAAGGTGGA

6181 AGACTGGTCT AAGCCTGTCG AGACTGTGTA CCATAACGTG GCCATCTATG CTTCCGTTTC

6241 GCAGGAGGAT GAGGCTGCCG GCCGTGACTC TGACTATGAG CATTGGTCGA TGCTTTTCAA

6301 GCAGCCTGTT GTGGGTGCCG GTTATCGTTG CCGGTGGCGT ATTCGGGGTG TGGTTTGGGA

6361 GGCGGACGGG TCTCCTATCG TGTGGCATCA TCCGATGTCT GGTTGGGATG CTGGTACGCA

6421 GGTTAATGTG AAGCGTAAGA AGGGCTGATG GGTTGTGGCT CAGGATGTGA ATGTGAAGCT

6481 GAACTTGCCG GGTATTCGTG AGGTGTTGAA GTCTTCTGGG GTGCAGTCGA TGTTGGCTGA

6541 GCGTGGCGAG CGGGTGAGGC GTGCGGCTTC GGCGAATGTT GGCGGTAATG CTTTTGATAG

6601 GGCCCAATAC CGTAGTGGTT TGTCGTCGGA GGTGCAGGTT CACCGTGTGG AGGCTGTGGC

6661 GAGGATTGGC ACCACCTATA AGGGTGGGAA GCGTATTGAG GCGAAGCATG GCACGTTGGC

6721 GAGGTCGATT GGGGCTGCGT CGTGATCGTT TACGGTGATC CGCGTGTGTG GGCTAAACGT

6781 GTGCTCAAGG ATGATGGCTG GCTGTCCGAT ATACCCTGTG TGGGGACGGT GCCTGACGAT

6841 TTCAGCGGTG ACCTGATTTG GTTGGCGTTG GATGGCGGCC CACAGTTGCA TGTTCGCGAG

6901 CAGGTGTTTT TGCGGGTGAA CGTGTTTTCT GATATGCCTG ATCGTGCCAT GTCGCTAGCC

6961 AGGCGGGTTG AGGCTGTCCT TGTAGACGGT GTGGACGGTG ACCCGGTGGT GTTTTGTCGA

7021 CGGTCTACTG GCCCTGATTT GCTGGTTGAT GGTGCACGTT TTGATGTGTA TTCGCTGTTT

7081 GAGCTGATAT GCAGGCCTGT CGAATCCGAG TAAACGTTTT GTTTTGATAT TGTTGTTTGT

7141 TTTTTGTTTG ATATTGTTTT TGGGGGTTAT GATGGCTGGA ACACGTAAAG CGTCTAATGT

7201 TCGTTCCGCG GTTACGGGTG ACGTCTATAT TGGTAAAGCT CATGCCGGTG ACACTATTGA

7261 TGGTGTGAAG ACGGTTCCTG ACGGGCTTAC AGCTTTAGGG TATCTGTCTG ATGACGGGTT

7321 TAAGATTAAA CCGGAGCGTA AAACGGATGA TTTGAAGGCT TGGCAGAATG CGGATGTTGT

7381 TCGCACTGTG GCTACGGAAT CGTCTATCGA GATTTCTTTC CAGCTGATCG AGTCTAAGAA

7441 GGAGGTTATC GAGCTGTTTT GGCAGTCGAA GGTTACTGCC GGAGCCGATT CGGGTTCGTT

7501 CGATATTTCT CCTGGTGCCA CGACGGGTGT TCATGCCCTG TTGATGGATA TTGTTGATGG

7561 CGATCAGGTT ATTCGCTACT ATTTCCCTGA GGTTGAGTTG ATCGATCGTG ACGAGATTAA

7621 GGGTAAGAAT GGCGAGGTGT ATGGGTATGG TGTGACGTTG AAGGCGTATC CTGCCCAGAT

7681 TAATAAGAAG GGTGATGCGG TGTCTGGTCG GGGGTGGATG ACGGCTTTAA AAGCTGATAC

7741 TCCTCCGACT CCTCCTCCGG CCCCGAATCC TCCGAAGCCT GAGCCGGATC CGAATCCGCC

7801 GTCTAATAAC TGATACACAT AGTTTGAGGG ATTGTTGATA GATGAGTGAC ACGGGTTACA

7861 CGTTGAAGAT TGGTGACCGT AGCTGGGTGT TGGCGGATGC GGAGGAGACG GCTCAGGCTG

7921 TTCCTGCCCG CGTTTTCCGT CGTGCTGCTA AGATTGCCCA GTCGGGTGAG TCTGCGGATT

7981 TCGCCCAGGT TGAGGTGATG TTTTCTATGT GGAGGCTGC CGCCCCGGCT GACGCGGTGG

8041 AGGCCCTGGA GGGGCTTCCT ATGGTTCGTG TGGCCGAGAT TTTCCGCCAG TGGATGGAAT
```

```
                    -continued
 8101 ACAAGCCTGA CGGTAAGGGT GCCTCGCTGG GGGAATAGTT TGGCTCCACG GCCTGATTGA

8161 TGATTATCGT GGGGCCATCG AATACGATTT CCGCACCAAG TTTGGTGTTT CTGTTTATAG

8221 TGTTGGTGGC CCGCAGATGT GTTGGGGTGA GGCTGTCCGG CTGGCTGGCG TGTTGTGTAC

8281 CGATACGTCT AGCCAGTTGG CGGCCCACCT GAATGGTTGG AAGCGCCCGT TGAGTGGTG

8341 CGAGTGGGCT GTGTTGGACA TGCTGGATCA TTACAGGTCT GCTAATAGTG AGGGGCAGCC

8401 GGAGCCTGTG GCGAGGCCTA CGGATGAGCG TAGGGCCCGG TTTACGTCTG GCAGGTGGA

8461 CGATATTTTG GCGCGTGTTC GTGCTGGTGG CGGGGTGTCT CGCGAGATTA ATATTATGGG

8521 GTGAATAGTG TATGTCTGGT GAGATTGCTT CCGCATATGT GTCGTTGTAT ACGAAGATGC

8581 CTGGTTTGAA GGCGGATGTT GGTAAACAGC TTTCTGGGGT GATGCCTGCT GAGGGTCAGC

8641 GTTCGGGTAG TTTGTTTGCT AAGGGAATGA AGTTGGCTCT TGGTGGTGCG GCGATGATGG

8701 GTGCCATCAA TGTTGCTAAG AAGGGCCTCA AGTCGATTTA TGATGTGACT ATTGGTGGCG

8761 GTATTGCTAG GGCGATGGCT ATTGATGAGG CTCAGGCTAA GTTGACTGGT TTGGGTCATA

8821 CGTCTTCTGA CACGTCTTCG ATTATGAATT CGGCTATTGA GGCTGTTACT GGTACGTCGT

8881 ATGCGTTGGG GGATGCGGCG TCTACGGCTG CGGCGTTGTC TGCTTCGGGT GTGAAGTCTG

8941 GCGGGCAGAT GACGGATGTG TTGAAGACTG TCGCCGATGT GTCTTATATT TCGGGTAAGT

9001 CGTTTCAGGA TACGGGCGCT ATTTTTACGT CTGTGATGGC TCGCGGTAAG TTGCAGGGCG

9061 ATGACATGTT GCAGCTTACT ATGGCGGGTG TTCCTGTCCT GTCTTTGCTT GCCAGGCAGA

9121 CTGGTAAAAC GTCTGCTGAG GTGTCGCAGA TGGTGTCAAA GGGGCAGATT GATTTTAACA

9181 CGTTTGCGGC TGCGATGAAG CTTGGCATGG GTGGTGCTGC GCAGGCGTCT GGTAAGACGT

9241 TTGAGGGCGC TATGAAGAAT GTTAAGGGCG CCCTGGGTTA TCTTGGTGCT ACGGCTATGG

9301 CCCCGTTTCT TAACGGGTTG CGGCAGATTT TTGTTGCGTT GAATCCGGTT ATCAAGTCTG

9361 TCACGGATTC CGTGAAGCCG ATGTTTGCTG CCGTCGATGC TGGTATTCAG CGTATGATGC

9421 CGTCTATTTT GGCGTGGATT AACCGTATGC CGGCTATGAT CACTCGAATG AATGCACAGA

9481 TGCGCGCCAA GGTGGAGCAG TTGAAGGGCG TTTTTGCAAG GTTGCATTTG CCTGTTCCTA

9541 AGGTGAATTT GGGTGCCATG TTTGCTGGCG GCACCGCAGT GTTCGGTATT GTTGCTGCGG

9601 GTGTTGGGAA GCTTGTCGCG GGGTTTGCCC CGTTGGCGGT GTCGTTGAAG AATCTGTTGC

9661 CGTCGTTTGG TGCTTTGAGG GGTGCCGCCG GGGGCTTGG TGGCGTGTTT CGCGCCTTGG

9721 GTGGCCCTGT TGGTATTGTG ATCGGCTTGT TTGCTGCCAT GTTTGCTACG AACGCCCAGT

9781 TCCGTGCCGC TGTTATGCAG CTTGTGGGGG TGGTTGGCCG GGCTTTGGGG CAGATTATGG

9841 TCGCCTTGCA GCCATTGTTC GGGATTGTTG CTGGCGTGGT TGCCAGGTTG GCTCCCGTTT

9901 TTGGCCAGAT TATTGGTATG GTTGCTGGTT TGGCTGCCCG GCTGGTGCCT GTTATTGGTA

9961 TGCTTATTGC CCGGCTGGTT CCTGTTATCA CCCAGATTAT TGGTATGGTA ACCCAGGTTG

10021 CTGCCATGTT GTTGCCTATG CTGATGCCGG TTATTCAGGC TGTTGTTGCT GTGATACGGC

10081 AGGTTATTGG TGTGGTCATG CAGTTGATAC CTGTTTTGAT GCCGGTTGTG CAGCAGATTT

10141 TGGGTGCTGT CATGTCTGTT TTGCCGCCGA TTGTTGGTTT GATACGGTCG CTGATACCGG

10201 TGATCATGTC GATTATGCGT GTGGTGGTGC AGGTTGTTGG TGCCGTGCTA CAGGTGGTGG

10261 CCCGTATTAT TCCGGTTGTT ATGCCGATTT ATGTTTCGGT GATTGGATTC ATTGCCAAGA

10321 TTTATGCTGC GGTTATCGTT TTTGAGGCTA AGGTTATTGG CGCTATTCTT CGTACTATTA

10381 CGTGGATTGT GAATCATTCA GTGTCTGGCG TGAGGTCTAT GGGCACGGCC ATCCAGAATG

10441 GCTGGAATCA TATCAAATCG TTTACGTCGG CGTTTATTAA CGGTTTCAAG TCGATCATTT

10501 CTGCCGGTGT TGCCGCGGTT GTGGGGTTTT TTACGCGGCT TGGTTTGTCG GTTGCCTCCC
```

-continued

```
10561 ATGTGAGGTC TGGTTTTAAC GCGGCCCGTG GTGCTGTTTC TTCTGCGATG AATGCTATTC
10621 GGAGTGTTGT GTCTTCGGTG GCGTCTGCTG TTGGCGGGTT TTTCGGGTCG ATGGCGTCTA
10681 GGGTTCGTAG TGGTGCTGTG CGCGGGTTTA ATGGTGCCCG GAGTGCGGCT TCTTCTGCTA
10741 TGCATGCTAT GGGGTCTGCG GTGTCTAACG GTGTGCATGG TGTGCTGGGG TTTTTCCGGA
10801 ATTTGCCTGG CAATATTAGG GGCGCCTTGG GTAGTATGGG GTCCCTGTTG GTGTCGGCTG
10861 GCCGTGATGT GGTGTCTGGT TTGGGTAACG GTATCCGGAA TGCTTTGAGT GGCCTGTTGG
10921 ATACGGTGCG TAACATGGGT TCCCAGATTG CGAACGCGGC GAAGTCTGCG CTGGGTATTC
10981 ATTCCCCGTC TCGGGTGTTT CGTGACGAGG TTGGCCGTCA GGTTGTTGCC GGTTTGGCTG
11041 AGGGGATCAC CGGGAATGCT GGTTTGGCGT TGGATGCGAT GTCTGGTGTG GCTGGCCGTC
11101 TTCCGGATGC TGTGGATGCC CGGTTTGGTG TGCGATCGTC TGTGGGCTCG TTTACCCCGT
11161 ACGACCGGTA TCGGCGTGCG AACGAGAAGA GTGTTGTGGT GAATGTGAAC GGACCCACGT
11221 ATGGGGATCC TGCCGAGTTT GCGAAGCGGA TTGAGCGTCA GCAGCGTGAC GCTTTGAATG
11281 CGTTGGCTTA CGTGTGATCG AGGGGGTGTT GTGCATGTTT ATTCCTGACC CGTCTGATCG
11341 TGCCGGTTTG ACTGTGGATT GGACTATGTT TCCGTTGGTG GGTAATGCTC CGGAGCGTGT
11401 GCTTCATTTG ACGGATTATA CGGGGTCGTC TCCGGTCATG TTGTTGAATG ATTCGTTGCG
11461 CGGCCTGGGT ATGCCTGAGG TGGAGCAGTT TTCTCAAACG CATGTTGGTG TGCATGGTTC
11521 GGAGTGGCGC GGGTTTAATG TGAAGCCTCG CGAGGTGACT TTGCCGGTGT TGGTGTCGGG
11581 TGTTGACCCG GATCCGGTGG GCGGGTTTCG TGACGGTTTT TTGAAGGCGT ATGACGCGTT
11641 GTGGTCTGCG TTTCCTCCGG GCGAGGTGGG GGAGTTGTCT GTGAAGACTC CTGCCGGTCG
11701 TGAGCGTGTG TTGAAGTGCC GGTTTGATTC GGCTGATGAC ACGTTTACGG TTGATCCGGT
11761 GAACCGTGGC TATGCGCGCT ATCTGTTGCA TTTGACAGCT TATGATCCGT TTTGGTATGG
11821 GGATGAGCAA AAGTTTCGTT TTAGTAACGC GAAGTTGCAG GATTGGTTGG GTGGCGGCCC
11881 TGTCGGCAAG AAGGGTACCG CGTTTCCTGT GGTGTTAACA CCGGGTGTGG GCTCGGGCTG
11941 GGATAACCTG TCTAATAAGG GTGATGTGCC TGCGTGGCCT GTGATTCGTG TTGAGGGTCC
12001 TTTGGAGTCG TGGTCTGTGC AGATTGATGG TTTGCGTGTG TCTTCGGACT ATCCGGTCGA
12061 GGAGTTTGAT TGGATCACTA TTGATACGGA TCCTCGCCAG CAGTCTGCGT TGTTGAACGG
12121 GTTTGAGGAT GTGATGGATC GTTTGACAGA GTGGGAGTTT GCGCCTATCC CGCCTGGCGG
12181 TTCTAAGAGT GTGAATATTG AGATGGTTGG TTTGGGTGCT ATTGTTGTGT CGGTGCAGTA
12241 CAGGTTTTTG AGGGCTTGGT GAATAGTTGA TGGCTGGTCT TGTTCCGCAT GTAACATTGT
12301 TTACACCTGA TTATCGCCGT GTGGCGCCTA TCAATTTTTT TGAGTCGTTG AAGTTGTCGT
12361 TGAAGTGGAA TGGTTTGTCG ACTTTGGAGT TGGTGGTGTC GGGGATCAT TCGAGGCTTG
12421 ACGGGTTGAC GAAGCCGGGT GCGCGGCTGG TTGTTGATTA TGGTGGTGGC CAGATTTTTT
12481 CTGGGCCTGT GCGTAAAGTG CATGGTGTGG GTCCGTGGCG TTCTTCCCGT GTGACTATAA
12541 CGTGTGAGGA TGATATTCGG CTGTTGTGGC GTATGTTGAT GTGGCCTGTG AATTATCGTC
12601 CTGGTTTGGT TGGTATGGAG TGGCGTGCGG ACAGGGATTA TGCCCACTAT TCGGGTGCGG
12661 CTGAGTCGGT TGCTAAGCAG GTGTTGGGGG ATAATGCTTG GCGTTTTCCG CCTGGTTTGT
12721 TTATGAACGA TGATGAGAGT CGTGGCCGCT ATATTAAGGA TTTTCAGGTG CGGTTTCACG
12781 TGTTTGCCGA TAAGTTGTTG CCGGTGTTGT CGTGGGCTCG GATGACTGTC ACGGTGAACC
12841 AGTTTGAGAA TGCGAAGTTT GATCAGCGTG GTTTGTTGTT TGATTGTGTG CCTGCTGTGA
12901 CCCGGACGCA TGTGTTGACT GCCGAGTCTG GTTCGATTGT GTCGTGGGAG TATGTGCGTG
```

-continued

```
12961 ACGCCCCGAA GGCTACTTCG GTGGTGGTTG GTGGCCGCGG CGAGGGCAAA GATCGGCTGT

13021 TTTGCGAGGA TGTTGATTCG ATGGCCGAGG ATGACTGGTT TGATCGTGTC GAGGTGTTTA

13081 AGGATGCCCG TAACACGGAT TCCGAGAATG TGCATCTTAT TGATGAGGCT GAGCGGGTGT

13141 TGTCCGAGTC GGGGGCTACG TCGGGGTTTA AGATCGAGTT GGCTGAGTCG GATGTGTTGC

13201 GGTTTGGGCC TGGCCGCCTG ATGCCGGGTG ATCTTATCTA TGTGGATGTG GGCTCGGGGC

13261 CTATTGCGGA GATTGTGCGC CAGATTGATG TGGAGTGTGA TTCGCCTGGT GATGGGTGGA

13321 CGAAGGTGAC TCCGGTTGCT GGGGATTATG AGGATAATCC GTCGGCGCTG TTGGCTCGCC

13381 GTGTGGCTGG TTTGGCTGCG GGTGTGCGGG ATTTGCAAAA ATTCTAATTG TTAGGGGTTT

13441 GTTGTGGGTA TTGTGTGTAA AGGGTTTGAT GGTGTGTTGA CCGAGTATGA TTGGGCTCAA

13501 ATGTCTGGTC TGATGGGTAA TATGCCGTCC GTGAAAGGGC CGGATGATTT TCGTGTCGGC

13561 ACTACGATTC AGGGTTCCAC GGTGTTGTGT GAGGTCCTGC CGGGGCAGGC TTGGGCTCAC

13621 GGGGTGATGT GCACGTCGAA TGCTGTTGAG ACGGTGACAG GTCAGCTTCC GGGCCCGGGT

13681 GAGACCCGCT ACGACTATGT TGTCCTGTCG CGGGATTGGC AGGAGAATAC GGCCAAGTTG

13741 GAGATTGTTC CTGGGGGGCG TGCGGAGCGT GCCCGTGACG TGTTGCGTGC GGAGCCTGGC

13801 GTGTACCATC AGCAGTTGTT GGCTACTTTG GTGGTGTCGT CTAACGGGTT GCAGCAGCAG

13861 CTTGACAGGA GGGCTATAGC GGCCCGTGTG GCGTTTGGGG AGTCTACTGC ATGTGATCCT

13921 ACCCCTGTGG AGGGTGACCG GGTGATGGTG CCTTCTGGGG CTGTGTTGGC TAATCATGCT

13981 AACGAGTGGA TGCTGTTGTC TCCGCGGATT GAGACGGGCA CTAAGTCGAT CATGTTTGGC

14041 GGGTCTGCTG TGTATGCTTA CACGATTCCG TTTGATCGCC AGTTTGCTAG TCCGCCTGTT

14101 GTGGTGGCGT CTATGGCTAC GGCGGCTGGG GGCACGACCC AGATTGATGT GAAAGCCTAC

14161 AATGTGACTG CCCAAAATTT TAGTTTGGCG TTTATTACGA ATGATGGTTC GAAGCCGAAT

14221 GGTGTGCCTG CGGTGGCTAA TTGGATTGCT GTCGGCGTGT GACTGTACAG GTGTTGTGGC

14281 GGATGGTGTG ATGTTGGGGG GCTGTGGTGT CGTGGTTTAC TCCTGCACTG GTGGCCTCTA

14341 TTTGTACCGC GTTGGCCACG GTTTTGGGTT CTGTTCAGGC TGTCACGTCT AAATCTAGGA

14401 GGCGTTTGCG CCGCCTGTCG GCGCAGGTGG ATGCGATGGA AGAGTATACG TGGGGTGTGC

14461 GGCGCGAGGT GCGAAGGTTT AACGCCGGGC TTCCTGACGA GGTGGAGCCT ATGCATCTCC

14521 CTGATTTGCC CGAGTTTTTG AAAGATACTG TTGATGGTGG AGGTGAGTAG GGTTGAGGGA

14581 GTTGGAGGAG GAGAAGCGGC AGCGCCGCAA TTTTGAGAAG GCTTCACTGG TGTTGCTGTT

14641 TTTGTCGCTT GTGTTATTGG CTGTGGTTGC TGCGGGTGCT TTGCGTTTCG GGGCTGTATC

14701 CTCTGAGCGG GATTCGGAGC AGGCGAGGGC CCAGTCGAAT GGTACAGCCG CCAAGGGTTT

14761 AGCCAGCAGT GTGCGGCAGG TGTGTGCTCA GGGTGGACGG GAGTCTGTGC GGCTTCACCA

14821 GTCTGGTTTG TGTGTGGATG CTCAGCGTGT TGAGCGTAGT GTGCAGGGTG TGCCGGGTCC

14881 TGCCGGTGAG CGCGGCCCGC AAGGCCCGGC AGGTGTGGAC GGCCGGGATG GTGTTAATGG

14941 TTCGGCTGGG CTGGTTGGCC CTGTGGGTCC GCAGGGGTCC CCGGGTTTGA ATGGTGTGAA

15001 AGGTCCTGAC GGGGTTGCCTG GCGCTAACGG TTCGGATGGC CGTGATGGTG TGGACGGTGT

15061 GAACGGCAAT GATGGCGCTG ATGGTCGGGA TGGTTCGGCC GGTGAGCGCG GTGATGTGGG

15121 CCCCTCAGGT CCTGCCGGCC CGCAAGGTGC ACAGGGTGAA CGGGGTGAGC GCGGCCCCGC

15181 CGGTGCGAAT GGCACGAATG GCAAGGACGG TAAGGATGGT GCCGACGGCC GTGATGGGCG

15241 TTCGGTTGTG TCTGTGTACT GTTTCGGTGG CCTGCCAGGG TGTGAAACCA TCACCTGTGG

15301 TTACCGTGTC ATCCCGTAAA TAGAAGAAGA GGGAAGGGTG TTACTAGTGT TGATTGTGGT

15361 TTTTGGTGGT GGTGTGTGGT GAGATACATT CCTGCAGCGC ATCACTCTGC CGGCTCTAAT
```

-continued

```
15421 AATCCGGTGA ACAGGGTTGT GATTCATGCA ACATGCCCGG ATGTGGGGTT TCCGTCCGCC
15481 TCACGTAAGG GGCGGGCGGT GTCTACAGCA AACTATTTCG CTTCCCCATC GTCTGGTGGT
15541 TCGGCGCATT ATGTGTGTGA TATTGGGGAG ACGGTGCAAT GCTTGTCGGA GTCTACGATT
15601 GGTTGGCATG CCCCGCCGAA TCCGCATTCT TTGGGTATCG AGATTTGCGC GGATGGGGGT
15661 TCGCATGCCT CGTTCCGTGT GCCGGGGCAT GCTTACACTC GGGAGCAGTG GCTTGATCCG
15721 CAGGTGTGGC CTGCCGTTGA GAGGGCGGCG GTGCTGTGTA GACGTTTGTG TGACAAATAT
15781 AATGTTCCGA AAAGGAAACT GTCGGCTGCC GATTTGAAGG CTGGCAGGCG GGGTGTGTGT
15841 GGCCATGTGG ATGTTACGGA TGCGTGGCAT CAGTCGGATC ATGACGATCC TGGGCCGTGG
15901 TTTCCGTGGG ACAAATTTAT GGCCGTCGTC AACGGCGGCA GTGGAGATAG TGGGGAGTTA
15961 ACTGTGGCTG ATGTGAAAGC CTTGCATGAT CAGATTAAAC AATTGTCTGC TCAGCTTACT
16021 GGTTCGGTGA ATAAGCTGCA CCATGATGTT GGTGTGGTTC AGGTTCAGAA TGGTGATTTG
16081 GGTAAACGTG TTGATGCCTT GTCGTGGGTG AAGAATCCTG TGACGGGGAA GCTGTGGCGC
16141 ACTAAGGATG CCCTGTGGAG TGTCTGGTAT TACGTGTTGG AGTGTCGTAG CCGTCTTGAC
16201 AGGCTCGAGT CTGCTGTCAA CGATTTGAAA AAGTGATGGT GGTTTGTTGT GGGTAAACAG
16261 TTTTGGTTAG GTTTGCTAGA GCGGGCGGCT AAGACTTTTG TGCAAACGTT TGTTGCTGTG
16321 TTGGGGGTGA CGGCGGGTGT CACGTATACG GCGGAGTCGT TTCGTGGTTT GCCGTGGGAG
16381 TCTGCGTTGA TTACGGCTAC GGTTGCTGCG GTCCTGTCGG TGGCTACCTC GTTTGGTAGC
16441 CCGTCGTTTG TGGCTGGTAA GCCGAAAACC ACGCCTGTGG ATGCGGGTTT GGTTCCGCCG
16501 GATGATCCCG GAATAGTGGA GCCTCACATG GTGGATGTGT CGGATCCTGG CATGATCGAG
16561 CCTGCAGATG ATGTGGATCT TGGTGTAGGC TATGTGCCGA AACATGCTGC CGAGTCGGAG
16621 GTTGGCACGG TAGAGTCGAC TGTTGCATAA GTGAATATAG ATGTGTGCCC CAGCGGTGCT
16681 GCCACGATTG TGTGGTGGTT GCCGCTGGGG CACTATTTTT GTATATTGCG GTGTGGCTAT
16741 GATTCGTTGC TGTCGATGGT GTCTTCGAGC ATCTGGTACA GGTGGAGGCA GGTAGAGATA
16801 GTTTCGCTGG CCTGGTCGAG AACGTTCCGG CCGATAACAT TTTTGTTGTT GTCGCGGTGG
16861 CGGATGATAG ACCACATGAT CTCGTCGGCT GCCGCCTGCA ATAGTTTTGC CTGGTATGCG
16921 ATTCCAGCGA GCCAGTCTAG TGCTTCCTGG CTTGCATAGG GTGTCTGGTC CTCGCTGTTG
16981 CTTGTGGGGT GTCCTGCACT GTCGCATAGC CACAGGATTT CGCTGCACTC GTCTAGCGTG
17041 TCCTGGTCTA TAGCGAGATC GTCGAGGCTG ACATTGTTGA CGGTAAGGTT CACGTTGTCG
17101 AGGGAGATGG GTACACCGTA CTGGTTTTCG ACACCGTCAA CAATGTTTTC CAATTGCTGC
17161 ATGTTGGTGG GCTGTTGTTG GACGATACGG TGTATCGCTG TGTTGAGGGT GGTGTAGGTG
17221 ATATTGTGTG TGTTGTTCAT CGTGTTATGC CATTCCTTCG TTATCGTCTG GCCTGTAGTA
17281 TGTGCTGTTT GCGTACTCGG TTAACGTCAT CAGTGTTTGG TCTGCCCACT GTTTCACAGT
17341 CTGCCTTGTC ACTCCGAGTC GTTGGGCGGC TGTGGCGTAG GTTTGGTCAT ACCCGTATAC
17401 TTCCCTGAAT GCTGCCAACC GTGCCAAATG TTTTCGCTGT TTGGATGGCT GGCAGGCGAG
17461 GGTGTAGTCG TCGATGGCTA GCTGTAGATC GATCATGGTG GCAATGTTGT TGCCGTGGTG
17521 TTGTGGCGCG GTTGGTGGGG GTGGCATTCC TGGCTCCACA CTGGGTTTCC ATGGGCCTCC
17581 GTTCCAGATC CATTGGGCGG CTTGGATGAT GTCTGCGGTG GTGTAGGTTC GGTTCACTGG
17641 TCATCCCCTG AACAGGTTGT CTGGGTTGCT GGTGCGGATT GTGTCGAATC GTCCGACGCA
17701 GTGGCAGTAG TCGTACATGA GTTTGATAAT GTGTTGGTGG TCTCCCAAAT AGGTGTTTCC
17761 GCTGATGCTG TAGGTGGCTG TGCCGTCTTT ACTAATAGTG TATTTGGCGG TGATGGTTTC
```

-continued

```
17821 GGGGTTTTCG GTGTCGGTGA TGATGGCTGT GGTGGTGGTG CCTACGGTTT GGAGCACGGT

17881 GGTTTGGGTT CCGTCGTCGA TGGTGGTTTT AACCATGAGG TGTGTTCTCC CTTTGTGTTA

17941 GTTGCTGGTT TGGTTGTCGG CTAGATGAAT GATGTCGGGT AAGGGTTTCG GCTGGTCTAA

18001 ATGTTGTGTG GTTTTGTTGG CTAGCCGTTT GGCTACCCTG TAGCACATTT TGGTGTAGTG

18061 TTTGTTGTCT AGGTTGTGGT ATTGTTCCCG CACCGCAATA TATAGCAGGG AGTCTTGGTA

18121 CAGGTCGTCT GCATTGATTG CGGGGTAGTG TGCGGCTGTT TTAGTGCATG CCCGGTTGAG

18181 TGTGCGTAGA TGATGGTCTG TGGCCCACAC CCACGATGCG GTGGTGGCTA GGTCGGCTTT

18241 TGTTGGTCGT CGGCTCATGG CATCTCTTTC ATCTGGCTAT CTGGTAGTTG TTTGGTGTTT

18301 TGTTGTTGAT AGTGTAGCAC ACGAGTCCGG GGTTTCCGGT GGTGCCCGTC TTGTGCCGGT

18361 ACCATGTGGA TTCGCCTTCC ATGGATGGGC ATTGGATGAA GGTGCGTTGT CCTTGTTCGG

18421 AGATTTCTAG GTGGTGCCTG TGTCCGGCCA TGAGGATGTG GGATGTGGTG CCGTTGTGGA

18481 ATTCTTGTCC GCGCCACCAA TCATAGTGTT TGCCGGTGCG CCATTGGTGG CCGTGGGCGT

18541 GTAGTATCCG TGTGCCGGCT ACTTCGACGG TGGTGGTCAT TTCGTCTCGG CTGGGGAAAT

18601 AAAAGTGTAG GTTGGGGTAT TGGTTGGTGA GCTGGTAGGC TTCTGCGATG GCGCGGCAGC

18661 AGTCTACGTC GAAGGAGTCG TCGTAGGTGG TGACTCCTTT GCCGAAGCGT ACGGCTTCTC

18721 CGTGGTTGCC GGGGATGGAT GTGATGGTCA CGTTTTTGCA GTGGTCGAAC ATGTGGATGA

18781 GTTGCATCAT GGCCATGCGG GTGAGCCTGA TTTGTTCCGT CAAGGGGGTT TGTGTGCGCC

18841 AGGCGTTGTT GCCTCCTTGT GACACGTATC CTTCGATCAT GTCGCCGAGG AATGCGATGT

18901 GGACTCGTTC GGGTTTGCCT GCCTGCTGCC AGTAGTGTTT AGCTGATGTG AGGGAGCGCA

18961 GGTAGTCGTC GGCGAAGTGT GATGTTTCCC CGCCGGGGAT GCCTTTGCCG ATTTGGAAGT

19021 CGCCTGCCCC GATGACGAAG GCCGCAGTGC TGTAGTCGGT GCGGGTGTCC TGTTCGGGTT

19081 TTGGGGGTGT CCATTCGGCT AGTTTATCGA CGAGTTCGTC TACAGGGTAG GGGTTTGTTG

19141 CGGGTTGGTG GTCGATGATT TTTTGTACGG ATCTGCCTGT TTCTCCGTTG GGGAGTGTCC

19201 ATTCGGAGAT GCGTGTGCGG CGTACGGTGC CGTTTGCGAG ATCATCGCAG ATGGTGTCTG

19261 CTTCGCTATC GTGGTTGGCT AGCTGGGTGA GTAGCCGGTC TATGTTGTCT ATCACTGGGT

19321 ATCCTCTTCT TGCGGGGTGG TGTTGGCTTG TTTGCGGCGG TAGTCTTTTA TAACGGTGGC

19381 GGAGATGGGG TATCCTGCCT GGGTGAGCTG TTTTGCTAGC CATGAGGCGG GGATGGTTTT

19441 GTCGGCGAGC ACGTCGGCAG CCTTGTTGCC GTAGCGTTGG ATGAGTGTTT CAGTTTTGGT

19501 TGCCATGGTG TCCTATCGGT TGTGTGGTGG GCTGCCATCC TGTGCGGCAG TCGCCGTCGT

19561 GGCCTGGTTT GCGTGTGCAC CACGATACGG TTCTGTCTGT GTGGTTGAGT GTTTTGCCGC

19621 ACATGACGTT TTGTAGATGC TCTGGCAGTG CGCCGTCACC CTGGTTGCTG GTTTGTGTGT

19681 CGAAGAGTGT TTTCTGGTTG GTGAAATGCT CGGACACGGT GCCATTATGT ACGGGTAGTA

19741 TCCATGTTTT CCATTGTTGT TGTAGCCGGG TGTTCCAGTG GAATTGTTTT GCTGCGTTCG

19801 TGGCTTGTTT GATGGTTTTG TAGTAGCCGA CGAGGATGCG CTGGTGTTCA CTGTCGGGAG

19861 GGTTTTGGCC TCGCCAGTAT TGTGCCGCCA CGGCGTAGCG GTTGCTGGCT GTGAAGGCGT

19921 CCCAGCAGTA TTCAATAATG TGTTGTAGTA CACTATCGGG CATGTCTCGT ACTTGGTTTT

19981 CGTCGAGCCA CGCGTCGACA ATGATGTTGC GTATGGCGCG TTTGTCTTTG GTGGTGGGTT

20041 TGAATGCGAT GCTCACAGTA CGGGCCTGTC GTCTTGCATG AAATCATTAA AGGATGATTC

20101 GCTTGCGCGG CGTGCTTGTG TGATTTGCTG GTCAGACCAG TCGGGGTGTT GCTGTTTCAG

20161 ATAGTACCAG TGGCACGCAT TGTAGGTTTC GTCTTGTAGC CGGGTGAGAT GGTTTTCGGT

20221 GATGATTTGT TTCCACATAG TCCATGACAC GTCGAGCCGG TCCAATATTT CCATTGCTGG
```

-continued

```
20281 AATGTTGAAC TGGTTCAGGA AGAGTATTTC GTGGGTGTAG TATTCCTTCT CGTACTGGTC

20341 CCATCCACTT CGGTGCCTGT TGGGCTGGTT TTTGGGGTAG GCTTCCCGGC ATACTTTGTG

20401 CAAATGTTTG GCCATGTCGT CGGGTAGTTT AATGTCAGGG TTGGCGCGGA TCATGGATCG

20461 CATCCCATCA TAGGTGGTGC CCCAGGTGTG CATGATGTAG GTGGGGTCTT CACCATCAGC

20521 CCATTTTTCT GCACAGATGG CGAGGCGGAT GCGTCTCCTG GCTGATTGGC TGGTGTTGCG

20581 CCGGTTGGGG ATGGGGCACG TGTCGAGGGG ATCCATGATG TTTTGGTGTA CCTTTCTTGG

20641 TTTAGGTTGC TTGTGTGGTT TTATTGTAGC ACTGTGTCTA GTGCTTGTGT CAACCCTGTT

20701 TTGCCGGCCT GAAGGTAGGT GTCTGTGACA TCCCCCAGGG TGAGGGCAC ATGGGTGGCT

20761 TGGGGGAGTG CGGCCTGGAG TGTTTGGGCC ATCTGGTGGC CCGCCTTGTC TGGGTCTGAC

20821 CAGATGTAGA TGTGGTCGTA GCCTTCAAAA AATTTGGTCC AAAAAGTTTG CCACGAGGTT

20881 GCGCCGGGTA GGGCTACGGC TGGCCATCCG CATTGTTCGA GGATCATGGA GTCGAATTCG

20941 CCTTCGCAAA TGTGCATTTC GGCTGCCGGG TTGGCCATGG CGGCCATGTT GTAGATGGAG

21001 CCTGTGTCTC CTGCCGGGGT TAGATATTTG GGGTGGTTGT GGGTTTTGCA ATCATGTTGG

21061 AGTGAGCAGC GGAAACGCAT TTTTCGTATT TCGGCTGGCC CTTCCCAGAC GGGGTACATG

21121 TATGGGATGG TGATGCACTG GTTGTAGTTT TCGTGGCCTT GGATGGGGTC ATTGTCGATG

21181 TATCCAAGGT GGTGGTAGCG GGCTGTTTCT TCGCTGATGC CTCTTGCCGA GAGCAGGTCG

21241 AGTATGTTTT CGAGGTGGGT TTCGTAGCGG GCTGAGGCTT TCTGGATTCG GCGGCGTTCC

21301 GCAATGTTGT AGGGGCGTAT GCTGTCGTAC ATTCGGGTTT CTTCCTCTA ATCGTTGTTT

21361 CAGTTTGTGG AGTCCGCCTC CGATACCGCA TGTGTGGCAG TACCAGACGC CCTTGTCGAG

21421 GTTGATGCTC ATGGAGGGCT GGTGGTCGTC GTGGAACGGG CAGAGGATGT GTTGCTCGTT

21481 CCGTGACGGG TTGTAGCGTA TCTGGTGGGC GTCTAGGAGG CGGCAGGTGT CAGAGGTGTG

21541 GGAGGAGCTC GTTGAGGGTT GATACCACAT AGGCTTCGCT CCAGGGTTTG TTGCGCTGTT

21601 TCATGATGAC GAGTCCGATG GTGGATTGGT TTTCGCGGTT TCGGTGTGTT TCGTAGTTGC

21661 GTGCCTCCCG GCTGGCTTGT TTCACGAATT CGGCTAGGTG TGCCTGTCCT GCTTTGGCTT

21721 CGATCACATA GGTTTTGTTG CCGGTTGTGA GGATGAGGTC GCCTTCGTCT TCTTTACCGT

21781 TGAGGTGGAG GCGTTCTATA TCATAGCCGG TGTCGCGTAG CTGGTGGAGG AGTCTTGTTT

21841 CCCATTCGGC GCCGGCTCGG CGGTTGCGTG CCTGTTGTGT TGACATGATA GTCCTTTATG

21901 TTCTTGTGTC ATGTTCCAGG GCTGTTTTTC TACTAGGGGC CCGAAGAATG TGTATTCGGG

21961 GTAGGCTCGT AGTCGTTCGT ATTTTGTTCC GTCTGGGCTG GATTTGCCGG TTCTCTGTTT

22021 CAGGACGGCG ATGCGTGCCT CGGCGGGGAT GGTGAGGCCG TTGCCGTTGT CTTCGCCACC

22081 ATACAGGGAG ACTCCCAATA TGAGTTGTGG TTTTTCGGAG AGGCCGTTTT TGATTTCCCG

22141 CCTAGCTGGG GGGTGTTCGA TGTCGGTGCC GGTTTTGTCG GTTGCGTGGT GGGTGACGAT

22201 GATGGTGGAG CCAGTATCTC TACCTAAGGC TGTGATCCAT GCATGGCTT CTTGCTGTGC

22261 CTGATAGTCG GATTCGCAGT CTTGGATGTC CATCAGGTTG TCTATAACAA TAATGGGTGG

22321 GAAGGTGTTC CACATTTCCA TGTAGGCTTG CAGTTCCATG GTGATGTCTG TCCATGTGAT

22381 GGGTGACTGG AATGAGAAGG TGATGTGTCC GCCGTGGTGG ATGCTGTCTC GATAGTATTC

22441 TGGCCCGTAG TTGTCGATGT TGTGTTGTAT CTGTTGGGTG GTGTGTTGGG TGTTGAGTGA

22501 GATGATTCGT GTGGAGGCCT CCCAGGGTGT CATGTCCCCT GATATGTAGA GGGCTGGCTG

22561 GTTGAGCATC GCGGTGATGA ACATGGCTAG CCCTGATTTT TGGCTGCCGG ACCGCCCCGC

22621 GATCATGACC AAATCCCCTT TGTGGATGTG CATGTCCAGG TTGTCATACA AGGGTGCTAG
```

```
22681 TTGGGGTATG CGGGGCAGTT CGGCGGCTGT TTGGGAGGCC CTCTCGAAGG ATCTTTGGAG

22741 AGAGAGCATC GGGACCTTAA TCTATCTGTT GGTTGGGTGT GTTTTGGTGG TCAGATGGAG

22801 TCGATGTCGA TGTCAGCATC GGCGGGGGCT GTGGTGTCGT CTAGCTGGCC GTTGTCGCGT

22861 TTGTCTACAT ATTCGGCAAC CTTATCGTAG ATGGCGTCGT CGAGGGGTTT GAGGACGACC

22921 GCGTTGAACC CGTTTTTGGT GCGCACGGTG GCAAGTTTGA AGGCTTGTTC TTCGCCGAGA

22981 TATGCTTCTA GGTCGCGGAT CATGGAGTGT GGGCGGTCGT TGTTGCCGCG TGCTTTTTCG

23041 ATGATGGCGT TGGGGATGGT TTCTGGGGTG CCGTTGTTGA GATCCTGGAG GGTGTGGAAG

23101 ATTGTGACAT CAGCGTAGAT GCGGTCTGCG ACCTGTCCAC CGTAGCCTTC GGTGTTGTGT

23161 TCTACGTCGC GGATTTTGAA GGCGATGGCG GTGGCGTCCT GGTTTCGGGA GGGGTTGAAG

23221 AAGGTGCTGT TGCTGTTGTT GTGGTAGTTG GCGAGTGCCA TGATTGTGTT ATCCTTTACT

23281 GTTGTGTCTG TTTTTGTTGT CTTATATTGG TTTATCGGGT GAGGCTGTTT CGTTTGCTGC

23341 GGAAAGCCTC GGAAACGTCA CTGTTACTGG TGATGGTCTT CTTGTACTGT TTGAGTAGGT

23401 CTGCTAGCTG TGTCTTGCTG GTGGCTTTGT TTATCCGGTC GATGATGATG TCGTTTTCCT

23461 GTGATGCGAT TTTGTTGACG TAGTCTTTGG CGGCTTTATC GTATCGGTCT TGAAGCAGGA

23521 TTGCTGCGCT AGCGATGAGG GTTGCGAGAT CCCAGTCTTT GGATACGGTT TCGTCTTTCA

23581 ATCCTCCTAG CAGATCAATA ATGGATTGTT TGATGTCTTC TGCGGTGTCT CCGCGGATGA

23641 CTGTCCATGG GGCGGCATAG TCGCCACCGT ATTTGAGTGT GATAGTTAGT TTTCCGCTGT

23701 CTGTGGTGTG CTCGTCGGTC ACGTGTTTTC CTTTTCGTTG TTTTCGGCTT CTGGTGGCTG

23761 TACGGTGGTT TCTATCGGGT ATCTGTAGGC GTCTTTCCCG TTGACGGCCC AGCAGGCGTC

23821 CTTGACGGGG CATCCTTTGC AGAGTGTGGT GACGTGGGGT ACGAAGATGC CTTGGCTGAT

23881 TCCTTTCATT GCTTGACTGT ACATGGATGA TACATGCCGG TAGGTGTTGT TGTCAAGATC

23941 AATGAGTTCG GTTGCTGTGC CCTGCTCGAC TGATTGCTCG TCTCCCTTGG TGGTGGCGGG

24001 TGTCCAAAAC ATGCCTTTCG TCACATGGAT GCCGTGTTGG GCGAGCATGT ACCGGTATGT

24061 GTGCAGCTGC ATACTGTCTG CGGGTAGGCG TCCGGTTTTG AGGTCCAAAA TGAAGGTTTC

24121 GCCGGTGTCG GTGTCGGTGA ATACCCGGTC AATATATCCG ACTATTTTTG TGTCATCGTC

24181 GAGGGTGGTT TCTACCGGGT ATTCGATGCC TGGCTGGCCG TCAATAACAG CGGTGGCGTA

24241 TTCTGGGTGG TTGCGCCTCC ATGTTTTCCA GCGGTCCACA AAGGTGGGGC CGTACATCAT

24301 CCACCAATTG TAGTCTTTCT TGTGTGGCCC GCCTGACTCG CACATGTTTT TGCATATTCT

24361 GCCGGAGGGC TTTATGTTTG TGCCTTCGGA TTCGCGAGG GCGATTGGG TGTCGAAAAT

24421 GTTTGTGAAG GATGAGAGTT TGTCTGGCAG TGCAGGGTAT TCGGCGGGGT TGTACAGGTG

24481 TAGGTCGTAT TGTTCGGTGA TGTGGTGTAT GGCGCTTCCG GCGATGGTGG CGTACCAGGT

24541 GTGGTGTTGG GCGTGGTAGC CGTGTGCTAG GCGCCATTTT TCGCCGCATT CGGCCCACTG

24601 TGTGAGTGAA CTGTAGGAGA TGTGGCCTGG ATGGTTGATG GTTTTCGGGT ATTGTGCTAG

24661 GGGCATTACT TGTCGCCTTT GTGGGTGTTC CATGGGTTGC GGGTGTCTTT GCCGGCGTGG

24721 TGTTGCTGGT AGGCGAGGAG TGCAGGCAG TGCCAGGCAG CGTGTGCCAG ATGCGGCAAA

24781 TGTGATTCGT TGTCGAGGTT GTTGCCTTGC TGCCATGATA ACAGGTGCCG GTAGAGGGCG

24841 TCGACACTGT GGCTCCACGG GTATCCTCCG GTCCAGTTGT TGTCGCCGTA CTTGGTGGCA

24901 CCGTAGCCTG CCACGGAGCC TAGGGCGTGC AAGGCTGCGG GGTCGATGAG GGAGAGCCTG

24961 CAGAGTTTCA ATTCTTTTCG GGCACCGCTG TTGGGGTCGG TGTACATGCT GGTGGGCTCA

25021 TCCATGGTGT GTGTGCTCCT TAAGCGTGGG TTACTGGTTA TTGTCGTGGG CGAGTGCTAC

25081 GGCGAGAATA ATGATGGCGA GGGTTTCAGC GATCAGTATG GGTGTTGTGA TCATTTAGTG
```

```
25141 TCTCGGGGAT TATTGGTGAG TGTTGATGCA CCTAGGAGGG TGGCGAGGGC GCATGCGGCG
25201 ATGGTGGCGA GGGCTGCCTT GTGTGGGGTG CCGGTTGCGT ACATCCATGT GATGATGCCG
25261 CCTTGGATCC AGGCTAGACT GGTGAAGAAC GTTTCGTAAC TGTGTAGCTC AATGTTGTTG
25321 TTGGGTGTGT TCATGCTTGC TCCTGAAGAA TGGTGTTGAT GGTTTTATAA ATGTTGTACA
25381 GGTCGGTTTC GATAGATAAC AGTTGGTTGA TTTGGTGGTC GAGATCAATG TCTGGGTTGA
25441 GGGTGTCGAT GCGGGCGGCG ATATCGGTGG CGGTGCGTAG CTTACTGCT GCACCGTGGA
25501 TGATGTGGCA CATGTCGGTG AGGCCGACTT TGGCGATATA GTGTGACATG AGAGGCATAA
25561 TAGGTGTGCT GTCTTTCTGG TCAGCGTGAA GGGTTGATGG ACATATCCTC TACCTGTGGT
25621 TTGTCTTCGG TGCCGGAGAC TTGGCAGAAG ACTTTCACAT GCGTCTTGGA TGCTCCGGCC
25681 TGTTTGGCGG TGGCACCGTA GGCGATAGTA AAGGTGTCTT TGTGGGCGCC GATGACTTTG
25741 TGTAGGAAGA GGTCGATGTC GGGGTTGCCG TTCCATTTGA CACCGTTTTC TGCGGCTGTC
25801 TGGGTGGCTT TCTGATTGCA GGCGTGTGCG GCGGTGATCA TGGTGAGACC CTTGCTGGTT
25861 TCTTCACCCC TTGCTTGGGC TTGCCGGTGG GCTTTGGCCT GCTCGGCTTG TAGGGAGCGG
25921 ACTGCTGCGG CCTGGCGGGC CTTCTTCTCA GCCTTGCGCT GCTGGACGGT TTTGGGTGTC
25981 CATTCGGTGT TGGCTGTGGT TACCTGTGGT GCGGGTTGTG AGGCGAGTGG CGGATTGTCG
26041 TCTGGGGCTG GCATGAAGGA TGCTGCGGCA ATAATGGCGA CTGTGGCGCC TGCGATGGTG
26101 TAGCCTGTTT TCTTGTTCAT GATTTTATGT TCCCCTTTCC GGGGTGTTGT TCGTTGCTGA
26161 CATGGTTAAT ACTTTCAGCG GCTGGGCCCA CTGTCAAGGC TGCGCTCAGT TTGTGTGAGC
26221 GTTTCTTGTG TGGCTAGGGG TGATGGCTTC TTTCGCCCAA TAGGATGTGC CACCGCTGGT
26281 CCAGTATCCG AGTTTGTTGC GCTGCATGCC CTTGGCGTCC ATCTCGTCGA TAGTGAGGCA
26341 CCTGCGGCGA TTGGGGCCTG TCTTGACCCC GTGGTCGCCT GTCCGGTGCA TGTCGCCTGA
26401 GGTGGTACTC GTGAATGTTT CATGGCAGAT GGTACAGTGC TCTGGTCGAT ATCCGGTGAT
26461 TGTGCTATCG CACTTGTGGC ATGTCCATTC CATGATTGCT CCTATTTTCC ATTATAAGAC
26521 TTCCTGTAGT GCCATTTTAG CGCCTTGCGG GTCTTGGGGG TACAACTATA TAGGTCAGGT
26581 GTTTCTAGGC GATTCTAGGC TCATTGTGTG TGGCTGGGGT TTTATCGGGC ACACAGGGTG
26641 AGCAGGTGGC CAACATTGAT GCGGGTCACA TTCCAGTAGA GTTGCGTGGC TTCCCCACTG
26701 GTGAGCGGCT TCCACTCGTC ATGGCTGAAC ACGGTGCCAT CGGATGCGAT GAACGTGTTG
26761 GGGCGTAGCT TGTGGAGTTC GGCTTCCACG CTCTGCCGGT AGGCTTCGGC GAGGCCCTCA
26821 AAATCCATGT GGTCGCAGGG GAGGTTTTCG AGGCGTGTCA GGTCGAAGGG TGTGGGCAG
26881 TCGTAGCTGG CGGGGGTGTA GAGCTGGGTG AAGTGGTTGG CGATCTTCTG CATCATGATT
26941 CCTTTTCTGA TGATGGTGTG TTGAGGGTTT ATCGGGTGGA TGCGACAAGG ATGGCGTCTA
27001 CATCGATCAT GTCGATGAGA TCGTGGAGTT CCTCGGCCTC GTTCTCAGTG AGTGGCTGCC
27061 AGGCGTAGTC GCCGTATACG GCGCCGTCGA GGGTGACAGT CCACGGGGC CGGATGAGTC
27121 GTATGGCTTC TTGTACTTTA GCGTGGTACA TGCGGCGCAC CATATCCAGA TCGATGTCGT
27181 CTGAATGGTT TCCGGTGAGG CTGTGGAGGC TGAGCGGGTC GATGTCTGTC TGCCTGTAGA
27241 GGGATGTGAA GGATGGGGTG ATGAGTGTGC CATCCATGAG TGTGCTCCTT TCGGTGGTTG
27301 TAGGGGTTGT TGTGGTTTCT AGAGTGTGCG GGCTGCGACC CCACAGTCAA GGTGTCGCTC
27361 AAACTCAGTG AGCGTTTCAT ATGGGTGTGT TGGGTGTGAC AGATGTCACT TAAGCCTTGA
27421 TGGCCTCTCT CAGCGCCTCA AATCTTCTAG GGTAGGATT ATGAAGGGTT GGCCCTGCTG
27481 ATCGATTCTA GGCCCCATAC AGGGCGTCTG AGGGGTGTGT CTGAGTGATA GTGGGTGTGG
```

```
-continued
27541 CAGATGATCT AGCGAGTCAA GGTGCCGAGC TGAGACATAA GATCTATCAT CTAGGTGTGT

27601 GAGATGTATC ACATCCTCCC GGCTTGGTGT GCACCCTCAA GGCCACCCAG TCGATCTGAC

27661 GTGGAGGGTG TAGCCCAGAA ATACTGTTTA AAGCCTTCAC ACGGCGCCTA GGAGCGCCTT

27721 ACAGGGTGGG GGCTAGGTAT TTATACCCCC AGCACATTCT GATCGATTCT AGACGCCTAC

27781 AGGAGCCCGA TACACGATCA GCCATCCAGA CGCAGATCAT CAGCACCTAT CATGGTTAGC

27841 TAAGCCTCAA CTATGTGGAC AGTGTTGGTT ACTGTGGGGG AAGAAGGACA CGGTAAAAGA

27901 AAGAGGGGGA GTATCAGCTT TAAAGCCTTA AGGTCTTAGC GCTTAGCACC GATGGTCTTA

27961 GCAGTTAGCA CCGAGCCCCC TCAAGGGCTC GGCATCAGCC CGAACAGGCA CAGCCATGAA

28021 AGGAGTACAC GCCATCAGGG AAGGCTTTCG AGTACGAGGA GCCTCAGCGA CGAGTACTCG

28081 AAAGCCTGAG GGAACACCCA TCAGCACTGA TGAGCCTAGC GTATTCGGAA AGGACACAAG

28141 AGTGAAGTGT GACAGCTGTC CGGGAGTGAA CCCCGTTCTG ACTAGGGGTT TCAGCCTTAA

28201 CCACCCTCAA AGGTTACAAG ACTCTAAGAA AATTTAAGGA AAAGTTTAGG TTTAATTTTT

28261 GGACCTTTAC TACCAAAAAC ACCCGTTTAC AGCCCTCAAA CCCGCCTATA GAGCCAAAAC

28321 CACCAGTTTG ACTCATCCCA GGTGGGGTAT GATAGGCTGG ACAGGTAGCC AGCTGGACGC

28381 AAGGCCGGAA AGTGCTAACG CACTTTCCAA CCTCGCTTAC CATCAGTCTA CCAAACACTT

28441 AAAGACCTAA GGGCTTAGCG CTAAGGTGCT GATAGCTTAG CACCGAGCCC CCTCAAGGGC

28501 TCGGCATCAG TCTTAAAGCC TTAAATACTT AAAGTAACTA TAAAACTTTA AAAGCTTAAC

28561 ACTTAAGGAT ATAAACTTTA CATCAGTGTT TAAGACTTAA AAACTTAAAA TAACTATTAA

28621 GACTTAAAGT AACTATAAAA CATTAAAGAC CTTAAGTACT TAAAGTTAAC CATCAGTCTT

28681 AAACTTTACT ATGATAACCT ATAAGTCTTA AAGCTTATAG GTATAATAAT ATAATATAAG

28741 TATTAAAGCT TATAAGTTAT AAAAGTTTTA GAAGAGTTAA AGGGTTAACT TCTTTACTTC

28801 TCTTCTCTCT TTGGTTCTTT CTCTCTTCTC TTCTTTTCTT CATCGGGGGA GAAGAGGAAC

28861 CTTTAACGTC AACGCTGATG GACTTTTCGC CGTGTGTCTC GTGTGCTTCT GGTCGCAAGC

28921 TCCCATCGCA CACTCCCCAC ACTCTTTCAC CTGTGTCCCT TTCAGGCTTA GCGTGTTCAG

28981 CTGAAGGCGT ACAGCGTGTC ACGCTTAAAC CCTTAACACC AGGTAAGACT TAAAGTGCAT

29041 ATTATAAGTA GAAGACTTTA AAACCTTAAG GGTGTTCCTG CTTAGCCTGT GTCCTTTAAC

29101 GCTAGGCGCT AAGCCGTGAA ACGTGAACAC CCATCCACCC CTCTTCTTTT TACCGTGTCC

29161 TTCTTCTTTT GACACCGCTG GGGGGCGATG TGATCTTTTT AACATGCCAG GGGGTGCGGG

29221 TAGAAAACAA CCACCCCACC ACAAACAGAA CACCCCCTCA AACGCACAAA ACAGCCCCCA

29281 GGATCGATGA ACAGGGCAAG GGCAAGGTAT TCATACCCCC AGACGATTCC AGGCCGTTAG

29341 AGAGGCAAAT AAGACCCGTA CAGGGCTAGG TGAGGAATAG ACACATCATG GCACGCACCA

29401 ATCGCACAGC TAGCCAAGCC CACCGACGCT GGCGGCAACG ACTCATCACC CAAGCCCAAC

29461 AACAAGGCCA AACCGAATGC CCACTCTGCG GAGTCACCAT CACCTGGGAC ACACACGACC

29521 TACCAACCAG CCCCGAAGCC GACCACATCA CACCCGTCAG CAGGGGAGGA CTCAACACCC

29581 TCGACAACGG GCAAATCATC TGCAGAACAT GCAACAGAAG CAAAGGCAAT CGCAGCGAAC

29641 CAAACATCAA ATTCCAACAA CAAACCACAA AAACATTGAT TCCATGGTGA CAAACCCGCC

29701 AACCCCCACC GGGGACACCC CCTGCACAGG CGTGCAAGAC CTCGTACGGC TT
```

In embodiments, the bacteriophage is a bacteriophage as deposited under Accession No. NCIMB 41349, 41350, or 41351. In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genome of the bacteriophage deposited under Accession No. NCIMB 41349. In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genome of the bacteriophage deposited under Accession No. NCIMB 41350. In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genome of the bacteriophage deposited under Accession No. NCIMB 41351.

In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the nucleotide sequence of SEQ ID NO: 1. In embodiments, the bacteriophage has a genome with a nucleotide sequence that is identical to the nucleotide sequence of SEQ ID NO: 1.

In embodiments, the genome of the bacteriophage encodes, from the 5' to the 3' end, a small terminase, a large terminase, a portal protein, gp4, a scaffold protein, a major head protein, gp7, gp8, gp9, gp10, a major tail protein, gp12, gp13, a tape measure protein, a minor tail subunit, optionally a protease, gp17, gp18, a tail protein, an amidase, a holin, gp22, gp23, a sigma factor, gp25, gp26, gp27, gp28, gp29, gp30, a DNA primase, a DNA primase 2, gp33, a DNA helicase, gp35, gp36, an exonuclease, gp38, gp39, gp40, gp41, gp42, gp43, gp44, gp45, gp46, gp47, and gp48.

In embodiments, the composition further includes a *P. acnes* biofilm degrading enzyme.

In embodiments, the enzyme is an anti-aging enzyme. In embodiments, the anti-aging enzyme is a superoxide dismutase or a peroxidase.

In embodiments, the enzyme is a *P. acnes* biofilm degrading enzyme. In embodiments, the enzyme is a glycosidase, a protease, a DNAse, or a restriction endonuclease. In embodiments, the enzyme is a glycosidase. In embodiments, the glycosidase is a glycoside hydrolase. In embodiments, the enzyme catalyzes the hydrolysis of linear polymers of N-acetyl-D-glucosamines. In embodiments, the enzyme is a β-hexosaminidase. In embodiments, the enzyme hydrolyzes β-1,6-glycosidic linkages of acetylglucosamine polymers. In embodiments, the enzyme is a DNAse I, a restriction endonuclease, papain, bromelain, Trypsin, Proteinase K, Subtilisin, serratiopeptidase, dispersin, alginate lyase, amylase, or cellulase. In embodiments, the enzyme is Dispersin B. In embodiments, the enzyme is a protease, and the protease is proteinase K or subtilisin.

In embodiments, the enzyme is a dispersin. In embodiments, the enzyme is Dispersin B. In embodiments, the enzyme is a naturally occurring form, homolog, isoform or variant of a dispersin (such as Dispersin B) that maintains the enzymatic activity (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes Dispersin B is as follows:

(SEQ ID NO: 11)
ATGAATTGTTGCGTAAAAGGCAATTCCATATATCCGCAAAAAACAAGTACC

AAGCAGACCGGATTAATGCTGGACATCGCCCGACATTTTTATTCACCCGAG

GTGATTAAATCCTTTATTGATACCATCAGCCTTTCCGGCGGTAATTTTCTG

CACCTGCATTTTTCCGACCATGAAAACTATGCGATAGAAAGCCATTTACTT

AATCAACGTGCGGAAAATGCCGTGCAGGGCAAAGACGGTATTTATATTAAT

CCTTATACCGGAAAGCCATTCTTGAGTTATCGGCAACTTGACGATATCAAA

GCCTATGCTAAGGCAAAAGGCATTGAGTTGATTCCCGAACTTGACAGCCCG

AATCACATGACGGCGATCTTTAAACTGGTGCAAAAAGACAGAGGGGTCAAG

TACCTTCAAGGATTAAAATCACGCCAGGTAGATGATGAAATTGATATTACT

AATGCTGACAGTATTACTTTTATGCAATCTTTAATGAGTGAGGTTATTGAT

ATTTTTGGCGACACGAGTCAGCATTTTCATATTGGTGGCGATGAATTTGGT

TATTCTGTGGAAAGTAATCATGAGTTTATTACGTATGCCAATAAACTATCC

TACTTTTTAGAGAAAAAGGGTTGAAAACCCGAATGTGGAATGACGGATTA

ATTAAAAATACTTTTGAGCAAATCAACCCGAATATTGAAATTACTTATTGG

AGCTATGATGGCGATACGCAGGACAAAAATGAAGCTGCCGAGCGCCGTGAT

ATGCGGGTCAGTTTGCCGGAGTTGCTGGCGAAAGGCTTTACTGTCCTGAAC

TATAATTCCTATTATCTTTACATTGTTCCGAAAGCTTCACCAACCTTCTCG

CAAGATGCCGCCTTTGCCGCCAAAGATGTTATAAAAAATTGGGATCTTGGT

GTTTGGGATGGACGAAACACCAAAACCGCGTACAAAATACTCATGAAATA

GCCGGCGCAGCATTATCGATCTGGGGAGAAGATGCAAAAGCGCTGAAAGAC

GAAACAATTCAGAAAAACACGAAAAGTTTATTGGAAGCGGTGATTCATAAG

ACGAATGGGGATGAGTGA

A non-limiting example of a Dispersin B amino acid sequence is as follows:

(SEQ ID NO: 12)
MNCCVKGNSIYPQKTSTKQTGLMLDIARHFYSPEVIKSFIDTISLSGGNF

LHLHFSDHENYAIESHLLNQRAENAVQGKDGIYINPYTGKPFLSYRQLDD

IKAYAKAKGIELIPELDSPNHMTAIFKLVQKDRGVKYLQGLKSRQVDDEI

DITNADSITFMQSLMSEVIDIFGDTSQHFHIGGDEFGYSVESNHEFITYA

NKLSYFLEKKGLKTRMWNDGLIKNTFEQINPNIEITYWSYDGDTQDKNEA

AERRDMRVSLPELLAKGFTVLNYNSYYLYIVPKASPTFSQDAAFAAKDVI

KNWDLGVWDGRNTKNRVQNTHEIAGAALSIWGEDAKALKDETIQKNTKSL

LEAVIHKTNGDE

In embodiments, the enzyme is an alginate lyase. In embodiments, the enzyme is a naturally occurring form, a homolog, an isoform or a variant of an alginate lyase that maintains the enzymatic activity of the alginate lyase (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes an alginate lyase is as follows:

```
                                         (SEQ ID NO: 13)
ATGAAAACGTCCCACCTGATCCGTATCGCCCTGCCCGGTGCCCTCGCCGC

GGCATTGCTCGCCAGCCAGGTCAGCCAGGCCGCCGACCTGGTACCCCCGC

CCGGCTACTACGCGGCGGTCGGCGAGCGCAAGGGCAGCGCCGGCAGCTGC

CCCGCGGTGCCGCCGCCGTATACCGGCAGCCTGGTCTTCACCAGCAAGTA

CGAAGGCTCCGATTCGGCGCGGGCGACCCTCAACGTCAAGGCGGAGAAGA

CCTTCCGCTCGCAGATCAAGGACATCACCGACATGGAGCGCGGCGCCACC

AAGCTGGTCACCCAGTACATGCGCAGCGGCCGCGACGGCGACCTGGCCTG

CGCACTGAACTGGATGAGCGCCTGGGCCCGCGCCGGCGCCCTGCAGAGCG

ACGACTTCAACCACACCGGCAAGTCCATGCGCAAATGGGCGCTGGGCAGC

CTCTCCGGCGCCTACATGCGCCTGAAGTTCTCCAGCTCGCGGCCGCTCGC

GGCCCACGCCGAGCAGAGCCGGGAAATCGAGGACTGGTTCGCCCGGCTCG

GCACCCAGGTAGTCCGCGACTGGAGCGGCCTGCCGCTGAAGAAGATCAAC

AACCATTCCTACTGGGCGGCCTGGTCGGTGATGTCCACCGCGGTGGTGAC

CAACCGCCGCGACCTCTTCGACTGGGCGGTGAGCGAGTTCAAGGTCGCCG

CCAACCAGGTCGACGAGCAGGGCTTCCTGCCCAACGAACTCAAGCGCCGC

CAGCGCGCCCTCGCCTACCACAACTATGCGCTGCCACCGCTGGCGATGAT

CGCCGCGTTCGCCCAGGTCAACGGCGTCGACCTGCGCCAGGAGAACCACG

GCGCCCTGCAGCGCCTGGCCGAGCGGGTGATGAAGGGAGTCGACGACGAG

GAAACCTTCGAGGAGAAGACCGGCGAGGACCAGGACATGACCGACCTCAA

GGTCGACAACAAGTACGCCTGGCTGGAGCCCTACTGCGCCCTCTACCGCT

GCGAGCCGAAGATGCTCGAGGCGAAGAAGGACCGCGAGCCGTTCAACAGT

TTCCGCCTCGGCGGCGAAGTGACGCGGGTGTTCAGCCGCGAAGGGGAAG

TTG
```

A non-limiting example of an alginate lyase amino acid sequence is as follows:

```
                                         (SEQ ID NO: 14)
MKTSHLIRIALPGALAAALLASQVSQAADLVPPPGYYAAVGERKGSAGSC

PAVPPPYTGSLVFTSKYEGSDSARATLNVKAEKTFRSQIKDITDMERGAT

KLVTQYMRSGRDGDLACALNWMSAWARAGALQSDDFNHTGKSMRKWALGS

LSGAYMRLKFSSSRPLAAHAEQSREIEDWFARLGTQVVRDWSGLPLKKIN

NHSYWAAWSVMSTAVVTNRRDLFDWAVSEFKVAANQVDEQGFLPNELKRR

QRALAYHNYALPPLAMIAAFAQVNGVDLRQENHGALQRLAERVMKGVDDE

ETFEEKTGEDQDMTDLKVDNKYAWLEPYCALYRCEPKMLEAKKDREPFNS

FRLGGEVTRVFSREGGS
```

In embodiments, the enzyme is an amylase. In embodiments, enzyme is a naturally occurring form, a homolog, an isoform or a variant of an amylase that maintains the enzymatic activity of the amylase (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes an amylase is as follows:

```
                                         (SEQ ID NO: 15)
ATGAAACAACAAAAACGGCTTTACGCCCGATTGCTGACGCTGTTATTTGC

GCTCATCTTCTTGCTGCCTCATTCTGCAGCAGCGGCGGCAAATCTTAATG

GGACGCTGATGCAGTATTTTGAATGGTACATGCCCAATGACGGCCAACAT

TGGAAGCGTTTGCAAAACGACTCGGCATATTTGGCTGAACACGGTATTAC

TGCCGTCTGGATTCCCCCGGCATATAAGGGAACGAGCCAAGCGGATGTGG

GCTACGGTGCTTACGACCTTTATGATTTAGGGGAGTTTCATCAAAAAGGG

ACGGTTCGGACAAAGTACGGCACAAAAGGAGAGCTGCAATCTGCGATCAA

AAGTCTTCATTCCCGCGACATTAACGTTTACGGGGATGTGGTCATCAACC

ACAAAGGCGGCGCTGATGCGACCGAAGATGTAACCGCGGTTGAAGTCGAT

CCCGCTGACCGCAACCGCGTAATTTCAGGAGAACACCTAATTAAAGCCTG

GACACATTTTCATTTTCCGGGGCGCGGCAGCACATACAGCGATTTTAAAT

GGCATTGGTACCATTTTGACGGAACCGATTGGGACGAGTCCCGAAAGCTG

AACCGCATCTATAAGTTTCAAGGAAAGGCTTGGGATTGGGAAGTTTCCAA

TGAAAACGGCAACTATGATTATTTGATGTATGCCGACATCGATTATGACC

ATCCTGATGTCGCAGCAGAAATTAAGAGATGGGGCACTTGGTATGCCAAT

GAACTGCAATTGGACGGTTTCCGTCTTGATGCTGTCAAACACATTAAATT

TTCTTTTTTGCGGGATTGGGTTAATCATGTCAGGGAAAAAACGGGGAAGG

AAATGTTTACGGTAGCTGAATATTGGCAGAATGACTTGGGCGCGCTGGAA

AACTATTTGAACAAAACAAATTTTAATCATTCAGTGTTTGACGTGCCGCT

TCATTATCAGTTCCATGCTGCATCGACACAGGGAGGCGGCTATGATATGA

GGAAATTGCTGAACGGTACGGTCGTTTCCAAGCATCCGTTGAAATCGGTT

ACATTTGTCGATAACCATGATACACAGCCGGGGCAATCGCTTGAGTCGAC

TGTCCAAACATGGTTTAAGCCGCTTGCTTACGCTTTTATTCTCACAAGGG

AATCTGGATACCCTCAGGTTTTCTACGGGGATATGTACGGGACGAAAGGA

GACTCCCAGCGCGAAATTCCTGCCTTGAAACACAAAATTGAACCGATCTT

AAAAGCGAGAAAACAGTATGCGTACGGAGCACAGCATGATTATTTCGACC

ACCATGACATTGTCGGCTGGACAAGGGAAGGCGACAGCTCGGTTGCAAAT

TCAGGTTTGGCGGCATTAATAACAGACGGACCCGGTGGGGCAAAGCGAAT

GTATGTCGGCCGGCAAAACGCCGGTGAGACATGGCATGACATTACCGGAA

ACCGTTCGGAGCCGGTTGTCATCAATTCGGAAGGCTGGGGAGAGTTTCAC

GTAAACGGCGGGTCGGTTTCAATTTATGTTCAAAGATAG
```

A non-limiting example of an amylase amino acid sequence is as follows:

```
                                         (SEQ ID NO: 16)
MKQQKRLYARLLTLLFALIFLLPHSAAAAANLNGTLMQYFEWYMPNDGQH

WKRLQNDSAYLAEHGITAVWIPPAYKGTSQADVGYGAYDLYDLGEFHQKG

TVRTKYGTKGELQSAIKSLHSRDINVYGDVVINHKGGADATEDVTAVEVD

PADRNRVISGEHLIKAWTHFHFPGRGSTYSDFKWHWYHFDGTDWDESRKL
```

NRIYKFQGKAWDWEVSNENGNYDYLMYADIDYDHPDVAAEIKRWGTWYAN

ELQLDGFRLDAVKHIKFSFLRDWVNHVREKTGKEMFTVAEYWQNDLGALE

NYLNKTNFNHSVFDVPLHYQFHAASTQGGGYDMRKLLNGTVVSKHPLKSV

TFVDNHDTQPGQSLESTVQTWFKPLAYAFILTRESGYPQVFYGDMYGTKG

DSQREIPALKHKIEPILKARKQYAYGAQHDYFDHHDIVGWTREGDSSVAN

SGLAALITDGPGGAKRMYVGRQNAGETWHDITGNRSEPVVINSEGWGEFH

VNGGSVSIYVQR

In embodiments, the enzyme is a cellulase. In embodiments, enzyme is a naturally occurring form, a homolog, an isoform or a variant of a cellulase that maintains the enzymatic activity of the cellulase (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes a cellulase is as follows:

(SEQ ID NO: 17)
ATGAAGTTTCAGAGCACTTTGCTTCTTGCCGCCGCGGCTGGTTCCGCGTT

GGCTGTGCCTCATGGCTCCGGACATAAGAAGAGGGCGTCTGTGTTTGAAT

GGTTCGGATCGAACGAGTCTGGTGCTGAATTTGGGACCAATATCCCAGGC

GTCTGGGGAACCGACTACATCTTCCCCGACCCCTCGACCATCTCTACGTT

GATTGGCAAGGGAATGAACTTCTTCCGCGTCCAGTTCATGATGGAGAGGT

TGCTTCCTGACTCGATGACTGGTTCATACGACGAGGAGTATCTGGCCAAC

TTGACGACTGTGGTGAAAGCGGTCACGGATGGAGGCGCGCATGCGCTCAT

CGACCCTCATAACTATGGCAGATACAACGGGGAGATCATCTCCAGTACAT

CGGATTTCCAGACTTTCTGGCAGAATCTGGCGGGCCAGTACAAAGATAAC

GACTTGGTCATGTTTGATACCAACAACGAATACTACGACATGGACCAGGA

TCTCGTGCTGAATCTCAACCAAGCAGCCATTAACGGCATCCGCGCTGCAG

GTGCAAGCCAGTACATTTTCGTCGAAGGCAACTCCTGGACCGGAGCTTGG

ACATGGGTCGATGTCAACGATAATATGAAGAATTTGACCGACCCAGAAGA

CAAGATCGTCTATGAAATGCACCAGTACCTAGACTCCGACGGTTCCGGCA

CTTCGGAGACCTGTGTCTCCGGGACAATCGGAAAGGAGCGGATCACTGAT

GCTACACAGTGGCTCAAGGACAATAAGAAGGTCGGCTTCATCGGCGAATA

TGCCGGGGGGTCCAATGATGTGTGTCGGAGTGCCGTGTCCGGGATGCTAG

AGTACATGGCGAACAACACCGACGTATGGAAGGGTGCGTCGTGGTGGGCA

GCCGGGCCATGGTGGGGAGACTACATTTTCAGCCTGGAGCCCCCAGATGG

AACTGCTTACACGGGTATGCTGGATATCCTGGAGACGTATCTCTGA

A non-limiting example of a cellulase amino acid sequence is as follows:

(SEQ ID NO: 18)
MKFQSTLLLAAAAGSALAVPHGSGHKKRASVFEWFGSNESGAEFGTNIPG

VWGTDYIFPDPSTISTLIGKGMNFFRVQFMMERLLPDSMTGSYDEEYLAN

LTTVVKAVTDGGAHALIDPHNYGRYNGEIISSTSDFQTFWQNLAGQYKDN

DLVMFDTNNEYYDMDQDLVLNLNQAAINGIRAAGASQYIFVEGNSWTGAW

TWVDVNDNMKNLTDPEDKIVYEMHQYLDSDGSGTSETCVSGTIGKERITD

ATQWLKDNKKVGFIGEYAGGSNDVCRSAVSGMLEYMANNTDVWKGASWWA

AGPWWGDYIFSLEPPDGTAYTGMLDILETYL

In embodiments, the enzyme is proteinase K. In embodiments, the enzyme is a naturally occurring form, a homolog, an isoform or a variant of proteinase K that maintains the enzymatic activity of proteinase K (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes proteinase K is as follows:

(SEQ ID NO: 19)
ATGCGTTTGTCTGTTCTTCTGAGTCTTCTTCCCCTCGCTCTCGGCGCTCC

TGCCGTTGAGCAGCGCTCCGAGGCTGCTCCTCTGATCGAGGCCCGCGGCG

AGATGGTTGCCAACAAGTACATTGTCAAGTTCAAGGAGGGTAGCGCTCTT

TCTGCTCTCGATGCTGCCATGGAGAAGATTTCTGGCAAGCCCGACCACGT

CTACAAGAACGTCTTCAGTGGTTTCGCTGCGACCCTTGACGAGAACATGG

TTCGGGTTCTCCGCGCCCATCCCGATGTTGAGTACATTGAGCAGGATGCT

GTTGTCACCATCAACGCTGCGCAGACCAACGCTCCCTGGGGCCTTGCTCG

CATCTCCAGCACCAGCCCCGGTACCTCTACTTACTACTATGACGAATCTG

CCGGCCAAGGCTCCTGCGTCTACGTGATTGACACCGGTATCGAGGCATCG

CACCCCGAGTTTGAGGGTCGTGCCCAGATGGTCAAGACCTACTACTACTC

CAGTCGCGACGGTAACGGTCACGGCACTCACTGCGCTGGTACCGTTGGCT

CCCGAACCTACGGTGTCGCCAAGAAGACCCAGCTCTTTGGTGTCAAGGTC

CTCGATGACAACGGCAGTGGCCAGTACTCCACCATCATCGCCGGTATGGA

CTTTGTTGCCAGCGACAAGAACAACCGCAACTGCCCCAAAGGTGTCGTTG

CCTCCTTGTCCCTTGGCGGTGGTTACTCCTCCTCCGTGAACAGCGCCGCT

GCCAGGCTCCAGAGCTCTGGTGTCATGGTCGCCGTCGCTGCCGGTAACAA

CAACGCTGACGCCCGCAACTACTCCCCTGCTTCTGAGCCCTCGGTCTGCA

CTGTCGGTGCTTCTGACCGCTACGACAGACGCTCCAGCTTCTCCAACTAC

GGCAGCGTTTTGGACATCTTTGGCCCTGGTACCAGCATTCTCTCCACCTG

GATCGGCGGCAGCACCCGCTCCATCTCTGGAACTTCCATGGCTACTCCCC

ACGTTGCCGGTCTCGCTGCCTACCTCATGACTCTTGGAAAGACTACCGCC

GCCAGCGCTTGCCGATACATTGCCGACACCGCCAACAAGGGCGACTTGAG

CAACATTCCCTTCGGCACTGTCAACCTGCTTGCCTACAACAACTACCAGG

CTTAA

A non-limiting example of a proteinase K amino acid sequence is as follows:

(SEQ ID NO: 20)
MRLSVLLSLLPLALGAPAVEQRSEAAPLIEARGEMVANKYIVKFKEGSAL

SALDAAMEKISGKPDHVYKNVFSGFAATLDENMVRVLRAHPDVEYIEQDA

VVTINAAQTNAPWGLARISSTSPGTSTYYYDESAGQGSCVYVIDTGIEAS

HPEFEGRAQMVKTYYYSSRDGNGHGTHCAGTVGSRTYGVAKKTQLFGVKV

LDDNGSGQYSTIIAGMDFVASDKNNRNCPKGVVASLSLGGGYSSSVNSAA

ARLQSSGVMVAVAAGNNNADARNYSPASEPSVCTVGASDRYDRRSSFSNY

GSVLDIFGPGTSILSTWIGGSTRSISGTSMATPHVAGLAAYLMTLGKTTA

ASACRYIADTANKGDLSNIPFGTVNLLAYNNYQA

In embodiments, the enzyme is subtilisin. In embodiments, the enzyme is a naturally occurring form, a homolog, an isoform or a variant of subtilisin that maintains the enzymatic activity of subtilisin (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes subtilisin is as follows:

(SEQ ID NO: 21)
ATGATGAGGAAAAAGAGTTTTTGGCTTGGGATGCTGACGGCCTTCATGCT

CGTGTTCACGATGGCATTCAGCGATTCCGCTTCTGCTGCTCAACCGGCGA

AAAATGTTGAAAAGGATTATATTGTCGGATTTAAGTCAGGAGTGAAAACC

GCATCTGTCAAAAAGGACATCATCAAAGAGAGCGGCGGAAAAGTGGACAA

GCAGTTTAGAATCATCAACGCGGCAAAAGCGAAGCTAGACAAAGAAGCGC

TTAAGGAAGTCAAAAATGATCCGGATGTCGCTTATGTGGAAGAGGATCAT

GTGGCCCATGCCTTGGCGCAAACCGTTCCTTACGGCATTCCTCTCATTAA

AGCGGACAAAGTGCAGGCTCAAGGCTTTAAGGGAGCGAATGTAAAAGTAG

CCGTCCTGGATACAGGAATCCAAGCTTCTCATCCGGACTTGAACGTAGTC

GGCGGAGCAAGCTTTGTGGCTGGCGAAGCTTATAACACCGACGGCAACGG

ACACGGCACACATGTTGCCGGTACAGTAGCTGCGCTTGACAATACAACGG

GTGTATTAGGCGTTGCGCCAAGCGTATCCTTGTACGCGGTTAAAGTACTG

AATTCAAGCGGAAGCGGAACTTACAGCGGCATTGTAAGCGGAATCGAGTG

GGCGACGACAAACGGCATGGATGTTATCAACATGAGTCTTGGAGGACCAT

CAGGCTCAACAGCGATGAAACAGGCGGTTGACAATGCATATGCAAGAGGG

GTTGTCGTTGTGGCGGCTGCTGGGAACAGCGGATCTTCAGGAAACACGAA

TACAATCGGCTATCCTGCGAAATACGACTCTGTCATCGCAGTTGGCGCGG

TAGACTCTAACAGCAACAGAGCTTCATTTTCCAGCGTCGGAGCAGAGCTT

GAAGTCATGGCTCCTGGCGCAGGCGTGTACAGCACTTACCCAACCAGCAC

TTATGCAACATTGAACGGAACGTCAATGGCTTCTCCTCATGTAGCGGGAG

CAGCAGCTTTGATCTTGTCAAAACATCCGAACCTTTCAGCTTCACAAGTC

CGCAACCGTCTCTCCAGTACGGCGACTTATTTGGGAAGCTCCTTCTACTA

TGGAAAAGGTCTGATCAATGTCGAAGCTGCCGCTCAATAA

A non-limiting example of a subtilisin amino acid sequence is as follows:

(SEQ ID NO: 22)
MMRKKSFWLGMLTAFMLVFTMAFSDSASAAQPAKNVEKDYIVGFKSGVKT

ASVKKDIIKESGGKVDKQFRIINAAKAKLDKEALKEVKNDPDVAYVEEDH

VAHALAQTVPYGIPLIKADKVQAQGFKGANVKVAVLDTGIQASHPDLNVV

GGASFVAGEAYNTDGNGHGTHVAGTVAALDNTTGVLGVAPSVSLYAVKVL

NSSGSGSYSGIVSGIEWATTNGMDVINMSLGGASGSTAMKQAVDNAYAKG

VVVVAAAGNSGSSGNTNTIGYPAKYDSVIAVGAVDSNSNRASFSSVGAEL

EVMAPGAGVYSTYPTNTYATLNGTSMASPHVAGAAALILSKHPNLSASQV

RNRLSSTATYLGSSFYYGKGLINVEAAAQ

In embodiments, the enzyme is trypsin. In embodiments, the enzyme is a naturally occurring form, a homolog, an isoform or a variant of trypsin that maintains the enzymatic activity of trypsin (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes trypsin is as follows:

(SEQ ID NO: 23)
ATCGTCGGGGGCTACACCTGCGCAGAGAATTCCGTCCCTTACCAGGTGTC

CCTGAATGCTGGCTACCACTTCTGCGGGGGCTCCCTCATCAATGACCAGT

GGGTGGTGTCCGCGGCTCACTGCTACCAGTACCACATCCAGGTGAGGCTG

GGAGAATACAACATTGATGTCTTGGAGGGTGGTGAGCAGTTCATCGATGC

GTCCAAGATCATCCGCCACCCCAAGTACAGCAGCTGGACTCTGGACAATG

ACATCCTGCTGATCAAACTCTCCACGCCTGCGGTCATCAATGCCCGGGTG

TCCACCTTGCTGCTGCCCAGTGCCTGTGCTTCCGCAGGCACAGAGTGCCT

CATCTCCGGCTGGGGCAACACCCTGAGCAGTGGCGTCAACTACCCGGACC

TGCTGCAATGCCTGGTGGCCCCGCTGCTGAGCCACGCCGACTGTGAAGCC

TCATACCCTGGACAGATCACTAACAACATGATCTGCGCTGGCTTCCTGGA

AGGAGGCAAGGATTCCTGCCAGGGTGACTCTGGCGGCCCTGTGGCTTGCA

ACGGACAGCTCCAGGGCATTGTGTCCTGGGGCTACGGCTGTGCCCAGAAG

GGCAAGCCTGGGGTCTACACCAAGGTCTGCAACTACGTGGACTGGATTCA

GGAGACCATCGCCGCCAAC

A non-limiting example of a trypsin amino acid sequence is as follows:

(SEQ ID NO: 24)
IVGGYTCGANTVPYQVSLNSGYHFCGGSLINSQWVVSAAHCYKSGIQVRL

GEDNINVVEGNEQFISASKSIVHPSYNSNTLNNDIMLIKLKSAASLNSRV

ASISLPTSCASAGTQCLISGWGNTKSSGTSYPDVLKCLKAPILSDSSCKS

AYPGQITSNMFCAGYLEGGKDSCQGDSGGPVVCSGKLQGIVSWGSGCAQK

NKPGVYTKVCNYVSWIKQTIASN

In embodiments, the enzyme is serratiopeptidase. In embodiments, the enzyme is a naturally occurring form, a homolog, an isoform or a variant of serratiopeptidase that maintains the enzymatic activity of serratiopeptidase (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. A non-limiting example of a DNA sequence that encodes serratiopeptidase is as follows:

(SEQ ID NO: 25)
ATGCAATCTACTAAAAAGGCAATTGAAATTACTGAATCCAGCCTCGCTGC

CGCGACAACCGGTTACGATGCTGTAGACGACCTGCTGCATTATCATGAGC

GGGGTAACGGGATTCAGATTAATGGCAAGGATTCATTTTCTAACGAGCAA

GCTGGGCTGTTTATTACCCGTGAGAACCAAACCTGGAACGGTTACAAGGT

ATTTGGCCAGCCGGTCAAATTAACCTTCTCGTTCCCGGACTATAAGTTCT

CTTCCACCAACGTCGCCGGCGACACCGGGCTGAGCAAGTTCAGCGCGGAA

CAGCAGCAGCAGGCTAAGCTGTCGCTGCAGTCCTGGGCCGACGTCGCCAA

TATCACCTTCACCGAAGTGGCGGCCGGTCAAAAGGCCAATATCACCTTCG

GCAACTACAGCCAGGATCGTCCCGGCCACTATGATTACGGCACCCAGGCC

TACGCCTTCCTGCCGAACACCATTTGGCAGGGCCAGGATTTGGGCGGCCA

GACTTGGTACAACGTAAACCAATCCAACGTGAAGCATCCGGCGACCGAAG

ACTACGGCCGCCAGACGTTCACCCATGAGATTGGCCATGCGCTGGGCCTG

AGCCACCCGGGCGACTACAACGCCGGTGAGGGCAACCCGACCTATAGAGA

TGTCACCTATGCGGAAGATACCCGCCAGTTCAGCCTGATGAGCTACTGGA

CTGCTGGATGACATTGCCGCCATTCAGCATCTGTATGGCGTGAAACCAAT

ACCGGTGGCGACAACGGCGGTCACTATGCCGCGGCTCCGGCCAACCTGTC

GACCCGCACCGGCGACACCGTGTACGGCTTTAACTCCAATACCGGTCGTG

ACTTCCTCAGCACCACCAGCAACTCGCAGAAAGTGATCTTTGCGGCCTGG

GATGCGGGCGGCAACGATACCTTCGACTTCTCCGGTTACACCGCTAACCA

GCGCATCAACCTGAACGAGAAATGGTTCTCCGACGTGGGCGGCCTGAAGG

GCAACGTGTCGATCGCCGCCGGTGTGACCATTGAGAACGCCATTGGCGGT

TCCGGCAACGACGTGATCGTCGGCAACGCGGCCAATAACGTGCTGAAAGG

CGGCGCGGGTAACGACGTGCTGTTCGGCGGCGGCGGGGCGGATGAATTGT

GGGGCGGTGCCGGCAAAGACATCTTCGTGTTCTCTGCCGCCAGCGATTCC

GCACCGGGCGCTTCAGACTGGATCCGCGACTTCCAGAAAGGGATCGACAA

GATCGACCTGTCGTTCTTCAATAAAGAAGCGCAGAGCAGCGATTTCATTC

ACTTCGTCGATCACTTCAGCGGCACGGCCGGTGAGGCGCTGCTGAGCTAC

AACGCGTCCAGCAACGTGACCGATTTGTCGGTGAACATCGGTGGGCATCA

GGCGCCGGACTTCCTGGTGAAAATCGTCGGCCAGGTAGACGTCGCCACGG

ACTTTATCGTGTAA

A non-limiting example of a serratiopeptidase amino acid sequence is as follows:

(SEQ ID NO: 26)
MQSTKKAIEITESSLAAATTGYDAVDDLLHYHERGNGIQINGKDSFSNEQ

AGLFITRENQTWNGYKVFGQPVKLTFSFPDYKFSSTNVAGDTGLSKFSAE

QQQQAKLSLQSWADVANITFTEVAAGQKANITFGNYSQDRPGHYDYGTQA

YAFLPNTIWQGQDLGGQTWYNVNQSNVKHPATEDYGRQTFTHEIGHALGL

SHPGDYNAGEGNPTYRDVTYAEDTRQFSLMSYWSETNTGGDNGGHYAAAP

LLDDIAAIQHLYGANLSTRTGDTVYGENSNTGRDFLSTTSNSQKVIFAAW

DAGGNDTFDFSGYTANQRINLNEKWFSDVGGLKGNVSIAAGVTIENAIGG

SGNDVIVGNAANNVLKGGAGNDVLFGGGGADELWGGAGKDIFVFSAASDS

APGASDWIRDFQKGIDKIDLSFFNKEAQSSDFIHFVDHFSGTAGEALLSY

NASSNVTDLSVNIGGHQAPDFLVKIVGQVDVATDFIV

In embodiments, the enzyme is a DNAse. In embodiments, the enzyme is a naturally occurring form, a homolog, an isoform or a variant of a DNAse that maintains the enzymatic activity of the DNAse (e.g., within at least 50%, 80%, 90%, 95%, 96%, 97%, 98%, 99% or 100% activity compared to the native protein). In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the enzyme is a DNAse I. In embodiments, the DNAse I is bovine pancreatic DNAse I. A non-limiting example of a DNA sequence that encodes a bovine pancreatic DNAse I is as follows:

(SEQ ID NO: 27)
TTGAAGATTGCTGCTTTCAACATTAGAACTTTCGGTGAAACTAAAATGTC

TAACGCTACTTTGGCATCTTACATCGTTAGAATTGTCAGAAGATATGATA

TCGTTTTAATTCAAGAAGTTAGAGACTCTCACTTGGTTGCAGTTGGTAAA

TTCTGAACCATTGGGTAGAAACTCTTACTTGTTAGACTACTTGAACCAAG

ATGACCCAAACACTTACCACTACGTTGTAAAGAAAGATACTTATTCTTGT

TCAGACCAAACAAAGTTTCAGTTTTGGATACTTACCAATACGACGACGGT

TGCGAATCTTGTGGTAACGATTCTTTCTCCAGAGAACCTGCTGTTGTTAA

ATTCTCATCACACTCTACCAAGGTTAAAGAGTTCGCTATCGTTGCTTTGC

ATTCTGCTCCTTCTGACGCTGTTGCTGAAATTAACTCTTTGTACGACGTT

TACTTAGATGTTCAACAGAAATGGCACTTGAACGACGTCATGTTGATGGG

TGACTTTAACGCTGATTGCTCTTATGTTACTTCTTCTCAATGGTCTTCAA

TTAGATTGAGAACATCTTCAACTTTCCAATGGTTAATTCCTGATTCCGCT

GATACCACTGCTACTAGTACCAACTGTGCTTACGATAGAATCGTTGTTGC

TGGATCATTATTGCAATCTTCTGTTGTCCCAGGTTCAGCGGCCCCTTTCG

-continued

ATTTCCAAGCTGCATATGGTTTGTCTAATGAAATGGCTTTAGCCATTTCT

GATCACTACCCAGTTGAAGTCACATTGACATAA

A non-limiting example of a bovine pancreatic DNAse I amino acid sequence is as follows:

(SEQ ID NO: 28)
LKIAAFNIRTFGETKMSNATLASYIVRIVRRYDIVLIQEVRDSHLVAVGK

LLDYLNQDDPNTYHYVVSEPLGRNSYKERYLFLFRPNKVSVLDTYQYDDG

CESCGNDSFSREPAVVKFSSHSTKVKEFAIVALHSAPSDAVAEINSLYDV

YLDVQQKWHLNDVMLMGDFNADCSYVTSSQWSSIRLRTSSTFQWLIPDSA

DTTATSTNCAYDRIVVAGSLLQSSVVPGSAAPFDFQAAYGLSNEMALAIS

DHYPVEVTLT

In embodiments, the composition or combination includes a probiotic bacterium.

In embodiments, the probiotic bacterium is a probiotic a *P.* sp., *Staphylococcus* sp., and/or *Corynebacterium* sp. bacterium.

In embodiments, the probiotic bacterium is a bacterium within the class Betaproteobacteria.

In embodiments, the probiotic bacterium is a probiotic *P. acnes* bacterium.

In embodiments, the *P. acnes* bacterium (a) has a 16S ribosomal DNA (rDNA) sequence with a T992C mutation compared to the KPA171202 type strain 16S rDNA sequence set forth as SEQ ID NO: 2; (b) has a 16S rDNA sequence with a T838C mutation compared to the KPA171202 type strain 16S rDNA sequence set forth as SEQ ID NO: 2; (c) has a 16S rDNA sequence with a C1322T mutation compared to the KPA171202 type strain 16S rDNA sequence set forth as SEQ ID NO: 2; (d) has a 16S rDNA sequence with a C986T mutation compared to the KPA171202 type strain 16S rDNA sequence set forth as SEQ ID NO: 2; (e) has a 16S rDNA sequence that is identical to the sequence of SEQ ID NO: 3; (f) has a 16S rDNA sequence that is identical to the sequence of SEQ ID NO: 4; (g) does not comprise a linear plasmid; (h) does not comprise a plasmid that has a virulence factor; and/or (i) does not have a plasmid that encodes an extrachromosomal lipase and/or a tight adhesion virulence factor.

In embodiments, the *P. acnes* bacterium (a) produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in a planktonic culture; (b) produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in an adherent culture; (c) adheres to epithelial cells at least 50% less than a pathogenic *P. acnes* strain; and/or (d) is less inflammatory than a pathogenic *P. acnes* strain.

In embodiments, the combination or composition includes at least one additional probiotic bacterium. In embodiments, the at least one additional probiotic bacterium includes *Propionibacterium granulosum* and/or *Propionibacterium avidum*.

In embodiments, a pathogenic *P. acnes* strain (a) has a 16S rDNA sequence with a G1058C mutation compared to the KPA171202 type strain 16S rDNA sequence set forth as SEQ ID NO: 2; (b) has a 16S rDNA sequence with a G1058C and an A1201C mutation compared to the KPA171202 type strain 16S rDNA sequence set forth as SEQ ID NO: 2; (c) has a 16S rDNA sequence with a G529A mutation compared to the KPA171202 type strain 16S rDNA sequence set forth as SEQ ID NO: 2; (d) has a 16S rDNA sequence with a G1004A and a T1007C mutation compared to the KPA171202 type strain 16S rDNA sequence set forth as SEQ ID NO: 2; (e) has a 16S rDNA sequence with a G1268A mutation compared to the KPA171202 type strain 16S rDNA sequence set forth as SEQ ID NO: 2; (f) has a 16S rDNA sequence with a T554C and a G1058C mutation compared to the KPA171202 type strain 16S rDNA sequence set forth as SEQ ID NO: 2; (g) has a 16S rDNA sequence that is identical to the sequence of SEQ ID NO: 5; (h) has a 16S rDNA sequence that is identical to the sequence of SEQ ID NO: 6; (i) has a 16S rDNA sequence that is identical to the sequence of SEQ ID NO: 7; (j) has a 16S rDNA sequence that is identical to the sequence of SEQ ID NO: 8; (k) has a 16S rDNA sequence that is identical to the sequence of SEQ ID NO: 9; and/or (l) has a 16S rDNA sequence that is identical to the sequence of SEQ ID NO: 10.

In embodiments, the combination or composition further includes at least one additional *P. acnes* bacteriophage.

In embodiments, the composition or combination includes a pharmaceutically acceptable carrier. In embodiments, the pharmaceutically acceptable carrier includes an emulsion. In embodiments, the emulsion is an oil-in-water emulsion or a water-in-oil emulsion. In embodiments, a combination or combination includes or is in the form of a cream, lotion, suspension, or aqueous solution.

In embodiments, a composition that includes a bacteriophage is provided. In embodiments, the composition is formulated for topical application to the skin (i.e., the composition is a topical composition). In embodiments, the composition is a pharmaceutical composition.

In an aspect, there is provided a pharmaceutical composition including a wild-type *P. acnes* bacteriophage and an isolated probiotic *P. acnes* bacterium. In embodiments, the composition further includes a pharmaceutically acceptable carrier.

In an aspect, there is provided a pharmaceutical composition including a bacteriophage and/or an isolated probiotic *P. acnes* bacterium and a pharmaceutically acceptable carrier.

In embodiments, the pharmaceutical composition is formulated for topical administration to the skin. In embodiments, the pharmaceutically acceptable carrier includes an emulsion. In embodiments, the emulsion is an oil-in-water emulsion or a water-in-oil emulsion. In embodiments, the pharmaceutical composition is in the form of a cream, lotion, suspension, or aqueous solution.

In embodiments, a composition or combination includes at least about 2, 3, 4, 5, 6, 7, 8, 9, or 10 *P. acnes* bacteriophages. In embodiments, the *P. acnes* bacteriophages include more than one type of *P. acnes* bacteriophage.

In embodiments, a combination or composition including an isolated probiotic *P. acnes* bacterium may further comprise at least one additional bacterium.

In embodiments, a *P. acnes* bacterium has a 16S rDNA sequence that includes a T992C, T838C, C1322T, and/or a C986T mutation compared to the KPA171202 type strain 16S rDNA sequence set forth as SEQ ID NO: 2. In embodiments, the *P. acnes* bacterium includes a 16S rDNA sequence with a T838C and a C1322T mutation compared to the KPA171202 type strain 16S rDNA sequence set forth as SEQ ID NO: 2. In embodiments, the *P. acnes* bacterium is the ProI strain. In embodiments, the *P. acnes* bacterium includes a 16S rDNA sequence with a C986T and a T992C mutation compared to the KPA171202 type strain 16S rDNA sequence set forth as SEQ ID NO: 2. In embodiments, the *P. acnes* bacterium is the ProII strain. In embodiments, the *P. acnes* bacterium: (a) includes a 16S rDNA sequence with a T992C mutation compared to the KPA171202 type strain 16S rDNA sequence set forth as SEQ ID NO: 2; (b) includes a 16S rDNA sequence with a T838C mutation compared to the KPA171202 type strain 16S rDNA sequence set forth as SEQ ID NO: 2; (c) includes a 16S rDNA sequence with a C1322T mutation compared to the KPA171202 type strain 16S rDNA sequence set forth as SEQ ID NO: 2; (d) includes a 16S rDNA sequence with a C986T mutation compared to the KPA171202 type strain 16S rDNA sequence set forth as SEQ ID NO: 2; (e) includes a 16S rDNA sequence that is identical to the sequence of SEQ ID NO: 3; (f) includes a 16S rDNA sequence that is identical to the sequence of SEQ ID NO: 4; (g) does not comprise a linear plasmid; (h) does not include a plasmid that includes a virulence factor; and/or (i) does not include a plasmid that encodes an extrachromosomal lipase and/or a tight adhesion virulence factor. In embodiments, the *P. acnes* bacterium has a 16S rDNA sequence that is identical to the sequence of SEQ ID NO: 3 or 4.

In embodiments, the *P. acnes* bacterium: (a) produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in a planktonic culture; (b) produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in an adherent culture; (c) adheres to epithelial cells at least 50% less than a pathogenic *P. acnes* strain; and/or (d) is less inflammatory than a pathogenic *P. acnes* strain. In embodiments, the pathogenic *P. acnes* strain (a) has a 16S rDNA sequence with a G1058C mutation compared to the KPA171202 type strain 16S rDNA sequence set forth as SEQ ID NO: 2; (b) has a 16S rDNA sequence with a G1058C and an A1201C mutation compared to the KPA171202 type strain 16S rDNA sequence set forth as SEQ ID NO: 2; (c) has a 16S rDNA sequence with a G529A mutation compared to the KPA171202 type strain 16S rDNA sequence set forth as SEQ ID NO: 2; (d) has a 16S rDNA sequence with a G1004A and a T1007C mutation compared to the KPA171202 type strain 16S rDNA sequence set forth as SEQ ID NO: 2; (e) has a 16S rDNA sequence with a G1268A mutation compared to the KPA171202 type strain 16S rDNA sequence set forth as SEQ ID NO: 2; (f) has a 16S rDNA sequence with a T554C and a G1058C mutation compared to the KPA171202 type strain 16S rDNA sequence set forth as SEQ ID NO: 2; (g) has a 16S rDNA sequence that is identical to the sequence of SEQ ID NO: 5; (h) has a 16S rDNA sequence that is identical to the sequence of SEQ ID NO: 6; (i) has a 16S rDNA sequence that is identical to the sequence of SEQ ID NO: 7; (j) has a 16S rDNA sequence that is identical to the sequence of SEQ ID NO: 8; (k) has a 16S rDNA sequence that is identical to the sequence of SEQ ID NO: 9; and/or (1) has a 16S rDNA sequence that is identical to the sequence of SEQ ID NO: 10.

SEQ ID NO: 2 is the 16S rDNA sequence for the KPA171202 type strain, and is as follows:

```
   1 TTTTTCATTG GAGAGTTTGA TCCTGGCTCA GGACGAACGC TGGCGGCGTG CTTAACACAT
  61 GCAAGTCGAA CGGAAAGGCC CTGCTTTTGT GGGGTGCTCG AGTGGCGAAC GGGTGAGTAA
 121 CACGTGAGTA ACCTGCCCTT GACTTTGGGA TAACTTCAGG AAACTGGGGC TAATACCGGA
 181 TAGGAGCTCC TGCTGCATGG TGGGGGTTGG AAAGTTTCGG CGGTTGGGGA TGGACTCGCG
 241 GCTTATCAGC TTGTTGGTGG GGTAGTGGCT TACCAAGGCT TTGACGGGTA GCCGGCCTGA
 301 GAGGGTGACC GGCCACATTG GGACTGAGAT ACGGCCCAGA CTCCTACGGG AGGCAGCAGT
 361 GGGGAATATT GCACAATGGG CGGAAGCCTG ATGCAGCAAC GCCGCGTGCG GGATGACGGC
 421 CTTCGGGTTG TAAACCGCTT TCGCCTGTGA CGAAGCGTGA GTGACGGTAA TGGGTAAAGA
 481 AGCACCGGCT AACTACGTGC CAGCAGCCGC GGTGATACGT AGGGTGCGAG CGTTGTCCGG
 541 ATTTATTGGG CGTAAAGGGC TCGTAGGTGG TTGATCGCGT CGGAAGTGTA ATCTTGGGGC
 601 TTAACCCTGA GCGTGCTTTC GATACGGGTT GACTTGAGGA AGGTAGGGGA GAATGGAATT
 661 CCTGGTGGAG CGGTGGAATG CGCAGATATC AGGAGGAACA CCAGTGGCGA AGGCGGTTCT
 721 CTGGGCCTTT CCTGACGCTG AGGAGCGAAA GCGTGGGGAG CGAACAGGCT TAGATACCCT
 781 GGTAGTCCAC GCTGTAAACG GTGGGTACTA GGTGTGGGGT CCATTCCACG GGTTCCGTGC
 841 CGTAGCTAAC GCTTTAAGTA CCCCGCCTGG GGAGTACGGC CGCAAGGCTA AAACTCAAAG
 901 GAATTGACGG GGCCCCGCAC AAGCGGCGGA GCATGCGGAT TAATTCGATG CAACGCGTAG
 961 AACCTTACCT GGGTTTGACA TGGATCGGGA GTGCTCAGAG ATGGGTGTGC CTCTTTTGGG
1021 GTCGGTTCAC AGGTGGTGCA TGGCTGTCGT CAGCTCGTGT CGTGAGATGT TGGGTTAAGT
1081 CCCGCAACGA GCGCAACCCT TGTTCACTGT TGCCAGCACG TTATGGTGGG GACTCAGTGG
1141 AGACCGCCGG GGTCAACTCG GAGGAAGGTG GGGATGACGT CAAGTCATCA TGCCCCTTAT
```

-continued

```
1201 GTCCAGGGCT TCACGCATGC TACAATGGCT GGTACAGAGA GTGGCGAGCC TGTGAGGGTG

1261 AGCGAATCTC GGAAAGCCGG TCTCAGTTCG GATTGGGGTC TGCAACTCGA CCTCATGAAG

1321 TCGGAGTCGC TAGTAATCGC AGATCAGCAA CGCTGCGGTG AATACGTTCC CGGGGCTTGT

1381 ACACACCGCC CGTCAAGTCA TGAAAGTTGG TAACACCCGA AGCCGGTGGC CTAACCGTTG

1441 TGGGGAGCC GTCGAAGGTG GGACTGGTGA TTAGGACTAA GTCGTAACAA GGTAGCCGTA

1501 CCGGAAGGTG CGGCTGGATC ACCTCCTTTC TAAGGAG
```

SEQ ID NO: 3 is the 16S rDNA sequence for the ProI probiotic strain, and is as follows:

```
  1 TTTTTCATTG GAGAGTTTGA TCCTGGCTCA GGACGAACGC TGGCGGCGTG CTTAACACAT

61 GCAAGTCGAA CGGAAAGGCC CTGCTTTTGT GGGGTGCTCG AGTGGCGAAC GGGTGAGTAA

121 CACGTGAGTA ACCTGCCCTT GACTTTGGGA TAACTTCAGG AAACTGGGGC TAATACCGGA

181 TAGGAGCTCC TGCTGCATGG TGGGGGTTGG AAAGTTTCGG CGGTTGGGGA TGGACTCGCG

241 GCTTATCAGC TTGTTGGTGG GGTAGTGGCT TACCAAGGCT TTGACGGGTA GCCGGCCTGA

301 GAGGGTGACC GGCCACATTG GGACTGAGAT ACGGCCCAGA CTCCTACGGG AGGCAGCAGT

361 GGGGAATATT GCACAATGGG CGGAAGCCTG ATGCAGCAAC GCCGCGTGCG GGATGACGGC

421 CTTCGGGTTG TAAACCGCTT TCGCCTGTGA CGAAGCGTGA GTGACGGTAA TGGGTAAAGA

481 AGCACCGGCT AACTACGTGC CAGCAGCCGC GGTGATACGT AGGGTGCGAG CGTTGTCCGG

541 ATTTATTGGG CGTAAAGGGC TCGTAGGTGG TTGATCGCGT CGGAAGTGTA ATCTTGGGGC

601 TTAACCCTGA GCGTGCTTTC GATACGGGTT GACTTGAGGA AGGTAGGGGA GAATGGAATT

661 CCTGGTGGAG CGGTGGAATG CGCAGATATC AGGAGGAACA CCAGTGGCGA AGGCGGTTCT

721 CTGGGCCTTT CCTGACGCTG AGGAGCGAAA GCGTGGGGAG CGAACAGGCT TAGATACCCT

781 GGTAGTCCAC GCTGTAAACG GTGGGTACTA GGTGTGGGGT CCATTCCACG GGTTCCGCGC

841 CGTAGCTAAC GCTTTAAGTA CCCCGCCTGG GGAGTACGGC CGCAAGGCTA AAACTCAAAG

901 GAATTGACGG GGCCCCGCAC AAGCGGCGGA GCATGCGGAT TAATTCGATG CAACGCGTAG

961 AACCTTACCT GGGTTTGACA TGGATCGGGA GTGCTCAGAG ATGGGTGTGC CTCTTTTGGG

1021 GTCGGTTCAC AGGTGGTGCA TGGCTGTCGT CAGCTCGTGT CGTGAGATGT TGGGTTAAGT

1081 CCCGCAACGA GCGCAACCCT TGTTCACTGT TGCCAGCACG TTATGGTGGG GACTCAGTGG

1141 AGACCGCCGG GGTCAACTCG GAGGAAGGTG GGGATGACGT CAAGTCATCA TGCCCCTTAT

1201 GTCCAGGGCT TCACGCATGC TACAATGGCT GGTACAGAGA GTGGCGAGCC TGTGAGGGTG

1261 AGCGAATCTC GGAAAGCCGG TCTCAGTTCG GATTGGGGTC TGCAACTCGA CCTCATGAAG

1321 TTGGAGTCGC TAGTAATCGC AGATCAGCAA CGCTGCGGTG AATACGTTCC CGGGGCTTGT

1381 ACACACCGCC CGTCAAGTCA TGAAAGTTGG TAACACCCGA AGCCGGTGGC CTAACCGTTG

1441 TGGGGAGCC GTCGAAGGTG GGACTGGTGA TTAGGACTAA GTCGTAACAA GGTAGCCGTA

1501 CCGGAAGGTG CGGCTGGATC ACCTCCTTTC TAAGGAG
```

Nucleotides 986 . . . 986
 ProII Mutation C986T
Nucleotides 992 . . . 992
 ProII Mutation T992C

```
  1 TTTTTCATTG GAGAGTTTGA TCCTGGCTCA GGACGAACGC TGGCGGCGTG CTTAACACAT

61 GCAAGTCGAA CGGAAAGGCC CTGCTTTTGT GGGGTGCTCG AGTGGCGAAC GGGTGAGTAA
```

-continued

```
 121 CACGTGAGTA ACCTGCCCTT GACTTTGGGA TAACTTCAGG AAACTGGGGC TAATACCGGA

181 TAGGAGCTCC TGCTGCATGG TGGGGGTTGG AAAGTTTCGG CGGTTGGGGA TGGACTCGCG

241 GCTTATCAGC TTGTTGGTGG GGTAGTGGCT TACCAAGGCT TTGACGGGTA GCCGGCCTGA

301 GAGGGTGACC GGCCACATTG GGACTGAGAT ACGGCCCAGA CTCCTACGGG AGGCAGCAGT

361 GGGGAATATT GCACAATGGG CGGAAGCCTG ATGCAGCAAC GCCGCGTGCG GGATGACGGC

421 CTTCGGGTTG TAAACCGCTT TCGCCTGTGA CGAAGCGTGA GTGACGGTAA TGGGTAAAGA

481 AGCACCGGCT AACTACGTGC CAGCAGCCGC GGTGATACGT AGGGTGCGAG CGTTGTCCGG

541 ATTTATTGGG CGTAAAGGGC TCGTAGGTGG TTGATCGCGT CGGAAGTGTA ATCTTGGGGC

601 TTAACCCTGA GCGTGCTTTC GATACGGGTT GACTTGAGGA AGGTAGGGGA GAATGGAATT

661 CCTGGTGGAG CGGTGGAATG CGCAGATATC AGGAGGAACA CCAGTGGCGA AGGCGGTTCT

721 CTGGGCCTTT CCTGACGCTG AGGAGCGAAA GCGTGGGGAG CGAACAGGCT TAGATACCCT

781 GGTAGTCCAC GCTGTAAACG GTGGGTACTA GGTGTGGGGT CCATTCCACG GGTTCCGTGC

841 CGTAGCTAAC GCTTTAAGTA CCCCGCCTGG GGAGTACGGC CGCAAGGCTA AAACTCAAAG

901 GAATTGACGG GGCCCCGCAC AAGCGGCGGA GCATGCGGAT TAATTCGATG CAACGCGTAG

961 AACCTTACCT GGGTTTGACA TGGATTGGGA GCGCTCAGAG ATGGGTGTGC CTCTTTTGGG

1021 GTCGGTTCAC AGGTGGTGCA TGGCTGTCGT CAGCTCGTGT CGTGAGATGT TGGGTTAAGT

1081 CCCGCAACGA GCGCAACCCT TGTTCACTGT TGCCAGCACG TTATGGTGGG GACTCAGTGG

1141 AGACCGCCGG GGTCAACTCG GAGGAAGGTG GGGATGACGT CAAGTCATCA TGCCCCTTAT

1201 GTCCAGGGCT TCACGCATGC TACAATGGCT GGTACAGAGA GTGGCGAGCC TGTGAGGGTG

1261 AGCGAATCTC GGAAAGCCGG TCTCAGTTCG GATTGGGGTC TGCAACTCGA CCTCATGAAG

1321 TCGGAGTCGC TAGTAATCGC AGATCAGCAA CGCTGCGGTG AATACGTTCC CGGGGCTTGT

1381 ACACACCGCC CGTCAAGTCA TGAAAGTTGG TAACACCCGA AGCCGGTGGC CTAACCGTTG

1441 TGGGGAGCC GTCGAAGGTG GGACTGGTGA TTAGGACTAA GTCGTAACAA GGTAGCCGTA

1501 CCGGAAGGTG CGGCTGGATC ACCTCCTTTC TAAGGAG
```

In embodiments, the *P. acnes* bacterium produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in a planktonic culture. In embodiments, the *P. acnes* bacterium produces about 1-5%, 1-10%, 1-20%, 1-30%, 5-50%, 5-40%, 5-30%, 5-20%, 5-10%, 10-50%, 10-40%, 10-30%, 10-20%, 20-50%, 20-40%, or 20-30% of the level of lipase that is produced by a pathogenic *P. acnes* strain when grown in a planktonic culture. In embodiments, the *P. acnes* bacterium produces less than about 5% of the level of lipase that is produced by a pathogenic *P. acnes* strain when grown in a planktonic culture. In embodiments, the *P. acnes* bacterium produces less than about 10% of the level of lipase that is produced by a pathogenic *P. acnes* strain when grown in a planktonic culture. In embodiments, the *P. acnes* bacterium produces less than about 20% of the level of lipase that is produced by a pathogenic *P. acnes* strain when grown in a planktonic culture. In embodiments, the *P. acnes* bacterium produces less than about 30% of the level of lipase that is produced by a pathogenic *P. acnes* strain when grown in a planktonic culture. In embodiments, the *P. acnes* bacterium produces less than about 40% of the level of lipase that is produced by a pathogenic *P. acnes* strain when grown in a planktonic culture. In embodiments, the *P. acnes* bacterium produces less than about 50% of the level of lipase that is produced by a pathogenic *P. acnes* strain when grown in a planktonic culture. In embodiments, the *P. acnes* bacterium produces less than about 1%, 5%, 10%, 15%, 20%, 25%, 30%, 35%, 40%, 45%, 50%, 55%, 60%, 65%, 70%, 75%, 80%, 85%, 90% or 95% of the level of lipase that is produced by a pathogenic *P. acnes* strain when grown in an adherent culture. In embodiments, the *P. acnes* bacterium produces less than about 5% of the level of lipase that is produced by a pathogenic *P. acnes* strain when grown in an adherent culture. In embodiments, the *P. acnes* bacterium produces less than about 10% of the level of lipase that is produced by a pathogenic *P. acnes* strain when grown in an adherent culture. In embodiments, the *P. acnes* bacterium produces less than about 20% of the level of lipase that is produced by a pathogenic *P. acnes* strain when grown in an adherent culture. In embodiments, the *P. acnes* bacterium produces less than about 30% of the level of lipase that is produced by a pathogenic *P. acnes* strain when grown in an adherent culture. In embodiments, the *P. acnes* bacterium produces less than about 40% of the level of lipase that is produced by a pathogenic *P. acnes* strain when grown in an adherent culture. In embodiments, the *P. acnes* bacterium produces less than about 50% of the level of lipase that is produced by a pathogenic *P. acnes* strain when grown in an adherent culture. In embodiments, the *P. acnes* bacterium produces about 1-5%, 1-10%, 1-20%, 1-30%, 5-50%, 5-40%, 5-30%, 5-20%, 5-10%, 10-50%, 10-40%, 10-30%, 10-20%, 20-50%, 20-40%, or 20-30% of the level of lipase that is produced by a pathogenic *P. acnes* strain when grown in an adherent culture. In embodiments, the lipase is extracellular lipase.

In embodiments, the level of lipase produced by a *P. acnes* bacterium (e.g., a probiotic or a pathogenic *P. acnes* bacterium, such as for comparison) is the level of lipase in culture supernatant. In embodiments, the culture supernatant is filtered. In embodiments, the culture supernatant is from a liquid (planktonic) culture. In embodiments, the culture supernatant is from an adherent culture. Non-limiting examples of methods for detecting a level of lipase include absorbance, Bradford protein assays, Biuret test derived assays, fluorescamine, amino black, colloidal gold, nitrogen detection, High-performance liquid chromatography (HPLC), Liquid chromatography-mass spectrometry (LC/MS), enzyme-linked immunosorbent assay (ELISA), protein immunoprecipitation, immunoelectrophoresis, and Western blot.

In embodiments, the *P. acnes* bacterium adheres to epithelial cells at least about 1%, 5%, 10%, 15%, 20%, 25%, 30%, 35%, 40%, 45%, 50%, 55%, 60%, 65%, 70%, 75%, 80%, 85%, 90% or 95% less than a pathogenic *P. acnes* strain. In embodiments, the *P. acnes* bacterium adheres to epithelial cells at least about 50% less than a pathogenic *P. acnes* strain. In embodiments, the *P. acnes* bacterium adheres to epithelial cells at least about 60% less than a pathogenic *P. acnes* strain. In embodiments, the *P. acnes* bacterium adheres to epithelial cells at least about 70% less than a pathogenic *P. acnes* strain. In embodiments, the *P. acnes* bacterium adheres to epithelial cells at least about 80% less than a pathogenic *P. acnes* strain. In embodiments, the *P. acnes* bacterium adheres to epithelial cells at least about 90% less than a pathogenic *P. acnes* strain. In embodiments, the *P. acnes* bacterium adheres to epithelial cells 1-5%, 1-10%, 1-20%, 1-30%, 5-50%, 5-40%, 5-30%, 5-20%, 5-10%, 10-50%, 10-40%, 10-30%, 10-20%, 20-50%, 20-40%, 20-30%, 50-60, 50-70, 50-80, 50-90, 60-80, 70-90 less than a pathogenic *P. acnes* strain.

In embodiments, adherence of a *P. acnes* bacterium (e.g., a probiotic or a pathogenic *P. acnes* bacterium, such as for comparison) to epithelial cells is determined using A-432 epithelial cells. In embodiments, the epithelial cells are confluent on a tissue culture plate or flask. In embodiments, adherence is detected by determining a number of colonies that are formed by *P. acnes* bacteria that have adhered to cultured epithelial cells.

In embodiments, the *P. acnes* bacterium is less inflammatory than a pathogenic *P. acnes* strain.

In embodiments, a *P. acnes* bacterium is less inflammatory than a pathogenic *P. acnes* strain if a lower level of an inflammatory cytokine (e.g., at least about 10%, 20%, 30%, 40%, 50%, 60%, 70%, 80%, or 90% less) is released by an immune cell that contacts the *P. acnes* bacterium or a compound produced by the *P. acnes* bacterium compared to a bacterium of the pathogenic *P. acnes* strain or a compound produced by the bacterium of the pathogenic *P. acnes* strain. In embodiments, a *P. acnes* bacterium is less inflammatory than a pathogenic *P. acnes* strain if a lower level of an inflammatory cytokine is released in tissue (such as skin tissue) that is contacted with *P. acnes* bacterium. In embodiments, the tissue is skin tissue. In embodiments, the tissue is ear tissue, e.g., of a mouse. In embodiments, the inflammatory cytokine is IL-1β, IL-6, IL-17, or TNFα, or any combination thereof.

In embodiments, the pathogenic *P. acnes* strain (a) has a 16S rDNA sequence with a G1058C mutation compared to the KPA171202 type strain 16S rDNA sequence set forth as SEQ ID NO: 2; (b) has a 16S rDNA sequence with a G1058C and an A1201C mutation compared to the KPA171202 type strain 16S rDNA sequence set forth as SEQ ID NO: 2; (c) has a 16S rDNA sequence with a G529A mutation compared to the KPA171202 type strain 16S rDNA sequence set forth as SEQ ID NO: 2; (d) has a 16S rDNA sequence with a G1004A and a T1007C mutation compared to the KPA171202 type strain 16S rDNA sequence set forth as SEQ ID NO: 2; (e) has a 16S rDNA sequence with a G1268A mutation compared to the KPA171202 type strain 16S rDNA sequence set forth as SEQ ID NO: 2; (f) has a 16S rDNA sequence with a T554C and a G1058C mutation compared to the KPA171202 type strain 16S rDNA sequence set forth as SEQ ID NO: 2; (g) has a 16S rDNA sequence that is identical to the sequence of SEQ ID NO: 5; (h) has a 16S rDNA sequence that is identical to the sequence of SEQ ID NO: 6; (i) has a 16S rDNA sequence that is identical to the sequence of SEQ ID NO: 7; (j) has a 16S rDNA sequence that is identical to the sequence of SEQ ID NO: 8; (k) has a 16S rDNA sequence that is identical to the sequence of SEQ ID NO: 9; and/or (1) has a 16S rDNA sequence that is identical to the sequence of SEQ ID NO: 10.

SEQ ID NO: 5 is as follows (mutations compared to the 16S sequence of the type strain KPA171202 are underlined):

```
AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

GGTGAGTAACACGTGAGTAACCTGCCCTTGACTTTGGGATAACTTCAGGA

AACTGGGGCTAATACCGGATAGGAGCTCCTGCTGCATGGTGGGGGTTGGA

AAGTTTCGGCGGTTGGGGATGGACTCGCGGCTTATCAGCTTGTTGGTGGG

GTAGTGGCTTACCAAGGCTTTGACGGGTAGCCGGCCTGAGAGGGTGACCG

GCCACATTGGGACTGAGATACGGCCCAGACTCCTACGGGAGGCAGCAGTG

GGGAATATTGCACAATGGGCGAAAGCCTGATGCAGCAACGCCGCGTGCGG

GATGACGGCCTTCGGGTTGTAAACCGCTTTCGCCTGTGACGAAGCGTGAG

TGACGGTAATGGGTAAAGAAGCACCGGCTAACTACGTGCCAGCAGCCGCG

GTGATACGTAGGGTGCGAGCGTTGTCCGGATTTATTGGGCGTAAAGGGCT

CGTAGGTGGTTGATCGCGTCGGAAGTGTAATCTTGGGGCTTAACCCTGAG

CGTGCTTTCGATACGGGTTGACTTGAGGAAGGTAGGGGAGAATGGAATTC

CTGGTGGAGCGGTGGAATGCGCAGATATCAGGAGGAACACCAGTGGCGAA

GGCGGTTCTCTGGGCCTTTCCTGACGCTGAGGAGCGAAAGCGTGGGGAGC

GAACAGGCTTAGATACCCTGGTAGTCCACGCTGTAAACGGTGGGTACTAG

GTGTGGGGTCCATTCCACGGGTTCCGTGCCGTAGCTAACGCTTTAAGTAC

CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGGAGTGCTCAGAGATGGGTGTGCC

TCTTTTGGGGTCGGTTCACAGGTGGTGCATGCCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG
```

```
AGGAAGGTGGGGATGACGTCAAGTCCTCATGCCCCTTATGTCCAGGGCTT

CACGCATGCTACAATGGCTGGTACAGAGAGTGGCGAGCCTGTGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGCTTGTACACACCGCCCGTCAAGTCATGAAAGTTGGT

AACACCCGAAGCCGGTGGCCTAACCGTTGTGGGGGAGCCGTCGAAGGTGG

GACTGGTGATTAGGACTAAGTCGTAACAAGGTAGCCGTACCGGAAGGTGC

GGCTGGATCACCTCCTTTCTAAGGA
```

SEQ ID NO: 6 is as follows (a mutation compared to the 16S sequence of the type strain KPA171202 is underlined):

```
AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

GGTGAGTAACACGTGAGTAACCTGCCCTTGACTTTGGGATAACTTCAGGA

AACTGGGGCTAATACCGGATAGGAGCTCCTGCTGCATGGTGGGGGTTGGA

AAGTTTCGGCGGTTGGGATGGACTCGCGGCTTATCAGCTTGTTGGTGGG

GTAGTGGCTTACCAAGGCTTTGACGGGTAGCCGGCCTGAGAGGGTGACCG

GCCACATTGGGACTGAGATACGGCCCAGACTCCTACGGGAGGCAGCAGTG

GGGAATATTGCACAATGGGCGGAAGCCTGATGCAGCAACGCCGCGTGCGG

GATGACGGCCTTCGGGTTGTAAACCGCTTTCGCCTGTGACGAAGCGTGAG

TGACGGTAATGGGTAAAGAAGCACCGGCTAACTACGTGCCAGCAGCCGCG

GTGATACGTAGGGTGCGAGCGTTGTCCGGATTTATTGGGCGTAAAGGGCT

CGTAGGTGGTTGATCGCGTCGGAAGTGTAATCTTGGGGCTTAACCCTGAG

CGTGCTTTCGATACGGGTTGACTTGAGGAAGGTAGGGGAGAATGGAATTC

CTGGTGGAGCGGTGGAATGCGCAGATATCAGGAGGAACACCAGTGGCGAA

GGCGGTTCTCTGGGCCTTTCCTGACGCTGAGGAGCGAAAGCGTGGGGAGC

GAACAGGCTTAGATACCCTGGTAGTCCACGCTGTAAACGGTGGGTACTAG

GTGTGGGGTCCATTCCACGGGTTCCGTGCCGTAGCTAACGCTTTAAGTAC

CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGGAGTGCTCAGAGATGGGTGTGCC

TCTTTTGGGGTCGGTTCACAGGTGGTGCATGCCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG

AGGAAGGTGGGGATGACGTCAAGTCATCATGCCCCTTATGTCCAGGGCTT

CACGCATGCTACAATGGCTGGTACAGAGAGTGGCGAGCCTGTGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGCTTGTACACACCGCCCGTCAAGTCATGAAAGTTGGT

AACACCCGAAGCCGGTGGCCTAACCGTTGTGGGGGAGCCGTCGAAGGTGG

GACTGGTGATTAGGACTAAGTCGTAACAAGGTAGCCGTACCGGAAGGTGC

GGCTGGATCACCTCCTTTCTAAGGA
```

SEQ ID NO: 7 is as follows (a mutation compared to the 16S sequence of the type strain KPA171202 is underlined):

```
AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

GGTGAGTAACACGTGAGTAACCTGCCCTTGACTTTGGGATAACTTCAGGA

AACTGGGGCTAATACCGGATAGGAGCTCCTGCTGCATGGTGGGGGTTGGA

AAGTTTCGGCGGTTGGGATGGACTCGCGGCTTATCAGCTTGTTGGTGGG

GTAGTGGCTTACCAAGGCTTTGACGGGTAGCCGGCCTGAGAGGGTGACCG

GCCACATTGGGACTGAGATACGGCCCAGACTCCTACGGGAGGCAGCAGTG

GGGAATATTGCACAATGGGCGGAAGCCTGATGCAGCAACGCCGCGTGCGG

GATGACGGCCTTCGGGTTGTAAACCGCTTTCGCCTGTGACGAAGCGTGAG

TGACGGTAATGGGTAAAGAAGCACCGGCTAACTACGTGCCAGCAGCCGCG

GTAATACGTAGGGTGCGAGCGTTGTCCGGATTTATTGGGCGTAAAGGGCT

CGTAGGTGGTTGATCGCGTCGGAAGTGTAATCTTGGGGCTTAACCCTGAG

CGTGCTTTCGATACGGGTTGACTTGAGGAAGGTAGGGGAGAATGGAATTC

CTGGTGGAGCGGTGGAATGCGCAGATATCAGGAGGAACACCAGTGGCGAA

GGCGGTTCTCTGGGCCTTTCCTGACGCTGAGGAGCGAAAGCGTGGGGAGC

GAACAGGCTTAGATACCCTGGTAGTCCACGCTGTAAACGGTGGGTACTAG

GTGTGGGGTCCATTCCACGGGTTCCGTGCCGTAGCTAACGCTTTAAGTAC

CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGGAGTGCTCAGAGATGGGTGTGCC

TCTTTTGGGGTCGGTTCACAGGTGGTGCATGGCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG

AGGAAGGTGGGGATGACGTCAAGTCATCATGCCCCTTATGTCCAGGGCTT

CACGCATGCTACAATGGCTGGTACAGAGAGTGGCGAGCCTGTGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGCTTGTACACACCGCCCGTCAAGTCATGAAAGTTGGT

AACACCCGAAGCCGGTGGCCTAACCGTTGTGGGGGAGCCGTCGAAGGTGG

GACTGGTGATTAGGACTAAGTCGTAACAAGGTAGCCGTACCGGAAGGTGC

GGCTGGATCACCTCCTTTCTAAGGA
```

SEQ ID NO: 8 is as follows (mutations compared to the 16S sequence of the type strain KPA171202 are underlined):

```
AGAGTTTGATCCTGGCTCAGGACGAACGCTGGCGGCGTGCTTAACACATG

CAAGTCGAACGGAAAGGCCCTGCTTTTGTGGGGTGCTCGAGTGGCGAACG

GGTGAGTAACACGTGAGTAACCTGCCCTTGACTTTGGGATAACTTCAGGA
```

AACTGGGGCTAATACCGGATAGGAGCTCCTGCTGCATGGTGGGGGTTGGA
AAGTTTCGGCGGTTGGGGATGGACTCGCGGCTTATCAGCTTGTTGGTGGG
GTAGTGGCTTACCAAGGCTTTGACGGGTAGCCGGCCTGAGAGGGTGACCG
GCCACATTGGGACTGAGATACGGCCCAGACTCCTACGGGAGGCAGCAGTG
GGGAATATTGCACAATGGGCGGAAGCCTGATGCAGCAACGCCGCGTGCGG
GATGACGGCCTTCGGGTTGTAAACCGCTTTCGCCTGTGACGAAGCGTGAG
TGACGGTAATGGGTAAAGAAGCACCGGCTAACTACGTGCCAGCAGCCGCG
GTGATACGTAGGGTGCGAGCGTTGTCCGGATTTATTGGGCGTAAAGGGCT
CGTAGGTGGTTGATCGCGTCGGAAGTGTAATCTTGGGCTTAACCCTGAG
CGTGCTTTCGATACGGGTTGACTTGAGGAAGGTAGGGGAGAATGGAATTC
CTGGTGGAGCGGTGGAATGCGCAGATATCAGGAGGAACACCAGTGGCGAA
GGCGGTTCTCTGGGCCTTTCCTGACGCTGAGGAGCGAAAGCGTGGGGAGC
GAACAGGCTTAGATACCCTGGTAGTCCACGCTGTAAACGGTGGGTACTAG
GTGTGGGGTCCATTCCACGGGTTCCGTGCCGTAGCTAACGCTTTAAGTAC
CCCGCCTGGGGAGTACGGCCGCAAGGCTAAAACTCAAAGGAATTGACGGG
GCCCCGCACAAGCGGCGGAGCATGCGGATTAATTCGATGCAACGCGTAGA
ACCTTACCTGGGTTTGACATGGATCGG<u>AAGC</u>GCTCAGAGATGGGTGTGCC
TCTTTTGGGGTCGGTTCACAGGTGGTGCATGGCTGTCGTCAGCTCGTGTC
GTGAGATGTTGGGTTAAGTCCCGCAACGAGCGCAACCCTTGTTCACTGTT
GCCAGCACGTTATGGTGGGGACTCAGTGGAGACCGCCGGGGTCAACTCGG
AGGAAGGTGGGGATGACGTCAAGTCATCATGCCCCTTATGTCCAGGGCTT
CACGCATGCTACAATGGCTGGTACAGAGAGTGGCGAGCCTGTGAGGGTGA
GCGAATCTCGGAAAGCCGGTCTCAGTTCGGATTGGGGTCTGCAACTCGAC
CTCATGAAGTCGGAGTCGCTAGTAATCGCAGATCAGCAACGCTGCGGTGA
ATACGTTCCCGGGCTTGTACACACCGCCCGTCAAGTCATGAAAGTTGGT
AACACCCGAAGCCGGTGGCCTAACCGTTGTGGGGGAGCCGTCGAAGGTGG
GACTGGTGATTAGGACTAAGTCGTAACAAGGTAGCCGTACCGGAAGGTGC
GGCTGGATCACCTCCTTTCTAAGGA

SEQ ID NO: 9 is as follows (a mutation compared to the 16S sequence of the type strain KPA171202 is underlined):

AGAGTTTGATCCTGGCTCAGGACGAACGCTGGCGGCGTGCTTAACACATG
CAAGTCGAACGGAAAGGCCCTGCTTTTGTGGGGTGCTCGAGTGGCGAACG
GGTGAGTAACACGTGAGTAACCTGCCCTTGACTTTGGGATAACTTCAGGA
AACTGGGGCTAATACCGGATAGGAGCTCCTGCTGCATGGTGGGGGTTGGA
AAGTTTCGGCGGTTGGGGATGGACTCGCGGCTTATCAGCTTGTTGGTGGG
GTAGTGGCTTACCAAGGCTTTGACGGGTAGCCGGCCTGAGAGGGTGACCG
GCCACATTGGGACTGAGATACGGCCCAGACTCCTACGGGAGGCAGCAGTG
GGGAATATTGCACAATGGGCGGAAGCCTGATGCAGCAACGCCGCGTGCGG
GATGACGGCCTTCGGGTTGTAAACCGCTTTCGCCTGTGACGAAGCGTGAG
TGACGGTAATGGGTAAAGAAGCACCGGCTAACTACGTGCCAGCAGCCGCG
GTGATACGTAGGGTGCGAGCGTTGTCCGGATTTATTGGGCGTAAAGGGCT
CGTAGGTGGTTGATCGCGTCGGAAGTGTAATCTTGGGCTTAACCCTGAG
CGTGCTTTCGATACGGGTTGACTTGAGGAAGGTAGGGGAGAATGGAATTC
CTGGTGGAGCGGTGGAATGCGCAGATATCAGGAGGAACACCAGTGGCGAA
GGCGGTTCTCTGGGCCTTTCCTGACGCTGAGGAGCGAAAGCGTGGGGAGC
GAACAGGCTTAGATACCCTGGTAGTCCACGCTGTAAACGGTGGGTACTAG
GTGTGGGGTCCATTCCACGGGTTCCGTGCCGTAGCTAACGCTTTAAGTAC
CCCGCCTGGGGAGTACGGCCGCAAGGCTAAAACTCAAAGGAATTGACGGG
GCCCCGCACAAGCGGCGGAGCATGCGGATTAATTCGATGCAACGCGTAGA
ACCTTACCTGGGTTTGACATGGATCGGGAGTGCTCAGAGATGGGTGTGCC
TCTTTTGGGGTCGGTTCACAGGTGGTGCATGGCTGTCGTCAGCTCGTGTC
GTGAGATGTTGGGTTAAGTCCCGCAACGAGCGCAACCCTTGTTCACTGTT
GCCAGCACGTTATGGTGGGGACTCAGTGGAGACCGCCGGGGTCAACTCGG
AGGAAGGTGGGGATGACGTCAAGTCATCATGCCCCTTATGTCCAGGGCTT
CACGCATGCTACAATGGCTGGTACAGAGAGTGGCGAGCCT<u>A</u>TGAGGGTGA
GCGAATCTCGGAAAGCCGGTCTCAGTTCGGATTGGGGTCTGCAACTCGAC
CTCATGAAGTCGGAGTCGCTAGTAATCGCAGATCAGCAACGCTGCGGTGA
ATACGTTCCCGGGCTTGTACACACCGCCCGTCAAGTCATGAAAGTTGGT
AACACCCGAAGCCGGTGGCCTAACCGTTGTGGGGGAGCCGTCGAAGGTGG
GACTGGTGATTAGGACTAAGTCGTAACAAGGTAGCCGTACCGGAAGGTGC
GGCTGGATCACCTCCTTTCTAAGGA

SEQ ID NO: 10 is as follows (mutations compared to the 16S sequence of the type strain KPA171202 are underlined):

AGAGTTTGATCCTGGCTCAGGACGAACGCTGGCGGCGTGCTTAACACATG
CAAGTCGAACGGAAAGGCCCTGCTTTTGTGGGGTGCTCGAGTGGCGAACG
GGTGAGTAACACGTGAGTAACCTGCCCTTGACTTTGGGATAACTTCAGGA
AACTGGGGCTAATACCGGATAGGAGCTCCTGCTGCATGGTGGGGGTTGGA
AAGTTTCGGCGGTTGGGGATGGACTCGCGGCTTATCAGCTTGTTGGTGGG
GTAGTGGCTTACCAAGGCTTTGACGGGTAGCCGGCCTGAGAGGGTGACCG
GCCACATTGGGACTGAGATACGGCCCAGACTCCTACGGGAGGCAGCAGTG
GGGAATATTGCACAATGGGCGGAAGCCTGATGCAGCAACGCCGCGTGCGG
GATGACGGCCTTCGGGTTGTAAACCGCTTTCGCCTGTGACGAAGCGTGAG
TGACGGTAATGGGTAAAGAAGCACCGGCTAACTACGTGCCAGCAGCCGCG
GTGATACGTAGGGTGCGAGCGTTG<u>C</u>CCGGATTTATTGGGCGTAAAGGGCT
CGTAGGTGGTTGATCGCGTCGGAAGTGTAATCTTGGGCTTAACCCTGAG
CGTGCTTTCGATACGGGTTGACTTGAGGAAGGTAGGGGAGAATGGAATTC
CTGGTGGAGCGGTGGAATGCGCAGATATCAGGAGGAACACCAGTGGCGAA
GGCGGTTCTCTGGGCCTTTCCTGACGCTGAGGAGCGAAAGCGTGGGGAGC
GAACAGGCTTAGATACCCTGGTAGTCCACGCTGTAAACGGTGGGTACTAG
GTGTGGGGTCCATTCCACGGGTTCCGTGCCGTAGCTAACGCTTTAAGTAC

-continued

```
CCCGCCTGGGGAGTACGGCCGCAAGGCTAAAACTCAAAGGAATTGACGGG

GCCCCGCACAAGCGGCGGAGCATGCGGATTAATTCGATGCAACGCGTAGA

ACCTTACCTGGGTTTGACATGGATCGGGAGTGCTCAGAGATGGGTGTGCC

TCTTTTGGGGTCGGTTCACAGGTGGTGCATGCCTGTCGTCAGCTCGTGTC

GTGAGATGTTGGGTTAAGTCCCGCAACGAGCGCAACCCTTGTTCACTGTT

GCCAGCACGTTATGGTGGGGACTCAGTGGAGACCGCCGGGGTCAACTCGG

AGGAAGGTGGGGATGACGTCAAGTCATCATGCCCCTTATGTCCAGGGCTT

CACGCATGCTACAATGGCTGGTACAGAGAGTGGCGAGCCTGTGAGGGTGA

GCGAATCTCGGAAAGCCGGTCTCAGTTCGGATTGGGGTCTGCAACTCGAC

CTCATGAAGTCGGAGTCGCTAGTAATCGCAGATCAGCAACGCTGCGGTGA

ATACGTTCCCGGGGCTTGTACACACCGCCCGTCAAGTCATGAAAGTTGGT

AACACCCGAAGCCGGTGGCCTAACCGTTGTGGGGGAGCCGTCGAAGGTGG

GACTGGTGATTAGGACTAAGTCGTAACAAGGTAGCCGTACCGGAAGGTGC

GGCTGGATCACCTCCTTTCTAAGGA
```

In embodiments, the at least one additional bacterium comprises, consists essentially of, or consists of a probiotic bacterium. In embodiments, the at least one bacterium includes 1, 2, 3, 4, 5, 6, 7, 8, 9, or 10 bacterial strains and/or species, less than about 10, 9, 8, 7, 6, 5, 4, 3, or 2 bacterial strains and/or species, or 1-10, 2-10, 3-10, 4-10, 5-10, 1-5, 2-5, 3-5, or 4-5 bacterial strains and/or species. In embodiments, the at least one bacterium includes a plurality of bacterial strains and/or species, e.g., at least about 2, 3, 4, 5, 6, 7, 8, 9, 10 bacterial strains and/or species. In embodiments, the least one bacterium includes an isolated *Propionibacterium granulosum* bacterium, an isolated *Propionibacterium avidum* bacterium, an isolated *Staphylococcus epidermidis* bacterium, an isolated *Staphylococcus aureus* bacterium, and/or an isolated *Corynebacterium jeikeium* bacterium. In embodiments, the least one bacterium includes 1, 2 (of any combination of), 3 (of any combination of), 4 (of any combination of), or 5 of an isolated *Propionibacterium granulosum* bacterium, an isolated *Propionibacterium avidum* bacterium, an isolated *Staphylococcus epidermidis* bacterium, an isolated *Staphylococcus aureus* bacterium, and/or an isolated *Corynebacterium jeikeium* bacterium.

In embodiments, a composition or combination provided herein includes an enhancing peptide or enzyme. In embodiments, the enhancing peptide or enzyme has one or more or any combination of the following properties: biofilm degradation, improving skin penetration, antibacterial, reducing inflammation (e.g., of the skin), reducing irritation (e.g., of the skin), reducing redness (e.g., of the skin), firming skin, removing lines, removing wrinkles, or otherwise improving appearance (e.g., of the skin).

In an aspect, a composition that includes a *P. acnes* bacteriophage and an anti-acne compound is provided. In embodiments, the composition includes a pharmaceutically acceptable carrier. In embodiments, the dose of the *P. acnes* bacteriophage is adjusted (e.g., increased or decreased) for stability. In embodiments, the dose of the *P. acnes* bacteriophage is adjusted up or down depending on the anti-acne compound to adjust for its stability in combination with the anti-acne compound.

In an aspect, a combination or system that includes a *P. acnes* bacteriophage and one or more anti-acne compounds is provided. In an example, the bacteriophage is within one composition (e.g., within one vessel such as a bottle, tube, or other container), and the one or more anti-acne compounds are in a separate composition (within another vessel such as a bottle, tube, or other container). In embodiments, the composition that includes the bacteriophage includes a pharmaceutically acceptable carrier. In embodiments, the composition that includes the anti-acne compound includes a pharmaceutically acceptable carrier. In embodiments, an additional one or more compounds (e.g. an enzyme, a hydrating compound, an ultraviolet radiation absorbing or blocking compound, etc.) are present in the composition that includes the bacteriophage, the composition that includes the one or more anti-acne compounds, or a third separate composition (within a third vessel such as a bottle, tube, or other container). In embodiments, one or more probiotic bacteria are present in the composition that includes the bacteriophage, the composition that includes the one or more anti-acne compounds, or a third separate composition (within a third vessel such as a bottle, tube, or other container). In embodiments, the combination or system further includes instructions for administration. In embodiments, the combination or system includes at least about 2, 3, 4, 5, 6, 7, 8, 9, or 10 *P. acnes* bacteriophages.

In an aspect, a combination or system that includes a *P. acnes* bacteriophage and one or more probiotic bacteria and/or one or more compounds (such as one or more enzymes or anti-acne compounds) is provided. In an example, the bacteriophage is within one composition (e.g., within one vessel such as a bottle, tube, or other container), and the one or more probiotic bacteria are in a separate composition (within another vessel such as a bottle, tube, or other container), and optionally, an additional one or more compounds are present in the composition that includes the bacteriophage, the composition that includes the one or more probiotic bacteria, or a third separate composition (within a third vessel such as a bottle, tube, or other container). In embodiments, the combination or system further includes instructions for administration. In embodiments, the combination or system includes at least about 2, 3, 4, 5, 6, 7, 8, 9, or 10 *P. acnes* bacteriophages.

In embodiments, a system, combination, or composition includes an enzyme such as a biofilm degradation enzyme or an anti-aging enzyme. Non-limiting examples of biofilm degradation enzymes include DNAses (e.g., DNAse I), proteases (e.g., papain, bromelain, Trypsin, Proteinase K, Subtilisin, or serratiopeptidase), glycosidases (e.g., dispersin, alginate lyase, amylase, or cellulase). Non-limiting examples of anti-aging enzymes include superoxide dismutase, and peroxidase.

In embodiments, a system, combination, or composition includes a topical retinoid, an antibiotic, and/or an alpha-hydroxy acid. In embodiments, a system or composition further includes a topical retinoid. In embodiments, a system or composition further includes an antibiotic. In embodiments, a system or composition further includes an alpha-hydroxy acid. In embodiments, the system or composition further includes benzoyl peroxide, salicylic acid, sulfur, resorcinol, resorcinol monoacetate, or any combination thereof. In embodiments, the benzoyl peroxide is present at a concentration of 2.5% to 10%, e.g., about 2.5%, 3%, 3.5%, 4%, 4.5%, 5%, 5.5%, 6%, 6.5%, 7%, 7.5%, 8%, 8.5%, 9%, 9.5%, or 10% (weight/volume). In embodiments, the benzoyl peroxide is present at a concentration of less than 2.5% but greater than about 0.1%, 0.5%, 1%, 1.5%, or 2% (weight/volume). In embodiments, the salicylic acid is present at a concentration of 0.5% to 2%, e.g., about 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (weight/volume). In embodiments, the salicylic acid is present at a concentration of less than 0.5% but greater than about 0.1% (weight/volume). In embodiments, the sulfur is present at a concentration of 3% to 10%, e.g., about 3%, 3.5%, 4%, 4.5%, 5%, 5.5%, 6%, 6.5%, 7%, 7.5%, 8%, 8.5%, 9%, 9.5%, or 10% (weight/volume). In embodiments, the sulfur is present at a concentration of less than 3% but greater than about 0.1%, 0.5%, 1, 1.5%, 2%, or 2.5% (weight/volume). In embodiments, resorcinol is present at a concentration of 2% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume). In embodiments, resorcinol monoacetate is present at a concentration of 3% and sulfur is present at a concentration of 3% to 8% (e.g., about 2.5%, 3%, 3.5%, 4%, 4.5%, 5%, 5.5%, 6%, 6.5%, 7%, 7.5%, or 8%) (weight/volume). In embodiments, the resorcinol is present at a concentration of less than 2% but greater than about 0.1%, 0.5%, 1%, 1.5% (weight/volume). In embodiments, the resorcinol monoacetate is present at a concentration of less than 3% but greater than about 0.1%, 0.5%, 1%, 1.5%, 2%, or 2.5% (weight/volume).

In embodiments, a composition provide herein includes a moisturizer.

Methods of Treating Acne

In an aspect, provided herein is a method of preventing or treating acne in a subject in need thereof, the method including administering an effective amount of a composition or combination provided herein. In embodiments, an effective amount of a composition comprising, consisting essentially of, or consisting of at least one *P. acnes* bacteriophage, at least one anti-acne compound, and a pharmaceutically acceptable carrier is administered to the subject. In embodiments, an effective amount of a composition that includes at least one *P. acnes* bacteriophage, at least one anti-acne compound and a pharmaceutically acceptable carrier, wherein the composition does not comprise a probiotic bacterium, is administered to the subject. In embodiments, an effective amount of a composition that includes a *P. acnes* bacteriophage and an enzyme is administered to the subject.

In embodiments, an effective amount of a composition that includes a bacteriophage as described herein, including embodiments thereof, is administered to the subject. In embodiments, the bacteriophage is a wild-type bacteriophage.

In embodiments, the bacteriophage is administered topically. In embodiments, the bacteriophage is in a composition (e.g., a pharmaceutical or cosmetic composition) that further includes a pharmaceutically or cosmetically acceptable carrier.

In embodiments, the method further includes administering a probiotic bacterium to the subject.

In an aspect, a method of treating acne in a subject in need thereof is provided. The method includes administering an effective amount of a probiotic *P. acnes* bacterium to the subject. In embodiments, the method further includes administering a bacteriophage to the subject.

In embodiments, the *P. acnes* bacterium has a 16S rDNA sequence that includes a T992C, T838C, C1322T, and/or a C986T mutation compared to the KPA171202 type strain 16S rDNA sequence set forth as SEQ ID NO: 2. In embodiments, the *P. acnes* bacterium includes a 16S rDNA sequence with a T838C and a C1322T mutation compared to the KPA171202 type strain 16S rDNA sequence set forth as SEQ ID NO: 2. In embodiments, the *P. acnes* bacterium is the ProI strain. In embodiments, the *P. acnes* bacterium includes a 16S rDNA sequence with a C986T and a T992C mutation compared to the KPA171202 type strain 16S rDNA sequence set forth as SEQ ID NO: 2. In embodiments, the *P. acnes* bacterium is the ProII strain.

In embodiments, the *P. acnes* bacterium: (a) includes a 16S rDNA sequence with a T992C mutation compared to the KPA171202 type strain 16S rDNA sequence set forth as SEQ ID NO: 2; (b) includes a 16S rDNA sequence with a T838C mutation compared to the KPA171202 type strain 16S rDNA sequence set forth as SEQ ID NO: 2; (c) includes a 16S rDNA sequence with a C1322T mutation compared to the KPA171202 type strain 16S rDNA sequence set forth as SEQ ID NO: 2; (d) includes a 16S rDNA sequence with a C986T mutation compared to the KPA171202 type strain 16S rDNA sequence set forth as SEQ ID NO: 2; (e) includes a 16S rDNA sequence that is identical to the sequence of SEQ ID NO: 3; (g) includes a 16S rDNA sequence that is identical to the sequence of SEQ ID NO: 4; (h) does not comprise a linear plasmid; (i) does not include a plasmid that includes a virulence factor; and/or (j) does not include a plasmid that encodes an extrachromosomal lipase and/or a tight adhesion virulence factor.

In embodiments, the method further includes administering at least one additional probiotic bacterium to the subject.

In embodiments, the at least one additional bacterium comprises, consists essentially of, or consists of a probiotic bacterium. In embodiments, the at least one bacterium includes 1, 2, 3, 4, 5, 6, 7, 8, 9, or 10 bacterial strains and/or species, less than about 10, 9, 8, 7, 6, 5, 4, 3, or 2 bacterial strains and/or species, or 1-10, 2-10, 3-10, 4-10, 5-10, 1-5, 2-5, 3-5, or 4-5 bacterial strains and/or species. In embodiments, the at least one bacterium includes a plurality of bacterial strains and/or species, e.g., at least about 2, 3, 4, 5, 6, 7, 8, 9, 10 bacterial strains and/or species. In embodiments, the least one bacterium includes a *Propionibacterium* sp., *Staphylococcus* sp., and/or *Corynebacterium* sp. bacterium. In embodiments, the least one bacterium includes bacterium within the class Betaproteobacteria. In embodiments, the least one bacterium includes an isolated *Propionibacterium granulosum* bacterium, an isolated *Propionibacterium avidum* bacterium, an isolated *Staphylococcus epidermidis* bacterium, an isolated *Staphylococcus aureus* bacterium, and/or an isolated *Corynebacterium jeikeium* bacterium. In embodiments, the least one bacterium includes 1, 2, 3, 4, or 5 of an isolated *Propionibacterium granulosum* bacterium, an isolated *Propionibacterium avidum* bacterium, an isolated *Staphylococcus epidermidis* bacterium, an isolated *Staphylococcus aureus* bacterium, and/or an isolated *Corynebacterium jeikeium* bacterium.

In embodiments, the subject has been administered a bacteriophage as described herein, including embodiments thereof.

In embodiments, the subject has been administered an antibiotic that kills *P. acnes*. In embodiments, the antibiotic is clindamycin, doxycycline, erythromycin, or tetracycline, or a derivative of clindamycin, doxycycline, erythromycin, or tetracycline.

In embodiments, the antibiotic is clindamycin, doxycycline, erythromycin, or tetracycline, or a derivative of clindamycin, doxycycline, erythromycin, or tetracycline.

In embodiments, the method further includes administering an enzyme to the subject such as a biofilm degradation enzyme or an anti-aging enzyme. Non-limiting examples of biofilm degradation enzymes include DNAses (e.g., DNAse I), restriction endonucleases, proteases (e.g., papain, bromelain, Trypsin, Proteinase K, Subtilisin, or serratiopeptidase), glycosidases (e.g., dispersin, alginate lyase, amylase, or cellulase). Non-limiting examples of anti-aging enzymes include superoxide dismutase, and peroxidase.

In embodiments, the method further includes administering a topical retinoid, an antibiotic, and/or an alpha-hydroxy acid. In embodiments, the method further includes administering a topical retinoid. In embodiments, the method further includes administering an antibiotic. In embodiments, the method further includes administering an alpha-hydroxy acid. In embodiments, the method further includes administering benzoyl peroxide, salicylic acid, sulfur, resorcinol, and/or resorcinol monoacetate to the subject. In embodiments, the method further includes administering benzoyl peroxide. In embodiments, the method further includes administering salicylic acid. In embodiments, the method further includes administering sulfur. In embodiments, the method further includes administering resorcinol and/or sulfur. In embodiments, the method further includes administering resorcinol and/or resorcinol monoacetate.

In embodiments, the method further includes administering an enhancing peptide or enzyme. In embodiments, the enhancing peptide or enzyme has one or more or any combination of the following properties: biofilm degradation, improving skin penetration, antibacterial, reducing inflammation (e.g., of the skin), reducing irritation (e.g., of the skin), reducing redness (e.g., of the skin), firming skin, removing lines, removing wrinkles, or otherwise improving appearance (e.g., of the skin).

In embodiments, at least about 2, 3, 4, 5, 6, 7, 8, 9, or 10 P. acnes bacteriophages are administered to the subject. In embodiments, the P. acnes bacteriophages include more than one types of P. acnes bacteriophage.

Exemplary Methods and Compositions for Treating Acne

In an aspect, provided herein is a composition that includes a bacteriophage. In embodiments, the bacteriophage is present in a composition, such as a therapeutic or cosmetic composition. In embodiments, the composition further includes a strain of probiotic bacteria. In embodiments, the composition further includes an enzyme that degrades a bacterial biofilms (e.g., a component thereof) in or on human skin pores. In embodiments, the enzyme enhances penetration of the bacteriophage and/or the probiotic bacteria. In embodiments, a bacteriophage ("phage") destroys an acne-causing (i.e., pathogenic) strain of P. acnes with a high degree of specificity and efficacy, without killing beneficial skin bacteria. In embodiments, the biofilm-degrading enzyme dissolves the biofilm to increase the susceptibility of the pathogen (e.g., by reducing pathogen adherence to host cells and/or by increasing access of the bacteriophage to pathogenic cells). In embodiments, the probiotic bacteria are immune to the bacteriophage (e.g., the bacteria lack a cellular receptor to which the bacteriophage specifically binds). In embodiments, the probiotic bacteria occupy the niche left by a killed P. acnes pathogenic strain. In embodiments the probiotic bacteria reduce or prevent the recolonization or growth of a subject's skin (such as a pore) by surviving pathogenic bacteria.

In an aspect a composition for the therapeutic treatment of the skin disease acne is provided. In embodiments, the composition includes a lytic P. acnes bacteriophage, and optionally a probiotic bacterium sourced from healthy skin, and/or optionally a biofilm-degrading enzyme in the composition as an adjuvant to increase penetration of the active components.

In embodiments, a lytic P. acnes bacteriophage infects virulent P. acnes in a skin comedone. In embodiments, the bacteriophage replicates and lyses within the P. acnes. In embodiments, when the P. acnes lyses, it releases new virions. In embodiments, enzymes unclog the blocked comedones, dissolve the P. acnes biofilms and increase access of virions to P. acnes. In embodiments, the exponential proliferation of lytic P. acnes phages rapidly kills the P. acnes with high specificity, without disturbing the growth beneficial skin commensal bacteria. In embodiments, the niche vacated by the P. acnes is then be filled by the probiotic bacteria. In embodiments, the bacteria are sourced from healthy skin and expand to occupy the niche, thereby preventing any surviving P. acnes bacteria from growing back. In embodiments, this strategy helps to balance the skin microbiome in subjects and recalibrates their microbiome toward a healthy skin bacterial community. In embodiments, the biofilm-degrading enzyme is in a formulation as an adjuvant that helps unclog blocked comedones and increase access of the phage and probiotic bacteria to the pores.

In an aspect, a combination that includes a bacteriophage, a probiotic bacterium, and (optionally) an enzyme that enhances the penetration of the bacteriophage is provided. In embodiments, the pathogens are killed and the probiotic bacterium replaces the pathogen. In embodiments, a "kill and replace" approach to is used to treat acne. In embodiments, a biologic that selectively kills pathogenic bacteria that cause acne is administered to a subject. In embodiments, probiotic bacteria sourced from healthy skin are applied to occupy the niche of the killed pathogen. In embodiments, this approach avoids the problems of rampant drug resistance associated with antibiotics. In embodiments, the presence of actively dividing probiotic bacteria prevents relapses by not allowing any pathogens to grow back. In embodiments, dysbiosis on the skin of the subject is treated. In embodiments, a microbiome associated with acne is recalibrated into a healthy one.

In embodiments, the bacteriophage is a naturally occurring P. acnes bacteriophage.

Non-limiting examples of enzymes that may be co-administered with a bacteriophage include BL00275 from Bacillus licheniformis; DNase I; restriction endonucleases; deoxyribonucleases (e.g. from Staphylococcus aureus thermonuclease, B. licheniformis NucB, DNase 1L2); glycoside hydrolases (e.g. Dispersin B, alginate lyase, amylase, cellulase, glycanase); and proteases (e.g. subtlisin, proteinase K, trypsin, serratiopeptidase).

Non-limiting examples of probiotic bacteria that may be administered or present in a system or composition include one or more or any combination of the following bacterial species: Propionibacterium acnes, Propionibacterium granulosum, Propionibacterium avidum, Staphylococcus epidermidis, Staphylococcus aureus, and Corynebacterium jeikeium. In embodiments, a probiotic bacterial strain is be selected based on its ability to (a) colonize the skin without eliciting an adverse immune response, characterized by low lipase activity and reduced adhesion to human keratinocytes; and (b) occupy a niche similar to Propionibacterium acnes.

In embodiments, a biofilm degrading enzyme is present in the formulation and acts as an adjuvant, to increase the efficacy of the active ingredients (such as a bacteriophage). In embodiments, the enzyme has the capacity to degrade P. acnes biofilms in vitro.

EMBODIMENTS

Embodiments and examples are provided below to facilitate a more complete understanding of the invention. The following embodiments and examples illustrate the exemplary modes of making and practicing the invention. However, the scope of the invention is not limited to specific embodiments disclosed in these embodiments and examples, which are for purposes of illustration only, since alternative methods can be utilized to obtain similar results.

Embodiments include Embodiments P1 to P56 following:

Embodiment P1. A composition consisting essentially of at least one *Propionibacterium acnes* bacteriophage, at least one anti-acne compound, and a pharmaceutically acceptable carrier.

Embodiment P2. A composition comprising at least one *Propionibacterium acnes* bacteriophage, at least one anti-acne compound, and a pharmaceutically acceptable carrier, wherein the composition does not comprise a probiotic bacterium.

Embodiment P3. The composition of Embodiment P2, wherein the composition further comprises a *P. acnes* biofilm degrading enzyme.

Embodiment P4. The composition of any one of Embodiments P1-P3, wherein the at least one anti-acne compound is benzoyl peroxide.

Embodiment P5. The composition of Embodiment P4, wherein the benzoyl peroxide is present at a concentration of 2.5% to 10% (weight/volume).

Embodiment P6. The composition of Embodiment P4, wherein the benzoyl peroxide is present at a concentration of less than 2.5% but greater than about 0.1%, 0.5%, 1%, 1.5%, or 2% (weight/volume).

Embodiment P7. The composition of any one of Embodiments P1-P3, wherein the at least one anti-acne compound is salicylic acid.

Embodiment P8. The composition of Embodiment P7, wherein the salicylic acid is present at a concentration of 0.5% to 2% (weight/volume).

Embodiment P9. The composition of Embodiment P7, wherein the salicylic acid is present at a concentration of less than 0.5% but greater than about 0.1% (weight/volume).

Embodiment P10. The composition of any one of Embodiments P1-P3, wherein the at least one anti-acne compound is sulfur.

Embodiment P11. The composition of Embodiment P10, wherein the sulfur is present at a concentration of 3% to 10% (weight/volume).

Embodiment P12. The composition of Embodiment P10, wherein the sulfur is present at a concentration of less than 3% but greater than about 0.1%, 0.5%, 1%, 1.5%, 2%, or 2.5% (weight/volume).

Embodiment P13. The composition of any one of Embodiments P1-P3, wherein the at least one anti-acne compound is resorcinol and sulfur.

Embodiment P14. The composition of Embodiment P13, wherein the resorcinol is present at a concentration of 2% and sulfur is present at a concentration of 3% to 8% (weight/volume).

Embodiment P15. The composition of any one of Embodiments P1-P3, wherein the at least one anti-acne compound comprises resorcinol monoacetate and sulfur.

Embodiment P16. The composition of Embodiment P15, wherein the resorcinol monoacetate is present at a concentration of 3% and sulfur is present at a concentration of 3% to 8% (weight/volume).

Embodiment P17. The composition of any one of Embodiments P1-P3, wherein the anti-acne compound is an antibiotic, a retinoid, or an alpha-hydroxy acid.

Embodiment P18. A composition comprising a *Propionibacterium acnes* bacteriophage and an enzyme.

Embodiment P19. The composition of any one of Embodiments P1-P18, wherein the *P. acnes* bacteriophage is a lytic *P. acnes* bacteriophage.

Embodiment P20. The composition of any one of Embodiments P1-P19, wherein the *P. acnes* bacteriophage comprises a linear double stranded DNA genome.

Embodiment P21. The composition of any one of Embodiments P1-P20, wherein the *P. acnes* bacteriophage is within the bacteriophage family Siphoviridae.

Embodiment P22. The composition of any one of Embodiments P1-P21, wherein the genome of the *P. acnes* bacteriophage comprises a nucleotide sequence that is at least about 80%, 85%, 90%, 95%, 96%, 97%, 98%, or 99% identical to the nucleotide sequence of SEQ ID NO: 1.

Embodiment P23. The composition of any one of Embodiments P18-P21, wherein the enzyme is a *P. acnes* biofilm degrading enzyme.

Embodiment P24. The composition of any one of Embodiments P3 or P18-P23, wherein the enzyme is a glycosidase, a protease, a DNAse, or a restriction endonuclease.

Embodiment P25. The composition of any one of Embodiments P3 or P18-P24, wherein the enzyme is a glycosidase.

Embodiment P26. The composition of Embodiment P25, wherein the glycosidase is a glycoside hydrolase.

Embodiment P27. The composition of Embodiment P26, wherein the enzyme catalyzes the hydrolysis of linear polymers of N-acetyl-D-glucosamines.

Embodiment P28. The composition of Embodiment P27, wherein the enzyme is a (3-hexosaminidase.

Embodiment P29. The composition of Embodiment P28, wherein the enzyme is hydrolyzes β-1,6-glycosidic linkages of acetylglucosamine polymers.

Embodiment P30. The composition of any one of Embodiments P3 or P18-P24, wherein the enzyme is a DNAse I, a restriction endonuclease, papain, bromelain, Trypsin, Proteinase K, Subtilisin, serratiopeptidase, dispersin, alginate lyase, amylase, or cellulase.

Embodiment P31. The composition of any one of Embodiments P3 or P18-P24, wherein the enzyme is Dispersin B.

Embodiment P32. The composition of any one of Embodiments P3 or P18-P24, wherein the enzyme is a protease, and the protease is proteinase K or subtilisin.

Embodiment P33. composition of any one of Embodiments P18-P22, wherein the enzyme is an anti-aging enzyme.

Embodiment P34. The composition of Embodiment P33, wherein the anti-aging enzyme is a superoxide dismutase or a peroxidase.

Embodiment P35. The composition of any one of Embodiments P18-P34, further comprising a probiotic bacterium.

Embodiment P36. The composition of Embodiment P35, wherein the probiotic bacterium is a probiotic a *P.* sp., *Staphylococcus* sp., and/or *Corynebacterium* sp. bacterium.

Embodiment P37. The composition of Embodiment P35, wherein the probiotic bacterium is a bacterium within the class Betaproteobacteria.

Embodiment P38. The composition of Embodiment P36, wherein the probiotic bacterium is a probiotic *P. acnes* bacterium.

Embodiment P39. The composition of Embodiment P38, wherein the *P. acnes* bacterium
 (a) comprises a 16S DNA sequence with a T992C mutation compared to the KPA171202 type strain 16S DNA sequence set forth as SEQ ID NO: 2;

(b) comprises a 16S DNA sequence with a T838C mutation compared to the KPA171202 type strain 16S DNA sequence set forth as SEQ ID NO: 2;
(c) comprises a 16S DNA sequence with a C1322T mutation compared to the KPA171202 type strain 16S DNA sequence set forth as SEQ ID NO: 2;
(d) comprises a 16S DNA sequence with a C986T mutation compared to the KPA171202 type strain 16S DNA sequence set forth as SEQ ID NO: 2;
(e) comprises a 16S DNA sequence that is identical to the sequence of SEQ ID NO: 3;
(f) comprises a 16S DNA sequence that is identical to the sequence of SEQ ID NO: 4;
(g) does not comprise a linear plasmid;
(h) does not comprise a plasmid that comprises a virulence factor; and/or
(i) does not comprises a plasmid that encodes an extrachromosomal lipase and/or a tight adhesion virulence factor.

Embodiment P40. The composition of Embodiment P38, wherein the *P. acnes* bacterium:
(a) produces less than about 20% of the level of lipase that is produced by a pathogenic *P. acnes* strain when grown in a planktonic culture;
(b) produces less than about 10% of the level of lipase that is produced by a pathogenic *P. acnes* strain when grown in an adherent culture;
(c) adheres to epithelial cells at least 50% less than a pathogenic *P. acnes* strain; and/or
(d) is less inflammatory than a pathogenic *P. acnes* strain.

Embodiment P41. The composition of any one of Embodiments P35-P40, further comprising at least one additional probiotic bacterium.

Embodiment P42. The composition of Embodiment P41, wherein said at least one additional probiotic bacterium comprises *Propionibacterium granulosum* and/or *Propionibacterium avidum*.

Embodiment P43. The composition of Embodiment P40, wherein said pathogenic *P. acnes* strain
(a) comprises a 16S DNA sequence with a G1058C mutation compared to the KPA171202 type strain 16S DNA sequence set forth as SEQ ID NO: 2;
(b) comprises a 16S DNA sequence with a G1058C and an A1201C mutation compared to the KPA171202 type strain 16S DNA sequence set forth as SEQ ID NO: 2;
(c) comprises a 16S DNA sequence with a G529A mutation compared to the KPA171202 type strain 16S DNA sequence set forth as SEQ ID NO: 2;
(d) comprises a 16S DNA sequence with a G1004A and a T1007C mutation compared to the KPA171202 type strain 16S DNA sequence set forth as SEQ ID NO: 2;
(e) comprises a 16S DNA sequence with a G1268A mutation compared to the KPA171202 type strain 16S DNA sequence set forth as SEQ ID NO: 2;
(f) comprises a 16S DNA sequence with a T554C and a G1058C mutation compared to the KPA171202 type strain 16S DNA sequence set forth as SEQ ID NO: 2;
(g) comprises a 16S DNA sequence that is identical to the sequence of SEQ ID NO: 5;
(h) comprises a 16S DNA sequence that is identical to the sequence of SEQ ID NO: 6;
(i) comprises a 16S DNA sequence that is identical to the sequence of SEQ ID NO: 7;
(j) comprises a 16S DNA sequence that is identical to the sequence of SEQ ID NO: 8;
(k) comprises a 16S DNA sequence that is identical to the sequence of SEQ ID NO: 9; and/or
(l) comprises a 16S DNA sequence that is identical to the sequence of SEQ ID NO: 10.

Embodiment P44. The composition of any one of Embodiments P18-P43, further comprising at least one additional *P. acnes* bacteriophage.

Embodiment P45. The composition of any one of Embodiments P1-P44, comprising a pharmaceutically acceptable carrier.

Embodiment P46. The composition of Embodiment P45, wherein the pharmaceutically acceptable carrier comprises an emulsion.

Embodiment P47. The composition of Embodiment P46, wherein the emulsion is an oil-in-water emulsion or a water-in-oil emulsion.

Embodiment P48. The composition of any one of Embodiments P1-P47, which is in the form of a cream, lotion, suspension, or aqueous solution.

Embodiment P49. A combination consisting essentially of at least one *Propionibacterium acnes* bacteriophage, and at least one anti-acne compound, wherein each of the at least one *Propionibacterium acnes* bacteriophage and the at least one anti-acne compound is in a composition that further comprises a pharmaceutically acceptable carrier.

Embodiment P50. The combination of Embodiment P49, wherein the at least one *P. acnes* bacteriophage and the at least one anti-acne compound are within separate compositions.

Embodiment P51. The combination of Embodiment P50, wherein the at least one *P. acnes* bacteriophage and the at least one anti-acne compound are within separate containers.

Embodiment P52. A combination comprising a *Propionibacterium acnes* bacteriophage and an enzyme.

Embodiment P53. The combination of Embodiment P52, wherein the *P. acnes* bacteriophage and the enzyme are within separate compositions.

Embodiment P54. The combination of Embodiment P53, wherein the *P. acnes* bacteriophage and the enzyme are within separate containers.

Embodiment P55. A method of treating acne in a subject in need thereof, the method comprising administering an effective amount of the composition of any one of Embodiments P1-P46 or the combination of any one of Embodiments P49-P54 to the subject.

Embodiment P56. The method of Embodiment P55, wherein the composition is administered topically.

Additional embodiments include Embodiments 1 to 55 following:

Embodiment 1. A composition comprising at least one *Propionibacterium acnes* bacteriophage, at least one anti-acne compound, and a pharmaceutically acceptable carrier.

Embodiment 2. The composition of Embodiment 1, which does not comprise a probiotic bacterium.

Embodiment 3. The composition of Embodiment 1 or 2, wherein the composition further comprises a *P. acnes* biofilm degrading enzyme.

Embodiment 4. The composition of any one of Embodiments 1-3, wherein the at least one anti-acne compound is salicylic acid.

Embodiment 5. The composition of Embodiment 4, wherein the salicylic acid is present at a concentration of 0.5% to 2% (weight/volume).

Embodiment 6. The composition of Embodiment 5, wherein the salicylic acid is present at a concentration of less than 0.5% but greater than about 0.1% (weight/volume).

Embodiment 7. The composition of any one of Embodiments 1-3, wherein the at least one anti-acne compound is sulfur.

Embodiment 8. The composition of Embodiment 7, wherein the sulfur is present at a concentration of 3% to 10% (weight/volume).

Embodiment 9. The composition of Embodiment 7, wherein the sulfur is present at a concentration of less than 3% but greater than about 0.1%, 0.5%, 1%, 1.5%, 2%, or 2.5% (weight/volume).

Embodiment 10. The composition of any one of Embodiments 1-3, wherein the at least one anti-acne compound is resorcinol and sulfur.

Embodiment 11. The composition of Embodiment 10, wherein the resorcinol is present at a concentration of 2% and sulfur is present at a concentration of 3% to 8% (weight/volume).

Embodiment 12. The composition of any one of Embodiments 1-3, wherein the at least one anti-acne compound comprises resorcinol monoacetate and sulfur.

Embodiment 13. The composition of Embodiment 12, wherein the resorcinol monoacetate is present at a concentration of 3% and sulfur is present at a concentration of 3% to 8% (weight/volume).

Embodiment 14. The composition of any one of Embodiments 1-3, wherein the anti-acne compound is an antibiotic, a retinoid, or an alpha-hydroxy acid.

Embodiment 15. The composition of any one of Embodiments 1-14, wherein the *Propionibacterium acnes* bacteriophage is a naturally occurring *Propionibacterium acnes* bacteriophage.

Embodiment 16. The composition of any one of Embodiments 1-15, wherein the *P. acnes* bacteriophage is a lytic *P. acnes* bacteriophage.

Embodiment 17. The composition of any one of Embodiments 1-16, wherein the *P. acnes* bacteriophage comprises a linear double stranded DNA genome.

Embodiment 18. The composition of any one of Embodiments 1-17, wherein the *P. acnes* bacteriophage is within the bacteriophage family Siphoviridae.

Embodiment 19. The composition of any one of Embodiments 1-19, wherein the genome of the *P. acnes* bacteriophage comprises a nucleotide sequence that is at least about 80%, 85%, 90%, 95%, 96%, 97%, 98%, or 99% identical to the nucleotide sequence of SEQ ID NO: 1.

Embodiment 20. The composition of any one of Embodiments 3-19, wherein the enzyme is a *P. acnes* biofilm degrading enzyme.

Embodiment 21. The composition of any one of Embodiments 3-20, wherein the enzyme is a glycosidase, a protease, a DNAse, or a restriction endonuclease.

Embodiment 22. The composition of any one of Embodiments 3-21, wherein the enzyme is a glycosidase.

Embodiment 23. The composition of Embodiment 22, wherein the glycosidase is a glycoside hydrolase.

Embodiment 24. The composition of Embodiment 23, wherein the enzyme catalyzes the hydrolysis of linear polymers of N-acetyl-D-glucosamines.

Embodiment 25. The composition of Embodiment 24, wherein the enzyme is a (3-hexosaminidase.

Embodiment 26. The composition of Embodiment 25, wherein the enzyme is hydrolyzes β-1,6-glycosidic linkages of acetylglucosamine polymers.

Embodiment 27. The composition of any one of Embodiments 3-20, wherein the enzyme is a DNAse I, a restriction endonuclease, papain, bromelain, Trypsin, Proteinase K, Subtilisin, serratiopeptidase, dispersin, alginate lyase, amylase, or cellulase.

Embodiment 28. The composition of any one of Embodiments 3-20, wherein the enzyme is Dispersin B.

Embodiment 29. The composition of any one of Embodiments 3-20, wherein the enzyme is a protease, and the protease is proteinase K or subtilisin.

Embodiment 30. The composition of any one of Embodiments 1-29, further comprising an anti-aging enzyme.

Embodiment 31. The composition of Embodiment 30, wherein the anti-aging enzyme is a superoxide dismutase or a peroxidase.

Embodiment 32. The composition of any one of Embodiments 1-31, further comprising a probiotic bacterium.

Embodiment 33. The composition of Embodiment 32, wherein the probiotic bacterium is a probiotic a P. sp., *Staphylococcus* sp., and/or *Corynebacterium* sp. bacterium.

Embodiment 34. The composition of Embodiment 32, wherein the probiotic bacterium is a bacterium within the class Betaproteobacteria.

Embodiment 35. The composition of Embodiment 33, wherein the probiotic bacterium is a probiotic *P. acnes* bacterium.

Embodiment 36. The composition of Embodiment 35, wherein the *P. acnes* bacterium
  (a) comprises a 16S rDNA sequence with a T992C mutation compared to the KPA171202 type strain 16S rDNA sequence set forth as SEQ ID NO: 2;
  (b) comprises a 16S rDNA sequence with a T838C mutation compared to the KPA171202 type strain 16S rDNA sequence set forth as SEQ ID NO: 2;
  (c) comprises a 16S rDNA sequence with a C1322T mutation compared to the KPA171202 type strain 16S rDNA sequence set forth as SEQ ID NO: 2;
  (d) comprises a 16S rDNA sequence with a C986T mutation compared to the KPA171202 type strain 16S rDNA sequence set forth as SEQ ID NO: 2;
  (e) comprises a 16S rDNA sequence that is identical to the sequence of SEQ ID NO: 3;
  (f) comprises a 16S rDNA sequence that is identical to the sequence of SEQ ID NO: 4;
  (g) does not comprise a linear plasmid;
  (h) does not comprise a plasmid that comprises a virulence factor; and/or
  (i) does not comprises a plasmid that encodes an extrachromosomal lipase and/or a tight adhesion virulence factor.

Embodiment 37. The composition of Embodiment 35 or 36, wherein the *P. acnes* bacterium:
  (a) produces less than about 20% of the level of lipase that is produced by a pathogenic *P. acnes* strain when grown in a planktonic culture;
  (b) produces less than about 10% of the level of lipase that is produced by a pathogenic *P. acnes* strain when grown in an adherent culture;
  (c) adheres to epithelial cells at least 50% less than a pathogenic *P. acnes* strain; and/or
  (d) is less inflammatory than a pathogenic *P. acnes* strain.

38. The composition of any one of Embodiments 32-37, further comprising at least one additional probiotic bacterium.

Embodiment 39. The composition of Embodiment 38, wherein said at least one additional probiotic bacterium comprises *Propionibacterium granulosum* and/or *Propionibacterium avidum*.

Embodiment 40. The composition of Embodiment 37, wherein said pathogenic *P. acnes* strain
  (a) comprises a 16S rDNA sequence with a G1058C mutation compared to the KPA171202 type strain 16S rDNA sequence set forth as SEQ ID NO: 2;

(b) comprises a 16S rDNA sequence with a G1058C and an A1201C mutation compared to the KPA171202 type strain 16S rDNA sequence set forth as SEQ ID NO: 2;

(c) comprises a 16S rDNA sequence with a G529A mutation compared to the KPA171202 type strain 16S rDNA sequence set forth as SEQ ID NO: 2;

(d) comprises a 16S rDNA sequence with a G1004A and a T1007C mutation compared to the KPA171202 type strain 16S rDNA sequence set forth as SEQ ID NO: 2;

(e) comprises a 16S rDNA sequence with a G1268A mutation compared to the KPA171202 type strain 16S rDNA sequence set forth as SEQ ID NO: 2;

(f) comprises a 16S rDNA sequence with a T554C and a G1058C mutation compared to the KPA171202 type strain 16S rDNA sequence set forth as SEQ ID NO: 2;

(g) comprises a 16S rDNA sequence that is identical to the sequence of SEQ ID NO: 5;

(h) comprises a 16S rDNA sequence that is identical to the sequence of SEQ ID NO: 6;

(i) comprises a 16S rDNA sequence that is identical to the sequence of SEQ ID NO: 7;

(j) comprises a 16S rDNA sequence that is identical to the sequence of SEQ ID NO: 8;

(k) comprises a 16S rDNA sequence that is identical to the sequence of SEQ ID NO: 9; and/or (l) comprises a 16S rDNA sequence that is identical to the sequence of SEQ ID NO: 10.

Embodiment 41. The composition of any one of Embodiments 1-40, further comprising at least one additional *P. acnes* bacteriophage.

Embodiment 42. The composition of any one of Embodiments 1-41, wherein the pharmaceutically acceptable carrier comprises an emulsion.

Embodiment 43. The composition of Embodiment 42, wherein the emulsion is an oil-in-water emulsion or a water-in-oil emulsion.

Embodiment 44. The composition of any one of Embodiments 1-44, which is in the form of a cream, lotion, suspension, or aqueous solution.

Embodiment 45. A combination comprising at least one *Propionibacterium acnes* bacteriophage and at least one anti-acne compound, wherein each of the at least one *Propionibacterium acnes* bacteriophage and the at least one anti-acne compound is in a composition that further comprises a pharmaceutically acceptable carrier.

Embodiment 46. The combination of Embodiment 45, wherein the at least one *P. acnes* bacteriophage and the at least one anti-acne compound are within separate compositions.

Embodiment 47. The combination of Embodiment 46, wherein the at least one anti-acne compound is benzoyl peroxide.

Embodiment 48. The combination of Embodiment 47, wherein the benzoyl peroxide is present at a concentration of 2.5% to 10% (weight/volume).

Embodiment 49. The combination of Embodiment 47, wherein the benzoyl peroxide is present at a concentration of less than 2.5% but greater than about 0.1%, 0.5%, 1%, 1.5%, or 2% (weight/volume).

Embodiment 50. A method of treating acne in a subject in need thereof, the method comprising administering an effective amount of the composition of any one of Embodiments 1-44 to the subject.

Embodiment 51. The method of Embodiment 50, wherein the composition is administered topically.

Embodiment 52. A method of treating acne in a subject in need thereof, the method comprising administering an effective amount of the combination of any one of Embodiments 45-49 to the subject.

Embodiment 53. A composition comprising a *Propionibacterium acnes* bacteriophage and an enzyme.

Embodiment 54. A combination comprising a *Propionibacterium acnes* bacteriophage and an enzyme.

Embodiment 55. A composition consisting essentially of at least one *Propionibacterium acnes* bacteriophage, at least one anti-acne compound, and a pharmaceutically acceptable carrier.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1. *P. acnes* Bacteriophage PHIT-101 Kills *P. acnes* Selectively and Efficiently

*P. acnes* bacteriophages have been shown to be genetically highly similar and exhibit a broad range against multiple strains of *P. acnes*. A lead bacteriophage (PHIT-101) was used for experimentation. PHIT-101 is a single lytic phage that killed all the strain types of *P. acnes* tested (data not shown). PHIT-101 has the sequence of SEQ ID NO: 1. In order to showcase the efficacy and specificity of this phage, a plate assay was performed as follows. *P. acnes* KPA171202 and *P. granulosum* (a closely related but benign skin bacterium) were plated on separate BHI-agar plates. Sterile cotton pads were placed on each plate. The sterile cotton pads were soaked in either minocycline, an antibiotic commonly used to treat acne, or a phage solution with a titer of $2\times10^7$ pfu/mL. After incubating the plates anaerobically for 72 hours at 37° C., the minocycline pads killed bacteria indiscriminately, showing a zone of killing on both the acne-causing *P. acnes* and the commensal *P. granulosum* (FIG. 1). In contrast, the PHIT-101 pads killed only the *P. acnes*, without disturbing the growth of beneficial *P. granulosum*.

Figure 2:
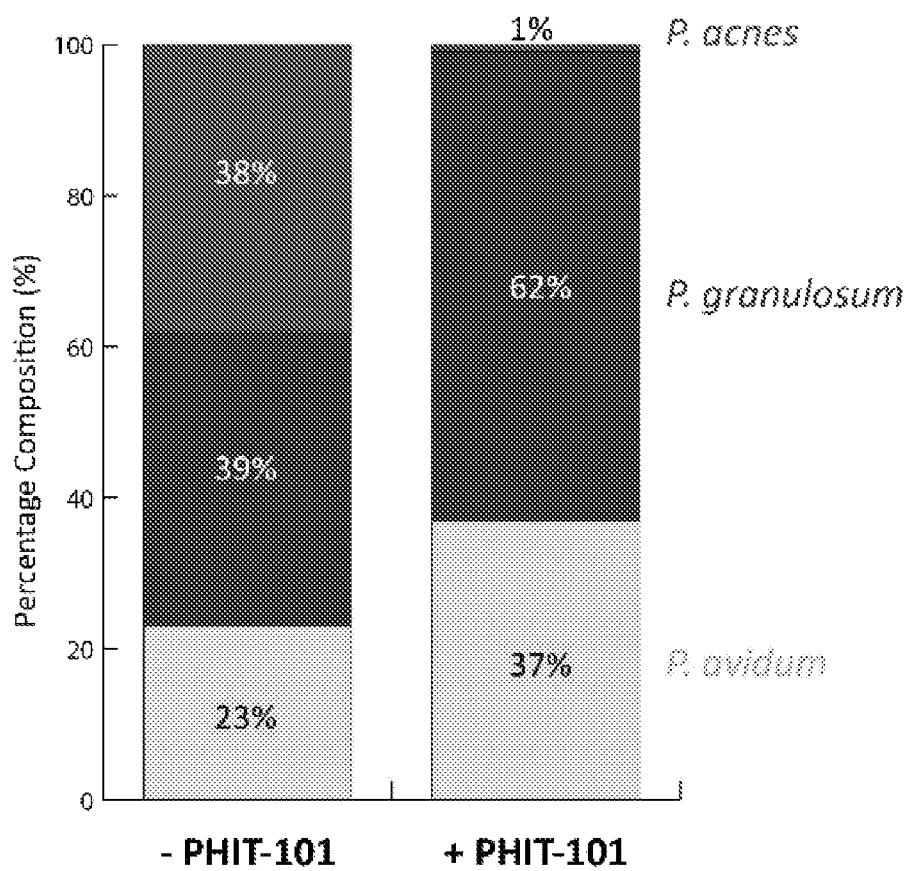
FIG. 2. A synthetic skin microbiome that includes *P. acnes, P. granulosum*, and *P. avidum* was grown to confluence in a test tube. It was then incubated in the presence or absence of PHIT-101 for 48 hours. The relative proportions of the three species were quantified by NGS sequencing of the 16S amplicon of the washed bacterial pellets using the Illumina MiSeq platform. PHIT-101 was able to almost completely wipe out acne-causing *P. acnes*, without affecting the growth of the other two commensal species.

Further evidence of the ability of PHIT-101 to kill selectively was obtained in a synthetic skin microbiome assay. A synthetic skin microbiome was formulated comprising *P. acnes*, *P. granulosum*, and *P. avidum*, three skin bacteria that comprise 60-80% of microbiota in the skin pore [Science (2009) 324:1190-1192]. This synthetic skin microbiome was grown anaerobically in the presence or absence of PHIT-101 (final concentration $5\times10^5$ pfu/mL). After 48 hours of incubation at 37° C., the cells were pelleted and washed, and the relative proportions of the three species was determined using 16S amplicon next-generation sequencing (NGS) on Illumina MiSeq. The results in FIG. 2 show that PHIT-101 is able to kill *P. acnes* almost completely, without negatively affecting the growth of the commensal *P. granulosum* and *P. avidum*.

Screening Biofilm Degrading Enzymes (BDEs) to Disrupt *P. acnes* Biofilms.

Figure 3:
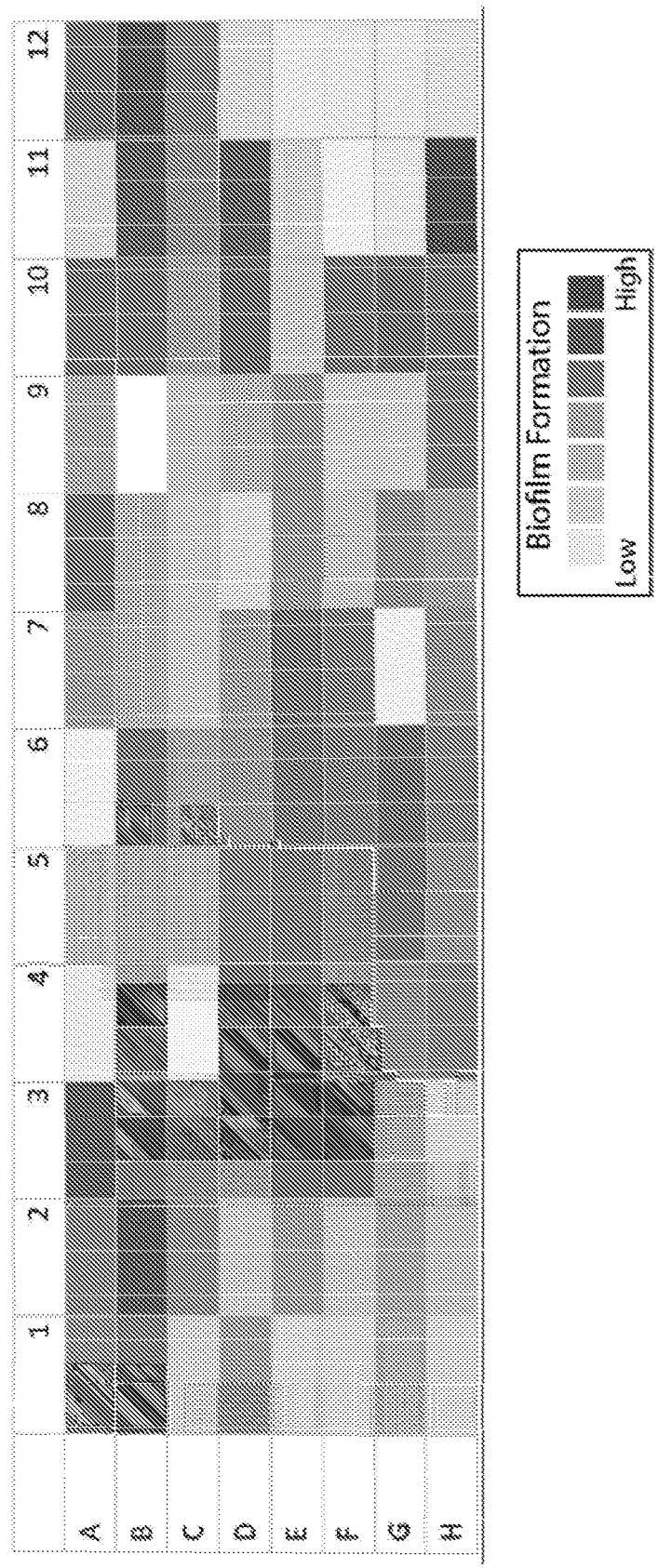
FIG. 3. Biofilm production amongst *P. acnes* strains is highly variable. 96 strains of *P. acnes* were grown in a 96-well polystyrene microtiter plate to stimulate biofilm production, and the biofilm produced by each strain was quantified. The variability demonstrated within this set of strains demonstrates the need to quantify biofilm formation under growth conditions more similar to those found in the human pore.

Several recent reports (Exp Dermatol (2014) 23:687, Br J Dermatol (2015) 172:13) have established that *P. acnes* produces significant amounts of biofilm in skin pores, which prevents antibiotic penetration and results in poor treatment outcomes. In order to validate this, biofilm production of several strains of *P. acnes* was quantified. FIG. 3 shows that adherent cultures of multiple strains isolated from the microbiota of a single subject produce markedly different levels of biofilm under similar conditions. Thus the previous proof-of-concept using planktonic cells did not reflect the true conditions under which *P. acnes* grows on the skin.

Figure 4:
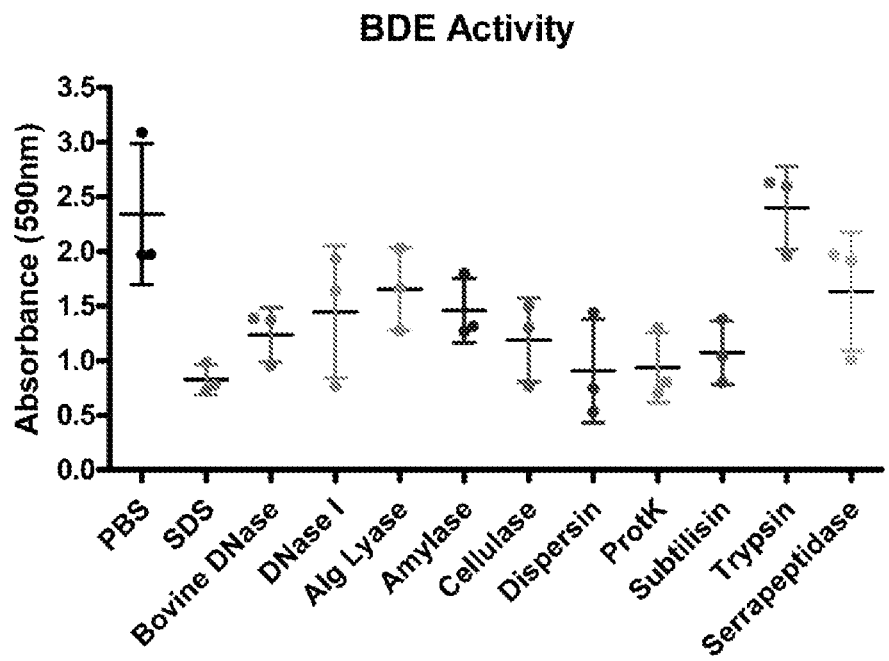
FIG. 4. A screen to select enzymes that can degrade *P. acnes* biofilms. *P. acnes* was grown in polystyrene microtiter plates to stimulate biofilm production. Enzymes were added at 0.01 mg/mL to the wells and incubated at 30° C. for 30 mins. The degraded biofilm was washed away with phosphate buffered saline (PBS), and the residual biofilm in each well was quantified by staining with crystal violet and recording absorbance at 590 nm. Proteases like proteinase K and subtilisin showed good activity, and dispersin was the best glycoside depolymerase amongst those tested.

Without being bound by any scientific theory, we hypothesized that biofilms might present a significant barrier to phage killing of sessile *P. acnes* cells. This hypothesis was validated in a cell survival assay (FIG. 5) which showed that unlike planktonic *P. acnes* (99% killing, FIG. 2), PHIT-101 was only able to kill about 50% of the *P. acnes* cells encased in biofilms. In order to determine whether biofilm degradation would improve phage killing, a number of enzymes was screened to find a BDE specific for *P. acnes*. The screen comprised three classes of enzymes that might degrade types of materials that may be found in biofilms: DNA, polysaccharides, and proteins. FIG. 4 shows that in the screen, DNAses had moderate activity while the best rates of biofilm degradation were found in proteases and dispersin, a glycoside hydrolase from Aggregatibacter *actinomycetemcomitans*.

Figure 5:
FIG. 5. Enhancement of phage with biofilm degrading enzyme (BDE) greatly increases bacterial killing. Sessile *P. acnes* cells were incubated with PBS (untreated), PHIT-101, or PHIT-101 and Dispersin. Cell survival was measured using the CellTiter-Blue reagent, and fluorescence was recorded at $560_{Ex}/590_{Em}$. PHIT-101 was unable to kill *P. acnes* as effectively as in liquid culture, but addition of the biofilm degrading enzyme Dispersin greatly increased the bacterial killing to levels similar to liquid culture.
Figure 6:
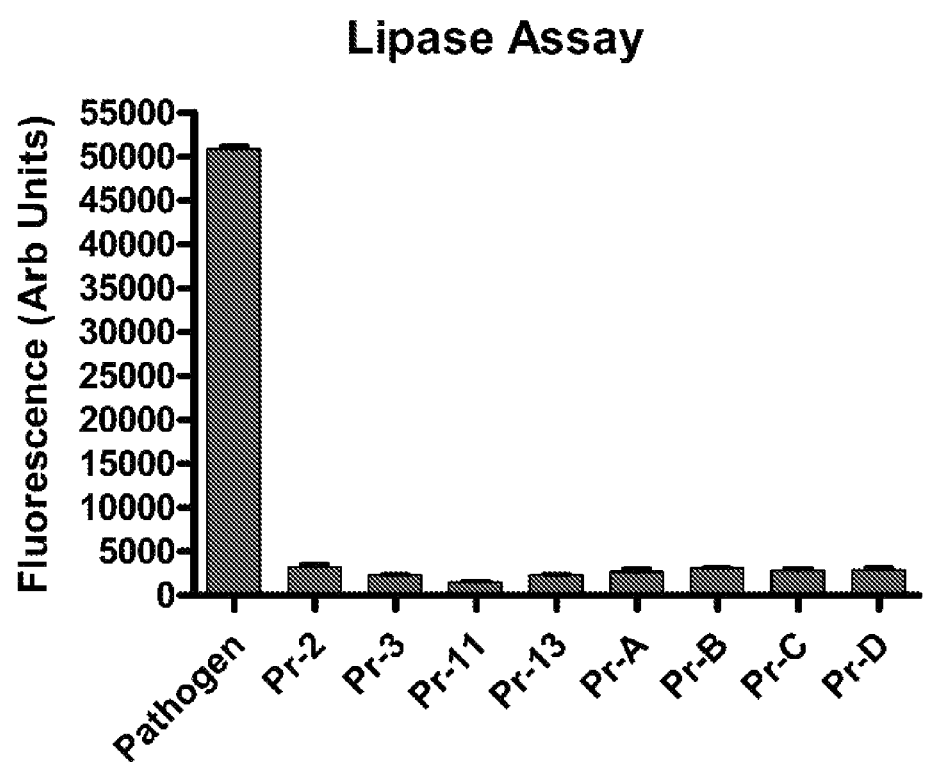
FIG. 6. Probiotic strains produce low levels of lipase in adherent culture. Probiotic *P. acnes* strains with known genotypes were grown under biofilm conditions in a microtiter plate. After 72 hrs of growth, the culture supernatant was filter-sterilized and incubated with 4-MU palmitate at 37 C for 4 hours to determine extracellular lipase production. The lipase production of the probiotic strains (Pr #X) was very low in comparison to pathogen, indicating a lower inflammatory potential.
Figure 7:
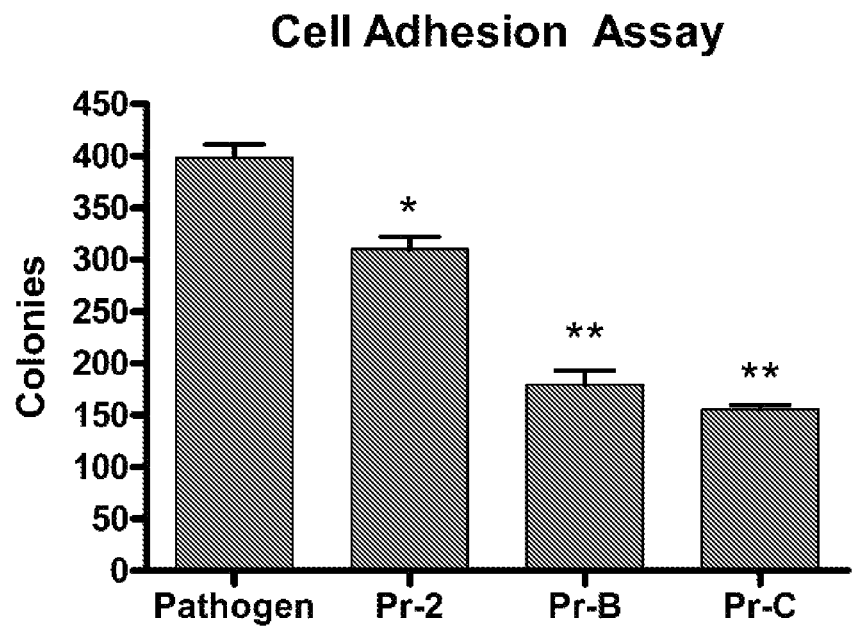
FIG. 7. Probiotic strains adhere significantly less to epithelial cells than pathogenic *P. acnes*. Select probiotic strains were incubated with confluent A-431 epithelial cells (MOI 10). After washing the wells, cells were lifted using 0.1% Tween 80 solution and plated on BHI plates. After anaerobic incubation for 72 hours, colonies were counted. The data show that probiotic strains showed significantly lower binding to epithelial cells (* $p<0.05$, ** $p<0.005$).
Figure 8A:
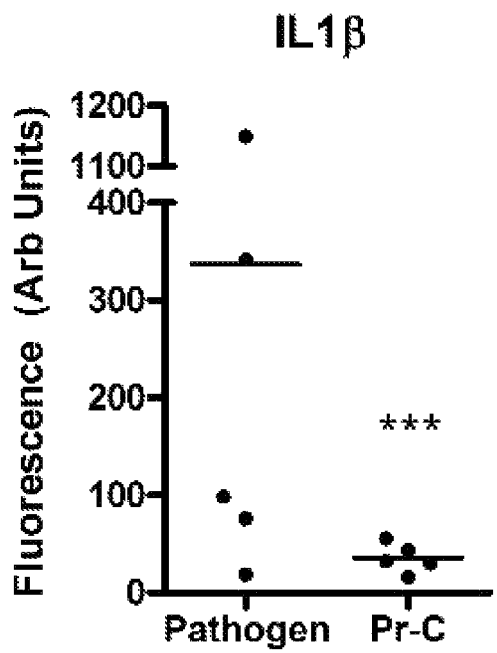
FIGS. 8A-8D. Lower inflammatory potential of probiotic strain in mouse ear inflammation model. CBA/J mice (5 mice per cohort) were injected with *P. acnes* strains, and cytokine analysis was performed at day 5. The probiotic strain Pr #C showed significantly lower levels (* $p<0.05$,  $p<0.01$, * $p<0.0001$) of inflammatory cytokines IL-1β (FIG. 8A), IL-6 (FIG. 8B), IL-17 (FIG. 8C), and TNFα (FIG. 8D) than the pathogenic strain. Pr-C has the ProII 16S sequence.
Figure 8B:
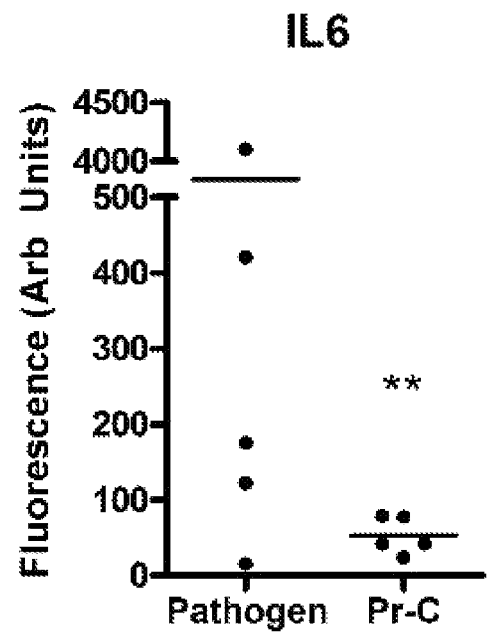
Figure 8C:
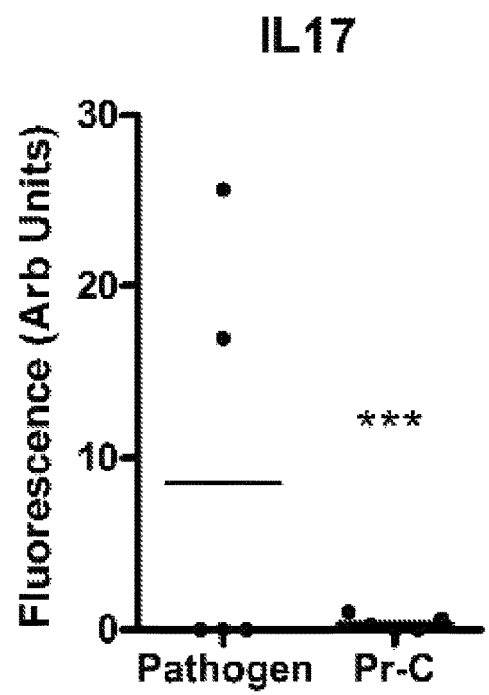
Figure 8D:
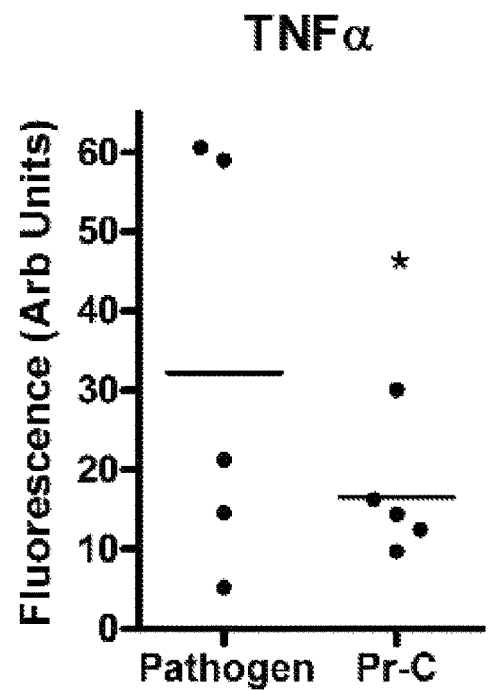

In selecting the BDE to pair with the phage, dispersin was selected for two reasons: firstly, as a glycoside hydrolase it was unlikely to attack the protein coat of the phage itself, thereby avoiding possible degradation of the phage. Secondly, *P. acnes* co-forms robust biofilms with *Staphylococcus aureus* [Anaerobe (2016) 40:63-67] and dispersin is active against biofilms from both organisms. Whether the addition of dispersin would increase the efficiency of phage killing in sessile *P. acnes* was determined. FIG. 5 shows that bacterial killing of PHIT-101 was enhanced in the presence of dispersin, restoring a ~99% killing efficiency to the phage.

Example 2. Probiotic Bacteria

Genotypic Characterization of Probiotic Strains.

Strains of *P. acnes* were characterized based on point mutations in the 16S rDNA sequence which leads to phylogenetic sorting into pathogenic and probiotic strain types, and the absence of a linear plasmid found in pathogenic strains, which carries virulence factors. Using 16S-specific primers the full 16S rDNA sequence of each *P. acnes* strain was amplified and Sanger-sequenced. A probiotic strain was identified as having ribosequence (RS) of ProI or ProII. ProI strains have T838C and C1322T mutations relative to the KPA171202 type strain's 16S rDNA sequence (NIH Accession No. NC_006085.1). ProII strains have C986T and T992C mutations relative to the KPA171202 sequence. Further, using specific primer pairs, the presence or absence of a linear plasmid within each strain was determined. Probiotic strains were identified as lacking this plasmid, which carries an extrachromosomal lipase as well as the Tad (tight adhesion) virulence factor.

In embodiments, the probiotic strains are characterized primarily by their 16S sequences, e.g., SEQ ID NO: 3 and SEQ ID NO: 4. In embodiments, they can be genotypically identified by the lack of the plasmid bearing virulence factors, such as an extrachromosomal lipase and a Tad locus.

The cohort of probiotic strains was further characterized for their immunogenic potential. A lead probiotic candidate based on two factors: low lipase production, and less tight adherence to epithelial cells. The phenotypic validation of these features was important in selecting the probiotic lead candidate.

Testing the Immunogenic Potential of Probiotic *P. acnes* Strains: Lipase Activity.

Lipases play an important role in pathogenesis of acne by hydrolyzing sebum triglycerides and releasing irritating free fatty acids in the pilosebaceous follicles. Lipase is a strong chemotactic and proinflammatory antigen. Therefore, lipase is of high interest as a pharmacological target for anti-acne drugs. In embodiments, the overall strategy is to replace the pathogenic *P. acnes* that secretes high levels of lipase with a low-secreting probiotic *P. acnes*. In order to quantify the lipase expression phenotype for each strain in our panel, lipase production of the probiotic *P. acnes* strains was compared against pathogenic *P. acnes* strains with a fluorescent lipase activity assay.

Figure 11:
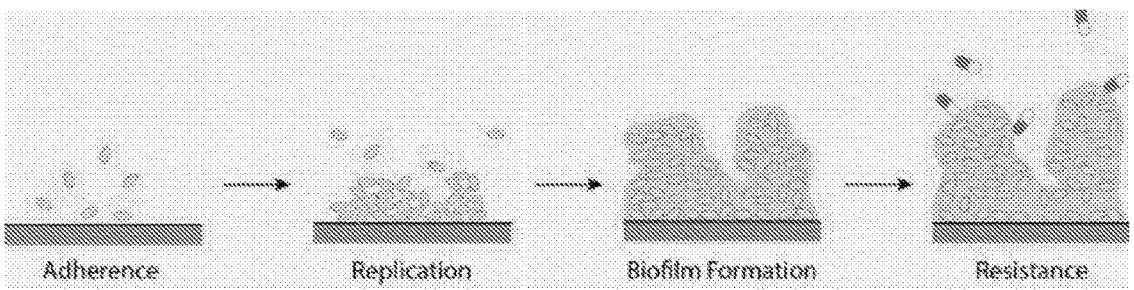
FIG. 11 illustrates the formation of exemplary bacterial biofilms. Bacterial cells land and adhere to a surface with favorable conditions for growth. They replicate to form a colony, until a certain threshold of cell density (quorum) triggers biofilm formation. The biofilm includes a mixture of polysaccharides, proteins, DNA and lipids in varying proportions. The biofilm is a physical barrier that protects the bacterial colony from harsh external conditions and grants resistance to antibiotics, toxins and immune cells.
Figure 12:
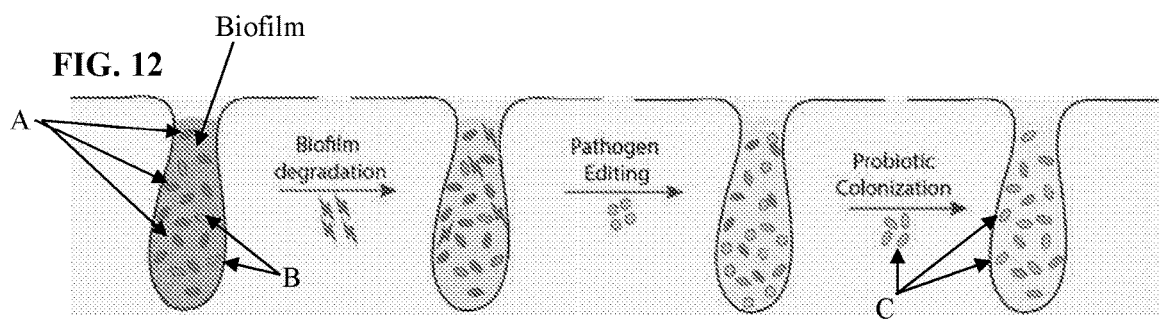
FIG. 12 illustrates an embodiment of three components act in concert; their effects are described sequentially for exposition. An inflamed comedone is typically clogged with the biofilm produced by overgrown *P. acnes* (A), along with commensal skin bacteria (B). The biofilm-degrading enzyme (bolts) breaks down the *P. acnes* biofilm to provide better access for the other components. The bacteriophage (hexagons) then edits or specifically kills the pathogenic *P. acnes* and clears the infection. Finally, the probiotic bacteria (C) colonize the pore and occupy the niche of the pathogen, preventing it from growing back and recalibrating the microbiome to a healthy state.
Figure 13:
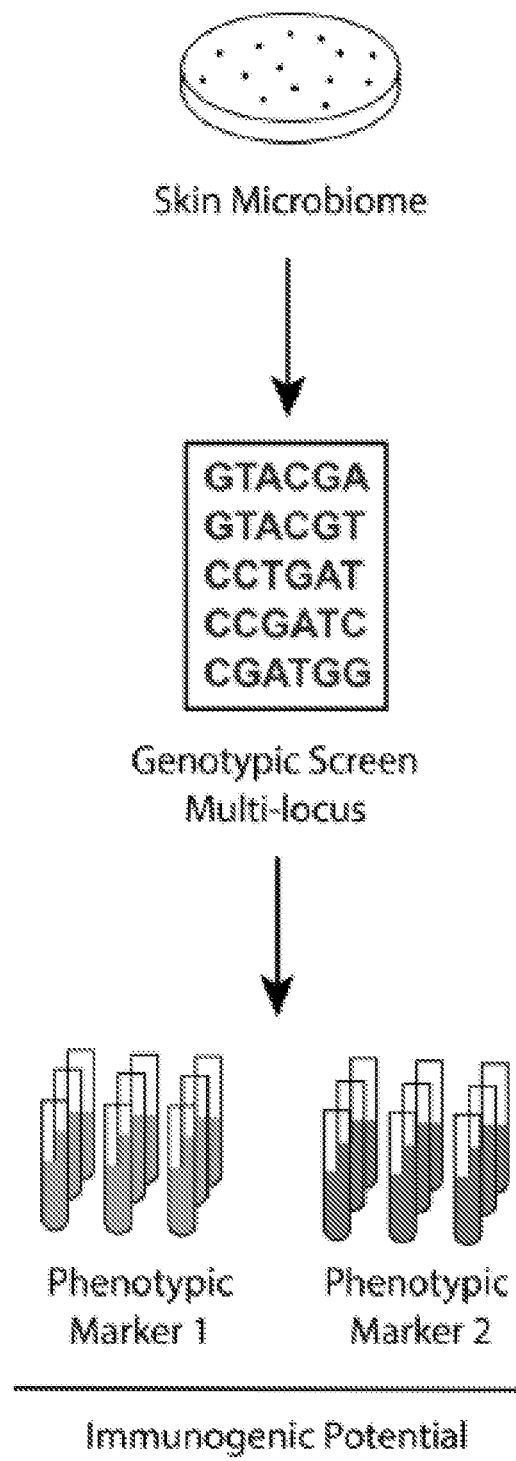
FIG. 13 is a cartoon of a non-limiting probiotic bacterium screening process.
Figure 14:
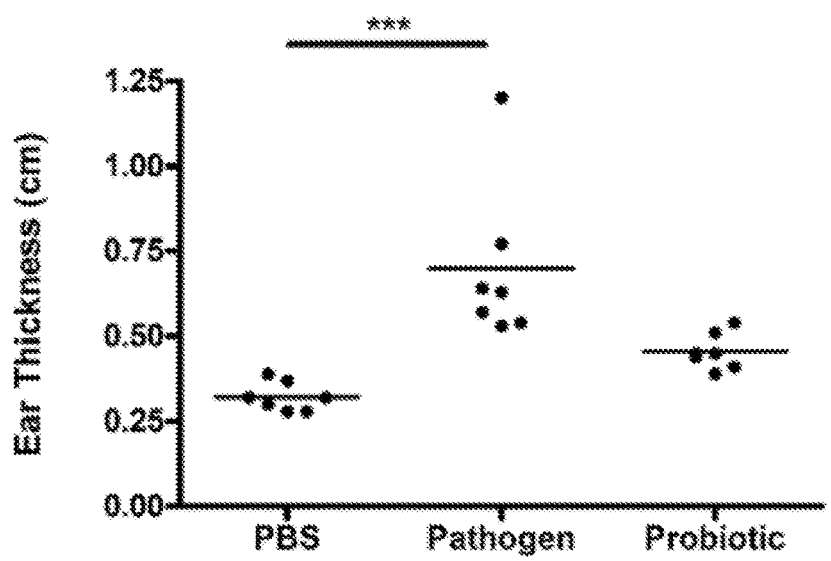
FIG. 14 is a graph showing that the pathogenic strain produces significantly higher ear inflammation than PBS control, while the lead probiotic strain Pr-C induces ear inflammation not significantly different from PBS control.

One of the most interesting findings was that each strain secreted different amounts of lipases when grown in planktonic vs adherent culture. This has been previously reported in *P. acnes* strains [Res Microbiol, (2007) 158:386-392]. Further, the data showed that when these strains were grown in liquid culture, there was no significant difference between the lipase output of the pathogenic and probiotic strains. However, when these strains were grown under biofilm conditions, an interesting change was seen. While variability in production between strains could still be observed, several probiotic strains had significantly less lipase activity than pathogenic strains (FIG. 11). Interestingly, not all strains within the probiotic cohort had low lipase activity. For example, the lipase production of strains Pr-1 and Pr-5 was over the threshold for a probiotic strain, and was not developed further. Thus by quantifying lipase production in sessile *P. acnes* cells, it was possible to screen amongst probiotic strains and select those lead candidates with the most consistent low levels of lipase activity.

Thus, while pathogenic and probiotic strains secreted similar amounts of lipase in planktonic culture, the probiotic strains secreted far less lipase in adherent culture than pathogenic strains. FIG. 8 shows that the top probiotic candidates had a low lipase profile compared to the pathogenic strain.

Testing the Immunogenic Potential of Probiotic *P. acnes* Strains: Cell Adherence.

Figure 9:
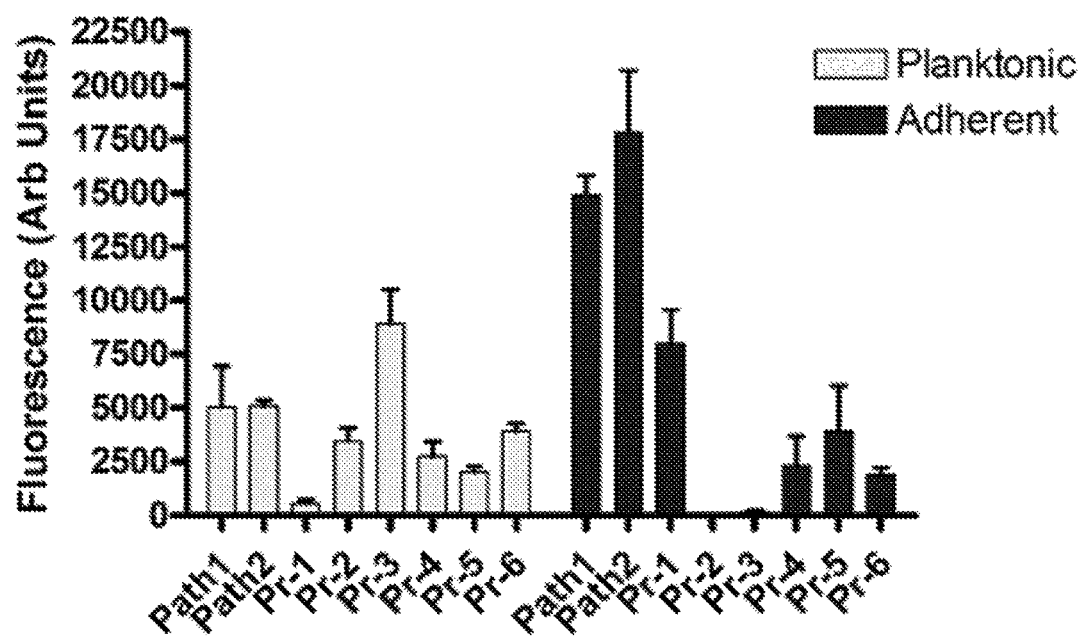
FIG. 9. *P. acnes* strains have different lipase profiles in planktonic and sessile cultures. A set of two pathogenic (Path-1, Path-2) and two probiotic (Pr-1 to Pr-6) *P. acnes* strains were evaluated for lipase production in planktonic (gray bars) and sessile (black bars) cultures. While the lipase production of probiotic strains was not significantly different from the pathogenic strains in liquid (planktonic) culture, their lipase output in adherent culture was consistently lower than corresponding pathogenic cultures. Interestingly, variability in lipase production amongst probiotic strains was observed. The strains with lowest lipase activity were selected.

Available pathogenic strains were confirmed to possess a tight adhesion (tad) locus that plays a role in the virulence of other mammalian pathogens [J Bacteriol (2000) 182: 6169-6176; Nat Rev Microbiol (2007) 5:363-375; PNAS (2003) 100:7295-7300]. Greater adherence to host cells may increase virulence or induce an inflammatory host response. The probiotic strains were previously genotypically verified to not contain the tad locus, and thus predicted to adhere less tightly to epithelial cells. The adhesion of pathogenic and probiotic strains to A-431 dermal epithelial cells was compared, in order to assess whether there was an appreciable difference in adherence. FIG. 9 shows that the top three probiotic candidates adhered less tightly to epithelial cells than the pathogenic strain. Interestingly, once again a subtle but persistent difference in cell adhesion was found between different strain families of *P. acnes*. Thus the strains of *P. acnes* with ProI ribosequence exhibited a slightly higher cell adherence (Pr-2 in FIG. 9) while the ProII strains adhered to cells less tightly (Pr-B, Pr-C in FIG. 9).

Comparison of Pathogenic and Probiotic P. acnes in Mouse Ear Inflammation Model.

Figure 10:
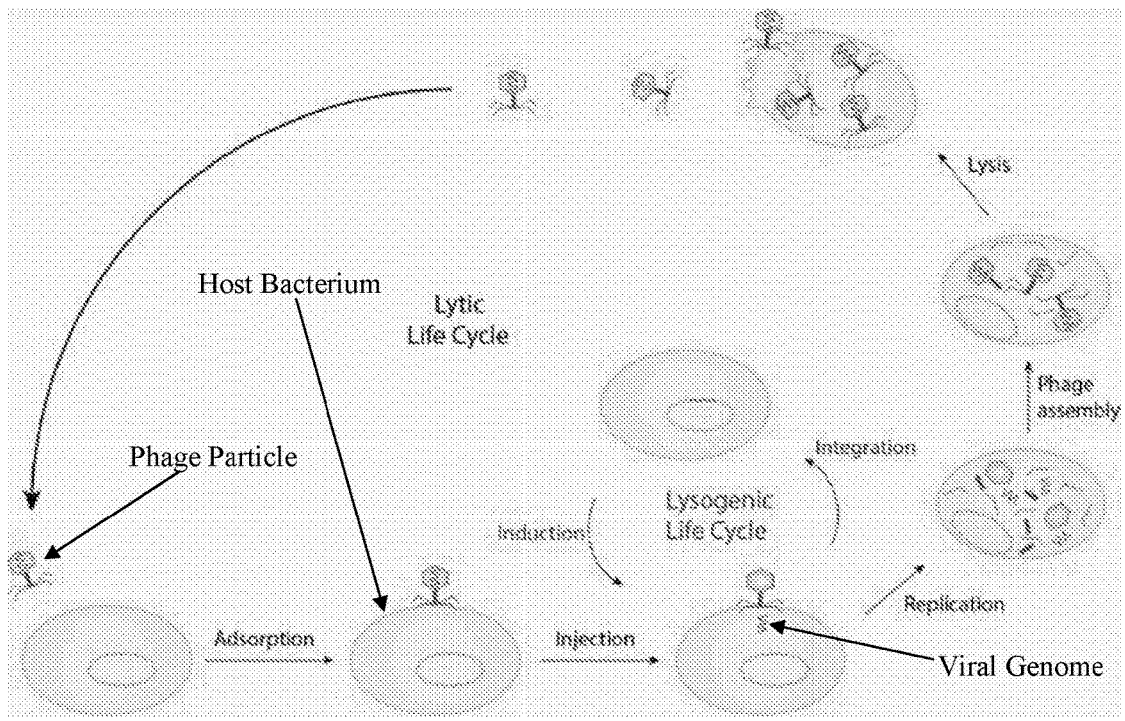
FIG. 10. illustrates life-cycles of exemplary bacteriophages. Anticlockwise from bottom left: A phage particle recognizes and adsorbs onto the surface of the host bacterium. The phage genome is injected into the bacteria. In the lysogenic life cycle, this DNA gets integrated into the bacterial genome and replicates with it for several cycles. In the lytic life cycle, the genome does not integrate and proceeds to hijack the host machinery to replicate its genome and phage structural components. The fully assembled phage then lyses the cell, typically by producing endolysins and holins at the late stage of infection. The liberated phages are now free to seek out and infect a new host bacterium, initiating another lytic cycle.

Upon validating the low immunogenic potential of the probiotic strains showing that they produced less lipase and adhered less tightly to epithelial cells, the inflammatory response of these strains was tested in a mouse ear inflammation model, which is well established and has been used previously to evaluate the inflammatory potential of P. acnes in the context of acne. The inflammatory potential of pathogenic and probiotic strains was compared in the following study: $10^{10}$ cfu of a strain was injected into the ears of CBA/J mice. A cohort of 5 mice was assigned to each strain. After 5 days the ears were excised and examined for inflammation. The levels of several inflammatory cytokines (IL-1 β, IL-6, IL-17, TNFα) were measured and the sections of the tissue were examined by histology. FIG. 10 shows that the pathogenic strain had significantly higher levels of IL-1β, IL-6, IL-17, and TNFα compared to the probiotic strain.

Acute Dermal Safety and Toxicity of Probiotic Strains in Miniswine Skin Model.

A miniswine model was used to test the probiotic strain for skin irritation. Swine are one of the major animals used in translational research, and pig skin is physiologically, anatomically, biochemically and immunologically similar to human skin. Miniswine are particularly commonly used to model human dermal diseases and conditions like acne [Vet Pathol (2012) 49:344-356]. The probiotic strain was applied to the skin of three separate miniswine in two doses—$10^8$ cfu and $10^9$ cfu—in delimited skin areas. The animals were observed daily for clinical signs and the dosing site skin was scored using the Draize Scoring System at pre-dose, 0.5, 1, 4, 8, and 24 hours post dose administration. There was no erythema or edema associated with the lead probiotic strain during the entire period (Table 1), and a Draize score of 0 was observed throughout. This demonstrates the safety to acute exposure of our probiotic strain in an animal skin model.

Table 1: Acute dermal safety/tox in miniswine skin model shows good safety profile of probiotic strain. Probiotic bacteria was applied at normal ($10^8$ cfu) and acute ($10^9$ cfu) doses on delimited skin areas in 3 male miniswine and monitored for 24 hours post-application. Erythema and edema were quantified using the Draize Scoring System. The Draize score provides the relative severity of erythema and edema. A Draize score of 0, indicating complete absence of erythema and edema, was observed on all the skin areas throughout the monitoring period.

| Group (Animal) | Dose Site | Treatment | Dose Level | Total Sites with non-zero Draize score* |
|---|---|---|---|---|
| 3 Male | Left #1 | P. acnes Normal | ~$10^8$ CFU | 0 |
| | Right #1 | P. acnes Acute | ~$10^9$ CFU | 0 |
| | Left #2 | PHIT-101 Normal | ~$10^8$ CFU | 0 |
| | Right #2 | PHIT-101 Acute | ~$10^9$ CFU | 0 |

Example 3. Bacteriophage Stability in Compositions with Anti-Acne Compounds

Figure 15:
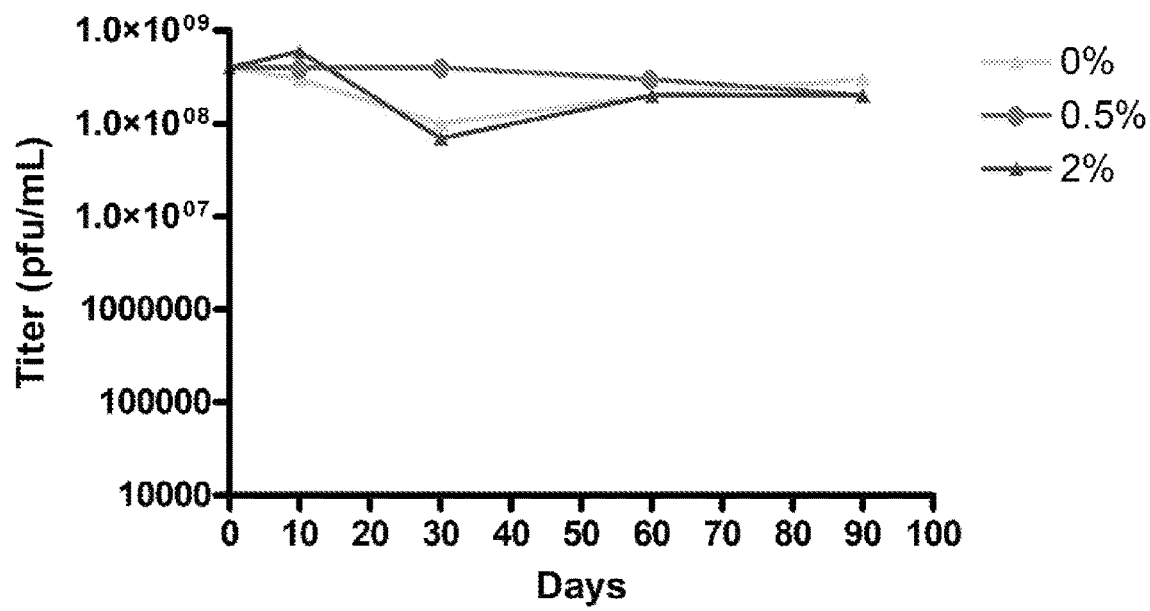
FIG. 15 is a graph showing that a phage remains stable in the presence of low (0.5% w/v) and high (2% w/v) concentrations of salicylic acid.
Figure 16:
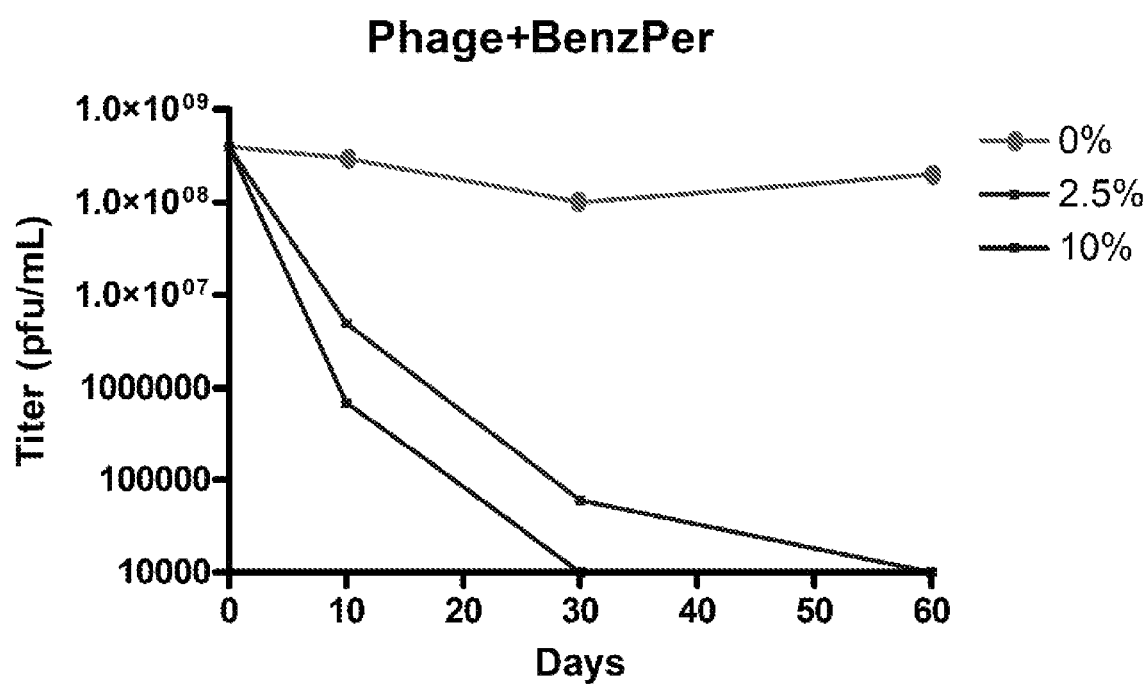
FIG. 16 is a graph showing that a phage loses its viability in the presence of benzoyl peroxide over 60 days. The rate of loss of phage viability is greater at the higher concentration (10% w/v) compared to the lower concentration (2.5% w/v).

In order to determine whether the phage was stable in co-formulation with either salicylic acid or benzoyl peroxide (BPO), the phage was co-incubated with these agents at a low and high concentration. The range of concentrations was determined by the permitted concentrations of these agents specified in the United States Food and Drug Administration (FDA) acne monograph for over-the-counter use. For salicylic acid, this is 0.5% to 2% (w/v), while for BPO the range is 2.5% to 10% (w/v). Buffered solutions of phage were added to these agents, and its stability at 4° C. was tested over 60-90 days. FIG. 15 shows that the phages are stable in the presence of both low and high doses of salicylic acid. In contrast, FIG. 16 shows that benzoyl peroxide destabilizes the phages, and the observed rate of decrease in phage viability is steeper at a higher concentration of BPO.

Example 4 (Prophetic). Treatment with a Combination of Bacteriophage with Salicylic Acid A double-blind, placebo-controlled study of a composition comprising *Propionibacterium acnes* bacteriophage and salicylic acid is conducted determine the comparative efficacy of this treatment with placebo, *Propionibacterium acnes* bacteriophage alone, and salicylic acid alone. Concentrations of 0.5% and 2% (w/v) salicylic acid are administered with and without *Propionibacterium acnes* bacteriophage. In all conditions that include the *Propionibacterium acnes* bacteriophage, the phage is present in a dose of $10^9$ pfu (plaque forming units) per dose. Ten subjects who have comparably severe acne are treated for each of the following groups:
  (i) Placebo (no active agent)
  (ii) 0.5% salicylic acid as the sole active agent
  (iii) 2% salicylic acid as the sole active agent
  (iv) *Propionibacterium acnes* bacteriophage as the sole active agent
  (v) the combination of 0.5% salicylic acid and *Propionibacterium acnes* bacteriophage (in a single composition)
  (vi) the combination of 2% salicylic acid and *Propionibacterium acnes* bacteriophage (in a single composition)

The combination of the *Propionibacterium* acne bacteriophage with salicylic acid achieves more than an additive effect, i.e., a synergistic effect (the combined effect of the bacteriophage and the salicylic acid is greater than the sum of the effects of the bacteriophage and the salicylic acid when each agent is used separately) in treating acne. The effectiveness of treatment is measured using lesion counts and an IGA (investigator global assessment) score.

Example 5 (Prophetic). Treatment with a Combination of Bacteriophage with Sulfur A double-blind, placebo-controlled study of a composition comprising *Propionibacterium acnes* bacteriophage and sulfur is conducted determine the comparative efficacy of this treatment with placebo, *Propionibacterium acnes* bacteriophage alone, and sulfur alone. Concentrations of 3% and 10% (w/v) sulfur are administered with and without *Propionibacterium acnes* bacteriophage. In all conditions that include the *Propionibacterium acnes* bacteriophage, the phage is present in a dose of $10^9$ pfu per dose. Ten subjects who have comparably severe acne are treated for each of the following groups:
  (i) Placebo (no active agent)
  (ii) 3% sulfur as the sole active agent
  (iii) 10% sulfur as the sole active agent (iv) *Propionibacterium acnes* bacteriophage as the sole active agent
(v) the combination of 3% sulfur and *Propionibacterium acnes* bacteriophage (in a single composition)
(vi) the combination of 10% sulfur and *Propionibacterium acnes* bacteriophage (in a single composition)

The combination of the *Propionibacterium* acne bacteriophage with sulfur achieves more than an additive effect, i.e., a synergistic effect (the combined effect of the bacteriophage and the sulfur is greater than the sum of the effects of the bacteriophage and the sulfur when each agent is used separately) in treating acne. The effectiveness of treatment is measured using lesion counts and an IGA (investigator global assessment) score.

Example 6 (Prophetic). Treatment with a Combination of Bacteriophage with Benzoyl Peroxide A double-blind, placebo-controlled study of a composition comprising *Propionibacterium acnes* bacteriophage and BPO is conducted determine the comparative efficacy of this treatment with placebo, *Propionibacterium acnes* bacteriophage alone, and BPO alone. Concentrations of 2.5% and 10% (w/v) BPO are administered with and without *Propionibacterium acnes* bacteriophage. In all conditions that include the *Propionibacterium acnes* bacteriophage, the phage is present in a dose of $10^9$ pfu per dose. Ten subjects who have comparably severe acne are treated for each of the following groups:
(i) Placebo (no active agent)
(ii) 2.5% BPO as the sole active agent
(iii) 10% BPO as the sole active agent
(iv) *Propionibacterium acnes* bacteriophage as the sole active agent
(v) the combination of 2.5% BPO and *Propionibacterium acnes* bacteriophage (in separate compositions)
(vi) the combination of 10% BPO and *Propionibacterium acnes* bacteriophage (in a single compositions)

The combination of the *Propionibacterium* acne bacteriophage with BPO achieves more than an additive effect, i.e., a synergistic effect (the combined effect of the bacteriophage and the BPO is greater than the sum of the effects of the bacteriophage and the BPO when each agent is used separately) in treating acne. The effectiveness of treatment is measured using lesion counts and an IGA (investigator global assessment) score.

Example 7 (Prophetic). Assay with a Combination of Bacteriophage with Benzoyl Peroxide An in vitro study is performed to determine the efficacy of (i) BPO; (ii) *Propionibacterium* acne bacteriophage; or (iii) *Propionibacterium* acne bacteriophage+BPO in killing planktonic and sessile pathogenic *P. acnes* bacteria.

The combination of the *Propionibacterium* acne bacteriophage with BPO achieves more than an additive effect, i.e., a synergistic effect (the combined effect of the bacteriophage and the BPO is greater than the sum of the effects of the bacteriophage and the BPO when each agent is used separately) in killing sessile pathogenic *P. acnes* bacteria. The keratolytic action of BPO (similar to salicylic acid and retinoids) assists the phage in penetrating skin pores to access the *P. acnes* deep within the pores.

What is claimed is:

1. A composition comprising therapeutically effective amounts of: (a) at least one *Propionibacterium* bacteriophage, wherein the genome of the *Propionibacterium* bacteriophage comprises a nucleotide sequence that is at least 90%, 95%, 96%, 97%, 98%, or 99% identical to the nucleotide sequence of SEQ ID NO: 1; (b) at least one anti-acne compound; and (c) a pharmaceutically acceptable carrier.

2. The composition of claim 1, wherein the anti-acne compound is one or more of salicylic acid, benzoyl peroxide, and sulfur.

3. The composition of claim 1, wherein the *Propionibacterium* bacteriophage has one or more of the following properties:
   a) it is a lytic *Propionibacterium acnes* (*P. acnes*) bacteriophage;
   b) it is a linear double stranded DNA genome;
   c) it is within the bacteriophage family Siphoviridae.

4. The composition of claim 1, further comprising a biofilm degrading enzyme.

5. The composition of claim 4, wherein the enzyme is a *P. acnes* biofilm degrading enzyme.

6. The composition of claim 4, wherein the enzyme is one of:
   a glycosidase;
   a protease;
   a DNAse;
   a restriction endonuclease;
   catalyst of hydrolysis of linear polymers of N-acetyl-D-glucosamines;
   a β-hexosaminidase;
   hydrolyzes β-1,6-glycosidic linkages of acetylglucosamine polymers;
   a restriction endonuclease;
   papain;
   bromelain;
   Trypsin;
   Proteinase K;
   Subtilisin;
   Serratiopeptidase;

Dispersin;
alginate lyase;
amylase;
cellulase;
Dispersin B;
a protease;
an anti-aging enzyme;
superoxide dismutase; or
a peroxidase.

7. The composition of claim 1, further comprising a probiotic bacterium, *P. acnes* bacterium comprising at least one of the following characteristics:
   (a) comprises a 16S rDNA sequence with a T992C mutation compared to the KPA171202 type strain 16S rDNA sequence set forth as SEQ ID NO: 2;
   (b) comprises a 16S rDNA sequence with a T838C mutation compared to the KPA171202 type strain 16S rDNA sequence set forth as SEQ ID NO: 2;
   (c) comprises a 16S rDNA sequence with a C1322T mutation compared to the KPA171202 type strain 16S rDNA sequence set forth as SEQ ID NO: 2;
   (d) comprises a 16S rDNA sequence with a C986T mutation compared to the KPA171202 type strain 16S rDNA sequence set forth as SEQ ID NO: 2;
   (e) comprises a 16S rDNA sequence that is identical to the sequence of SEQ ID NO: 3;
   (f) comprises a 16S rDNA sequence that is identical to the sequence of SEQ ID NO: 4;
   (g) does not comprise a linear plasmid;
   (h) does not comprise a plasmid that comprises a virulence factor;
   (i) does not comprises a plasmid that encodes an extrachromosomal lipase and/or a tight adhesion virulence factor;
   (j) produces less than about 20% of the level of lipase that is produced by a pathogenic *P. acnes* strain when grown in a planktonic culture;
   (k) produces less than about 10% of the level of lipase that is produced by a pathogenic *P. acnes* strain when grown in an adherent culture;
   (l) adheres to epithelial cells at least 50% less than a pathogenic *P. acnes* strain; or
   (m) is less inflammatory than a pathogenic *P. acnes* strain.

8. The composition of claim 7, wherein the probiotic bacterium includes at least one of:
   *Propionibacterium* sp.;
   *Staphylococcus* sp.;
   *Corynebacterium* sp.;
   a bacterium within class Betaproteobacteria;
   *Propionibacterium acnes*;
   *Propionibacterium granulosum*; or
   *Propionibacterium avidum*.

9. A composition comprising therapeutically effective amounts of at least one *Propionibacterium acnes* bacteriophage, wherein the genome of the *P. acnes* bacteriophage comprises a nucleotide sequence that is at least 90%, 95%, 96%, 97%, 98%, or 99% identical to the nucleotide sequence of SEQ ID NO: 1, and at least one compound selected from the group consisting of salicylic acid, benzoyl peroxide, and sulfur.

10. The composition of claim 1, wherein at least one of the *Propionibacterium* bacteriophage is a *Propionibacterium acnes* (*P. acnes*) bacteriophage, wherein the genome of the *P. acnes* bacteriophage comprises a nucleotide sequence of SEQ ID NO: 1, and wherein the anti-acne compound is salicylic acid.

11. The composition of claim 9, wherein the genome of the *P. acnes* bacteriophage comprises a nucleotide sequence of SEQ ID NO: 1, and wherein the anti-acne compound is sulfur.

12. The composition of claim 9, wherein the genome of the *P. acnes* bacteriophage comprises a nucleotide sequence of SEQ ID NO: 1, and wherein the anti-acne compound is benzoyl peroxide.

13. A method for treating acne in a subject in need thereof, the method comprising: topically administering a therapeutically effective amount of the composition of claim 9 to a region of the subject's skin comprising the acne.

14. The composition of claim 1, wherein the genome of the *P. acnes* bacteriophage comprises a nucleotide sequence of SEQ ID NO: 1, and wherein the anti-acne compound is sulfur.

15. The composition of claim 1, wherein the genome of the *P. acnes* bacteriophage comprises a nucleotide sequence of SEQ ID NO: 1, and wherein the anti-acne compound is benzoyl peroxide.

16. A method for treating acne in a subject in need thereof, the method comprising: topically administering a therapeutically effective amount of the composition of claim 1 to a region of the subject's skin comprising the acne.

17. The method of claim 16, comprising: prior to topical administration, pretreating the region of the subject's skin with a composition comprising benzoyl peroxide.

18. The method of claim 16, wherein the benzoyl peroxide composition is washed off of the region of the subject's skin prior to the topical administration of the composition.

\* \* \* \* \*

UNITED STATES PATENT AND TRADEMARK OFFICE
CERTIFICATE OF CORRECTION

PATENT NO. : 11,903,984 B1
APPLICATION NO. : 17/819050
DATED : February 20, 2024
INVENTOR(S) : Yug Varma et al.

It is certified that error appears in the above-identified patent and that said Letters Patent is hereby corrected as shown below:

In the Specification

Column 1, Lines 8-11, "This application claims the benefit of priority to U.S. Provisional Application No. 62/488,326, filed Apr. 21, 2017, which is hereby incorporated by reference in its entirety and or all purposes." should be --This application is a continuation of U.S. Application No. 16/606,158, which is a United States national stage filing under 35 U.S.C. 371 of International Patent Application No. PCT /US2018/028556, filed April 20, 2018, which claims the benefit of priority to U.S. Provisional Application No. 62/488,326, filed Apr. 21, 2017, all of which are hereby incorporated by reference in their entirety for all purposes.--.

Column 11, Line 29, "an a" should be --an α--.

Column 74, Line 29, "(3-" should be --β– --.

Column 77, Line 57, "(3-" should be --β– --.

Signed and Sealed this
Fifteenth Day of April, 2025

Coke Morgan Stewart
*Acting Director of the United States Patent and Trademark Office*

SEQUENCE LISTING

```
Sequence total quantity: 28
SEQ ID NO: 1              moltype = DNA   length = 29752
FEATURE                   Location/Qualifiers
misc_feature              1..29752
                          note = Propionibacterium acnes bacteriophage
source                    1..29752
                          mol_type = genomic DNA
                          organism = Cutibacterium acnes
SEQUENCE: 1
agtgaaatac ctcccttttg tggttttgtc tgtttgtcga cttttttgtgt tggtggtgag    60
tgttgtgcag cctgagcttc ctgagtctcg tgagtggtgt ggggagacgc gtcgttggtg   120
gcgtgtgtgg ggtgaggata gtcgcgcgcc gtatgtgtct gatgaggagt ggttgtttct   180
tatggatgct gcggtgattc atgattgtgt gtggcgtgag ggtcgcgcgg atttggtggc   240
ttcgcttcgt gcgcatgtga aggcttttat gggcatgttg gataggtatt cggttgatgt   300
ggcgtctggt ggccgtggtg ggggttctgc tgtggcgatg attgaccggt ataggaagcg   360
taggggggct tgagtaggtg tctggtgttg ttgggtctca ggttcctcgt caccgtgtgg   420
ctgcggcgta ttcggtgtct gctgggggtg atgctgggga gcttggtcgt gcgtatgggt   480
tgacgcctga tccgtggcag cagcaggtgt tggatgattg gctggctgtc ggtagcaatg   540
gcaggcttgc ttctggtgtg tgtggggtgt ttgttccgcg gcagaatggc aagaatgcta   600
ttttggagat tgtggagttg tttaaggcga ctattcaggg tcgccgtatt ttgcatacgg   660
ctcacgagtt gaagtcggct cgtaaggcgt ttatgcggtt gaggtcgttt tttgagaatg   720
agcggcagtt tcctgacttg tatcgtatgg tgaagtcgat tcgtgcgacg aatggtcagg   780
aggctattgt gttgcatcat ccggattgtg ccacttttga gaagaagtgt ggctgcagcg   840
gttggggttc ggttgagttt gtggctcgta gccgggttc ggctcgcggg tttacggttg   900
atgatttggt gtgtgatgag gctcaggagt tgtcggatga gcagttggag gctttgcttc   960
ctacggtaag tgctgccccg tctggtgatc cgcagcagat tttccttggt acgccgcctg  1020
ggccgttggc tgatggttct gtggtgttgc gtttgcgttg ggagcgctt ggtggcggta  1080
aaaggtttgc gtggacggag ttttcgattc ctgacgagtc tgatccggat gatgtgtcgc  1140
ggcagtggcg gaagttggcg ggggatacga atccggcgtt ggggcgtcgc ctgaattttg  1200
ggaccgtaag cgatgagcat gagtcgatgt ctgctgccgg ttttgctcgg gagcggcttg  1260
gctggtggga tcgtggccag tctgctgcgt ctgtggttcc tgctgataag tgggctcagt  1320
ctgcggtgga tgaggcgagt ctggttggcg ggaaagtgtt tggtgctctcg ttttctcgtt  1380
ctggggatcg ggttgctttg gcgggtgccg gcaagactga tgctgggtt catgttgagg  1440
ttattgatgg gctgtcggga acgattgttg atggtgtggg ccggttggct gactggttgg  1500
cggttcgttg gggtgatact gaccggatca tggttgccgg gtctggtgcg gtgttgttgc  1560
agaaggcgtt gacggatcgt ggtattccgg gccgtggcgt ggtggttgct gatactggcg  1620
tttatgtgga ggcttgtcag gcgtttcttg agggtgtcag gtcgggtgtg atcagtcatc  1680
```

```
ctcgtgctga ttctcgccgt gacatgttgg atattgctgt gaggtcggct gtgcagaagc  1740
gtaaggggtc tgcgtggggt tggggttcct cgtttaagga tggttctgag gttcctttgg  1800
aggctgtgtc tttggcgttt ttgggggcta aacgtgttcg tcgtggccgt cgggagcgta  1860
gtggtaggaa gcgggtgtct gtggtatgaa ctcggatgag ttggctctga ttgagggcat  1920
gtacgatcgt atccaaaggt tgtcttcgtg gcattgtttgt attgagggct actatgaggg  1980
ctctaatcgg gtgcgtgacc ttggtgtggc tattccgccg gagttgcagc gtgtgcagac  2040
tgtggtgtcg tggcctggta tagctgtgga tgctttggag gagcgtctgg attggcttgg  2100
ctggactaat ggtgacggct acggccttga tggtgtgtat gctgcgaatc ggcttgctac  2160
ggcgtcgtgt gatgtgcatt tggatgcgct gattttttggg ttgtcgtttg ttgcgatcat  2220
tcctcatggt gatggtacgg tgtcggttcg tccgcagtca ccaaagaatt gtacgggcaa  2280
gttttcggct gacgggtctc gtttggatgc gggtttggtg gtgcagcaga cgtgtgatcc  2340
tgaggttgtt gaggctgagc ttttgcttcc tgatgtgatt gttcaggtgg agcggcgggg  2400
ttcgcgtgaa tgggttgagg tggatcgtat accgaatgtg ttgggtgcgg ttccgttggt  2460
gcctattgtg aatcgtcgcc gtacttctag gattgatgcc cgttcggaga ttacgaggtc  2520
tattagggct tacacggatg aggctgtgcg cacactgttg gggcagtctg tgaatcgtga  2580
ttttttatgcg tatcctcagc gttgggtgac tggcgtgagc gcggatgagt tttcgcagcc  2640
tggctgggtc ctgtcgatgg cttctgtgtg ggctgtggat aaggatgatg acggtgacac  2700
tccgaaggtg gggtcgtttc ctgtcaatag tcctacaccg tattcggatc agatgagact  2760
gttggcgcag ttgactgcgg gtgaggcggc tgttccggaa cgctatttcg ggtttatcac  2820
gtctaaccca cctagtgggg aggctttggc tgccgaggaa tctcggcttg tgaagcgtgc  2880
tgagcggcgt caaacgtcgt ttggtcaggg ttggctgtcg gttggttttt tggctgccaa  2940
ggcgttggat tctcgtgttg atgaggccga ttttttggt gatgttggtt tgcgttggcg  3000
tgatgcttcg acgcctaccc gggcggctac ggctgatgct gtgacgaagc ttgttggtgc  3060
cggtattttg cctgctgatt ctcgtacggt gttggagatg ttggggcttg atgatgtgca  3120
ggttgaggct gtgatgcgtc atcgtgctga gtcgtctgac ccgttggcgg tgcttgctgg  3180
ggctatatcg cgtcaaacta acgaggtatg ataggccgtg tcggggtattg ttgaggcgag  3240
gcttgcggcg actgagtatc agcgtgaggc ggtcaggttt gctgggaagt atgcgggcta  3300
ttattctgag cttggtcgtt tgtgcggtgc cggcaggatg agtgacacgc agtatgtgcg  3360
tttgtgtgtg gagttggagc gtgccggcca tgatggttcg gcatcgttgg ctgccaggtt  3420
tgtgtcggat tttcgccgtt tgaatgtggt ggatccggtt ttgattgtgt atgacgagtt  3480
tgatgctgcg gcggctttgg ctaggtctat ttcgaccacg aagattcttg agagtgaccc  3540
ggatagggcg aatgacacga ttgatgcgat ggcggcgggt tttgatcggg ctgttatgaa  3600
tgctggccgt gacacggttg agtggtctgc gggtgcgcag ggtaggtcgt ggcgtcgggt  3660
gacggatggt gatccgtgtg cttttttgtgc catgttggct acgaggtcgg attatacgac  3720
aaaagagagg gcacttacta ctggacatac tcggcgtcat acgacggtgt gtaagcgtcc  3780
gtttggttcg aagtatcatg atcattgtgg ttgtacggtg gttgaggttg ttggcccttg  3840
ggaaccaaat agggctgatg ccgagtatca gaggacgtat gagaaggcct gtgagtgggt  3900
tgatgatcat gggttgcagc aatcgcctgg caatattttg aaggctatgc gtactgttgg  3960
cgacatgaga taatttgatg tggtttccgg ttgtgcgccg ccggttattg gtgcacaggg  4020
ttgtctcccg cacggggtc aacaatattg tgttgttttc cgcaaggagt gtagggttag  4080
gctatgccg atcagagtgt tgaggaacag aatgttgaca atgatgttgt ggagtccgga  4140
aaggataacg gcattgttga tacagtaaaa gacgatggcg ggcaggaggt agccgacaat  4200
cagttgaaga atgaaggcga gggtaaatcg ccggggacgt attggaaggc tgaggccccgt  4260
aagtgggagt ctcgtgctaa aagtaattttt gccgagttgg agaagcttcg cgcctcggat  4320
ggtgatgcgg ggtctacgat tgatgagctt cgccgcaaga atgaggaact cgaagaccgg  4380
atcaatgggt ttgttcttga gggtgtgaag cgcgaggtgg ctgccgagtg tggcctgtcg  4440
ggtgatgtcg tcgcttttctt gtcgggtggc gataaggagt cgcttgccga gtctgcgaaa  4500
gctttgaagg gtttgatcga ccatagtagt ggtggcgcgg gtgtgcgccg tcttgcgggg  4560
agtgccccg ttgatgatgt taaacgacgt gagggtgtcg cgtttgtgga tgctcttgtc  4620
aataattcta ggagatgatt tgtgatggct gacgattttc tttctgcagg gaagcttgag  4680
cttcctggtt ctatgattgg tgcggttcgt gaccgtgcta tcgattctgg tgtttttggcg  4740
aagctttcgc cggagcagcc gactattttc gggcctgtga agggtgccgt gtttagtggt  4800
gttcctcgcg ccaagattgt tggtgagggc gaggttaagc cttccgcgtc tgttgatgtt  4860
tcggcgttta ctgcgcagcc tatcaaggtt gtgactcagc agcgtgtctc ggatgagttt  4920
atgtgggctg atgctgatta ccgtctgggt gtgcttcagg atctgatttc cccggctctt  4980
ggtgcttcga ttggtcgcgc cgtgtggatctg attgctttcc atggtattga tcctgccact  5040
ggtaaagcgg cttccgctgt gcatacttcg ctgaataaga cgaagaatat tgttgatgcc  5100
acggattctg ctacgcgtga tcttgttaag gctgtcggcc tgattgctgg tgctggtttg  5160
caggttccta acggggttgc tttggatccg gcgttctcgt ttcgctgtc tactgaggtg  5220
tatccgaagg ggtctccgct tgccggtcag cctatgtatc ctgccgccgg gtttgccggt  5280
ttggataatt ggcgcgggct gaatgttggt gcttcttcga ctgtttctgg cgccccggag  5340
atgtcgcctg cctctggcgt taaggctatt gttggtgatt tctctcgtgt tcattgggt  5400
ttccagcgta acttcccgat cgagcttatc gagtatggtg acccggatca gactgggcgt  5460
gacttgaagg gccataatga ggttatgtt cgtgccgagg ctgtcctgta tgttgcgatt  5520
gagtcgcttg attcgtttgc tgttgtgaag gagaaggctg ccccgaagcc taatccgccg  5580
gccgagaact gattcatttg ttgcggtgat gttttctatg tgcagggggt ggtgttgatg  5640
ggtatcattt tgaagcctga ggatattgag cctttcgccg atattcctag agagaagctt  5700
gaggcgatga ttgccgatgt ggaggctgtg gctgtcagtg tcgcccctg tatcgctaaa  5760
ccggatttca aatacaagga tgccgctaag gctattctgc gcagggccct gttgcgctgg  5820
aatgataccg gggtttcggg tcaggtgcag tacgagtctg cgggccgtt tgctcagact  5880
acacggtcga atactcccac gaatttgttt tggccttctg agattgccgc gttgaagaag  5940
ttgtgtgagg tgatggtgg ggctggtaaa gcgttcacta ttacaccgac catgaggagt  6000
agtgtgaatc atttctgaggt gtgttccacg gtgtggggtg agggttgctc gtgcggatct  6060
gatattaacg gcgtatggt ccctttgtgg gagatatgat atgaccggtt ttccttacgg  6120
tgaaacggtt gtgatgcttc aaccgactgt tcgtgtcgat gatcttggcg acaaggtgga  6180
agactggtct aagcctgtcg agactgtgta ccataacgtg gccatctatg cttccgtttc  6240
gcaggaggat gaggctgccg gccgtgactc tgactatgag cattggtcga tgcttttcaa  6300
gcagcctgtt gtgggtgccg gttatcgttg ccggtgcgt attcggggtg tggtttggga  6360
ggcggacggg tctcctatcg tgtggcatca tccgatgtct ggttgggatg ctggtacgca  6420
```

```
ggttaatgtg aagcgtaaga agggctgatg ggttgtggct caggatgtga atgtgaagct   6480
gaacttgccg ggtattcgtg aggtgttgaa gtcttctggg gtgcagtcga tgttggctga   6540
gcgtggcgag cgggtgaggc gtgcggcttc ggcgaatgtt ggcggtaatg cttttgatag   6600
ggcccaatac cgtagtggtt tgtcgtcgga ggtgcaggtt caccgtgtgg aggctgtggc   6660
gaggattggc accacctata agggtgggaa gcgtattgag gcgaagcatg gcacgttggc   6720
gaggtcgatt ggggctgcgt cgtgatcgtt tacggtgatc cgcgtgtgtg ggctaaacgt   6780
gtgctcaagg atgatggctg gctgtccgat ataccctgtg tggggacggt gcctgacgat   6840
ttcagcggtg acctgatttg gttggcgttg atggcggcc cacagttgca tgttcgcgag    6900
caggtgtttt tgcgggtgaa cgtgttttct gatatgcctg atcgtgccat gtcgctagcc   6960
aggcgggttg aggctgtcct tgtagacggt gtggacggtg acccggtggt gttttgtcga   7020
cggtctactg gccctgattt gctggttgat ggtgcacgtt ttgatgtgta ttcgctgttt   7080
gagctgatat gcaggcctgt cgaatccgag taaacgtttt gttttgatat tgttgtttgt   7140
tttttgtttg atattgtttt tgggggttat gatggctgga acacgtaaag cgtctaatgt   7200
tcgttccgcg gttacgggtg acgtctatat tggtaaagct catgccggtg acactattga   7260
tggtgtgaag acggttcctg acgggcttac agctttaggg tatctgtctg atgacgggtt   7320
taagattaaa ccggagcgta aaacggatga tttgaaggct tggcagaatg cggatgttgt   7380
tcgcactgtg gctacggaat cgtctatcga gatttcttc cagctgatcg agtctaagaa     7440
ggaggttatc gagctgtttt ggcagtcgaa ggttactgcc ggagccgatt cgggttcgtt   7500
cgatatttct cctggtgcca cgacgggtgt tcatgccctg ttgatggata ttgttgatgg   7560
cgatcaggtt attcgctact atttcccctga ggttgagttg atcgatcgtg acgagattaa   7620
gggtaagaat ggcgaggtgt atgggtatgg tgtgacgttg aaggcgtatc ctgcccagat   7680
taataagaag ggtgatgcgg tgtctggtcg gggtgggatg aggctttaa aagctgatac     7740
tcctccgact cctcctccgg ccccgaatcc tccgaagcct gagccggatc cgaatccgcc   7800
gtctaataac tgatacacat agtttgaggg attgttgata gatgagtgac acgggttaca   7860
cgttgaagat tggtgaccgt agctgggtgt tggcggatgc ggaggagacg gctcaggctg   7920
ttcctgcccg cgttttccgt cgtgctgcta agattgccca gtcgggtgag tctgcggatt   7980
tcgcccaggt tgaggtgatg ttttctatgt tggaggctgc cgccccgcgt gacgcggtgg   8040
aggccctgga ggggcttcct atggttcgtg tggccgagat tttccgccag tggatggaat   8100
acaagcctga cggtaagggt gcctcgctgg gggaatagtt tggctccacg gcctgattga   8160
tgattatcgt ggggccatcg aatacgattt ccgcaccaag ttggtgtttt ctgttttatag   8220
tgttggtggc ccgcagatgt gttggggtga ggctgtccgg ctggctggcg tgttgtgtac   8280
cgatacgtct agccagttgg cggcccacct gaatggttgg aagcgcccgt ttgagtggtg   8340
cgagtgggct gtgttggaca tgctggatca ttacaggtct gctaatagtt aggggcagcc   8400
ggagcctgtg gcgaggccta cggatgagcg taggggcccgg tttacgtctg ggcaggtgga   8460
cgatattttg gcgcgtgttc gtgctggtgg cggggtgtct cgcagatta atattatggg     8520
gtgaatagtg tatgtctggt gagattgctt ccgcatatgt gtcgttgtat acgaagatgc   8580
ctggtttgaa ggcggatgtt ggtaaacagc tttctggggt gatgcctgct gagggtcagc   8640
gttcgggtag tttgtttgct aagggaatga agttggctct tggtggtgcg gcgatgatgg   8700
gtgccatcaa tgttgctaag aagggcctca agtcgattta tgatgtgact attggtgggg   8760
gtattgctag ggcgatggct attgatgagg ctcaggctaa gttgactggt ttgggtcata   8820
cgtcttctga cacgtcttcg attatgaatt cggctattga ggctgttact ggtacgtcgt   8880
atgcgttggg ggatgcggcg tctacggctg cggcgttgtc tgcttcgggt gtgaagtctg   8940
gcgggcagat gacggatgtg ttgaagactg tcgccgatgt gtcttatatt tcgggtaagt   9000
cgtttcagga tacgggcgct atttttacgt ctgtgatggc tcgcggtaag ttgcagggtg   9060
atgacatgtt gcagcttact atggcggggt ttcctgtcct gtctttgctt gccaggcaga   9120
ctggtaaaac gtctgctgag gtgtcgcaga tggtgtcaaa ggggcagatt gattttaaca   9180
cgtttgcggc tgcgatgaag cttggcatgg gtggtgctgc gcaggcgtct ggtaagacgt   9240
ttgagggcgc tatgaagaat gttaaggcg cccctgggtta tcttggtgct acggctatgg    9300
ccccgtttct taacggggttg cggcagattt ttgttgcgtt gaatccggtt atcaagtctg   9360
tcacggattc cgtgaagccg atgtttgctg ccgtcgatgc tggtattcag cgtatgatgc   9420
cgtctatttt ggcgtgatt aaccgtatgc cggctatgat cactccgaatg aatgcacaga    9480
tgcgcgccaa ggtggagcag ttgaagggcg tttttgcaag gttgcatttg cctgttccta   9540
aggtgaattt gggtgccatg tttgctggcg gcaccgcagt gttcggtatt gttgctgcgg   9600
gtgttgggaa gcttgtcgcg gggtttgccc cgttggcggt gtcgtgaag aatctgttgc    9660
cgtcgtttgg tgctttgagg ggtgccgccg gggggcttgg tggcgtgttt cgcgccttgg   9720
gtggccctgt tggtattgtg atcggcttgt ttgctgccat gttttgctacg aacgcccagt    9780
tccgtgccgc tgttatgcag cttgtggggg tggtggccgg gctttgggg cagattatgg     9840
tcgccttgca gccattgttc gggattgttg ctggcgtggt tgccaggttg gctcccgttt    9900
ttggccagat tattggtatg gttgctggtt tggctgcccg gctggtgcct gttattggta   9960
tgcttattgc ccggctggtt cctgttatca cccagattat tggtatggta acccaggttg  10020
ctgccatgtt gttgccatg ctgatgccgg ttattcagge tgttgttgct gtgatacggc   10080
aggttattgg tgtggtcatg cagttgatac ctgttttgat gccggttgtg cagcagtttt  10140
tgggtgctgt catgtctgtt ttgccgccga tgttggttt gatacggtcg ctgataccgg    10200
tgatcatgtc gattatgcgt gtggtggtgc aggttgttgg tgccgtgcta caggtggtgg   10260
cccgtattat tccggttgtt atgccgattt atgtttcggt gattggattc attgccaaga  10320
tttatgctgc ggttatcgtt tttgaggcta aggttattgg cgctattctt cgtactatta   10380
cgtgattgtt gaatcattca gtgtctggcg tgaggtctat gggcacggcc atccagaatg  10440
gctggaatca tatcaaatcg tttacgtcgg cgttttattaa cggtttcaag tcgatcattt   10500
ctgccggtgt tgccgcgtgt gtggggtttt ttacgcgtgg tggtttgtcg gttgcctccc   10560
atgtgaggtc tggttttaac gcggcccgtg gtgctgtttc ttctgcgatg aatgctattc    10620
ggagtgttgt gtcttcggtg gcgtctgctg ttggcggggt tttcgggtcg atggcgtcta  10680
gggttcgtag tggtgctgtg cgcgggttta atggtgcccg gagtgcggct tcttctgcta    10740
tgcatgctat ggggtctgcg gtgtctaacg gtgtgcatgg tgtgctgggg ttttttccgga   10800
atttgcctga caattattagg ggcgccttgg gtagtatggg tgtgtcgtag gtgtcggctg   10860
gccgtgatgt ggtgtctggt ttgggtaacg gtatccggaa tgctttgagt ggcctgttgg   10920
atacggtgcg taacatgggt tcccagattg cgaacgcggc gaagtctgcg ctgggtattc   10980
attcccgtc tcgggtgttt cgtgacgagg ttggccgtca ggtgttgcc ggtttggctg     11040
aggggatcac cgggaatgct ggtttggcgt tggatgcgat gtctggtgtg gctggccgtc   11100
ttccggatgc tgtggatgcc cggtttggtg tgcgatcgtc tgtgggctcg tttacccgt    11160
```

```
acgaccggta tcggcgtgcg aacgagaaga gtgttgtggt gaatgtgaac ggacccacgt  11220
atggggatcc tgccgagttt gcgaagcgga ttgagcgtca gcagcgtgac gctttgaatg  11280
cgttggctta cgtgtgatcg aggggtgtt gtgcatgttt attcctgacc cgtctgatcg  11340
tgccggtttg actgtggatt ggactatgtt tccgttggtg ggtaatgctc cggagcgtgt  11400
gcttcatttg acggattata cggggtcgtc tccggtcatg ttgttgaatg attcgttgcg  11460
cggcctgggt atgcctgagg tggagcagtt ttctcaaacg catgttggtg tgcatggttc  11520
ggagtggcgc gggtttaatg tgaagcctcg cgaggtgact ttgccggtgt tggtgtcggg  11580
tgttgacccg gatccggtgg gcgggtttcg tgacggtttt ttgaaggcgt atgacgcgtt  11640
gtggtctgcg tttcctccgg gcgaggtggg ggagttgtct gtgaagactc ctgccggtcg  11700
tgagcgtgtg ttgaagtgcc ggtttgattc ggctgatgac acgtttacgg ttgatccggt  11760
gaaccgtggc tatgcgcgct atctgttgca tttgacagct tatgatccgt tttggtatgg  11820
ggatgagcaa aagtttcgtt ttagtaacgc gaagttgcag gattggttgg gtggcggccc  11880
tgtcggcaag aagggtaccg cgtttcctgt ggtgttaaca ccgggtgtgg gctcgggctg  11940
ggataacctg tctaataagg gtgatgtgcc tgcgtgcct gtgattcgtg ttgagggtcc  12000
tttggagtcg tggtctgtgc agattgatgg tttgcgtgtg tcttcggact atccggtcga  12060
ggagtttgat tggatcacta ttgatacgga tcctcgccag cagtctgcgt tgttgaacgg  12120
gtttgaggat gtgatggatc gtttgacaga gtgggagttt gcgcctatcc cgcctggcgg  12180
ttctaagagt gtgaatattg agatggttgg tttgggtgct attgttgtgt cgtgtgcagta  12240
caggttttt agggcttggt gaatagttga tggctggtct tgttccgcat gtaacattgt  12300
ttacacctga ttatcgccgt gtggcgccta tcaatttttt tgagtcgttg aagttgtcgt  12360
tgaagtggaa tggtttgtcg actttggagt tggtggtgtc gggggatcat tcgaggcttg  12420
acgggttgac gaagccggat gcgcggctgg ttgttgatta tggtggtggc cagattttt  12480
ctgggcctgt gcgtaaagtg catggtgtgg gtccgtggcg ttcttcccgt gtgactataa  12540
cgtgtgagga tgatattcgg ctgttgtggc gtatgttgat gtggcctgtg aattatcgtc  12600
ctggtttggt tggtatggag tggcgtgcgg acagggatta tgcccactat tcgggtgcgg  12660
ctgagtcggt tgctaagcag tgttggggg ataatgcttg gcgttttcg cctggtttgt  12720
ttatgaacga tgatgagagt cgtggccgct atattaagga ttttcaggtg cggtttcacg  12780
tgtttgccga taagttgttg ccggtgttgt cgtgggctcg gatgactgtc acggtgaacc  12840
agtttgagaa tgcgaagttt gatcagcgtg gtttgttgtt tgattgtgtg cctgctgtga  12900
cccggacgca tgtgttgact gccgagtctg gttcgattgt gtcgtgggag tatgtgcgtg  12960
acgccccgaa ggctacttcg gtggtggttg gtgccgcgg cgagggcaaa gatcggctgt  13020
tttgcgagga tgttgattcg atggccgagg atgactggtt tgatcgtgtc gaggtgttta  13080
aggatgcccg taacacggat tccgagaatg tgcatcttat tgatgaggct gagcgggtgt  13140
tgtccgagtc gggggctacg tcggggttta agatcgagtt ggctgagtcg gatgtgttgc  13200
ggtttggcc tggccgcctg atgccggtg atcttatcta tgtggatgtg ggctcgggc  13260
ctattgcgga gattgtgcgc cagattgatg tggagtgtga ttcgcctggt gatgggtgga  13320
cgaaggtgac tccggttgct gggggattatg aggataatcc gtcggcgctg ttggctcgcc  13380
gtgtggctgg tttggctgcg ggtgtgcggg attttgcaaaa attctaattg ttagggggtt  13440
gttgtggtta ttgtgtgtaa aggggtttgat ggtgtgttga ccgagtatga ttgggctcaa  13500
atgtctggtc tgatgggtaa tatgccgtcc gtgaaagggc cggatgattt tcgtgtcggg  13560
actacgattc agggttccac ggtgttgtgt gaggtcctgc cggggcaggc ttgggctcac  13620
ggggtgatgt gcacgtcgaa tgctgttgag acggtgacag tcagcttcc gggcccgggt  13680
gagaccgct acgactatgt tgtcctgtcg cgggattggc aggagaatac ggccaagttg  13740
gagattgttc ctgggggggcg tgcggagcgt gcccgtgacg tgttgcgtgc ggagcctggc  13800
gtgtaccatc agcagttgtt ggctactttg gtggtgtcgt ctaacgggtt gcagcagcag  13860
cttgacagga gggctatagc ggcccgtgtg gcgtttgggg agtctactgc atgtgatcct  13920
accccctgtgg agggtgaccg ggtgatggtg ccttctgggg ctgtgttgcc taatcatgct  13980
aacgagtgga tgctgttgtc tccgcggatt gagacgggca ctaagtcgat catgtttggc  14040
gggtctgctg tgtatgctta cacgattccg tttgatcgcc agtttgctag tccgcctgtt  14100
gtggtggcgt ctatgctac ggcggctggg ggcacgaccc agattgatgt gaaagcctac  14160
aatgtgactg cccaaaattt tagttttggcg tttattacga atgatggttc gaagccgaat  14220
ggtgtgcctg cggtgctaa ttggattgct gtcggcgtgt gactgtacag gtgttgtggc  14280
ggatggtgtg atgttggggg gctgtggtgt cgtggtttac tcctgcactg gtggcctcta  14340
tttgtaccgc gttggccacg gttttgggtt ctgttcaggc tgtcacgtct aaatctagga  14400
ggcgttttcg ccgcctgtcg gcgcaggtgg atgcgatgga agagtatacg tggggtgtgc  14460
ggcgcgaggt gcgaaggttt aacgccgggc ttcctgacga ggtggagcct atgcatctcc  14520
ctgatttgcc cgagtttttg aaagatactg ttgatggtgg aggtgagtag ggtgaggga  14580
gttggaggag gagaagcggc agcgccgcaa ttttgagaag gcttcactgg tgttgctgtt  14640
tttgtcgctt gtgttattgg ctgtggttgc tgcgggtgct ttgcgtttcg gggctgtatc  14700
ctctgacggg gattcggacg aggcgagggc ccagtcgaat ggtacagccg ccaagggttt  14760
agccagcagt gtgcggcagg tgtgtgctca gggtggacgg gagtctgtgc ggcttcacca  14820
gtctggtttg tgtgtggatg ctcagcgtgt tgagcgtagt gtgcagggtg tgccgggtcc  14880
tgccggtgag cgcggcccgc aaggcccggc aggtgtggac ggccgggatg tgttaatgg  14940
ttcggctggg ctgttggcc ctgtgggtcc gcagggtcc ccgggtttga atggtgtgaa  15000
aggtcctgac gggttgcctg cgcgtaacgg ttcggatggt cgtgatggtt ggacggtgt  15060
gaacggcaat gatggcgctg atgtcggga tggttcggcc ggtgagcgcg tgatgtgggg  15120
cccctcaggt cctgccggcc cgcaaggtgc acagggtgaa cggggtgagc gcggcccgc  15180
cggtgcgaat ggcacgaatg gcaaggacgg taaggatggt gccgacggcc gtgatgggcg  15240
ttcggttgtg tctgtgtact gtttcggtgg cctgccaggg tgtgaaacca tcacctgtgg  15300
ttaccgtgtc atcccgtaaa tagaagaaga gggaagggtg ttactagtgt tgattgtggt  15360
ttttggtggt ggtgtgtggt gagatacatt cctgcagcgc atcactctgc cggctctaat  15420
aatccggtga acagggttgt gattcatgca acatgcccgg atgtggggtt tccgtccgcc  15480
tcacgtaagg ggcgggcggt gtctacagca aactatttcg cttccccatc gtctggtggt  15540
tcggcgcatt atgtgtga tattggggag acggtgcaat gcttgtcga gcttctacgatt  15600
ggttggcatg ccccgccgaa tccgcattct ttgggtatcg agatttgcgc ggatgggggt  15660
tcgcatgcct cgttccgtgt gccggggcat gcttacactc gggagcagtg gcttgatccg  15720
caggtgtggc ctgccgttga gagggcggcg gtgctgtgta gacgtttgtg tgacaaatat  15780
aatgttccga aaaggaaact gtcggctgcc gatttgaagg ctgcaggcg gggtgtgtgt  15840
ggccatgtgg atgttacgga tgcgtggcat cagtcggatc atgacgatcc tgggccgtgg  15900
```

```
tttccgtggg acaaatttat ggccgtcgtc aacggcggca gtggagatag tggggagtta 15960
actgtggctg atgtgaaagc cttgcatgat cagattaaac aattgtctgc tcagcttact 16020
ggttcggtga ataagctgca ccatgatgtt ggtgtggttc aggttcagaa tggtgatttg 16080
ggtaaacgtg ttgatgcctt gtcgtgggtg aagaatcctg tgacggggaa gctgtggcgc 16140
actaaggatg ccctgtggag tgtctggtat tacgtgttgg agtgtcgtag ccgtcttgac 16200
aggctcgagt ctgctgtcaa cgatttgaaa aagtgatggt ggtttgttgt gggtaaacag 16260
ttttggttag gtttgctaga gcgggcggct aagacttttg tgcaaacgtt tgttgctgtg 16320
ttgggggtga cggcgggtgt cacgtatacg gcggagtcgt ttcgtggttt gccgtgggag 16380
tctgcgttga ttacggctac ggttgctgcg gtcctgtcgg tggctacctc gtttggtagc 16440
ccgtcgtttg tggctggtaa gccgaaaacc acgcctgtgg atgcgggttt ggttccgccg 16500
gatgatcccg gaatagtgga gcctcacatg gtggatgtgt cggatcctgg catgatcgag 16560
cctgcagatg atgtggatct tggtgtaggc tatgtgccga acatgctgc cgagtcgag 16620
gttggcacgg tagagtcgac tgttgcataa gtgaatatag atgtgtgccc cagcggtgct 16680
gccacgattg tgtggtggtt gccgctgggg cactattttt gtatattgcg gtgtggctat 16740
gattcgttgc tgtcgatggt gtcttcgagc atctggtaca ggtggaggca ggtagagata 16800
gtttcgctgg cctggtcgag aacgttccgg ccgataacat ttttgttgtt gtcgcggtgg 16860
cggatgatag accacatgat ctcgtcggct gccgcctgca atagttttgc ctggtatgcg 16920
attccagcga gccagtctag tgcttcctgg cttgcatagg gtgtctggtc ctcgctgttg 16980
cttgtggggt gtcctgcact gtcgcatagc cacaggattt cgctgcactc gtctagcgtg 17040
tcctggtcta tagcgagatc gtcgaggctg acattgttga cggtaaggtt cacgttgtcg 17100
agggagatgg gtacaccgta ctggttttcg acaccgtcaa caatgttttc caattgctgc 17160
atgttggtgg gctgttgttg gacgatacgg tgtatcgctg tgttgagggt ggtgtaggtg 17220
atattgtgtg tgttgttcat cgtgttatgc cattccttcg ttatcgtctg gcctgtagta 17280
tgtgctgttt gcgtactcgg ttaacgtcat cagtgtttgg tctgcccact gtttcacagt 17340
ctgccttgtc actccgagtc gttgggcggc tgtggcgtag gttggtcat accgtatac 17400
ttccctgaat gctgccaacc gtgccaaatg ttttcgctgt ttggatggct ggcaggcgag 17460
ggtgtagtcg tcgatggcta gctgtagatc gatcatgctg gcaatgttgt tgccgtggtg 17520
ttgtggcgcg gttggtgggg gtggcattcc tggctccaca ctgggtttcc atgggcctcc 17580
gttccagatc cattgggcgg cttggatgat gtctgcggtg gtgtaggttc ggttcactgg 17640
tcatccccctg aacaggttgt ctgggttgct ggtgcgaatc gtgtcgaatc gtccgacgca 17700
gtggcagtag tcgtacatga gtttgataat gtgttggtgg tctcccaaat aggtgtttcc 17760
gctgatgctg taggtggctg tgccgtcttt actaatagtg tatttggcgg tgatggtttc 17820
ggggttttcg gtgtcggtga tgatggctgt ggtggtggtg cctacggttt ggagcacggt 17880
ggtttgggtt ccgtcgtcga tggtggtttt aaccatgagg tgtgttctcc ctttgtgtta 17940
gttgctggtt tggttgtcgg ctagatgaat gatgtcggtt aagggtttcg gctggtctaa 18000
atgttgtgtg gttttgttgg ctagccgttt ggctaccctg tagcacattt tggtgtagtg 18060
tttgttgtct aggttgtggt attgttcccg caccgcaata tatagcaggg agtcttggta 18120
caggtcgtct gcattgattg cggggtagtg tgcggctgtt ttagtgcatg cccggttgag 18180
tgtgcgtaga tgatggtctg tggcccacac ccacgatgcg gtggtggcta ggtcggcttt 18240
tgttggtcgt cggctcatgg catctctttc atctggctat ctggtagttg tttggtgttt 18300
tgttgttgat agtgtagcac acgagtccgg ggtttccggt ggtgcccgtc ttgtgccggt 18360
accatgtgga ttcgccttcc atggatgggc attggatgaa ggtgcgttgt ccttgttcgg 18420
agatttctag gtggtgcctg tgtccggcca tgaggatgtg ggatgtggtg ccgttgtggga 18480
attcttgtcc gcgccaccaa tcatagtgtt tgccggtgcg ccattggtgg ccgtgggcgt 18540
gtagtatccg tgtgccggct acttcgacgg tggtggtcat ttcgtctcgg ctggggaaat 18600
aaaagtgtag gttggggtat tggttggtga gctggtaggc ttctgcgatg gcgcggcagc 18660
agtcacgtc gaaggagtcg tcgtaggtgg tgactccttt gccgaagcgt acggcttctc 18720
cgtggttgcc ggggatggat gtgatggtca cgttttttgca gtggtcgaac atgtggatga 18780
gttgcatcat ggccatgcgg gtgagcctga tttgttccgt caaggggggtt tgtgtgcgcc 18840
aggcgttgtt gcctccttgt gacacgtatc cttcgatcat gtcgccgagg aatgcgatgt 18900
ggactcgttc gggtttgcct gcctgctgcc agtagtgttt agctgatgtg agggagcgca 18960
ggtagtcgtc ggcgaagtgt gatgtttccc cgccggggat gcctttgccg atttggaagt 19020
cgcctgcccc gatgacgaag gccgcagtgc tgtagtcggt gcgggtgtcc tgttcgggtt 19080
ttgggggtgt ccattcggct agtttatcga cgagttcgtc tacagggtag gggtttgttg 19140
cgggttggtg gtcgatgatt ttttgtacgg atctgcctgt ttctccgttg gggagtgtcc 19200
attcggagat gcgtgtgcgg cgtacggtgc cgtttgcgag atcatcgcag atggtgtctg 19260
cttcgctatc gtggttggct agctgggtga gtagccggtc tatgttgtct atcactgggt 19320
atcctcttct tgcggggtgg tgttggcttg tttgcggcgg tagtcttta taacggtggc 19380
ggagatgggg tatcctgcct gggtgagctg ttttgctagc catgaggcgg ggatggtttt 19440
gtcggcgagc acgtcggcag ccttgttgcc gtagcgttgg atgagtgttt cagttttggt 19500
tgccatggtg tcctatcggt tgtgtggtgg gctgccatcc tgtgcggcag tcgccgtcgt 19560
ggcctggttt gcgtgtgcac cacgatacgg ttctgtctgt gtggttgagt gttttgccgc 19620
acatgacgtt ttgtagatgc tctggcagtg cgccgtcacc ctggttgctg gtttgtgtgt 19680
cgaagagtgt ttttcggttg gtgaaatgct cggacacggt gccattatgt acgggtagta 19740
tccatgtttt ccattgttgt tgtagccggg tgttccagtg gaattgtttt gctgcgttcg 19800
tggcttgttt gatggttttg tagtagccga cgaggatgcg ctggtgttca ctgtcgggag 19860
ggttttggcc tcgccagtat tgtgccgcca cggcgtagcg gttgctggct gtgaaggcgt 19920
cccagcagta ttcaataatg tgttgtagta cactatcggg catgtctcgt acttggtttt 19980
cgtcgagcca cgcgtcgaca atgatgttgc gtatggcgcg tttgtctttg gtggtggggt 20040
tgaatgcgat gctcacagta cgggcctgtc gtcttgcatg aaatcattaa aggatgattc 20100
gcttgcgcgg cgtgcttgtg tgatttgctg gtcagaccag tcggggtgtt gctgtttcag 20160
atagtaccag tggcacgcat gtaggtttc gtcttgtagc cgggtgagat ggttttcggt 20220
gatgatttgt ttccacatag tccatgacac gtcgagccgg tccaatatttt ccattgctgg 20280
aatgttgaac tggttcagga agagtatttc gtggggtgtag tattccttct cgtactggtc 20340
ccatccactt cggtgcctgt tgggctggtt ttggggtag gcttcccggc atactttgtg 20400
caaatgtttg gccatgtcgt cgggtagttt aatgtcaggg ttggcgcgga tcatggatcg 20460
catcccatca taggtggtgc cccaggtgtg catgatgtag gtgggtcttt caccatcagc 20520
ccatttttct gcacagatgg cgaggcggat gcgtctcctg gctgattggc tggtgttgcg 20580
ccggttgggg atggggcacg tgtcgagggg atccatgatg ttttggtgta cctttcttgg 20640
```

```
tttaggttgc ttgtgtggtt ttattgtagc actgtgtcta gtgcttgtgt caaccctgtt   20700
ttgccggcct gaaggtaggt gtctgtgaca tcccccaggg tgaggggcac atgggtggct   20760
tgggggagtg cggcctggag tgtttgggcc atctggtggc ccgccttgtc tgggtctgac   20820
cagatgtaga tgtggtcgta gccttcaaaa aatttggtcc aaaaagtttg ccacgaggtt   20880
gcgccgggta gggctacggc tggccatccg cattgttcga ggatcatgga gtcgaattcg   20940
ccttcgcaaa tgtgcatttc ggctgccggg ttggccatgg cggccatgtt gtagatggag   21000
cctgtgtctc ctgccggggt tagatatttg gggtggttgt gggttttgca atcatgttgg   21060
agtgagcagc ggaaacgcat ttttcgtatt tcggctggcc cttccagac ggggtacatg    21120
tatgggatgg tgatgcactg gttgtagttt tcgtggcctt ggatggggtc attgtcgatg   21180
tatccaaggt ggtggtagcg ggctgtttct tcgctgatgc ctcttgccga gagcaggtcg   21240
agtatgtttt cgaggtgggt ttcgtagcgg gctgaggctt tctggattcg gcggcgttcc   21300
gcaatgttgt aggggcgtat gctgtcgtac attcggtttt tcttcctcta atcgttgttt   21360
cagtttgtgt agtccgcctc cgataccgca tgtgtggcag taccagacgc ccttgtcgag   21420
gttgatgctc atggagggct ggtggtcgtc gtggaacggt cagaggatgt gttgctcgtt   21480
ccgtgacggg ttgtagcgta tctggtgggc gtctaggagg cggcaggtgt cagaggtgtg   21540
ggaggagctc gttgagggtt gataccacat aggcttcgct ccagggtttg ttgcgctgtt   21600
tcatgatgac gagtccgatg gtggattggt tttcgcggtt tcggtgtgtt tcgtagttgc   21660
gtgcctcccg gctggcttgt ttcacgaatt cggctaggtg tgcctgtcct gctttggctt   21720
cgatcacata ggttttgttg ccggttgtga ggatgaggtc gccttcgtct tctttaccgt   21780
tgaggtggag gcgttctata tcatagccgg tgtcgcgtag ctggtggagg agtcttgttt   21840
cccattcggc gccggctcgg cggttgcgtg cctgttgtgt tgacatgata gtcctttatg   21900
ttcttgtgtc atgttccagg gctgttttc tactagggcc ccgaagaatg tgtattcggg   21960
gtaggctcgt agtcgttcgt attttgttcc gtctggctg gatttgccgg ttctctgttt    22020
caggacggcg atgcgtgcct cggcggggat ggtgaggccg ttgccgttgt cttcgccacc   22080
atacaggag actcccaata tgagttgtgg ttttcggag aggccgtttt tgatttcccg     22140
cctagctggg gggtgttcga tgtcggtgcc ggttttgtcg gttgcgtggt gggtgacgat   22200
gatggtggag ccagtatctc tacctaaggc tgtgatccat tgcatggctt cttgctgtgc   22260
ctgatagtcg gattcgcagt cttggatgtc catcaggttg tctataacaa taatgggtgg   22320
gaaggtgttc cacatttcca tgtaggcttg cagttccatg gtgatgtctg tccatgtgat   22380
gggtgactgg aatgagaagg tgatgtgtcc gccgtggtgg atgctgtctc gatagtattc   22440
tggcccgtag ttgtcgatgt tgtgttgtat ctgttgggtg gtgtgttggg tgttgagtga   22500
gatgattcgt gtggaggcct cccagggtgt catgtcccct gatatgtaga gggctggctg   22560
gttgagcatc gcggtgatga acatggctag ccctgatttt tggctgccgg accgccccgc   22620
gatcatgacc aaatcccctt tgtggatgtg catgtccagg ttgtcataca agggtgctag   22680
ttggggtatg cggggcagtt cggcgctgt ttgggaggcc ctctcgaagg atctttggag    22740
agagagcatc gggaccttaa tctatctgtt ggttgggtgt gttttggtgg tcagatggag   22800
tcgatgtcga tgtcagcatc ggcgggggct gtggtgtcgt ctagctgcc gttgtcgcgt    22860
ttgtctacat attcggcaac cttatcgtag atggcgtcgt cgaggggttt gaggacgacc   22920
gcgttgaacc cgttttttggt gcgcacggtg gcaagtttga aggcttgttc ttcgccgaga   22980
tatgcttcta ggtcgcggat catggagtgt gggcggtcgt tgttgccgcg tgcttttcg    23040
atgatggcgt tggggatggt ttctgggtg ccgttgttga atcctggag ggtgtggaag     23100
attgtgacat cagcgtagat gcggtctgcg acctgtccac cgtagcctcc ggtgttgtgt   23160
tctacgtcgc ggatttgaa ggcgatggcg gtggcgtcct ggttcggga ggggttgaag     23220
aaggtgctgt tgctgttgtt gtggtagttg gcgagtgcca tgattgtgtt atccttact    23280
gttgtgtctg tttttgttgt cttatattgg tttatcgggt gaggctgttt cgtttgctgc   23340
ggaaagcctc ggaaacgtca ctgttactgg tgatggtctt cttgtactgt ttgagtaggt   23400
ctgctagctg tgtcttgctg gtggcttttgt ttatccggtc gatgatgatg tcgttttcct  23460
gtgatgcgat tttgttgacg tagtctttgg cggcttatc gtatcggtct tgaagcagga    23520
ttgctgcgct agcgatgagg gttgcgagat cccagtcttt ggatacggtt tcgtctttca   23580
atcctcctag cagatcaata atggattgtt tgatgtcttc tgcggtgtct ccgcggatga   23640
ctgtccatgg ggcggcatag tcgccaccgt atttgagtgt gatagttagt tttccgctgt   23700
ctgtggtgtg ctcgtcggtc acgtgttttc cttttcgttg ttttcggctt ctggtggctg   23760
tacggtggtt tctatcgggt atctgtaggc gtctttcccg ttgacggccc agcaggcgtc   23820
cttgacgggg catcctttgc agagtgtggt gacgtgggt acgaagatgc cttggctgat    23880
tcctttcatt gcttgactgt acatggatga tacatgccag taggtgttgt tgtcaagatc   23940
aatgagttcg gttgctgtgc cctgctcgac tgattgctcg tctcccttgg tggtggcggg   24000
tgtccaaaac atgcctttcg tcacatggat gccgtgttgg gcgagcatgt accggtatgt   24060
gtgcagctgc atactgtctg cgggtaggcg tccggttttg aggtcaaaaa tgaaggtttc   24120
gccggtgtcg gtgtcggtga atacccggtc aatatatccg actattttg tgtcatcgtc   24180
gagggtggtt tctaccgggt attcgatgcc tggctggccg tcaataacag cggtggcgta   24240
ttctgggtgg ttgcgcctcc atgttttcca gcggtccaca aagtggggc cgtacatcat    24300
ccaccaattg tagtctttct tgtgtggccc gcctgactcg cacatgtttt tgcatattct   24360
gccggagggc tttatgtttg tgccttcgga ttcggcgagg gcgatttggg tgtcgaaaat   24420
gtttgtgaag gatgagagtt tgtctggcag tgcagggtt tcggcggggt tgtacaggtg    24480
taggtcgtat tgttcggtga tgtggtgtat ggcgcttccg gcgatggtgg cgtaccaggt   24540
gtggtcgttgg gcgtggtagc cgtgtgctag gcgccatttt tcgccgcatt cggcccactg   24600
tgtgagtgaa ctgtaggaga tgtggcctgg atggttgatg gttttcgggt attgtgctag   24660
gggcattact tgtcgccttt tgggtgtttc catgggttgc gggtgtcttt gccggcgtgg   24720
tgttgctggt aggcggagag tgcgaggcag tgccaggcaa cgtgtgccag atgcggcaaa   24780
tgtgattcgt tgtcgaggtt gttgccttgc tgccatgata acaggtgccg gtagagggcg   24840
tcgacactgt ggctccacgg gtatcctccg gtccagttgt tgtcgccgta cttggtggca   24900
ccgtagcctc ccacgagcc tagggcgtgc aaggctgcgg ggtcgatgag ggagagcctg    24960
cagagtttca attcttttcg ggcaccgctg ttggggtcgg tgtacatgct ggtgggctac   25020
tccatgtgtt gtgtgctcct taagctgggg ttactggtta ttgtcgtggg cgagtgctac   25080
ggcgagaata atgatggcga gggtttcagc gatcagtatg ggtgttgtga tcatttagtg   25140
tctcggggat tattggtgag tgttgatgca cctaggaggg tggcgagggc gcatgcggcg   25200
atggtggcga gggctgcctt gtgtggggtg ccggttgcgt acatccatgt gatgatgccg   25260
ccttggatcc aggctagact ggtgaagaac gtttcgtaac tgtgtagctc aatgttgttg   25320
ttgggtgtgt tcatgcttgc tcctgaagaa tggtgttgat ggttttataa atgttgtaca   25380
```

```
ggtcggtttc gatagataac agttggttga tttggtggtc gagatcaatg tctgggttga   25440
gggtgtcgat gcgggcggcg atatcggtgg cggtgcgtag gcttactgct gcaccgtgga   25500
tgatgtggca catgtcggtg aggccgactt tggcgatata gtgtgacatg agaggcataa   25560
taggtgtgct gtctttctgg tcagcgtgaa gggttgatgg acatatcctc tacctgtggt   25620
ttgtcttcgg tgccggagac ttggcagaag acttctcacat gcgtcttgga tgctccggcc   25680
tgtttggcgg tggcaccgta ggcgatagta aaggtgtctt tgtgggcgcc gatgactttg   25740
tgtaggaaga ggtcgatgtc gggggttgccg ttccatttga caccgttttc tgcggctgtc   25800
tgggtggctt tctgattgca ggcgtgtgcg gcggtgatca tggtgagacc cttgctggtt   25860
tcttcacccc ttgcttgggc ttgccggtgg gctttggcct gctcggcttg tagggagcgg   25920
actgctgcgg cctggcgggc cttcttctca gccttgcgct gctggacggt tttgggtgtc   25980
cattcggtgt tggctgtggt tacctgtggt gcgggttgtg aggcgagtgg cggattgtcg   26040
tctggggctg gcatgaagga tgctgcggca ataatgcga ctgtggcgcc tgcgatggtg    26100
tagcctgttt tcttgttcat gattttatgt tccccttttcc ggggtgttgt tcgttgctga   26160
catggttaat actttcagcg gctgggccca ctgtcaaggc tgcgctcagt ttgtgtgagc   26220
gtttcttgtg tggctagggg tgatggcttc tttcgcccaa taggatgtgc caccgctggt   26280
ccagtatccg agtttgttgc gctgcatgcc cttggcgtcc atctcgtcga tagtgaggca   26340
cctgcggcga ttggggcctg tcttgacccc gtggtcgcct gtccggtgca tgtcgcctga   26400
ggtggtactc gtgaatgttt catggcagat ggtacagtgc tctggtcgat atccggtgat   26460
tgtgctatcg cacttgtggc atgtccattc catgattgct cctatttttcc attataagac   26520
ttcctgtagt gccatttag cgccttgcgg gtcttggggg tacaactata taggtcaggt    26580
gtttctaggc gattctaggc tcattgtgtg tggctggggt tttatcgggc acacagggtg   26640
agcaggtggc caacattgat gcgggtcaca ttccagtaga gttgcgtggc ttccccactg   26700
gtgagcggct tccactcgtc atggctgaac acgtgccat cggatgcgat gaacgtgttg    26760
gggcgtagct tgtggagttc ggcttccacg ctctgccgt aggcttcggc gaggccctca    26820
aaatccatgt ggtcgcaggg gaggttttcg aggcgtgtca ggtcgaaggg tgtggggcag   26880
tcgtagctgg cggggggtgta gagctgagtgg aagtggttgg cgatcttctg catcatgatt   26940
cctttttctga tgatggtgtg ttgagggttt atcgggtgga tgcgacaagg atggcgtcta   27000
catcgatcat gtcgatgaga tcgtggagtt cctcggcctc gttctcagtg agtggctgcc   27060
aggcgtagtc gccgtatacg gcgccgtcga gggtgacagt ccacggggg cggatgagtc    27120
gtatggcttc ttgtacttta gcgtggtaca tgcggccgac catatccaga tcgatgtcgt   27180
ctgaatggtt tccggtgagg ctgtggaggc tgagcgggtc gatgtctgtc tgcctgtaga   27240
gggatgtgaa ggatggggtg atgagtgtgc catccatgag tgtgctcctt tcggtggttg   27300
tagggggttgt tgtggtttct agagtgtgcg ggctgcgacc ccacagtcaa ggtgtcgctc   27360
aaactcagtg agcgtttcat atgggtgtgt tgggtgtgac agatgtcact taagccttga   27420
tggcctctct cagcgcctca aatcttctag gggtaggatt atgaagggtt ggcctgctg    27480
atcgattcta ggccccatac agggcgtctg aggggtgtgt ctgagtgata gtgggtgtgg   27540
cagatgatct agcgagtcaa ggtgccgagc tgagacataa gatctatcat ctaggtgtgt   27600
gagatgtatc acatcctccc ggcttggtgt gcaccctcaa ggccacccag tcgatctgac   27660
gtggaggtg tagcccagaa atactgttta aagccttcac acggcgccta ggagcgcctt    27720
acagggtggg ggctaggtat ttataccccc agcacattct gatcgattct agacgcctac   27780
aggagcccga tacacgatca gccatccaga cgcagatcat cagcacctat catgttagc    27840
taagcctcaa ctatgtggac agtgttggtt actgtggggg aagaaggaca cggtaaaaga   27900
aagaggggga gtatcagctt taaagcctta aggtcttagc gcttagcacc gatggtctta   27960
gcagttagca ccgagcccc tcaagggctc ggcatcagcc cgaacaggca cagccatgaa    28020
aggagtacac gccatcaggg aaggctttcg agtacgagga gcctcagcga cgagtactcg   28080
aaagcctgag ggaacaccca tcagcactga tgagcctagc gtattcggaa aggacacaag   28140
agtgaagtgt gacagctgtc cgggagtgaa ccccgttctg actagggggtt tcagccttaa   28200
ccaccctcaa aggttacaag actctaagaa aatttaagga aaagtttagg tttaattttt   28260
ggaccttac taccaaaaac acccgtttac agccctcaaa cccgcctata gagccaaaac    28320
caccagtttg actcatccca ggtgggtat gataggctgg acaggtagcc agctggacgc    28380
aaggccggaa agtgctaacg cactttccaa cctcgcttac catcagtcta ccaaacactt   28440
aaagacctaa gggcttagcg ctaaggtgct gatagcttag caccgagccc cctcaagggc   28500
tcggcatcag tcttaaagcc ttaaatactt aaagtaacta taaaacttta aaagcttaac   28560
acttaaggat ataaactttta catcagtgtt taagacttaa aaacttaaaa taactattaa   28620
gacttaaagt aactataaaa cattaaagac cttaagtact taaagttaac catcagtctt   28680
aaactttact atgataacct ataagtctta aagcttatag gtataataat ataatataag   28740
tattaaagct tataagttat aaaagtttta gaagagttaa aggggttaact tctttacttc   28800
tcttctctct ttggttctt ctctcttctc ttcttttctt catcggggga gaagaggaac    28860
ctttaacgtc aacgctgatg gactttctcgc cgtgtgtctc gtgtgcttct ggtcgcaagc   28920
tcccatcgca cactccccac actctttcac ctgtgtccct ttcaggctta gcgtgttcag   28980
ctgaaggcgt acagcgtgtc acgcttaaac ccttaacacc aggtaagact taaagtgcat   29040
attataagta gaagacttta aaaccttaag ggtgttcctg cttagcctgt gtcctttaac    29100
gctaggcgct aagccgtgaa acgtgaacac ccatccaccc ctcttctttt taccgtgtcc   29160
ttcttctttt gacaccgctg gggggcgatg tgatctttt aacatgccag gggtgcgggg   29220
tagaaaacaa ccaccccacc acaaacagaa caccccctca aacgcacaaa acagccccca   29280
ggatcgatga acagggcaag ggcaaggtat tcataccccc agacgattcc aggccgttag   29340
agaggcaaat aagacccgta cagggctagg tgaggaatag acacatcatg gcacgcacca   29400
atcgcacagc tagccaagcc caccgacgct ggcggcaacg actcatcacc caagcccaac   29460
aacaaggcca aaccgaatgc ccactctgcg gagtcaccat cacctgggac acacacgagc   29520
taccaaccag ccccgaagcc gaccacatca caccgtcag caggggagga ctcaacaccc    29580
tcgacaacgg gcaaatcatc tgcagaacat gcaacagaag caaaggcaat cgcagcgaac   29640
caaacatcaa attccaacaa caaaccacaa aaacattgat tccatggtga caaacccgcc   29700
aacccccacc ggggacaccc cctgcacagg cgtgcaagac ctcgtacggc tt           29752
```

SEQ ID NO: 2           moltype = DNA   length = 1537
FEATURE                Location/Qualifiers
misc_feature           1..1537
                       note = 16S DNA sequence for the KPA171202 type strain
source                 1..1537

```
                        mol_type = other DNA
                        organism = synthetic construct
SEQUENCE: 2
tttttcattg gagagtttga tcctggctca ggacgaacgc tggcggcgtg cttaacacat    60
gcaagtcgaa cggaaaggcc ctgcttttgt ggggtgctcg agtggcgaac gggtgagtaa   120
cacgtgagta acctgccctt gactttggga taacttcagg aaactggggc taataccgga   180
taggagctcc tgctgcatgg tggggggtgg aaagtttcgg cggttgggga tggactcgcg   240
gcttatcagc ttgttggtgg ggtagtggct taccaaggct ttgacgggta gccggcctga   300
gagggtgacc ggccacattg ggactgagat acggcccaga ctcctacggg aggcagcagt   360
ggggaatatt gcacaatggg cggaagcctg atgcagcaac gccgcgtgcg ggatgacggc   420
cttcggggttg taaaccgctt tcgcctgtga cgaagcgtga gtgacggtaa tgggtaaaga   480
agcaccggct aactacgtgc cagcagccgc ggtgatacgt agggtgcgag cgttgtccgg   540
atttattggg cgtaaagggc tcgtaggtgg ttgatcgcgt cggaagtgta atcttggggc   600
ttaaccctga gcgtgctttc gatacgggtt gacttgagga aggtagggga gaatggaatt   660
cctggtggag cggtggaatg cgcagatatc aggaggaaca ccagtggcga aggcggttct   720
ctgggccttt cctgacgctg aggagcgaaa gcgtggggag cgaacaggct tagataccct   780
ggtagtccac gctgtaaacg gtgggtacta ggtgtgggtc ccattccacg ggttccgtgc   840
cgtagctaac gctttaagta ccccgcctgg ggagtacggc cgcaaggcta aaactcaaag   900
gaattgacgg ggccccgcac aagcggcgga gcatgcggat taattcgatg caacgcgtag   960
aaccttacct gggtttgaca tggatcggga gtgctcagaa atgggtgtgc ctcttttggg  1020
gtcggttcac aggtggtgca tggctgtcgt cagctcgtgt cgtgagatgt tgggttaagt  1080
cccgcaacga gcgcaaccct tgttcactgt tgccagcacg ttatggtggg gactcagtgg  1140
agaccgccgg ggtcaactcg gaggaaggtg gggatgacgt caagtcatca tgccccctat  1200
gtccagggct tcacgcatgc tacaatggct ggtacagaga gtggcgagcc tgtgagggtg  1260
agcgaatctc ggaaagccgg tctcagttcg gattgggggtc tgcaactcga cctcatgaag  1320
tcggagtcgc tagtaatcgc agatcagcaa cgctgcggtg aatacgttcc cggggccttgt  1380
acacaccgcc cgtcaagtca tgaaagttgg taacacccga agccgtggc  ctaaccgttg  1440
tgggggagcc gtcgaaggtg ggactggtga ttaggactaa gtcgtaacaa ggtagccgta  1500
ccggaaggtg cggctggatc acctcctttc taaggag                            1537

SEQ ID NO: 3               moltype = DNA  length = 1537
FEATURE                    Location/Qualifiers
misc_feature               1..1537
                        note = 16S DNA sequence for the ProI probiotic strain
source                     1..1537
                        mol_type = other DNA
                        organism = synthetic construct
SEQUENCE: 3
tttttcattg gagagtttga tcctggctca ggacgaacgc tggcggcgtg cttaacacat    60
gcaagtcgaa cggaaaggcc ctgcttttgt ggggtgctcg agtggcgaac gggtgagtaa   120
cacgtgagta acctgccctt gactttggga taacttcagg aaactggggc taataccgga   180
taggagctcc tgctgcatgg tggggggtgg aaagtttcgg cggttgggga tggactcgcg   240
gcttatcagc ttgttggtgg ggtagtggct taccaaggct ttgacgggta gccggcctga   300
gagggtgacc ggccacattg ggactgagat acggcccaga ctcctacggg aggcagcagt   360
ggggaatatt gcacaatggg cggaagcctg atgcagcaac gccgcgtgcg ggatgacggc   420
cttcggggttg taaaccgctt tcgcctgtga cgaagcgtga gtgacggtaa tgggtaaaga   480
agcaccggct aactacgtgc cagcagccgc ggtgatacgt agggtgcgag cgttgtccgg   540
atttattggg cgtaaagggc tcgtaggtgg ttgatcgcgt cggaagtgta atcttggggc   600
ttaaccctga gcgtgctttc gatacgggtt gacttgagga aggtagggga gaatggaatt   660
cctggtggag cggtggaatg cgcagatatc aggaggaaca ccagtggcga aggcggttct   720
ctgggccttt cctgacgctg aggagcgaaa gcgtggggag cgaacaggct tagataccct   780
ggtagtccac gctgtaaacg gtgggtacta ggtgtgggtc ccattccacg ggttccgcgc   840
cgtagctaac gctttaagta ccccgcctgg ggagtacggc cgcaaggcta aaactcaaag   900
gaattgacgg ggccccgcac aagcggcgga gcatgcggat taattcgatg caacgcgtag   960
aaccttacct gggtttgaca tggatcggga gtgctcagaa atgggtgtgc ctcttttggg  1020
gtcggttcac aggtggtgca tggctgtcgt cagctcgtgt cgtgagatgt tgggttaagt  1080
cccgcaacga gcgcaaccct tgttcactgt tgccagcacg ttatggtggg gactcagtgg  1140
agaccgccgg ggtcaactcg gaggaaggtg gggatgacgt caagtcatca tgccccctat  1200
gtccagggct tcacgcatgc tacaatggct ggtacagaga gtggcgagcc tgtgagggtg  1260
agcgaatctc ggaaagccgg tctcagttcg gattgggggtc tgcaactcga cctcatgaag  1320
ttggagtcgc tagtaatcgc agatcagcaa cgctgcggtg aatacgttcc cggggccttgt  1380
acacaccgcc cgtcaagtca tgaaagttgg taacacccga agccgtggc  ctaaccgttg  1440
tgggggagcc gtcgaaggtg ggactggtga ttaggactaa gtcgtaacaa ggtagccgta  1500
ccggaaggtg cggctggatc acctcctttc taaggag                            1537

SEQ ID NO: 4               moltype = DNA  length = 1537
FEATURE                    Location/Qualifiers
misc_feature               1..1537
                        note = 16S DNA sequence for the ProII probiotic strain
source                     1..1537
                        mol_type = other DNA
                        organism = synthetic construct
SEQUENCE: 4
tttttcattg gagagtttga tcctggctca ggacgaacgc tggcggcgtg cttaacacat    60
gcaagtcgaa cggaaaggcc ctgcttttgt ggggtgctcg agtggcgaac gggtgagtaa   120
cacgtgagta acctgccctt gactttggga taacttcagg aaactggggc taataccgga   180
taggagctcc tgctgcatgg tggggggtgg aaagtttcgg cggttgggga tggactcgcg   240
gcttatcagc ttgttggtgg ggtagtggct taccaaggct ttgacgggta gccggcctga   300
gagggtgacc ggccacattg ggactgagat acggcccaga ctcctacggg aggcagcagt   360
```

```
gggggaatatt gcacaatggg cggaagcctg atgcagcaac gccgcgtgcg ggatgacggc    420
cttcggggttg taaaccgctt tcgcctgtga cgaagcgtga gtgacggtaa tgggtaaaga    480
agcaccggct aactacgtgc cagcagccgc ggtgatacgt agggtgcgag cgttgtccgg    540
atttattggg cgtaaaggc tcgtaggtgg ttgatcgcgt cggaagtgta atcttggggc    600
ttaaccctga gcgtgctttc gatacgggtt gacttgaaga agtagggga gaatggaatt    660
cctggtggag cggtggaatg cgcagatatc aggaggaaca ccagtggcga aggcggttct    720
ctgggccttt cctgacgctg aggagcgaaa gcgtggggag cgaacaggct agatacccct    780
ggtagtccac gctgtaaacg gtgggtacta ggtgtgggt ccattccacg gttccgtgc     840
cgtagctaac gctttaagta ccccgcctgg ggagtacggc cgcaaggcta aaactcaaag    900
gaattgacgg ggccccgcac aagcggcgga gcatgcggat taattcgatg caacgcgtag    960
aaccttacct gggtttgaca tggattggga gcgctcagag atgggtgtgc ctcttttggg   1020
gtcggttcac aggtggtgca tggctgtcgt cagctcgtgt cgtgagatgt tgggttaagt   1080
cccgcaacga gcgcaaccct tgttcactgt tgccagcacg ttatggtggg gactcagtgg   1140
agaccgccgg ggtcaactcg gaggaaggtg gggatgacgt caagtcatca tgccccttat   1200
gtccagggct tcacgcatgc tacaatggct ggtacagaga gtggcgagcc tgtgagggtg   1260
agcgaatctc ggaaagccgg tctcagttcg gattggggtc tgcaactcga cctcatgaag   1320
tcggagtcgc tagtaatcgc agatcagcaa cgctgcggtg aatacgttcc ggggcttgt    1380
acacaccgcc cgtcaagtca tgaaagttgg taacacccga gccggtggcc ctaaccgttg   1440
tgggggagcc gtcgaaggtg ggactggtga ttaggactaa gtcgtaacaa ggtagccgta   1500
ccggaaggtg cggctggatc acctccttc taaggag                              1537

SEQ ID NO: 5             moltype = DNA  length = 1525
FEATURE                  Location/Qualifiers
misc_feature             1..1525
                         note = 16S DNA sequence
source                   1..1525
                         mol_type = other DNA
                         organism = synthetic construct
SEQUENCE: 5
agagtttgat cctggctcag gacgaacgct ggcggcgtgc ttaacacatg caagtcgaac     60
ggaaaggccc tgcttttgtg gggtgctcga gtggcgaacg ggtgagtaac acgtgagtaa    120
cctgcccttg actttgggat aacttcagga aactgggggct aataccggat aggagctcct   180
gctgcatggt gggggttgga aagtttcggc ggttgggat ggactcgcgg cttatcagct     240
tgttggtggg gtagtggctt accaaggctt tgacgggtag ccggcctgag agggtgaccg    300
gccacattgg gactgagata cggcccagac tcctacggga ggcagcagtg gggaatattg    360
cacaatgggc ggaagcctga tgcagcaacg ccgcgtgcgg gatgacgcc ttcgggttgt     420
aaaccgcttt cgcctgtgac gaagcgtgag tgacggtaat gggtaaagaa gcaccggcta    480
actacgtgcc agcagccgcg gtgatacgta gggtgcgagc gttgtccgga tttattgggc    540
gtaaagggct cgtaggtggt tgatcgcgtc ggaagtgtaa tcttggggct taaccctgag    600
cgtgctttcg atacgggttg acttgaggaa ggtaggggga aatggaattc ctggtggagc    660
ggtggaatgc gcagatatca ggaggaacac cagtggcgaa ggcggttctc tgggcctttc    720
ctgacgctga ggagcgaaag cgtggggagc gaacaggctt agatacctg gtagtccacg     780
ctgtaaacgt tgggtactag gtgtgggggtc cattccacgg ttccgtgcc gtagctaacg    840
ctttaagtac cccgcctggg gagtacggcc gcaaggctaa aactcaaagg aattgacggg    900
gcccccgcaca agcggcggag catgcggatt aattcgatgc aacgcgtaga accttacctg    960
gtttgacat ggatcgggag tgctcagaga tgggtgtgcc tcttttgggg tcggttcaca    1020
ggtggtgcat gcctgtcgtc agctcgtgtc gtgagatgtt gggttaagtc ccgcaacga    1080
cgcaacccctt gttcactgtt gccagcacgt tatggtgggg actcagtgga gaccgccggg   1140
gtcaactcgg aggaaggtgg ggatgacgtc aagtcctcat gccccttatg tcaggggctt   1200
cacgcatgct acaatggctg gtacagagag tggcgagcct gtgagggtga gcgaatctcg   1260
gaaagccggt ctcagttcgg attggggtct gcaactcgac ctcatgaagt cggagtcgc    1320
agtaatcgca gatcagcaac gctgcggtga atacgttccc ggggcttgta cacaccgccc   1380
gtcaagtcat gaaagttggt aacacccgaa gccgtggcc taaccgttgt gggggagccg    1440
tcgaaggtgg gactggtgat taggactaag tcgtaacaag gtagccgtac cggaaggtgc   1500
ggctggatca cctcctttct aagga                                          1525

SEQ ID NO: 6             moltype = DNA  length = 1525
FEATURE                  Location/Qualifiers
misc_feature             1..1525
                         note = 16S Sequence
source                   1..1525
                         mol_type = other DNA
                         organism = synthetic construct
SEQUENCE: 6
agagtttgat cctggctcag gacgaacgct ggcggcgtgc ttaacacatg caagtcgaac     60
ggaaaggccc tgcttttgtg gggtgctcga gtggcgaacg ggtgagtaac acgtgagtaa    120
cctgcccttg actttgggat aacttcagga aactgggggct aataccggat aggagctcct   180
gctgcatggt gggggttgga aagtttcggc ggttgggat ggactcgcgg cttatcagct     240
tgttggtggg gtagtggctt accaaggctt tgacgggtag ccggcctgag agggtgaccg    300
gccacattgg gactgagata cggcccagac tcctacggga ggcagcagtg gggaatattg    360
cacaatgggc ggaagcctga tgcagcaacg ccgcgtgcgg gatgacgcc ttcgggttgt     420
aaaccgcttt cgcctgtgac gaagcgtgag tgacggtaat gggtaaagaa gcaccggcta    480
actacgtgcc agcagccgcg gtgatacgta gggtgcgagc gttgtccgga tttattgggc    540
gtaaagggct cgtaggtggt tgatcgcgtc ggaagtgtaa tcttggggct taaccctgag    600
cgtgctttcg atacgggttg acttgaggaa ggtaggggga aatggaattc ctggtggagc    660
ggtggaatgc gcagatatca ggaggaacac cagtggcgaa ggcggttctc tgggcctttc    720
ctgacgctga ggagcgaaag cgtggggagc gaacaggctt agatacctg gtagtccacg     780
ctgtaaacgt tgggtactag gtgtgggggtc cattccacgg ttccgtgcc gtagctaacg    840
ctttaagtac cccgcctggg gagtacggcc gcaaggctaa aactcaaagg aattgacggg    900
```

-continued

```
gccccgcaca agcggcgag catgcggatt aattcgatgc aacgcgtaga accttacctg    960
ggtttgacat ggatcgggag tgctcagaga tgggtgtgcc tcttttgggg tcggttcaca  1020
ggtggtgcat ggctgtcgtc agctcgtgtc gtgagatgtt gggttaagtc ccgcaacgag  1080
cgcaaccctt gttcactgtt gccagcacgt tatggtgggg actcagtgga gaccgccggg  1140
gtcaactcgg aggaaggtgg ggatgacgtc aagtcatcat gccccttatg tccagggctt  1200
cacgcatgct acaatggctg gtacagagag tggcgagcct gtgagggtga gcgaatctcg  1260
gaaagccggt ctcagttcgg attggggtct gcaactcgac ctcatgaagt cggagtcgct  1320
agtaatcgca gatcagcaac gctgcggtga atacgttccc ggggcttgta cacaccgccc  1380
gtcaagtcat gaaagttggt aacacccgaa gccggtggcc taaccgttgt gggggagccg  1440
tcgaaggtgg gactggtgat taggactaag tcgtaacaag gtagccgtac cggaaggtgc  1500
ggctggatca cctcctttct aagga                                        1525

SEQ ID NO: 7          moltype = DNA  length = 1525
FEATURE               Location/Qualifiers
misc_feature          1..1525
                      note = 16S Sequence
source                1..1525
                      mol_type = other DNA
                      organism = synthetic construct
SEQUENCE: 7
agagtttgat cctggctcag gacgaacgct ggcggcgtgc ttaacacatg caagtcgaac    60
ggaaaggccc tgcttttgtg gggtgctcga gtggcgaacg ggtgagtaac acgtgagtaa   120
cctgcccttg actttgggat aacttcagga aactgggggct aataccggat aggagctcct  180
gctgcatggt gggggttgga aagtttcggc ggttggggat ggactcgcgg cttatcagct   240
tgttggtggg gtagtggctt accaaggctt tgacgggtag ccggcctgag agggtgaccg   300
gccacattgg gactgagata cggcccagac tcctacggga ggcagcagtg gggaatattg   360
cacaatgggc ggaagcctga tgcagcaacg ccgcgtgcgg gatgacggcc ttcgggttgt   420
aaaccgcttt cgcctgtgac gaagcgtgag tgacggtaat gggtaaagaa gcaccggcta   480
actacgtgcc agcagccgcg gtaatacgta gggtgcgagc gttgtccgga tttattgggc   540
gtaaagggct cgtaggtggt tgatcgcgtc ggaagtgtaa tcttgggggct taaccctaag  600
cgtgctttcg atacggggttg acttgaggaa ggtagggggag aatggaattc ctggtggagc  660
ggtggaatgc gcagatatca ggaggaacac cagtggcgaa ggcggttctc tgggcctttc   720
ctgacgctga ggagcgaaag cgtggggagc gaacaggctt agataccctg gtagtccacg   780
ctgtaaacga tgggtactag gtgtggggtc cattccacg gttccgtgcc gtagctaacg    840
ctttaagtac cccgcctggg gagtacggcc gcaaggctaa aactcaaagg aattgacggg   900
gccccgcaca agcggcgag catgcggatt aattcgatgc aacgcgtaga accttacctg    960
ggtttgacat ggatcgggag tgctcagaga tgggtgtgcc tcttttgggg tcggttcaca  1020
ggtggtgcat ggctgtcgtc agctcgtgtc gtgagatgtt gggttaagtc ccgcaacgag  1080
cgcaaccctt gttcactgtt gccagcacgt tatggtgggg actcagtgga gaccgccggg  1140
gtcaactcgg aggaaggtgg ggatgacgtc aagtcatcat gccccttatg tccagggctt  1200
cacgcatgct acaatggctg gtacagagag tggcgagcct gtgagggtga gcgaatctcg  1260
gaaagccggt ctcagttcgg attggggtct gcaactcgac ctcatgaagt cggagtcgct  1320
agtaatcgca gatcagcaac gctgcggtga atacgttccc ggggcttgta cacaccgccc  1380
gtcaagtcat gaaagttggt aacacccgaa gccggtggcc taaccgttgt gggggagccg  1440
tcgaaggtgg gactggtgat taggactaag tcgtaacaag gtagccgtac cggaaggtgc  1500
ggctggatca cctcctttct aagga                                        1525

SEQ ID NO: 8          moltype = DNA  length = 1525
FEATURE               Location/Qualifiers
misc_feature          1..1525
                      note = 16S Sequence
source                1..1525
                      mol_type = other DNA
                      organism = synthetic construct
SEQUENCE: 8
agagtttgat cctggctcag gacgaacgct ggcggcgtgc ttaacacatg caagtcgaac    60
ggaaaggccc tgcttttgtg gggtgctcga gtggcgaacg ggtgagtaac acgtgagtaa   120
cctgcccttg actttgggat aacttcagga aactgggggct aataccggat aggagctcct  180
gctgcatggt gggggttgga aagtttcggc ggttggggat ggactcgcgg cttatcagct   240
tgttggtggg gtagtggctt accaaggctt tgacgggtag ccggcctgag agggtgaccg   300
gccacattgg gactgagata cggcccagac tcctacggga ggcagcagtg gggaatattg   360
cacaatgggc ggaagcctga tgcagcaacg ccgcgtgcgg gatgacggcc ttcgggttgt   420
aaaccgcttt cgcctgtgac gaagcgtgag tgacggtaat gggtaaagaa gcaccggcta   480
actacgtgcc agcagccgcg gtgatacgta gggtgcgagc gttgtccgga tttattgggc   540
gtaaagggct cgtaggtggt tgatcgcgtc ggaagtgtaa tcttgggggct taaccctgag  600
cgtgctttcg atacggggttg acttgaggaa ggtagggggag aatggaattc ctggtggagc  660
ggtggaatgc gcagatatca ggaggaacac cagtggcgaa ggcggttctc tgggcctttc   720
ctgacgctga ggagcgaaag cgtggggagc gaacaggctt agataccctg gtagtccacg   780
ctgtaaacga tgggtactag gtgtggggtc cattccacg gttccgtgcc gtagctaacg    840
ctttaagtac cccgcctggg gagtacggcc gcaaggctaa aactcaaagg aattgacggg   900
gccccgcaca agcggcgag catgcggatt aattcgatgc aacgcgtaga accttacctg    960
ggtttgacat ggatcggaag cgctcagaga tgggtgtgcc tcttttgggg tcggttcaca  1020
ggtggtgcat ggctgtcgtc agctcgtgtc gtgagatgtt gggttaagtc ccgcaacgag  1080
cgcaaccctt gttcactgtt gccagcacgt tatggtgggg actcagtgga gaccgccggg  1140
gtcaactcgg aggaaggtgg ggatgacgtc aagtcatcat gccccttatg tccagggctt  1200
cacgcatgct acaatggctg gtacagagag tggcgagcct gtgagggtga gcgaatctcg  1260
gaaagccggt ctcagttcgg attggggtct gcaactcgac ctcatgaagt cggagtcgct  1320
agtaatcgca gatcagcaac gctgcggtga atacgttccc ggggcttgta cacaccgccc  1380
gtcaagtcat gaaagttggt aacacccgaa gccggtggcc taaccgttgt gggggagccg  1440
```

```
tcgaaggtgg gactggtgat taggactaag tcgtaacaag gtagccgtac cggaaggtgc    1500
ggctggatca cctcctttct aagga                                          1525

SEQ ID NO: 9            moltype = DNA  length = 1525
FEATURE                 Location/Qualifiers
misc_feature            1..1525
                        note = 16S Sequence
source                  1..1525
                        mol_type = other DNA
                        organism = synthetic construct
SEQUENCE: 9
agagtttgat cctggctcag gacgaacgct ggcggcgtgc ttaacacatg caagtcgaac     60
ggaaaggccc tgcttttgtg gggtgctcga gtggcgaacg ggtgagtaac acgtgagtaa    120
cctgcccttg actttgggat aacttcagga aactggggct aataccggat aggagctcct    180
gctgcatggt gggggttgga aagtttcggc ggttggggat ggactcgcgg cttatcagct    240
tgttggtggg gtagtggctt accaaggctt gacgggtag ccggcctgag agggtgaccg     300
gccacattgg gactgagata cggcccagac tcctacggga ggcagcagtg gggaatattg    360
cacaatgggc ggaagcctga tgcagcaacg ccgcgtgcgg gatgacggcc ttcgggttgt    420
aaaccgcttt cgcctgtgac gaagcgtgag tgacggtaat gggtaaagaa gcaccggcta    480
actacgtgcc agcagccgcg gtgatacgta gggtgcgagc gttgtccgga tttattgggc    540
gtaaagggct cgtaggtggt tgatcgcgtc ggaagtgtaa tcttgggggct taaccctgag    600
cgtgctttcg atacgggttg acttgaggaa ggtaggggag aatggaattc ctggtggagc    660
ggtggaatgc gcagatatca ggaggaacac cagtggcgaa ggcggttctc tgggcctttc    720
ctgacgctga ggagcgaaag cgtggggagc gaacaggctt agatacctg gtagtccacg     780
ctgtaaacg tgggtactag gtgtgggtc cattccacgg gttccgtgcc gtagctaacg      840
cttttaagtac cccgcctggg gagtacggcc gcaaggctaa aactcaaagg aattgacggg    900
gcccgcaca agcggcggag catgcggatt aattcgatgc aacgcgtaga accttacctg     960
ggtttgacat ggatcgggag tgctcagaga tgggtgtgcc tctttggggg tcggttcaca   1020
ggtggtgcat ggctgtcgtc agctcgtgtc gtgagatgtt gggttaagtc ccgcaacgag   1080
cgcaaccctt gttcactgtt gccagcacgt tatggtgggg actcagtgga gaccgccggg   1140
gtcaactcgg aggaaggtgg ggatgacgtc aagtcatcat gccccttatg tccagggctt   1200
cacgcatgct acaatggctg gtacagagag tggcgagcct atgagggtga gcgaatctcg   1260
gaaagccggt ctcagttcgg attggggtct gcaactcgac ctcatgaagt cggagtcgct   1320
agtaatcgca gatcagcaac gctgcggtga atacgttccc ggggcttgta cacaccgccc   1380
gtcaagtcat gaaagttggt aacacccgaa gccgtggcc taaccgttgt gggggagccg    1440
tcgaaggtgg gactggtgat taggactaag tcgtaacaag gtagccgtac cggaaggtgc   1500
ggctggatca cctcctttct aagga                                         1525

SEQ ID NO: 10           moltype = DNA  length = 1525
FEATURE                 Location/Qualifiers
misc_feature            1..1525
                        note = 16S Sequence
source                  1..1525
                        mol_type = other DNA
                        organism = synthetic construct
SEQUENCE: 10
agagtttgat cctggctcag gacgaacgct ggcggcgtgc ttaacacatg caagtcgaac     60
ggaaaggccc tgcttttgtg gggtgctcga gtggcgaacg ggtgagtaac acgtgagtaa    120
cctgcccttg actttgggat aacttcagga aactggggct aataccggat aggagctcct    180
gctgcatggt gggggttgga aagtttcggc ggttggggat ggactcgcgg cttatcagct    240
tgttggtggg gtagtggctt accaaggctt gacgggtag ccggcctgag agggtgaccg     300
gccacattgg gactgagata cggcccagac tcctacggga ggcagcagtg gggaatattg    360
cacaatgggc ggaagcctga tgcagcaacg ccgcgtgcgg gatgacggcc ttcgggttgt    420
aaaccgcttt cgcctgtgac gaagcgtgag tgacggtaat gggtaaagaa gcaccggcta    480
actacgtgcc agcagccgcg gtgatacgta gggtgcgagc gttgcccgga tttattgggc    540
gtaaagggct cgtaggtggt tgatcgcgtc ggaagtgtaa tcttgggggct taaccctgag    600
cgtgctttcg atacgggttg acttgaggaa ggtaggggag aatggaattc ctggtggagc    660
ggtggaatgc gcagatatca ggaggaacac cagtggcgaa ggcggttctc tgggcctttc    720
ctgacgctga ggagcgaaag cgtggggagc gaacaggctt agatacctg gtagtccacg     780
ctgtaaacgg tgggtactag gtgtgggtc cattccacgg gttccgtgcc gtagctaacg     840
cttttaagtac cccgcctggg gagtacggcc gcaaggctaa aactcaaagg aattgacggg    900
gcccgcaca agcggcggag catgcggatt aattcgatgc aacgcgtaga accttacctg     960
ggtttgacat ggatcgggag tgctcagaga tgggtgtgcc tctttggggg tcggttcaca   1020
ggtggtgcat ggctgtcgtc agctcgtgtc gtgagatgtt gggttaagtc ccgcaacgag   1080
cgcaaccctt gttcactgtt gccagcacgt tatggtgggg actcagtgga gaccgccggg   1140
gtcaactcgg aggaaggtgg ggatgacgtc aagtcatcat gccccttatg tccagggctt   1200
cacgcatgct acaatggctg gtacagagag tggcgagcct gtgagggtga gcgaatctcg   1260
gaaagccggt ctcagttcgg attggggtct gcaactcgac ctcatgaagt cggagtcgct   1320
agtaatcgca gatcagcaac gctgcggtga atacgttccc ggggcttgta cacaccgccc   1380
gtcaagtcat gaaagttggt aacacccgaa gccgtggcc taaccgttgt gggggagccg    1440
tcgaaggtgg gactggtgat taggactaag tcgtaacaag gtagccgtac cggaaggtgc   1500
ggctggatca cctcctttct aagga                                         1525

SEQ ID NO: 11           moltype = DNA  length = 1089
FEATURE                 Location/Qualifiers
misc_feature            1..1089
                        note = DNA sequence that encodes Dispersin B
source                  1..1089
                        mol_type = other DNA
```

```
                              organism = synthetic construct
SEQUENCE: 11
atgaattgtt  gcgtaaaagg  caattccata  tatccgcaaa  aaacaagtac  caagcagacc    60
ggattaatgc  tggacatcgc  ccgacatttt  tattcacccg  aggtgattaa  atcctttatt   120
gataccatca  gccttccgg   cggtaatttt  ctgcacctgc  attttccga   ccatgaaaac   180
tatgcgatag  aaagccattt  acttaatcaa  cgtgcggaaa  atgccgtgca  gggcaaagac   240
ggtatttata  ttaatcctta  taccggaaag  ccattcttga  gttatcggca  acttgacgat   300
atcaaagcct  atgctaaggc  aaaaggcatt  gagttgattc  ccgaacttga  cagcccgaat   360
cacatgacgg  cgatctttaa  actggtgcaa  aaagacagag  gggtcaagta  ccttcaagga   420
ttaaaatcac  gccaggtaga  tgatgaaatt  gatattacta  atgctgacag  tattacttt    480
atgcaatctt  taatgagtga  ggttattgat  atttttggcg  acacgagtca  gcattttcat   540
attggtggcg  atgaatttgg  ttattctgtg  gaaagtaatc  atgagtttat  tacgtatgcc   600
aataaactat  cctacttttt  agagaaaaaa  gggttgaaaa  cccgaatgtg  gaatgacgga   660
ttaattaaaa  atactttga   gcaaatcaac  ccgaatattg  aaattactta  ttggagctat   720
gatggcgata  cgcaggacaa  aaatgaagct  gccgagcgcc  gtgatatgcg  ggtcagttg    780
ccggagttgc  tggcgaaagg  ctttactgtc  ctgaactata  attcctatta  tctttacatt   840
gttccgaaag  cttcaccaac  cttctcgcaa  gatgccgcct  tgccgccaa   agatgttata   900
aaaaattggg  atcttggtgt  ttgggatgga  cgaaaacaca  aaaccgcgt   acaaaatact   960
catgaaatag  ccggcgcagc  attatcgatc  tggggagaag  atgcaaaagc  gctgaaagac  1020
gaaacaattc  agaaaaacac  gaaaagttta  ttggaagcgg  tgattcataa  gacgaatggg  1080
gatgagtga                                                              1089

SEQ ID NO: 12        moltype = AA  length = 362
FEATURE              Location/Qualifiers
source               1..362
                     mol_type = protein
                     organism = Aggregatibacter actinomycetemcomitans
SEQUENCE: 12
MNCCVKGNSI YPQKTSTKQT GLMLDIARHF YSPEVIKSFI DTISLSGGNF LHLHFSDHEN  60
YAIESHLLNQ RAENAVQGKD GIYINPYTGK PFLSYRQLDD IKAYAKAKGI ELIPELDSPN 120
HMTAIFKLVQ KDRGVKYLQG LKSRQVDDEI DITNADSITF MQSLMSEVID IFGDTSQHFH 180
IGGDEFGYSV ESNHEFITYA NKLSYFLEKK GLKTRMWNDG LIKNTFEQIN PNIEITYWSY 240
DGDTQDKNEA AERRDMRVSL PELLAKGFTV LNYNSYYLYI VPKASPTFSQ DAAFAAKDVI 300
KNWDLGVWDG RNTKNRVQNT HEIAGAALSI WGEDAKALKD ETIQKNTKSL LEAVIHKTNG 360
DE                                                                362

SEQ ID NO: 13        moltype = DNA  length = 1103
FEATURE              Location/Qualifiers
misc_feature         1..1103
                     note = DNA sequence that encodes an alginate lyase
source               1..1103
                     mol_type = other DNA
                     organism = synthetic construct
SEQUENCE: 13
atgaaaacgt  cccacctgat  ccgtatcgcc  ctgccggtg   ccctcgccgc  ggcattgctc    60
gccagccagg  tcagccaggc  cgccgacctg  gtaccccgc   ccggctacta  cgcggcggtc   120
ggcgagcgca  agggcagcgc  cggcagctgc  ccgcgccgta  taccggcagc               180
ctggtcttca  ccagcaagta  cgaaggctcc  gattcggcgc  gggcgaccct  caacgtcaag   240
gcggagaaga  ccttccgctc  gcagatcaag  gacatcaccg  acatggagcg  cggcgccacc   300
aagctggtca  cccagtacat  gcgcagcggc  cgcgacggcg  acctggcctg  cgcactgaac   360
tggatgagcg  cctgggcccg  cgccggcgcc  ctgcagagcg  acgactttcaa ccacaccgtc   420
aagtccatgc  gcaaatgggc  gctgggcagc  ctctccggcg  cctacatgcg  cctgaagttc   480
tccagctcgc  ggccgctcgc  ggcccacgcc  gagcagagcc  gggaaatcga  ggactggttc   540
gcccggctcg  gcacccaggt  agtccgcgac  tggagcggcc  tgccgctgaa  gaagatcaac   600
aaccattcct  actgggcggc  ctggtcggtg  atgtccaccg  ctgtggtgac  caaccgccgc   660
gacctcttcg  actgggcggt  gagcgagttc  aaggtcgccg  ccaaccaggt  cgacgagcag   720
ggcttcctgc  ccaacgaact  caagcgccgc  cagcgcgccc  tcgcctacca  caactatgcg   780
ctgccacccg  tggcgatgat  cgccgcgttc  gcccaggtca  acggcgtcga  cctgcgccag   840
gagaaccacg  gcgccctgca  gcgcctggcc  gagcgggtga  tgaagggagt  cgacgacgag   900
gaaaccttcg  aggagaagac  cggcgaggac  caggacatga  ccgacctcaa  ggtcgacaac   960
aagtacgcct  ggctggagcc  ctactgcgcc  ctctaccgct  gcgagccgaa  gatgctcgag  1020
gcgaagaagg  accgcgagcc  gttcaacagt  tccgcctcg   gcggcgaagt  gacgcgggtg  1080
ttcagccgcg  aaggggggaag ttg                                             1103

SEQ ID NO: 14        moltype = AA  length = 367
FEATURE              Location/Qualifiers
source               1..367
                     mol_type = protein
                     organism = Flavobacterium multivorum
SEQUENCE: 14
MKTSHLIRIA LPGALAAALL ASQVSQAADL VPPPGYYAAV GERKGSAGSC PAVPPPYTGS  60
LVFTSKYEGS DSARATLNVK AEKTFRSQIK DITDMERGAT KLVTQYMRSG RDGDLACALN 120
WMSAWARAGA LQSDDFNHTG KSMRKWALGS LSGAYMRLKF SSSRPLAAHA EQSREIEDWF 180
ARLGTQVVRD WSGLPLKKIN NHSYWAAWSV MSTAVVTNRR DLFDWAVSEF KVAANQVDEQ 240
GFLPNELKRR QRALAYHNYA LPPLAMIAAF AQVNGVDLRQ ENHGALQRLA ERVMKGVDDE 300
ETFEEKTGED QDMTDLKVDN KYAWLEPYCA LYRCEPKMLE AKKDREPFNS FRLGGEVTRV 360
FSREGGS                                                           367

SEQ ID NO: 15        moltype = DNA  length = 1539
```

```
FEATURE                 Location/Qualifiers
misc_feature            1..1539
                        note = DNA sequence that encodes an amylase
source                  1..1539
                        mol_type = other DNA
                        organism = synthetic construct
SEQUENCE: 15
atgaaacaac aaaaacggct ttacgcccga ttgctgacgc tgttatttgc gctcatcttc    60
ttgctgcctc attctgcagc agcggcggca aatcttaatg ggacgctgat gcagtatttt   120
gaatggtaca tgcccaatga cggccaacat tggaagcgtt tgcaaaacga ctcggcatat   180
ttggctgaac acggtattac tgccgtctgg attccccggg catataaggg aacgagccaa   240
gcggatgtgg gctacggtgc ttacgacctt tatgatttag gggagtttca tcaaaaaggg   300
acggttcgga caaagtacgg cacaaaagga gagctgcaat ctgcgatcaa aagtcttcat   360
tcccgcgaca ttaacgttta cggggatgtg gtcatcaaac acaaaggcgg cgctgatgcg   420
accgaagatg taaccgcggt tgaagtcgat cccgctgacc gcaaccgcgt aatttcagga   480
gaacacctaa ttaaagcctg gacacatttt catttccggg ggcgcggcag cacatacagc   540
gattttaaat ggcattggta ccattttgac ggaaccgatt gggacgagtc ccgaaagctg   600
aaccgcatct ataagtttca aggaaaggct tgggattggg aagtttccaa tgaaaacggc   660
aactatgatt atttgatgta tgccgacatc gattatgacc atcctgatgt cgcagcagaa   720
attaagagat gggcacttgg gtatgccaat gaactgcaat tggacggttt ccgtcttgat   780
gctgtcaaac acattaaatt ttcttttttg cgggattggg ttaatcatgt cagggaaaaa   840
acggggaagg aaatgtttac ggtagctgaa tattggcaga ttgacttggg cgcgctggaa   900
aactatttga acaaaacaaa ttttaatcat tcagtgtttg acgtgccgct tcattatcag   960
ttccatgctg catcgacaca gggaggcggc tatgatatga ggaaattgct gaacggtacg  1020
gtcgtttcca agcatccgtt gaaatcggtt acatttgtcg ataaccatga tacacagccg  1080
gggcaatcgc ttgagtcgac tgtccaaaca tggtttaaac cgcttgctta cgctttatt   1140
ctcacaaggg aatctggata ccctcaggtt ttctacgggg atatgtacgg gacgaaagga  1200
gactcccagc gcgaaattcc tgccttgaaa cacaaaattg aaccgatctt aaaagcgaga  1260
aaacagtatg cgtacggagc acagcatgat tatttcgacc accatgacat tgtcggctgg  1320
acaagggaag cgcgacagctc ggttgcaaat tcaggttttgg cggcattaat aacagacgga  1380
cccggtgggg caaagcgaat gtatgtcggc cggcaaaacg ccggtgagac atggcatgac  1440
attaccggaa accgttcgga gccggttgtc atcaattcgg aaggctgggg agagtttcac  1500
gtaaacggcg ggtcggtttc aatttatgtt caaagatag                         1539

SEQ ID NO: 16           moltype = AA   length = 512
FEATURE                 Location/Qualifiers
source                  1..512
                        mol_type = protein
                        organism = Bacillus licheniformis
SEQUENCE: 16
MKQQKRLYAR LLTLLFALIF LLPHSAAAAA NLNGTLMQYF EWYMPNDGQH WKRLQNDSAY    60
LAEHGITAVW IPPAYKGTSQ ADVGYGAYDL YDLGEFHQKG TVRTKYGTKG ELQSAIKSLH   120
SRDINVYGDV VINHKGGADA TEDVTAVEVD PADRNRVISG EHLIKAWTHF HPGRGSTYS    180
DFKWHWYHFD GTDWDESRKL NRIYKFQGKA WDWEVSNENG NYDYLMYADI DYDHPDVAAE   240
IKRWGTWYAN ELQLDGFRLD AVKHIKFSFL RDWVNHVREK TGKEMFTVAE YWQNDLGALE   300
NYLNKTNFNH SVFDVPLHYQ FHAASTQGGG YDMRKLLNGT VVSKHPLKSV TFVDNHDTQP   360
GQSLESTVQT WFKPLAYAFI LTRESGYPQV FYGDMYGTKG DSQREIPALK HKIEPILKAR   420
KQYAYGAQHD YFDHHDIVGW TREGDSSVAN SGLAALITDG PGGAKRMYVG RQNAGETWHD   480
ITGNRSEPVV INSEGWGEFH VNGGSVSIYV QR                                 512

SEQ ID NO: 17           moltype = DNA   length = 996
FEATURE                 Location/Qualifiers
misc_feature            1..996
                        note = DNA sequence that encodes a cellulase
source                  1..996
                        mol_type = other DNA
                        organism = synthetic construct
SEQUENCE: 17
atgaagtttc agagcacttt gcttcttgcc gccgcggctg ttccgcgtt ggctgtgcct     60
catggctccg gacataagaa gagggcgtct gtgtttgaat ggttcggatc gaacgagtct   120
ggtgctgaat ttgggaccaa tatcccaggc gtctggggaa ccgactacat cttccccgac   180
ccctcgacca tctctacgtt gattggcaag ggaatgaact tcttccgcgt ccagttcatg   240
atggagaggt tgcttcctga ctcgatgact ggttcatacg acgaggagta tctgccaac    300
ttgacgactg tggtgaaagc ggtcacggat ggaggccgac atgcgctcat cgaccctcat   360
aactatggca gatacaacgg ggagatcatc tccagtacat cggatttcca gactttctgt   420
cagaatctgg cgggccagta caagataac gacttggtca tgtttgatac caacaacgaa   480
tactacgaca tggaccagga tctcgtgctg aatctcaacc aagcagccat taacggcatc   540
cgcgctgcag gtgcaagcca gtacattttc gtcgaaggca actcctggac cggagcttgg   600
acatgggtcg atgtcaacga taatatgaag aatttgaccg acccagaaga caatcctcag   660
tatgaaatgc accagtacct agactccgac ggttccggca cttcggagac ctgtgtctcc   720
gggacaatcg aaaggagcg atcactgat gctacacagt ggctcaagga caataagaag   780
gtcggcttca tcggcgaata tgccgggggg tccaatgatg tgtgtcggag tgccgtgcc   840
gggatgctag agtacatggc gaacaacacc gacgtatgga aggtgcgtc gtggtgggca   900
gccgggcat ggtggggaga ctacattttc agcctggagc cccagatgg aactgcttac    960
acgggtatgc tggatatcct ggagacgtat ctctga                            996

SEQ ID NO: 18           moltype = AA   length = 331
FEATURE                 Location/Qualifiers
source                  1..331
```

```
                    mol_type = protein
                    organism = Aspergillus niger
SEQUENCE: 18
MKFQSTLLLA AAAGSALAVP HGSGHKKRAS VFEWFGSNES GAEFGTNIPG VWGTDYIFPD   60
PSTISTLIGK GMNFFRVQFM MERLLPDSMT GSYDEEYLAN LTTVVKAVTD GGAHALIDPH  120
NYGRYNGEII SSTSDFQTFW QNLAGQYKDN DLVMFDTNNE YYDMDQDLVL NLNQAAINGI  180
RAAGASQYIF VEGNSWTGAW TWVDVNDNMK NLTDPEDKIV YEMHQYLDSD GSGTSETCVS  240
GTIGKERITD ATQWLKDNKK VGFIGEYAGG SNDVCRSAVS GMLEYMANNT DVWKGASWWA  300
AGPWWGDYIF SLEPPDGTAY TGMLDILETY L                                331

SEQ ID NO: 19          moltype = DNA  length = 1155
FEATURE                Location/Qualifiers
misc_feature           1..1155
                       note = DNA sequence that encodes proteinase K
source                 1..1155
                       mol_type = other DNA
                       organism = synthetic construct
SEQUENCE: 19
atgcgtttgt ctgttcttct gagtcttctt ccctcgctc tcggcgctcc tgccgttgag    60
cagcgctccg aggctgctcc tctgatcgag gcccgcggcg agatggttgc caacaagtac   120
attgtcaagt tcaaggaggg tagcgctctt tctgctctcg atgctgccat ggagaagatt   180
tctggcaagc ccgaccacgt ctacaagaac gtcttcagtg gtttcgctgc gacccttgac   240
gagaacatgg ttcgggttct ccgcgcccat cccgatgttg agtacattga gcaggatgct   300
gttgtcacca tcaacgctgc gcagaccaac gctcccgtgg gccttgctcg catctccagc   360
accagccccg gtacctctac ttactactat gacgaatctg ccggcaagg ctcctgcgtc   420
tacgtgattg acaccggtat cgaggcatcg caccccgagt tgagggtcg tgcccagatg   480
gtcaagacct actactactc cagtcgcgac ggtaacggtc acggcactca ctgcgctggt   540
accgttggct cccgaaccta cggtgtcgcc aagaagaccc agctctttgg tgtcaaggtc   600
ctcgatgaca acggcagtgg ccagtactcc accatcatcg ccggtatgga ctttgttgcc   660
agcgacaaga acaaccgcaa ctgccccaaa ggtgtcgttg cctccttgtc ccttggcggt   720
ggttactcct cctccgtgaa cagcgccgct gccaggctcc agagctctgg tgtcatgggt   780
gccgtcgctg ccggtaacaa caacgctgac gcccgcaact actcccctgc ttctgagccc   840
tcggtctgca ctgtcggtgc ttctgaccgc tacgacagac gctccagctt ctccaactac   900
ggcagcgttt tggacatctt tggccctggt accagcattc tctccacctg gatcggcggc   960
agcacccgct ccatctctgg aacttccatg gctactcccc acgttgccgg tctcgctgcc  1020
tacctcatga ctcttggaaa gactaccgcc gccagcgctt gccgatacat tgccgacacc  1080
gccaacaagg gcgacttgag caacattccc tccggcactg tcaacctgct tgcctacaac  1140
aactaccagg cttaa                                                   1155

SEQ ID NO: 20          moltype = AA  length = 384
FEATURE                Location/Qualifiers
source                 1..384
                       mol_type = protein
                       organism = Parengyodontium album
SEQUENCE: 20
MRLSVLLSLL PLALGAPAVE QRSEAAPLIE ARGEMVANKY IVKFKEGSAL SALDAAMEKI   60
SGKPDHVYKN VFSGFAATLD ENMVRVLRAH PDVEYIEQAQ VVTINAAQTN APWGLARISS  120
TSPGTSTYYY DESAGQGSCV YVIDTGIEAS HPEFEGRAQM VKTYYYSSRD GNGHGTHCAG  180
TVGSRTYGVA KKTQLFGVKV LDDNGSGQYS TIIAGMDFVA SDKNNRNCPK GVVASLSLGG  240
GYSSSVNSAA ARLQSSGVMV AVAAGNNNAD ARNYSPASEP SVCTVGASDR YDRRSSFSNY  300
GSVLDIFGPG TSILSTWIGG STRSISGTSM ATPHVAGLAA YLMTLGKTTA ASACRYIADT  360
ANKGDLSNIP FGTVNLLAYN NYQA                                        384

SEQ ID NO: 21          moltype = DNA  length = 1140
FEATURE                Location/Qualifiers
misc_feature           1..1140
                       note = DNA sequence that encodes subtilisin
source                 1..1140
                       mol_type = other DNA
                       organism = synthetic construct
SEQUENCE: 21
atgatgagga aaagagtttt ttggcttggg atgctgacgg ccttcatgct cgtgttcacg    60
atggcattca gcgattccgc ttctgctgct caaccggcga aaaatgttga aaggattat   120
attgtcggat ttaagtcagg agtgaaaacc gcatctgtca aaaaggacat catcaaagag   180
agcggcggaa aagtggacaa gcagtttaga atcatcaacg cggcaaaagc gaagctagac   240
aaagaagcgc ttaaggaagt caaaaatgat ccggatgtcg cttatgtgga agaggatcat   300
gtggcccatg ccttggcgca aaccgttcct acggcattc ctctcattaa agcggacaaa   360
gtgcaggctc aaggctttaa gggagcgaat gtaaaagtga ccgtcctgga tacaggaatc   420
caagcttctc atccggactt gaactagtc ggcgagcaa gctttgtgc tggcgaagct   480
tataacaccg acggcaacgg acacggcaca catgttgccg gtacagtagc tgcgcttgac   540
aatacaacgg gtgtattagg cgttgcgcca agctatcct tgtacgcggt taaagtactg   600
aattcaagcg gaagcggaac ttacagcggg attgtaagcg gaatcgagtg ggcgacgaca   660
aacggcatgg atgttatcaa catgagtctt ggaggaccat caggctcaac agcgatgaaa   720
caggcggttg acaatgcata tgcaagaggg gttgtcgttg tggccgtcgc tgcaggaaacgc   780
ggatcttcag gaaacacgaa tacaatcggc tatcctgcga atacgactc tgtcatcgca   840
gttggcgcgt agactctaa cagcaacaga gcttcatttt ccagcgtcgg agcagagctt   900
gaagtcatgg ctcctggcgc aggcgtgtac agcacttacc caaccagcac ttatgcaaca   960
ttgaacggaa cgtcaatggc ttcctcat gtagcgggag cagcagcttt gatcttgtca  1020
aaacatccga acctttcagc ttcacaagtc cgcaaccgtc tctccagtac ggcgactat  1080
```

```
ttgggaagct ccttctacta tggaaaaggt ctgatcaatg tcgaagctgc cgctcaataa  1140

SEQ ID NO: 22            moltype = AA   length = 379
FEATURE                  Location/Qualifiers
source                   1..379
                         mol_type = protein
                         organism = Bacillus licheniformis
SEQUENCE: 22
MMRKKSFWLG MLTAFMLVFT MAFSDSASAA QPAKNVEKDY IVGFKSGVKT ASVKKDIIKE   60
SGGKVDKQFR IINAAKAKLD KEALKEVKND PDVAYVEEDH VAHALAQTVP YGIPLIKADK  120
VQAQGFKGAN VKVAVLDTGI QASHPDLNVV GGASFVAGEA YNTDGNGHGT HVAGTVAALD  180
NTTGVLGVAP SVSLYAVKVL NSSGSGSYSG IVSGIEWATT NGMDVINMSL GGASGSTAMK  240
QAVDNAYAKG VVVVAAAGNS GSSGNTNTIG YPAKYDSVIA VGAVDSNSNR ASFSSVGAEL  300
EVMAPGAGVY STYPTNTYAT LNGTSMASPH VAGAAALILS KHPNLSASQV RNRLSSTATY  360
LGSSFYYGKG LINVEAAAQ                                               379

SEQ ID NO: 23            moltype = DNA   length = 669
FEATURE                  Location/Qualifiers
misc_feature             1..669
                         note = DNA sequence that encodes trypsin
source                   1..669
                         mol_type = other DNA
                         organism = synthetic construct
SEQUENCE: 23
atcgtcgggg gctacacctg cgcagagaat tccgtcccct accaggtgtc cctgaatgct   60
ggctaccact tctgcggggg ctccctcatc aatgaccagt gggtggtcgt cgcggctcac  120
tgctaccagt accacatcca ggtgaggctg ggagaataca acattgatgt cttggagggt  180
ggtgagcagt tcatcgatgc gtccaagatc atccgccacc ccaagtacag cagctggact  240
ctggacaatg acatcctgct gatcaaactc tccacgcctg cggtcatcaa tgcccggtg   300
tccaccttgc tgctgcccag tgcctgtgct ccgcaggca tgactcccgg c            360
tggggcaaca ccctgagcag tggcgtcaac taccccggacc tgctgcaatg cctggtgctc  420
ccgctgctga gccacgccga ctgtgaagcc tcataccctg acagatcac taacaacatg   480
atctgcgctg cttcctgga aggaggcaag gattcctgcc agggtgactc tggcggcccct  540
gtggcttgca acgacagct ccagggcatt gtgtcctggg gctacggctg tgcccagaag   600
ggcaagcctg gggtctacac caaggtctgc aactacgtgg actggattca ggagaccatc  660
gccgccaac                                                          669

SEQ ID NO: 24            moltype = AA   length = 223
FEATURE                  Location/Qualifiers
source                   1..223
                         mol_type = protein
                         organism = Bos taurus
SEQUENCE: 24
IVGGYTCGAN TVPYQVSLNS GYHFCGGSLI NSQWVVSAAH CYKSGIQVRL GEDNINVVEG   60
NEQFISASKS IVHPSYNSNT LNNDIMLIKL KSAASLNSRV ASISLPTSCA SAGTQCLISG  120
WGNTKSSGTS YPDVLKCLKA PILSDSSCKS AYPGQITSNM FCAGYLEGGK DSCQGDSGGP  180
VVCSGKLQGI VSWGSGCAQK NKPGVYTKVC NYVSWIKQTI ASN                    223

SEQ ID NO: 25            moltype = DNA   length = 1464
FEATURE                  Location/Qualifiers
misc_feature             1..1464
                         note = DNA sequence that encodes serratiopeptidase
source                   1..1464
                         mol_type = other DNA
                         organism = synthetic construct
SEQUENCE: 25
atgcaatcta ctaaaaaggc aattgaaatt actgaatcca gcctcgctgc cgcgacaacc   60
ggttacgatg ctgtagacga cctgctgcat tatcatgagc ggggtaacgg gattcagatt  120
aatggcaagg attcattttc taacgagcaa gctgggctgt ttattacccg tgagaaccaa  180
acctggaacg gttacaaggt atttggccag ccggtcaaat taaccttctc gttcccggac  240
tataagttct cttccaccaa cgtcgccggc gacaccgggc tgagcaagtt cagcgcggaa  300
cagcagcagc aggctaagct gtcgctgcag tcctgggccg acgtcgccaa tatcaccttc  360
accgaagtgg cggccggtca aaaggccaat atcaccttcg gcaactacag ccaggatcgt  420
cccggccact atgattacgg cacccaggcc tacgccttcc tgccgaacac cattggccag  480
ggccaggatt tgggcggcca gacttggtac aacgtaaaac aatccaacgt gaagcatccg  540
gcgaccgaag actacggccg ccagacgttc cccatgagaa ttggccatgc gctgggcctg  600
agccaccggg cgactacaa cgccggtgag ggcaacccga cctatagaga tgtcacctat  660
gcggaagata cccgccagtt cagcctgatg agctactgga gtgaaaccaa taccggtgcc  720
dacaacgcg gtcactgatg cgcggctccg ctgctgaaca cgtagtgcc cattcagcat  780
ctgtatggcg ccaacctgtc gacccgcacc ggcgacaccg tgtacggctt taactccaat  840
accggtcgtg acttcctcag caccaccagc aactcgcaga aagtgatctt tgcggcctgg  900
gatgcgggcg gcaacgatac cttcgactc tccggttaca ccgctaacca gcgcatcaac  960
ctgaacgaga atggtttctc cgacgtgggc ggcctgaagg caacgtgtc gatcgccgcc 1020
ggtgtgacca ttgagaacgc cattggcggt tccggcaacg acgtgatcgt caacaacgcg 1080
gccaataacg tgctgaaagg cggcgcgggt aacgacgtgc tgttcggcgg cggcggggcg 1140
gatgaattgt ggggcggtgc cggcaaagac atcttcgtgt ctctgccgc cagcgattcc 1200
gcaccgggcg cttcagactg gatccgcgac ttccagaaag ggatcgacaa gatcgacctg 1260
tcgttcttca ataaagaagc gcagagcagc gatttcattc acttcgtcga tcacttcagc 1320
ggcacggccg tgaggcgct gctgagctac aacgcgtcca gcaacgtgac cgatttgtcg 1380
```

```
gtgaacatcg gtgggcatca ggcgccggac ttcctggtga aaatcgtcgg ccaggtagac    1440
gtcgccacgg actttatcgt gtaa                                            1464

SEQ ID NO: 26          moltype = AA  length = 487
FEATURE                Location/Qualifiers
source                 1..487
                       mol_type = protein
                       organism = Serratia sp.
SEQUENCE: 26
MQSTKKAIEI TESSLAAATT GYDAVDDLLH YHERGNGIQI NGKDSFSNEQ AGLFITRENQ     60
TWNGYKVFGQ PVKLTFSFPD YKFSSTNVAG DTGLSKFSAE QQQQAKLSLQ SWADVANITF    120
TEVAAGQKAN ITFGNYSQDR PGHYDYGTQA YAFLPNTIWQ GQDLGGQTWY NVNQSNVKHP    180
ATEDYGRQTF THEIGHALGL SHPGDYNAGE GNPTYRDVTY AEDTRQFSLM SYWSETNTGG    240
DNGGHYAAAP LLDDIAAIQH LYGANLSTRT GDTVYGFNSN TGRDFLSTTS NSQKVIFAAW    300
DAGGNDTFDF SGYTANQRIN LNEKWFSDVG GLKGNVSIAA GVTIENAIGG SGNDVIVGNA    360
ANNVLKGGAG NDVLFGGGGA DELWGGAGKD IFVFSAASDS APGASDWIRD FQKGIDKIDL    420
SFFNKEAQSS DFIHFVDHFS GTAGEALLSY NASSNVTDLS VNIGGHQAPD FLVKIVGQVD    480
VATDFIV                                                              487

SEQ ID NO: 27          moltype = DNA  length = 783
FEATURE                Location/Qualifiers
misc_feature           1..783
                       note = DNA sequence that encodes a bovine pancreatic DNAse I
source                 1..783
                       mol_type = other DNA
                       organism = synthetic construct
SEQUENCE: 27
ttgaagattg ctgctttcaa cattagaact ttcggtgaaa ctaaaatgtc taacgctact     60
ttggcatctt acatcgttag aattgtcaga agatatgata tcgttttaat tcaagaagtt    120
agagactctc acttggttgc agttggtaaa ttgttagact acttgaacca agatgaccca    180
aacacttacc actacgttgt ttctgaacca ttgggtagaa actcttacaa agaaagatac    240
ttattcttgt tcagaccaaa caaagtttca gttttggata cttaccaata cgacgacggt    300
tgcgaatctt gtggtaacga ttctttctcc agagaacctg ctgttgttaa attctcatca    360
cactctacca aggttaaaga gttcgctatc gttgctttgc attctgctcc ttctgacgct    420
gttgctgaaa ttaactcttt gtacgacgtt tacttagatg ttcaacagaa atggcacttg    480
aacgacgtca tgttgatggg tgactttaac gctgattgct cttatgttac ttcttctcaa    540
tggtcttcaa ttagattgag aacatcttca actttccaat ggttaattcc tgattccgct    600
gataccactg ctactagtac caactgtgct tacgatagaa tcgttgttgc tggatcatta    660
ttgcaatctt ctgttgtccc aggttcagcg gccccctttcg atttccaagc tgcatatggt    720
ttgtctaatg aaatggcttt agccatttct gatcactacc cagttgaagt cacattgaca    780
taa                                                                  783

SEQ ID NO: 28          moltype = AA  length = 260
FEATURE                Location/Qualifiers
source                 1..260
                       mol_type = protein
                       organism = Bos taurus
SEQUENCE: 28
LKIAAFNIRT FGETKMSNAT LASYIVRIVR RYDIVLIQEV RDSHLVAVGK LLDYLNQDDP     60
NTYHYVVSEP LGRNSYKERY LFLFRPNKVS VLDTYQYDDG CESCGNDSFS REPAVVKFSS    120
HSTKVKEFAI VALHSAPSDA VAEINSLYDV YLDVQQKWHL NDVMLMGDFN ADCSYVTSSQ    180
WSSIRLRTSS TFQWLIPDSA DTTATSTNCA YDRIVVAGSL LQSSVVPGSA APFDFQAAYG    240
LSNEMALAIS DHYPVEVTLT                                                260
```